US008980879B2

(12) United States Patent
Liu et al.

(10) Patent No.: US 8,980,879 B2
(45) Date of Patent: Mar. 17, 2015

(54) BROMODOMAIN INHIBITORS

(71) Applicant: AbbVie Inc., North Chicago, IL (US)

(72) Inventors: Dachun Liu, Vernon Hills, IL (US);
John Pratt, Kenosha, WI (US); Le Wang, Vernon Hills, IL (US); Lisa A. Hasvold, Grayslake, IL (US); Andrew Bogdan, Evanston, IL (US)

(73) Assignee: AbbVie Inc., North Chicago, IL (US)

(*) Notice: Subject to any disclaimer, the term of this patent is extended or adjusted under 35 U.S.C. 154(b) by 0 days.

(21) Appl. No.: 14/203,651

(22) Filed: Mar. 11, 2014

(65) Prior Publication Data

US 2014/0256710 A1    Sep. 11, 2014

Related U.S. Application Data

(60) Provisional application No. 61/776,547, filed on Mar. 11, 2013.

(51) Int. Cl.
| | |
|---|---|
| *C07D 471/04* | (2006.01) |
| *C07D 487/04* | (2006.01) |
| *A61K 31/407* | (2006.01) |
| *A61K 31/437* | (2006.01) |
| *A61K 31/5025* | (2006.01) |
| *A61K 31/519* | (2006.01) |
| *A61K 31/18* | (2006.01) |
| *C07D 471/16* | (2006.01) |
| *C07D 471/12* | (2006.01) |
| *C07D 471/22* | (2006.01) |

(52) U.S. Cl.
CPC ............ *C07D 471/16* (2013.01); *C07D 471/12* (2013.01); *C07D 471/22* (2013.01)
USPC ................... 514/211.1; 514/212.05; 514/215; 540/520; 540/546; 540/578

(58) Field of Classification Search
USPC .......... 540/520, 546, 578; 514/211.1, 212.05, 514/215
See application file for complete search history.

(56) References Cited

U.S. PATENT DOCUMENTS

| 4,010,159 A | 3/1977 | Tarzia et al. |
|---|---|---|
| 2008/0011457 A1 | 1/2008 | Mirolli et al. |

FOREIGN PATENT DOCUMENTS

| WO | 0204453 A2 | 1/2002 |
|---|---|---|
| WO | 2006129623 A1 | 12/2006 |
| WO | 2011054553 A1 | 5/2011 |
| WO | 2011161031 A1 | 12/2011 |
| WO | 2012075456 A1 | 6/2012 |
| WO | 2012143415 A1 | 10/2012 |
| WO | 2012143416 A2 | 10/2012 |
| WO | 2012150234 A1 | 11/2012 |
| WO | 2012151512 A2 | 11/2012 |
| WO | 2012174487 A2 | 12/2012 |
| WO | 2013024104 A1 | 2/2013 |
| WO | 2013027168 A1 | 2/2013 |

OTHER PUBLICATIONS

Banerjee C., et al., "BET Bromodomain Inhibition as a Novel Strategy for Reactivation of HIV-1," Journal of Leukocyte Biology, 2012, vol. 92 (6), pp. 1147-1154.
Barraja P., et al., "Synthesis of the New Ring System 6,8-dihydro-5H-pyrrolo[3,4-h]Quinazoline," Tetrahedron Letters, 2009, vol. 50 (38), pp. 5389-5391.
Berge, S. M. et al., "Pharmaceutical Salts," Journal of Pharmaceutical Sciences, 1977, vol. 66 (1), pp. 1-19.
Bew S.P., et al., "Stereoselective Synthesis of N-alkylaziridines from N-chloroamines," Chemical Communications, 2006, vol. 4 (41), pp. 4338-4340.
Dattolo G., et al., "Polycondensed Nitrogen Heterocycles. Part 22. Pyrrolo[3,4-d]-1,2,3-triazines: A New Ring System as Potential Antineoplastic Agent," Journal of Heterocyclic Chemistry, 1989, vol. 26 (6), pp. 1747-1749.
Dawson M.A., et al., "Inhibition of BET Recruitment to Chromatin as an Effective Treatment for MLL-fusion Leukaemia," Nature, 2011, vol. 478 (7370), pp. 529-533.
Delmore J.E., et al., "BET Bromodomain Inhibition as a Therapeutic Strategy to Target c-Myc," Cell, 2011, vol. 146 (6), pp. 904-917.
Denis G.V., "Bromodomain Coactivators in Cancer, Obesity, type 2 Diabetes, and Inflammation," Discovery Medicine, 2010, vol. 10 (55), pp. 489-499.
Eastwood B.J., et al., "The Minimum Significant Ratio: A Statistical Parameter to Characterize the Reproducibility of Potency Estimates from Concentration-Response Assays and Estimation by Replicate-Experiment Studies," Journal of Biomolecular Screening, 2006, vol. 11 (3), pp. 253-261.
Green, et al., "Protecting Groups in Organic Synthesis" in: Antibodies, 3rd Edition, John Wiley & Sons, NY, 1999, pp. 20.

(Continued)

*Primary Examiner* — Bruck Kifle
(74) *Attorney, Agent, or Firm* — Glen J. Gesicki

(57) ABSTRACT

The present invention provides for compounds of formula (I)

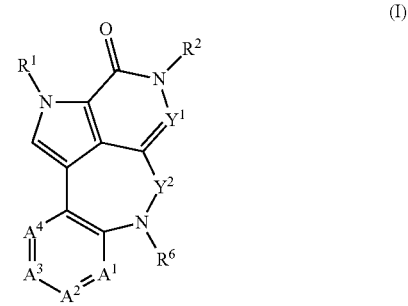

(I)

wherein $R^1$, $R^2$, $R^6$, $Y^1$, $Y^2$, $A^1$, $A^2$, $A^3$, and $A^4$ have any of the values defined in the specification, and pharmaceutically acceptable salts thereof, that are useful as agents in the treatment of diseases and conditions, including inflammatory diseases, cancer, and AIDS. Also provided are pharmaceutical compositions comprising one or more compounds of formula (I).

32 Claims, No Drawings

(56) References Cited

OTHER PUBLICATIONS

Huang B., et al., "Brd4 Coactivates Transcriptional Activation of NF-kappaB Via Specific Binding to Acetylated RelA," Molecular and Cellular Biology, 2009, vol. 29 (5), pp. 1375-1387.

International Search Report and Written Opinion for Application No. PCT/US20141023437, mailed on Jul. 11, 2014, 14 pages.

International Search Report and Written Opinion for Application No. PCT/US2014/023463, mailed on Jul. 2, 2014, 7 pages.

Jang M.K., et al., "The Bromodomain Protein Brd4 is a Positive Regulatory Component of P-TEFb and Stimulates RNA Polymerase II-dependent Transcription," Molecular Cell, 2005, vol. 19 (4), pp. 523-534.

Leroy G., et al., "The Double Bromodomain Proteins Brd2 and Brd3 Couple Histone Acetylation to Transcription," Molecular Cell, 2008, vol. 30 (1), pp. 51-60.

Matzuk M.M., et al., "Small-molecule Inhibition of BRDT for Male Contraception," Cell, 2012, vol. 150 (4), pp. 673-684.

Mertz J.A., et al., "Targeting MYC Dependence in Cancer by Inhibiting BET Bromodomains," Proceedings of the National Academy of Sciences, 2011, vol. 108 (40), pp. 16669-16674.

Miyaura N., et al., "Palladium-Catalyzed Cross-Coupling Reactions of Organoboron Compounds," Chemical Reviews, 1995, vol. 95 (7), pp. 2457-2483.

Nicodeme E., et al., "Suppression of Inflammation by a Synthetic Histone Mimic," Nature, 2010, vol. 468 (7327), pp. 1119-1123.

Prescott, Ed., Methods in Cell Biology, vol. XIV, Academic Press, New York, 1976, pp. 33.

Sutton, V.R. et al., "Bcl-2 Prevents Apoptosis Induced by Perforin and Granzyme B, But Not That Mediated by Whole Cytotoxic Lymphocytes," Journal of Immunology, 1997, vol. 158 (12), pp. 5783-5790.

Suzuki A, "Recent Advances in the Cross-Coupling Reactions of Organoboron Derivatives with Organic Electrophiles," Journal of Organometallic Chemistry, 1999, vol. 576, pp. 147-168.

Yang Z., et al., "Brd4 Recruits P-TEFb to Chromosomes at Late Mitosis to Promote G1 Gene Expression and Cell Cycle Progression," Molecular and Cellular Biology, 2008, vol. 28 (3), pp. 967-976.

Zhang G., et al., "Down-regulation of NF-κB Transcriptional Activity in HIV-associated Kidney Disease by BRD4 Inhibition," Journal of Biological Chemistry, 2012, vol. 287 (34), pp. 28840-28851.

Zuber J., et al., "RNAi Screen Identifies Brd4 as a Therapeutic Target in Acute Myeloid Leukaemia," Nature, 2011, vol. 478 (7370), pp. 524-528.

BROMODOMAIN INHIBITORS

BACKGROUND

Bromodomains refer to conserved protein structural folds which bind to N-acetylated lysine residues that are found in some proteins. The BET family of bromodomain containing proteins is comprised of four members (BRD2, BRD3, BRD4 and BRDt). Each member of the BET family employs two bromodomains to recognize N-acetylated lysine residues found primarily, but not exclusively, on the amino-terminal tails of histone proteins. These interactions modulate gene expression by recruiting transcription factors to specific genome locations within chromatin. For example, histone-bound BRD4 recruits the transcription factor P-TEFb to promoters, resulting in the expression of a subset of genes involved in cell cycle progression (Yang et al., Mol. Cell. Biol. 28: 967-976 (2008)). BRD2 and BRD3 also function as transcriptional regulators of growth promoting genes (LeRoy et al., Mol. Cell. 30: 51-60 (2008)). BET family members were recently established as being important for the maintenance of several cancer types (Zuber et al., Nature 478: 524-528 (2011); Mertz et al; Proc. Nat'l. Acad. Sci. 108: 16669-16674 (2011); Delmore et al., Cell 146: 1-14, (2011); Dawson et al., Nature 478: 529-533 (2011)). BET family members have also been implicated in mediating acute inflammatory responses through the canonical NF-κB pathway (Huang et al., Mol. Cell. Biol. 29: 1375-1387 (2009)) resulting in the upregulation of genes associated with the production of cytokines (Nicodeme et al., Nature 468: 1119-1123, (2010)). Suppression of cytokine induction by BET bromodomain inhibitors has been shown to be an effective approach to treat inflammation-mediated kidney disease in an animal model (Zhang, et al., J. Biol. Chem. 287: 28840-28851 (2012)). BRD2 function has been linked to predisposition for dyslipidemia or improper regulation of adipogenesis, elevated inflammatory profiles and increased susceptibility to autoimmune diseases (Denis, Discovery Medicine 10: 489-499 (2010)). The human immunodeficiency virus utilizes BRD4 to initiate transcription of viral RNA from stably integrated viral DNA (Jang et al., Mol. Cell, 19: 523-534 (2005)). BET bromodomain inhibitors have also been shown to reactivate HIV transcription in models of latent T cell infection and latent monocyte infection (Banerjee, et al, J. Leukocyte Biol. doi:10.1189/jlb.0312165). BRDt has an important role in spermatogenesis that is blocked by BET bromodomain inhibitors (Matzuk, et al., Cell 150: 673-684 (2012)). Thus, compounds that inhibit the binding of BET family bromodomains to their cognate acetylated lysine proteins are being pursued for the treatment of cancer, inflammatory diseases, kidney diseases, diseases involving metabolism or fat accumulation, and some viral infections, as well as for providing a method for male contraception. Accordingly, there is an ongoing medical need to develop new drugs to treat these indications.

SUMMARY

In one aspect the present invention provides for compounds of formula (I) or a salt thereof,

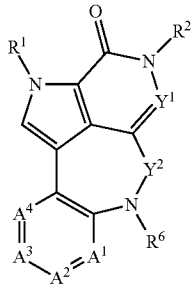

(I)

wherein
$R^1$ is $CD_3$, $C_1$-$C_3$ alkyl, or $C_1$-$C_3$ haloalkyl;
$R^2$ is H or $C_1$-$C_3$ alkyl;
$Y^1$ is N or $CR^3$;
$R^3$ is H, $C_1$-$C_6$ alkyl, $C_2$-$C_6$ alkenyl, $C_2$-$C_6$ alkynyl, halogen, $C_1$-$C_6$ haloalkyl, —C(O)$R^{3a}$, —C(O)O$R^{3a}$, —C(O)N$R^{3b}R^{3c}$, —C(O)N($R^{3b}$)N$R^{3b}R^{3c}$, —S(O)$R^{3d}$, —S(O)$_2R^{3a}$, —S(O)$_2$N$R^{3b}R^{3c}$ or $G^1$; wherein the $C_1$-$C_6$ alkyl, $C_2$-$C_6$ alkenyl, and $C_2$-$C_6$ alkynyl are each independently unsubstituted or substituted with 1 or 2 substituents independently selected from the group consisting of $G^1$, —C(O)$R^{3a}$, —C(O)O$R^{3a}$, —C(O)N$R^{3b}R^{3c}$, —S(O)$R^{3d}$, —S(O)$_2R^{3a}$, —S(O)$_2$N$R^{3b}R^{3c}$, —O$R^{3a}$, —OC(O)$R^{3d}$, —N$R^{3b}R^{3c}$, N($R^{3b}$)C(O)$R^{3d}$, N($R^{3b}$)SO$_2R^{3d}$, N($R^{3b}$)C(O)O$R^{3d}$, N($R^{3b}$)C(O)N$R^{3b}R^{3c}$, N($R^{3b}$)SO$_2$N$R^{3b}R^{3c}$, and N($R^{3b}$)C(N$R^{3b}R^{3c}$)=N$R^{3b}R^{3c}$;
$Y^2$ is C(O), S(O)$_2$, or $CR^4R^5$;
$R^4$ is H, deuterium, $C_1$-$C_6$ alkyl, halogen, or $C_1$-$C_6$ haloalkyl; and
$R^5$ is H, deuterium, $C_1$-$C_6$ alkyl, $C_2$-$C_6$ alkenyl, $C_2$-$C_6$ alkynyl, halogen, $C_1$-$C_6$ haloalkyl, —C(O)$R^{5a}$, —C(O)O$R^{5a}$, —C(O)N$R^{5b}R^{5c}$, —S(O)$R^{5d}$, —S(O)$_2R^{5a}$, —S(O)$_2$N$R^{5b}R^{5c}$, or $G^1$; wherein the $C_1$-$C_6$ alkyl, $C_2$-$C_6$ alkenyl, and $C_2$-$C_6$ alkynyl are each independently unsubstituted or substituted with 1 or 2 substituents independently selected from the group consisting of $G^1$, —C(O)$R^{5a}$, —C(O)O$R^{5c}$, —C(O)N$R^{5b}R^{5c}$, —C(O)N($R^{5b}$)N$R^{5b}R^{5c}$, —S(O)$R^{5d}$, —S(O)$_2R^{5a}$, —S(O)$_2$N$R^{5b}R^{5c}$, —O$R^{5a}$, —OC(O)$R^{5d}$—N$R^{5b}R^{5c}$, N($R^{5b}$)C(O)$R^{5d}$, N($R^{5b}$)SO$_2R^{5d}$, N($R^{5b}$)C(O)O$R^{5d}$, N($R^{5b}$)C(O)N$R^{5b}R^{5c}$, N($R^{5b}$)SO$_2$N$R^{5b}R^{5c}$, and N($R^{5b}$)C(N$R^{5b}R^{5c}$)=N$R^{5b}R^{5c}$;
$R^{3a}$, $R^{3b}$, $R^{3c}$, $R^{5a}$, $R^{5b}$, and $R^{5c}$, at each occurrence, are each independently H, $C_1$-$C_6$ alkyl, $C_2$-$C_6$ alkenyl, $C_2$-$C_6$ alkynyl, $C_1$-$C_6$ haloalkyl, $G^1$, or —($C_1$-$C_6$ alkylenyl)-$G^1$;
$R^{3d}$ and $R^{5d}$, at each occurrence, are each independently $C_1$-$C_6$ alkyl, $C_2$-$C_6$ alkenyl, $C_2$-$C_6$ alkynyl, $C_1$-$C_6$ haloalkyl, $G^1$, or —($C_1$-$C_6$ alkylenyl)-$G^1$;
$G^1$, at each occurrence, is independently aryl, heteroaryl, heterocycle, cycloalkyl, or cycloalkenyl; and each $G^1$ is optionally substituted with 1, 2, 3, 4, or 5 $R^{1g}$ groups;
$R^6$ is H, $C_1$-$C_6$ alkyl, $C_2$-$C_6$ alkenyl, $C_2$-$C_6$ alkynyl, halogen, $C_1$-$C_6$ haloalkyl, —C(O)$R^{6a}$, —C(O)O$R^{6a}$, —C(O)N$R^{6b}R^{6c}$, —S(O)$_2R^{6a}$, —S(O)$_2$N$R^{6b}R^{6c}$, or $G^2$; wherein the $C_1$-$C_6$ alkyl, $C_2$-$C_6$ alkenyl, and $C_2$-$C_6$ alkynyl are each independently unsubstituted or substituted with 1 or 2 substituents independently selected from the group consisting of $G^2$, —C(O)$R^{6a}$, —C(O)O$R^{6a}$, —C(O)N$R^{6b}R^{6c}$, —C(O)N($R^{6b}$)N$R^{6b}R^{6c}$, —S(O)$R^{6d}$, —S(O)$_2R^{6a}$, —S(O)$_2$N$R^{6b}R^{6c}$, —O$R^{6a}$, —OC(O)$R^{6d}$, —N$R^{6b}R^{6c}$, N($R^{6b}$)C(O)$R^{6d}$, N($R^{6b}$)SO$_2R^{6d}$, N($R^{6b}$)C(O)O$R^{6d}$, N($R^{6b}$)C(O)N$R^{6b}R^{6c}$, N($R^{6b}$)SO$_2$N$R^{6b}R^{6c}$, and N($R^{6b}$)C(N$R^{6b}R^{6c}$)=N$R^{6b}R^{6c}$;
$R^{6a}$, $R^{6b}$, and $R^{6c}$, at each occurrence, are each independently H, alkyl, $C_2$-$C_6$ alkenyl, $C_2$-$C_6$ alkynyl, haloalkyl, $G^2$, —($C_1$-$C_6$ alkylenyl)-$G^2$, —($C_1$-$C_6$ alkylenyl)-O$R^a$, —($C_1$-$C_6$ alkylenyl)-S(O)$_2R^a$, —($C_1$-$C_6$ alkylenyl)-S(O)$_2$N$R^cR^d$, —($C_1$-$C_6$ alkylenyl)-C(O)$R^a$, —($C_1$-$C_6$ alkylenyl)-C(O)O$R^a$, —($C_1$-$C_6$ alkylenyl)-C(O)N$R^cR^d$, —($C_1$-$C_6$ alkylenyl)-N$R^cR^d$, —($C_1$-$C_6$ alkylenyl)-N($R^e$)C(O)$R^b$, —($C_1$-$C_6$ alkylenyl)-N($R^e$)S(O)$_2R^b$, —($C_1$-$C_6$ alkylenyl)-N($R^e$)C(O)O($R^b$), —($C_1$-$C_6$ alkylenyl)-N($R^e$)C(O)N$R^cR^d$, or —($C_1$-$C_6$ alkylenyl)-N($R^e$)S(O)$_2$N$R^cR^d$;

$R^{6d}$, at each occurrence, is independently alkyl, $C_2$-$C_6$ alkenyl, $C_2$-$C_6$ alkynyl, haloalkyl, $G^2$, —($C_1$-$C_6$ alkylenyl)-$G^2$, —($C_1$-$C_6$ alkylenyl)-$OR^a$, —($C_1$-$C_6$ alkylenyl)-$S(O)_2R^a$, —($C_1$-$C_6$ alkylenyl)-$S(O)_2NR^cR^d$, —($C_1$-$C_6$ alkylenyl)-$C(O)R^a$, —($C_1$-$C_6$ alkylenyl)-$C(O)OR^a$, —($C_1$-$C_6$ alkylenyl)-$C(O)NR^cR^d$, —($C_1$-$C_6$ alkylenyl)-$NR^cR^d$, —($C_1$-$C_6$ alkylenyl)-$N(R^e)C(O)R^b$, —($C_1$-$C_6$ alkylenyl)-$N(R^e)S(O)_2R^b$, —($C_1$-$C_6$ alkylenyl)-$N(R^e)C(O)O(R^b)$, —($C_1$-$C_6$ alkylenyl)-$N(R^e)C(O)NR^cR^d$, or —($C_1$-$C_6$ alkylenyl)-$N(R^e)S(O)_2NR^cR^d$;

$G^2$, at each occurrence, is independently aryl, heteroaryl, heterocycle, cycloalkyl, or cycloalkenyl; and each $G^2$ is optionally substituted with 1, 2, 3, 4, or 5 $R^{2g}$ groups;

$A^1$ is $C(R^7)$ or N; $A^2$ is $C(R^8)$ or N; $A^3$ is $C(R^9)$ or N; and $A^4$ is $C(R^{10})$ or N; wherein zero, one, or two of $A^1$, $A^2$, $A^3$, and $A^4$ are N;

$R^7$, $R^8$, and $R^9$, are each independently H, $C_1$-$C_6$ alkyl, $C_2$-$C_6$ alkenyl, $C_2$-$C_6$ alkynyl, halogen, $C_1$-$C_6$ haloalkyl, —CN, $NO_2$, —$OR^{y1}$, —$OC(O)R^{y2}$, —$OC(O)NR^{y3}R^{y4}$, —$SR^{y1}$, —$S(O)_2R^{y1}$, —$S(O)_2NR^{y3}R^{y4}$, —$C(O)R^{y1}$, —$C(O)OR^{y1}$, —$C(O)NR^{y3}R^{y4}$, —$NR^{y3}R^{y4}$, —$N(R^{y3})C(O)R^{y2}$, —$N(R^{y3})S(O)_2R^{y2}$, —$N(R^{y3})C(O)O(R^{y2})$, —$N(R^{y3})C(O)NR^{y3}R^{y4}$, —$N(R^{y3})S(O)_2NR^{y3}R^{y4}$, $G^3$, —($C_1$-$C_6$ alkylenyl)-CN, —($C_1$-$C_6$ alkylenyl)-$OR^{y1}$, —($C_1$-$C_6$ alkylenyl)-$OC(O)R^{y2}$, —($C_1$-$C_6$ alkylenyl)-$OC(O)NR^{y3}R^{y4}$, —($C_1$-$C_6$ alkylenyl)-$S(O)_2R^{y1}$, —($C_1$-$C_6$ alkylenyl)-$S(O)_2NR^{y3}R^{y4}$, —($C_1$-$C_6$ alkylenyl)-$C(O)R^{y1}$, —($C_1$-$C_6$ alkylenyl)-$C(O)OR^{y1}$, —($C_1$-$C_6$ alkylenyl)-$C(O)NR^{y3}R^{y4}$, —($C_1$-$C_6$ alkylenyl)-$NR^{y3}R^{y4}$, —($C_1$-$C_6$ alkylenyl)-$N(R^{y3})C(O)R^{y2}$, —($C_1$-$C_6$ alkylenyl)-$N(R^{y3})S(O)_2R^{y2}$, —($C_1$-$C_6$ alkylenyl)-$N(R^{y3})C(O)O(R^{y2})$, —($C_1$-$C_6$ alkylenyl)-$N(R^{y3})C(O)NR^{y3}R^{y4}$, —($C_1$-$C_6$ alkylenyl)-$N(R^{y3})S(O)_2NR^{y3}R^{y4}$, —($C_1$-$C_6$ alkylenyl)-CN, or —($C_1$-$C_6$ alkylenyl)-$G^3$;

$R^{y1}$, $R^{y2}$, and $R^{y4}$, at each occurrence, are each independently H, $C_1$-$C_6$ alkyl, $C_2$-$C_6$ alkenyl, $C_2$-$C_6$ alkynyl, $C_1$-$C_6$ haloalkyl, $G^3$, —($C_1$-$C_6$ alkylenyl)-$G^3$, —($C_1$-$C_6$ alkylenyl)-$OR^a$, —($C_1$-$C_6$ alkylenyl)-$S(O)_2R^a$, —($C_1$-$C_6$ alkylenyl)-$S(O)_2NR^cR^d$, —($C_1$-$C_6$ alkylenyl)-$C(O)R^a$, —($C_1$-$C_6$ alkylenyl)-$C(O)OR^a$, —($C_1$-$C_6$ alkylenyl)-$C(O)NR^cR^d$, —($C_1$-$C_6$ alkylenyl)-$NR^cR^d$, —($C_1$-$C_6$ alkylenyl)-$N(R^e)C(O)R^b$, —($C_1$-$C_6$ alkylenyl)-$N(R^e)S(O)_2R^b$, —($C_1$-$C_6$ alkylenyl)-$N(R^e)C(O)O(R^b)$, —($C_1$-$C_6$ alkylenyl)-$N(R^e)C(O)NR^cR^d$, or —($C_1$-$C_6$ alkylenyl)-$N(R^e)S(O)_2NR^cR^d$;

$R^{y2}$, at each occurrence, is independently $C_1$-$C_6$ alkyl, $C_2$-$C_6$ alkenyl, $C_2$-$C_6$ alkynyl, $C_1$-$C_6$ haloalkyl, $G^3$, —($C_1$-$C_6$ alkylenyl)-$G^3$, —($C_1$-$C_6$ alkylenyl)-$OR^a$, —($C_1$-$C_6$ alkylenyl)-$S(O)_2R^a$, —($C_1$-$C_6$ alkylenyl)-$S(O)_2NR^cR^d$, —($C_1$-$C_6$ alkylenyl)-$C(O)R^a$, —($C_1$-$C_6$ alkylenyl)-$C(O)OR^a$, —($C_1$-$C_6$ alkylenyl)-$C(O)NR^cR^d$, —($C_1$-$C_6$ alkylenyl)-$NR^cR^d$, —($C_1$-$C_6$ alkylenyl)-$N(R^e)C(O)R^b$, —($C_1$-$C_6$ alkylenyl)-$N(R^e)S(O)_2R^b$, —($C_1$-$C_6$ alkylenyl)-$N(R^e)C(O)O(R^b)$, —($C_1$-$C_6$ alkylenyl)-$N(R^e)C(O)NR^cR^d$, or —($C_1$-$C_6$ alkylenyl)-$N(R^e)S(O)_2NR^cR^d$;

$G^3$, at each occurrence, is independently aryl, heteroaryl, cycloalkyl, cycloalkenyl, or heterocycle; and each $G^3$ group is optionally substituted with 1, 2, 3, 4, or 5 $R^{4g}$ groups;

$R^{10}$ is H, $C_1$-$C_3$ alkyl, halogen, $C_1$-$C_3$ haloalkyl, or —CN;

$R^{1g}$, $R^{2g}$, and $R^{4g}$, at each occurrence, is independently selected from the group consisting of oxo, $C_1$-$C_6$ alkyl, $C_2$-$C_6$ alkenyl, $C_2$-$C_6$ alkynyl, halogen, $C_1$-$C_6$ haloalkyl, —CN, $NO_2$, —$OR^a$, —$OC(O)R^b$, —$OC(O)NR^cR^d$, —$SR^a$, —$S(O)_2R^a$, —$S(O)_2NR^cR^d$, —$C(O)R^a$, —$C(O)OR^a$, —$C(O)NR^cR^d$, —$NR^cR^d$, —$N(R^e)C(O)R^b$, —$N(R^e)S(O)_2R^b$, —$N(R^e)C(O)O(R^b)$, —$N(R^e)C(O)NR^cR^d$, —$N(R^e)S(O)_2NR^cR^d$, —($C_1$-$C_6$ alkylenyl)-CN, —($C_1$-$C_6$ alkylenyl)-$G^{2a}$, —($C_1$-$C_6$ alkylenyl)-$OR^a$, —($C_1$-$C_6$ alkylenyl)-$OC(O)R^b$, —($C_1$-$C_6$ alkylenyl)-$OC(O)NR^cR^d$, —($C_1$-$C_6$ alkylenyl)-$S(O)_2R^a$, —($C_1$-$C_6$ alkylenyl)-$S(O)_2NR^cR^d$, —($C_1$-$C_6$ alkylenyl)-$C(O)R^a$, —($C_1$-$C_6$ alkylenyl)-$C(O)OR^a$, —($C_1$-$C_6$ alkylenyl)-$C(O)NR^cR^d$, —($C_1$-$C_6$ alkylenyl)-$NR^cR^d$, —($C_1$-$C_6$ alkylenyl)-$N(R^e)C(O)R^b$, —($C_1$-$C_6$ alkylenyl)-$N(R^e)S(O)_2R^b$, —($C_1$-$C_6$ alkylenyl)-$N(R^e)C(O)O(R^b)$, —($C_1$-$C_6$ alkylenyl)-$N(R^e)C(O)NR^cR^d$, —($C_1$-$C_6$ alkylenyl)-$N(R^e)S(O)_2NR^cR^d$, or —($C_1$-$C_6$ alkylenyl)-CN;

$R^a$, $R^c$, $R^d$, and $R^e$, at each occurrence, are each independently H, $C_1$-$C_6$ alkyl, $C_2$-$C_6$ alkenyl, $C_2$-$C_6$ alkynyl, $C_1$-$C_6$ haloalkyl, $G^{1a}$, or —($C_1$-$C_6$ alkylenyl)-$G^{2a}$;

$R^b$, at each occurrence, is independently $C_1$-$C_6$ alkyl, $C_2$-$C_6$ alkenyl, $C_2$-$C_6$ alkynyl, $C_1$-$C_6$ haloalkyl, $G^{1a}$, or —($C_1$-$C_6$ alkylenyl)-$G^{2a}$;

$G^{2a}$, at each occurrence, are each independently aryl, heteroaryl, heterocycle, cycloalkyl, or cycloalkenyl; and each $G^{2a}$ group is optionally substituted with 1, 2, 3, 4, or 5 $R^{3g}$ groups;

$R^{3g}$, at each occurrence, is independently oxo, $C_1$-$C_6$ alkyl, $C_2$-$C_6$ alkenyl, $C_2$-$C_6$ alkynyl, halogen, $C_1$-$C_6$ haloalkyl, —CN, $NO_2$, —$OR^{z1}$, —$OC(O)R^{z2}$, —$OC(O)NR^{z3}R^{z4}$, —$SR^{z1}$, —$S(O)_2R^{z1}$, —$S(O)_2NR^{z3}R^{z4}$, —$C(O)R^{z1}$, —$C(O)OR^{z1}$, —$C(O)NR^{z3}R^{z4}$, —$NR^{z3}R^{z4}$, —$N(R^{z3})C(O)R^{z2}$, —$N(R^{z3})S(O)_2R^{z2}$, —$N(R^{z3})C(O)O(R^{z2})$, —$N(R^{z3})C(O)NR^{z3}R^{z4}$, —$N(R^{z3})S(O)_2NR^{z3}R^{z4}$, —($C_1$-$C_6$ alkylenyl)-$OR^{z1}$, —($C_1$-$C_6$ alkylenyl)-$OC(O)R^{z2}$, —($C_1$-$C_6$ alkylenyl)-$OC(O)NR^{z3}R^{z4}$, —($C_1$-$C_6$ alkylenyl)-$S(O)_2R^{z1}$, —($C_1$-$C_6$ alkylenyl)-$S(O)_2NR^{z3}R^{z4}$, —($C_1$-$C_6$ alkylenyl)-$C(O)R^{z1}$, —($C_1$-$C_6$ alkylenyl)-$C(O)OR^{z1}$, —($C_1$-$C_6$ alkylenyl)-$C(O)NR^{z3}R^{z4}$, —($C_1$-$C_6$ alkylenyl)-$NR^{z3}R^{z4}$, —($C_1$-$C_6$ alkylenyl)-$N(R^{z3})C(O)R^{z2}$, —($C_1$-$C_6$ alkylenyl)-$N(R^{z3})S(O)_2R^{z2}$, —($C_1$-$C_6$ alkylenyl)-$N(R^{z3})C(O)O(R^{z2})$, —($C_1$-$C_6$ alkylenyl)-$N(R^{z3})C(O)NR^{z3}R^{z4}$, —($C_1$-$C_6$ alkylenyl)-$N(R^{z3})S(O)_2NR^{z3}R^{z4}$, or —($C_1$-$C_6$ alkylenyl)-CN;

$R^{z1}$, $R^{z3}$, and $R^{z4}$, at each occurrence, are each independently H, $C_1$-$C_6$ alkyl, $C_2$-$C_6$ alkenyl, $C_2$-$C_6$ alkynyl, or $C_1$-$C_6$ haloalkyl; and $R^{z2}$, at each occurrence, is independently $C_1$-$C_6$ alkyl, $C_2$-$C_6$ alkenyl, $C_2$-$C_6$ alkynyl, or $C_1$-$C_6$ haloalkyl.

In another aspect, the present invention provides for methods for treating or preventing disorders that are ameliorated by inhibition of BET. Such methods comprise of administering to the subject a therapeutically effective amount of a compound of formula (I), alone, or in combination with a pharmaceutically acceptable carrier.

Some of the methods are directed to treating or preventing an inflammatory disease or cancer or AIDS.

In another aspect, the present invention relates to methods of treating cancer in a subject comprising administering a therapeutically effective amount of a compound of formula (I) or a pharmaceutically acceptable salt thereof, to a subject in need thereof. In certain embodiments, the cancer is selected from the group consisting of: acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor. In certain embodiments, the methods further comprise administering a therapeutically effective amount of at least one additional therapeutic agent. In certain embodiments, the additional therapeutic agent is selected from the group consisting of cytarabine, bortezomib, and 5-azacitidine.

In another aspect, the present invention relates to methods of treating a disease or condition in a subject comprising administering a therapeutically effective amount of a compound of formula (I) or a pharmaceutically acceptable salt thereof, to a subject in need thereof, wherein said disease or condition is selected from the group consisting of: Addison's disease, acute gout, ankylosing spondylitis, asthma, atherosclerosis, Behcet's disease, bullous skin diseases, cardiac myopathy, cardiac hypertrophy, chronic obstructive pulmonary disease (COPD), Crohn's disease, dermatitis, eczema, giant cell arteritis, glomerulonephritis, heart failure, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis. In certain embodiments, the methods further comprise administering a therapeutically effective amount of at least one additional therapeutic agent.

In another aspect, the present invention relates to methods of treating a chronic kidney disease or condition in a subject comprising administering a therapeutically effective amount of a compound of formula (I) or a pharmaceutically acceptable salt thereof, to a subject in need thereof, wherein said disease or condition is selected from the group consisting of: diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease and tubular interstitial nephritis. In certain embodiments, the methods further comprise administering a therapeutically effective amount of at least one additional therapeutic agent.

In another aspect, the present invention relates to methods of treating an acute kidney injury or disease or condition in a subject comprising administering a therapeutically effective amount of a compound of formula (I) or a pharmaceutically acceptable salt thereof, to a subject in need thereof, wherein said acute kidney injury or disease or condition is selected from the group consisting of: ischemia-reperfusion induced kidney disease, cardiac and major surgery induced kidney disease, percutaneous coronary intervention induced kidney disease, radio-contrast agent induced kidney disease, sepsis induced kidney disease, pneumonia induced kidney disease, and drug toxicity induced and pharmaceutically acceptable salts thereof. In certain embodiments, the methods further comprise administering a therapeutically effective amount of at least one additional therapeutic agent.

In another aspect, the present invention relates to methods of treating AIDS in a subject comprising administering a therapeutically effective amount of a compound of formula (I) or a pharmaceutically acceptable salt thereof, to a subject in need thereof. In certain embodiments, the methods further comprise administering a therapeutically effective amount of at least one additional therapeutic agent.

In another aspect, the present invention relates to methods of treating obesity, dyslipidemia, hypercholesterolemia, Alzheimer's disease, metabolic syndrome, hepatic steatosis, type II diabetes, insulin resistance, diabetic retinopathy or diabetic neuropathy in a subject comprising administering a therapeutically effective amount of a compound of formula (I) or a pharmaceutically acceptable salt thereof, to a subject in need thereof. In certain embodiments, the methods further comprise administering a therapeutically effective amount of at least one additional therapeutic agent.

In another aspect, the present invention provides for contraception in a male subject comprising administering a therapeutically effective amount of a compound of formula (I), or a pharmaceutically acceptable salt thereof, to a subject in need thereof. In certain embodiments, the methods further comprise administering a therapeutically effective amount of at least one additional therapeutic agent.

A further aspect of the invention provides the use of a compound of formula (I), alone or in combination with a second active pharmaceutical agent, in the manufacture of a medicament for treating or preventing conditions and disorders disclosed herein, with or without a pharmaceutically acceptable carrier.

Pharmaceutical compositions comprising a compound of formula (I), or a pharmaceutically acceptable salt, alone or in combination with a second active pharmaceutical agent, are also provided. In certain embodiments, pharmaceutical compositions comprise a therapeutically effective amount of a compound of formula (I), or a pharmaceutically acceptable salt thereof, and a pharmaceutically acceptable carrier.

DETAILED DESCRIPTION

Disclosed herein are compounds of formula (I)

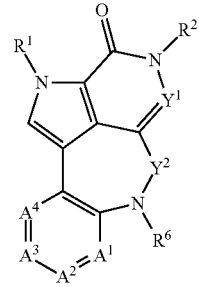

(I)

wherein $R^1$, $R^2$, $R^6$, $Y^1$, $Y^2$, $A^1$, $A^2$, $A^3$, and $A^4$ are defined above in the Summary of the Invention and below in the Detailed Description. Further, compositions comprising such compounds and methods for treating conditions and disorders using such compounds and compositions are also disclosed.

Compounds disclosed herein may contain one or more variable(s) that occur more than one time in any substituent or in the formulae herein. Definition of a variable on each occurrence is independent of its definition at another occurrence. Further, combinations of substituents are permissible only if such combinations result in stable compounds. Stable compounds are compounds, which can be isolated from a reaction mixture.

a). Definitions

It is noted that, as used in this specification and the intended claims, the singular form "a," "an," and "the" include plural referents unless the context clearly dictates otherwise. Thus, for example, reference to "a compound" includes a single compound as well as one or more of the same or different compounds, reference to "optionally a pharmaceutically acceptable carrier" refers to a single optional pharmaceutically acceptable carrier as well as one or more pharmaceutically acceptable carriers, and the like.

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond, optionally substituted with 1, 2, or 3 halogen atoms. The term "$C_2$-$C_6$ alkenyl" means an alkenyl group containing 2-6 carbon atoms. Non-limiting examples of alkenyl include buta-1,3-dienyl, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of 2 to 4 carbon atoms and contains at least one carbon-carbon double bond. Representative examples of alkenylene include, but are not limited to, —CH═CH— and —CH$_2$CH═CH—.

The term "alkyl" as used herein, means a saturated, straight or branched hydrocarbon chain radical. In some instances, the number of carbon atoms in an alkyl moiety is indicated by the prefix "$C_x$-$C_y$", wherein x is the minimum and y is the maximum number of carbon atoms in the substituent. Thus, for example, "$C_1$-$C_6$ alkyl" means an alkyl substituent containing from 1 to 6 carbon atoms and "$C_1$-$C_3$ alkyl" means an alkyl substituent containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 3,3-dimethylbutyl, 1,1-dimethylpropyl, 1,2-dimethylpropyl, 2,2-dimethylpropyl, 1-methylpropyl, 2-methylpropyl, 1-ethylpropyl, 1,2,2-trimethylpropyl, 2-ethylhexyl, 3-methylhexyl, 2,2-dimethylpentyl, 2,3-dimethylpentyl, n-heptyl, n-octyl, n-nonyl, and n-decyl.

The term "alkylene" or "alkylenyl" means a divalent radical derived from a straight or branched, saturated hydrocarbon chain, for example, of 1 to 10 carbon atoms, or of 1 to 6 carbon atoms ($C_1$-$C_6$ alkylenyl), or of 1 to 4 carbon atoms, or of 2 to 3 carbon atoms ($C_2$-$C_3$ alkylenyl). Examples of alkylene and alkylenyl include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon radical containing from 2 to 10 carbon atoms and containing at least one carbon-carbon triple bond, optionally substituted with 1, 2, or 3 halogen atoms. The term "$C_2$-$C_6$ alkynyl" means an alkynyl group of 2 to 6 carbon atoms. Representative examples of alkynyl include, but are not limited to, acetylenyl, 1-propynyl, 2-propynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Non-limiting examples of the aryl groups include dihydroindenyl (indanyl), indenyl, naphthyl, dihydronaphthalenyl, and tetrahydronaphthalenyl. The aryls are attached to the parent molecular moiety through any carbon atom contained within the bicyclic ring systems and can be unsubstituted or substituted.

The term "cycloalkyl" as used herein, refers to a radical that is a monocyclic cyclic alkyl, a bicyclic cycloalkyl, or a spiro cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring. The monocyclic and the bicyclic cycloalkyl groups may contain one or two alkylene bridges, each consisting of one, two, three, or four carbon atoms in length, and each bridge links two non-adjacent carbon atoms of the ring system. Non-limiting examples of bicyclic ring systems include bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane, tricyclo[3.3.1.0$^{3,7}$] nonane (octahydro-2,5-methanopentalene or noradamantane), and tricyclo[3.3.1.1$^{3,7}$]decane (adamantane). A spiro cycloalkyl is a monocyclic cycloalkyl wherein two substituents on the same carbon atom of the monocyclic cycloalkyl ring together with said carbon atom form a second monocyclic cycloalkyl ring. The monocyclic, the bicyclic, and the spiro cycloalkyl groups can be unsubstituted or substituted, and are attached to the parent molecular moiety through any substitutable atom contained within the ring system.

The term "cycloalkenyl" as used herein, refers to a monocyclic or a bicyclic hydrocarbon ring radical. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two, or three double bonds. Representative examples of monocyclic cycloalkenyl groups include, but are not limited to, cyclobutenyl, cyclopentenyl, cyclohexenyl, cycloheptenyl, and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic or bicyclic cycloalkenyl ring may contain one or two alkylene bridges, each consisting of one, two, or three carbon atoms, and each linking two non-adjacent carbon atoms of the ring system. Representative examples of the bicyclic cycloalkenyl groups include, but are not limited to, 4,5,6,7-tetrahydro-3aH-indene, octahydronaphthalenyl, and 1,6-dihydro-pentalene. The monocyclic and bicyclic cycloalkenyls can be attached to the parent molecular moiety through any substitutable atom contained within the ring systems, and can be unsubstituted or substituted.

The term "halo" or "halogen" as used herein, means Cl, Br, I, and F.

The term "haloalkyl" as used herein, means an alkyl group, as defined herein, in which one, two, three, four, five or six hydrogen atoms are replaced by halogen. The term "$C_1$-$C_6$ haloalkyl" means a $C_1$-$C_6$ alkyl group, as defined herein, in which one, two, three, four, five, six, or seven hydrogen atoms are replaced by halogen. The term "$C_1$-$C_3$ haloalkyl" means a $C_1$-$C_3$ alkyl group, as defined herein, in which one, two, three, four, five, or six hydrogen atoms are replaced by halogen. Representative examples of haloalkyl include, but are not limited to, chloromethyl, 2-fluoroethyl, 2,2-difluoroethyl, 2,2,2-trifluoroethyl, trifluoromethyl, difluoromethyl, pentafluoroethyl, 4-chlorobutyl, 2-chloro-3-fluoropentyl, trifluorobutyl, trifluoropropyl, 2,2,3,3,3-pentafluoropropyl, and 2,2,3,3,4,4,4-heptafluorobutyl.

The term "heterocycle" or "heterocyclic" as used herein, means a radical of a monocyclic heterocycle, a bicyclic heterocycle, and a spiro heterocycle. A monocyclic heterocycle is a three-, four-, five-, six-, seven-, or eight-membered carbocyclic ring also containing at least one heteroatom independently selected from the group consisting of O, N, and S. A three- or four-membered ring contains zero or one double bond, and one heteroatom selected from the group consisting of O, N, and S. When two O atoms or one O atom and one S atom are present in a heterocyclic ring, then the two O atoms or one O atom and one S atom are not bonded directly to each other. A five-membered ring contains zero or one double bond and one, two, or three heteroatoms selected from the group consisting of O, N, and S. Examples of five-membered heterocyclic rings include those containing in the ring: 1 O; 1 S; 1 N; 2 N; 3 N; 1 S and 1 N; 1 S, and 2 N; 1 O and 1 N; or 1 O and 2 N. Examples of 5-membered heterocyclic groups include tetrahydrofuranyl, dihydrofuranyl, tetrahydrothienyl, dihydrothienyl, imidazolidinyl, oxazolidinyl, imidazolinyl, isoxazolidinyl, pyrrolidinyl, 2-pyrrolinyl, and 3-pyrrolinyl. A six-membered ring contains zero, one, or two double bonds and one, two, or three heteroatoms selected from the group consisting of O, N, and S. Examples of six-membered heterocyclic rings include those containing in the ring: 1 O; 2 O; 1 S; 2 S; 1 N; 2 N; 3 N; 1 S, 1 O, and 1 N; 1 S and 1 N; 1 S and 2 N; 1 S and 1 O; 1 S and 2 O; 1 O and 1 N; and 1 O and 2 N. Examples of 6-membered heterocyclic groups include tetrahydropyranyl, dihydropyranyl, dioxanyl, 1,3-dioxolanyl, 1,4-dithianyl, hexahydropyrimidine, morpholinyl, piperazinyl, piperidinyl, 2H-pyranyl, 4H-pyranyl, pyrazolidinyl, pyrazolinyl, 1,2,3,6-tetrahydropyridinyl, tetrahydrothiopyranyl, 1,1-dioxo-hexahydro-1-thiopyranyl, 1,1-dioxo-1$\lambda^6$-thiomorpholinyl, thiomorpholinyl, thioxanyl, and trithianyl. Seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyridinyl, tetrahydropyranyl, tetrahydrothienyl, thiadiazolinyl, thiadiazolidinyl, thiazolinyl, thiazolidinyl, thiomorpholinyl, thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle. Representative examples of bicyclic heterocycles include, but are not limited to, benzo[d][1,3]dioxolyl, benzopyranyl, benzothiopyranyl, 2,3-dihydrobenzofuranyl, 2,3-dihydrobenzothienyl, 2,3-dihydro-1H-indolyl, isoindolinyl, 3,4-dihydroisoquinolin-2(1H)-yl, 2,3,4,6-tetrahydro-1H-pyrido[1,2-a]pyrazin-2-yl, hexahydropyrano[3,4-b][1,4]oxazin-1(5H)-yl. The monocyclic heterocycle and the bicyclic heterocycle may contain one or two alkylene bridges or an alkenylene bridge, or mixture thereof, each consisting of no more than four carbon atoms and each linking two non adjacent atoms of the ring system. Examples of such bridged heterocycle include, but are not limited to, azabicyclo[2.2.1] heptyl (including 2-azabicyclo[2.2.1]hept-2-yl), 8-azabicyclo[3.2.1]oct-8-yl, octahydro-2,5-epoxypentalene, hexahydro-2H-2,5-methanocyclopenta[b]furan, hexahydro-1H-1,4-methanocyclopenta[c]furan, aza-admantane (1-azatricyclo[3.3.1.1$^{3,7}$]decane), and oxa-adamantane (2-oxatricyclo[3.3.1.1$^{3,7}$]decane). A spiro heterocycle is a monocyclic heterocycle wherein two substituents on the same carbon atom of the monocyclic heterocycle ring together with said carbon atom form a second ring system selected from a monocyclic cycloalkyl, a bicyclic cycloalkyl, a monocyclic heterocycle, or a bicyclic heterocycle. Examples of spiro heterocycle include, but not limited to, 6-azaspiro[2.5]oct-6-yl, 1'H,4H-spiro[1,3-benzodioxine-2,4'-piperidin]-1'-yl, 1'H,3H-spiro[2-benzofuran-1,4'-piperidin]-1'-yl, and 1,4-dioxa-8-azaspiro[4.5]dec-8-yl. The monocyclic, the bicyclic, and the spiro heterocycles can be unsubstituted or substituted. The monocyclic, the bicyclic and the spiro heterocycles are connected to the parent molecular moiety through any carbon atom or any nitrogen atom contained within the ring systems. The nitrogen and sulfur heteroatoms in the heterocycle rings may optionally be oxidized (e.g. 1,1-dioxidotetrahydrothienyl, 1,2-dioxido-1,2-thiazolidinyl, 1,1-dioxidothiomorpholinyl)) and the nitrogen atoms may optionally be quarternized.

The term "heteroaryl" as used herein, means a monocyclic heteroaryl and a bicyclic heteroaryl. The monocyclic heteroaryl is a five- or six-membered monocyclic ring. The five-membered ring contains two double bonds. The five membered ring may contain one heteroatom selected from O or S; or one, two, three, or four nitrogen atoms and optionally one oxygen or one sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, phthalazinyl, 2,6-dihydropyrrolo[3,4-c]pyrazol-5(4H)-yl, 6,7-dihydro-pyrazolo[1,5-a]pyrazin-5(4H)-yl, 6,7-dihydro-1,3-benzothiazolyl, imidazo[1,2-c]pyridinyl, indazolyl, indolyl, isoindolyl, isoquinolinyl, naphthyridinyl, pyridoimidazolyl, quinolinyl, 2,4,6,7-tetrahydro-5H-pyrazolo[4,3-c]pyridin-5-yl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups can be substituted or unsubstituted and are connected to the parent molecular moiety through any substitutable carbon atom or any substitutable nitrogen atom contained within the ring systems. The nitrogen atom in the heteroaryl rings may optionally be oxidized and may optionally be quarternized.

The term "heteroatom" as used herein, means a nitrogen, oxygen, and sulfur.

The term "oxo" as used herein, means a =O group.

If a moiety is described as "substituted", a non-hydrogen radical is in the place of hydrogen radical of any substitutable atom of the moiety. Thus, for example, a substituted heterocycle moiety is a heterocycle moiety in which at least one non-hydrogen radical is in the place of a hydrogen radical on the heterocycle. It should be recognized that if there are more than one substitution on a moiety, each non-hydrogen radical may be identical or different (unless otherwise stated).

If a moiety is described as being "optionally substituted," the moiety may be either (1) not substituted or (2) substituted. If a moiety is described as being optionally substituted with up to a particular number of non-hydrogen radicals, that moiety may be either (1) not substituted; or (2) substituted by up to that particular number of non-hydrogen radicals or by up to the maximum number of substitutable positions on the moiety, whichever is less. Thus, for example, if a moiety is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

The terms "treat", "treating", and "treatment" refer to a method of alleviating or abrogating a disease and/or its attendant symptoms.

The terms "prevent", "preventing", and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The phrase "therapeutically effective amount" means an amount of a compound, or a pharmaceutically acceptable salt thereof, sufficient to prevent the development of or to alleviate to some extent one or more of the symptoms of the condition or disorder being treated when administered alone or in conjunction with another pharmaceutical agent or treatment in a particular subject or subject population. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated.

The term "subject" is defined herein to refer to animals such as mammals, including, but not limited to, primates (e.g., humans), cows, sheep, goats, horses, dogs, cats, rabbits, rats, mice and the like. In preferred embodiments, the subject is a human.

b. Compounds

Compounds of the invention have the general formula (I) as described above.

Particular values of variable groups in compounds of formula (I) are as follows. Such values may be used where appropriate with any of the other values, definitions, claims or embodiments defined hereinbefore or hereinafter.

In certain embodiments, $R^1$ is $CD_3$, $C_1$-$C_3$ alkyl, or $C_1$-$C_3$ haloalkyl.

In certain embodiments, $R^1$ is $C_1$-$C_3$ alkyl. In some such embodiments, $R^1$ is methyl.

In certain embodiments, $R^2$ is H or $C_1$-$C_3$ alkyl.

In certain embodiments, $R^2$ is H or methyl.

In certain embodiments, $R^2$ is H.

In certain embodiments, $R^2$ is $C_1$-$C_3$ alkyl. In some such embodiments, $R^2$ is methyl.

In certain embodiments, $Y^1$ is N or $CR^3$.

In certain embodiments, $Y^1$ is N.

In certain embodiments, $Y^1$ is $CR^3$.

In certain embodiments, $R^3$ is H, $C_1$-$C_6$ alkyl, $C_2$-$C_6$ alkenyl, $C_2$-$C_6$ alkynyl, halogen, $C_1$-$C_6$ haloalkyl, —$C(O)R^{3a}$, —$C(O)OR^{3a}$, —$C(O)NR^{3b}R^{3c}$, —$C(O)N(R^{3b})NR^{3b}R^{3c}$, —$S(O)R^{3d}$, —$S(O)_2R^{3a}$, —$S(O)_2NR^{3b}R^{3c}$ or $G^1$; wherein the $C_1$-$C_6$ alkyl, $C_2$-$C_6$ alkenyl, and $C_2$-$C_6$ alkynyl are each independently unsubstituted or substituted with 1 or 2 substituents independently selected from the group consisting of $G^1$, —$C(O)R^{3a}$, —$C(O)OR^{3a}$, —$C(O)NR^{3b}R^{3c}$, —$S(O)R^{3d}$, —$S(O)_2R^{3a}$, —$S(O)_2NR^{3b}R^{3c}$, —$OR^{3a}$, —$OC(O)R^{3d}$, —$NR^{3b}R^{3c}$, $N(R^{3b})C(O)R^{3d}$, $N(R^{3b})SO_2R^{3d}$, $N(R^{3b})C(O)OR^{3d}$, $N(R^{3b})C(O)NR^{3b}R^{3c}$, $N(R^{3b})SO_2NR^{3b}R^{3c}$, and $N(R^{3b})C(NR^{3b}R^{3c})$=$NR^{3b}R^{3c}$.

In certain embodiments, $R^3$ is H, —$C(O)R^{3a}$, —$C(O)OR^{3a}$, —$C(O)NR^{3b}R^{3c}$, or $C_1$-$C_6$ alkyl, wherein the $C_1$-$C_6$ alkyl is optionally substituted with a substituent selected from the group consisting of $G^1$, $NR^{3b}R^{3c}$, $N(R^{3b})C(O)R^{3d}$, $N(R^{3b})SO_2R^{3d}$, $N(R^{3b})C(O)OR^{3d}$, $N(R^{3b})C(O)NR^{3b}R^{3c}$, and $N(R^{3b})SO_2NR^{3b}R^{3c}$. In some such embodiments, the $G^1$ group is optionally substituted heterocycle.

In certain embodiments, $R^3$ is H, —$C(O)R^{3a}$, or —$C(O)NR^{3b}R^{3c}$. In some such embodiments, $R^{3a}$ is $G^1$. In some such embodiments, $R^{3a}$ is $G^1$ wherein $G^1$ is optionally substituted heterocycle.

In certain embodiments, $R^3$ is H or —$C(O)NR^{3b}R^{3c}$. In some such embodiments, $R^{3b}$ and $R^{3c}$ are each independently H or $C_1$-$C_6$ alkyl.

In certain embodiments, $R^3$ is H.

In certain embodiments, $R^3$ is —$C(O)NR^{3b}R^{3c}$. In some such embodiments, $R^{3b}$ and $R^{3c}$ are each independently H or $C_1$-$C_3$ alkyl.

In certain embodiments, $Y^2$ is $C(O)$, $S(O)_2$, or $CR^4R^5$.

In certain embodiments, $Y^2$ is $C(O)$.

In certain embodiments, $Y^2$ is $S(O)_2$.

In certain embodiments, $Y^2$ is $CR^4R^5$.

In certain embodiments, $R^4$ is H, deuterium, $C_1$-$C_6$ alkyl, halogen, or $C_1$-$C_6$ haloalkyl.

In certain embodiments, $R^4$ is H or deuterium.

In certain embodiments, $R^4$ is H.

In certain embodiments, $R^5$ is H, deuterium, $C_1$-$C_6$ alkyl, $C_2$-$C_6$ alkenyl, $C_2$-$C_6$ alkynyl, halogen, $C_1$-$C_6$ haloalkyl, —$C(O)R^{5a}$, —$C(O)OR^{5a}$, —$C(O)NR^{5b}R^{5c}$, —$S(O)R^{5d}$, —$S(O)_2R^{5a}$, —$S(O)_2NR^{5b}R^{5c}$, or $G^1$; wherein the $C_1$-$C_6$ alkyl, $C_2$-$C_6$ alkenyl, and $C_2$-$C_6$ alkynyl are each independently unsubstituted or substituted with 1 or 2 substituents independently selected from the group consisting of $G^1$, —$C(O)R^{5a}$, —$C(O)OR^{5a}$, —$C(O)NR^{5b}R^{5c}$—$C(O)N(R^{5b})NR^{5b}R^{5c}$, —$S(O)R^{5d}$, —$S(O)_2R^{5a}$, —$S(O)_2NR^{5b}R^{5c}$, —$OR^{5a}$, —$OC(O)R^{5d}$, —$NR^{5b}R^{5c}$, $N(R^{5b})C(O)R^{5d}$, $N(R^{5b})SO_2R^{5d}$, $N(R^{5b})C(O)OR^{5d}$, $N(R^{5b})C(O)NR^{5b}R^{5c}$, $N(R^{5b})SO_2NR^{5b}R^{5c}$, and $N(R^{5b})C(NR^{5b}R^{5c})$=$NR^{5b}R^{5c}$.

In certain embodiments, $R^5$ is H, deuterium, $C_1$-$C_6$ alkyl, $C_2$-$C_6$ alkenyl, $C_2$-$C_6$ alkynyl, $C_1$-$C_6$ haloalkyl, —$C(O)R^{5a}$, —$C(O)OR^{5a}$, or $G^1$; wherein the $C_1$-$C_6$ alkyl, $C_2$-$C_6$ alkenyl, and $C_2$-$C_6$ alkynyl are each independently unsubstituted or substituted with 1 or 2 substituents independently selected from the group consisting of $G^1$, —C(O)$R^{5a}$, —C(O)O$R^{5a}$, —C(O)N$R^{5b}R^{5c}$, —C(O)N($R^{5b}$)N$R^{5b}R^{5c}$, —O$R^{5a}$, —OC(O)$R^{5d}$, —N$R^{5b}R^{5c}$, N($R^{5b}$)C(O)$R^{5d}$, N($R^{5b}$)SO$_2R^{5d}$, N($R^{5b}$)C(O)O$R^{5d}$, N($R^{5b}$)C(O)N$R^{5b}R^{5c}$, and N($R^{5b}$)SO$_2$N$R^{5b}R^{5c}$.

In certain embodiments, $R^5$ is H, —C(O)O$R^{5a}$, $G^1$, or $C_1$-$C_6$ alkyl which is unsubstituted or substituted with a substituent selected from the group consisting of $G^1$, —C(O)O$R^{5c}$, and —O$R^5$.

In certain embodiments, $R^5$ is H, deuterium, or $C_1$-$C_6$ alkyl optionally substituted with a substituent selected from the group consisting of —C(O)O$R^{5a}$ and O$R^{5a}$. In some such embodiments, $R^{5a}$ is $C_1$-$C_6$ alkyl.

In certain embodiments, $R^5$ is H or $C_1$-$C_6$ alkyl optionally substituted with a substituent selected from the group consisting of —C(O)O$R^{5a}$ and O$R^{5a}$. In some such embodiments, $R^{5a}$ is $C_1$-$C_6$ alkyl.

In certain embodiments, $R^6$ is H, $C_1$-$C_6$ alkyl, $C_2$-$C_6$ alkenyl, $C_2$-$C_6$ alkynyl, halogen, $C_1$-$C_6$ haloalkyl, —C(O)$R^{6a}$, —C(O)O$R^{6a}$, —C(O)N$R^{6b}R^{6c}$, —S(O)$_2R^{6a}$, —S(O)$_2$N$R^{6b}R^{6c}$, or $G^2$; wherein the $C_1$-$C_6$ alkyl, $C_2$-$C_6$ alkenyl, and $C_2$-$C_6$ alkynyl are each independently unsubstituted or substituted with 1 or 2 substituents independently selected from the group consisting of $G^2$, —C(O)$R^{6a}$, —C(O)O$R^{6a}$, —C(O)N$R^{6b}R^{6c}$, —C(O)N($R^{6b}$)N$R^{66}R^{6e}$, —S(O)$R^{6d}$, —S(O)$_2R^{6a}$, —S(O)$_2$N$R^{6b}R^{6c}$, —O$R^{6a}$, —OC(O)$R^{6d}$, —N$R^{6b}R^{6c}$, N($R^{6b}$)C(O)$R^{6d}$, N($R^{6b}$)SO$_2R^{6d}$, N($R^{6b}$)C(O)O$R^{6d}$, N($R^{6b}$)C(O)N$R^{6b}R^{6c}$, N($R^{6b}$)SO$_2$N$R^{6b}R^{6c}$, and N($R^{6b}$)C(N$R^{6b}R^{6c}$)=N$R^{6b}R^{6c}$.

In certain embodiments, $R^6$ is H, $C_1$-$C_6$ alkyl, $C_2$-$C_6$ alkenyl, —C(O)$R^{6a}$, —C(O)O$R^{6a}$, —C(O)N$R^{6b}R^{6c}$, —S(O)$_2R^{6a}$, or $G^2$; wherein the $C_1$-$C_6$ alkyl and the $C_2$-$C_6$ alkenyl are each independently unsubstituted or substituted with 1 or 2 substituents independently selected from the group consisting of $G^2$, —C(O)O$R^{6a}$, —N$R^{6b}R^{6c}$, N($R^{6b}$)C(O)$R^{6d}$, N($R^{6b}$)SO$_2R^{6d}$, N($R^{6b}$)C(O)O$R^{6d}$, N($R^{6b}$)C(O)N$R^{6b}R^{6c}$, and N($R^{6b}$)SO$_2$N$R^{6b}R^{6c}$.

In certain embodiments, $R^6$ is H, $C_1$-$C_6$ alkyl, —C(O)$R^{6a}$, or $G^2$; wherein the $C_1$-$C_6$ alkyl is unsubstituted or substituted with a $G^2$ group.

In certain embodiments, $R^6$ is —C(O)$R^{6a}$, $G^2$, or $C_1$-$C_6$ alkyl which is unsubstituted or substituted with a $G^2$ group. In some such embodiments, $R^{6a}$ is $G^2$. In some such embodiments, $R^{6a}$ is $G^2$ wherein $G^2$ is optionally substituted cycloalkyl. In some such embodiments, $R^{6a}$ is $G^2$ wherein $G^2$ is optionally substituted cyclopropyl. In some such embodiments, $R^{6a}$ is $G^2$ wherein $G^2$ is optionally substituted phenyl.

In certain embodiments, $R^6$ is $G^2$ or $C_1$-$C_6$ alkyl which is unsubstituted or substituted with a $G^2$ group. In some such embodiments, $R^6$ is optionally substituted aryl, optionally substituted heteroaryl, optionally substituted heterocycle, or $C_1$-$C_6$ alkyl which is unsubstituted or substituted with an optionally substituted cycloalkyl. In some such embodiments, $R^6$ is optionally substituted aryl or $C_1$-$C_6$ alkyl which is unsubstituted or substituted with an optionally substituted cycloalkyl. In some such embodiments, $R^6$ is optionally substituted phenyl, optionally substituted pyridinyl, optionally substituted piperidinyl, or $C_1$-$C_6$ alkyl which is unsubstituted or substituted with an optionally substituted cyclopropyl. In some such embodiments, $R^6$ is optionally substituted phenyl or $C_1$-$C_6$ alkyl which is unsubstituted or substituted with an optionally substituted cyclopropyl. In some such embodiments, said optional substituents are independently selected from the group consisting of halogen, —C(O)($C_1$-$C_6$ alkyl), —C(O)O($C_1$-$C_6$ alkyl), —O($C_1$-$C_3$ alkyl), —O($C_1$-$C_3$ haloalkyl), $C_1$-$C_3$ alkyl, and $C_1$-$C_3$ haloalkyl. In some such embodiments, said optional substituents are independently selected from the group consisting of halogen, —O($C_1$-$C_3$ alkyl), —O($C_1$-$C_3$ haloalkyl), $C_1$-$C_3$ alkyl, and $C_1$-$C_3$ haloalkyl. In some such embodiments, said optional substituents are halogen. In some such embodiments, said halogen is F or Cl.

In certain embodiments, $A^1$ is C($R^7$) or N; $A^2$ is C($R^8$) or N; $A^3$ is C($R^9$) or N; and $A^4$ is C($R^{10}$) or N; wherein zero, one, or two of $A^1$, $A^2$, $A^3$, and $A^4$ are N.

In certain embodiments, $A^1$ is C($R^7$), $A^2$ is C($R^8$), $A^3$ is C($R^9$), and $A^4$ is C($R^{10}$).

In certain embodiments, one of $A^1$, $A^2$, $A^3$, and $A^4$ is N. In some such embodiments, $A^1$ is N; $A^2$ is C($R^8$); $A^3$ is C($R^9$); and $A^4$ is C($R^{10}$).

In certain embodiments, two of $A^1$, $A^2$, $A^3$, and $A^4$ are N. In some such embodiments, $A^1$ is N; $A^2$ is C($R^8$); $A^3$ is N; and $A^4$ is C($R^{10}$).

In certain embodiments, $A^1$ is C($R^7$), $A^2$ is C($R^8$), $A^3$ is C($R^9$), and $A^4$ is C($R^{10}$); or $A^1$ is N; $A^2$ is C($R^8$); $A^3$ is C($R^9$); and $A^4$ is C($R^{10}$); or $A^1$ is N; $A^2$ is C($R^8$); $A^3$ is N; and $A^4$ is) C($R^{10}$).

In certain embodiments, $R^7$, $R^8$, and $R^9$, are each independently H, $C_1$-$C_6$ alkyl, $C_2$-$C_6$ alkenyl, $C_2$-$C_6$ alkynyl, halogen, $C_1$-$C_6$ haloalkyl, —CN, NO$_2$, —O$R^{y1}$, —OC(O)$R^{y2}$, —OC(O)N$R^{y3}R^{y4}$, —S$R^{y1}$, —S(O)$_2R^{y1}$, —S(O)$_2$N$R^{y3}R^{y4}$, —C(O)$R^{y1}$, —C(O)O$R^{y1}$, —C(O)N$R^{y3}R^{y4}$, —N$R^{y3}R^{y4}$, —N($R^{y3}$)C(O)$R^{y2}$, —N($R^{y3}$)S(O)$_2R^{y2}$, —N($R^{y3}$)C(O)O($R^{y2}$), —N($R^{y3}$)C(O)N$R^{y3}R^{y4}$, —N($R^{y3}$)S(O)$_2$N$R^{y3}R^{y4}$, $G^3$, —($C_1$-$C_6$ alkylenyl)-CN, —($C_1$-$C_6$ alkylenyl)-O$R^{y1}$, —($C_1$-$C_6$ alkylenyl)-OC(O)$R^{y2}$, —($C_1$-$C_6$ alkylenyl)-OC(O)N$R^{y3}R^{y4}$, —($C_1$-$C_6$ alkylenyl)-S(O)$_2R^{y1}$, —($C_1$-$C_6$ alkylenyl)-S(O)$_2$N$R^{y3}R^{y4}$, —($C_1$-$C_6$ alkylenyl)-C(O)$R^{y1}$, —($C_1$-$C_6$ alkylenyl)-C(O)O$R^{y1}$, —($C_1$-$C_6$ alkylenyl)-C(O)N$R^{y3}R^{y4}$, —($C_1$-$C_6$ alkylenyl)-N$R^{y3}R^{y4}$, —($C_1$-$C_6$ alkylenyl)-N($R^{y3}$)C(O)$R^{y2}$, —($C_1$-$C_6$ alkylenyl)-N($R^{y3}$)S(O)$_2R^{y2}$, —($C_1$-$C_6$ alkylenyl)-N($R^{y3}$)C(O)O($R^{y2}$), —($C_1$-$C_6$ alkylenyl)-N($R^{y3}$)C(O)N$R^{y3}R^{y4}$, —($C_1$-$C_6$ alkylenyl)-N($R^{y3}$)S(O)$_2$N$R^{y3}R^{y4}$, —($C_1$-$C_6$ alkylenyl)-CN, or —($C_1$-$C_6$ alkylenyl)-$G^3$.

In certain embodiments, $R^7$ is H, halogen, $C_1$-$C_3$ alkyl, or optionally substituted cyclopropyl. In some such embodiments, the cyclopropyl is optionally substituted with 1, 2, 3, 4, or 5 $R^{4g}$ groups, wherein $R^{4g}$ is $C_1$-$C_3$ alkyl, halogen, or $C_1$-$C_3$ haloalkyl.

In certain embodiments, $R^7$ is H or halogen. In some such embodiments, the halogen is F or Cl. In some such embodiments, the halogen is F.

In certain embodiments, $R^7$ is H.

In certain embodiments, $R^8$ is H, $C_1$-$C_6$ alkyl, halogen, $C_1$-$C_6$ haloalkyl, —CN, optionally substituted heterocycle, —C(O)N$R^{y3}R^{y4}$, —($C_1$-$C_6$ alkylenyl)-N$R^{y3}R^{y4}$, —($C_1$-$C_6$ alkylenyl)-N($R^{y3}$)C(O)$R^{y2}$, —($C_1$-$C_6$ alkylenyl)-N($R^{y3}$)S(O)$_2R^{y2}$, —($C_1$-$C_6$ alkylenyl)-N($R^{y3}$)C(O)O($R^{y2}$), —($C_1$-$C_6$ alkylenyl)-N($R^{y3}$)C(O)N$R^{y3}R^{y4}$, —($C_1$-$C_6$ alkylenyl)-N($R^{y3}$)S(O)$_2$N$R^{y3}R^{y4}$, or —($C_1$-$C_6$ alkylenyl)-$G^3$ wherein $G^3$ is optionally substituted heterocycle.

In certain embodiments, $R^8$ is H.

In certain embodiments, $R^9$ is H, $C_1$-$C_6$ alkyl, halogen, $C_1$-$C_6$ haloalkyl, —CN, —S(O)$_2R^{y1}$, —S(O)$_2$N$R^{y3}R^{y4}$, —C(O)N$R^{y3}R^{y4}$, —N$R^{y3}R^{y4}$, —N($R^{y3}$)C(O)$R^{y2}$, —N($R^{y3}$)S(O)$_2R^{y2}$, —N($R^{y3}$)C(O)O($R^{y2}$), —N($R^{y3}$)C(O)N$R^{y3}R^{y4}$, —N($R^{y3}$)S(O)$_2$N$R^{y3}R^{y4}$, —($C_1$-$C_6$ alkylenyl)-S(O)$_2R^{y1}$, —($C_1$-$C_6$ alkylenyl)-S(O)$_2$N$R^{y3}R^{y4}$, —($C_1$-$C_6$ alkylenyl)-C(O)N$R^{y3}R^{y4}$, —($C_1$-$C_6$ alkylenyl)-N$R^{y3}R^{y4}$, —($C_1$-$C_6$ alkylenyl)-N($R^{y3}$)C(O)$R^{y2}$, —($C_1$-$C_6$ alkylenyl)-N($R^{y3}$)S(O)$_2R^{y2}$, —($C_1$-$C_6$ alkylenyl)-N($R^{y3}$)C(O)O($R^{y2}$), —($C_1$-$C_6$ alkylenyl)-N($R^{y3}$)C(O)N$R^{y3}R^{y4}$, or —($C_1$-$C_6$ alkylenyl)-N($R^{y3}$)S(O)$_2$N$R^{y3}R^{y4}$.

In certain embodiments, $R^9$ is H, halogen, $-S(O)_2R^{y1}$, $-C(O)NR^{y3}R^{y4}$, $-NR^{y3}R^{y4}$, $-N(R^{y3})C(O)R^{y2}$, $-N(R^{y3})S(O)_2R^{y2}$, $-N(R^{y3})C(O)NR^{y3}R^{y4}$, or $-(C_1\text{-}C_6 \text{ alkylenyl})\text{-}S(O)_2R^{y1}$.

In certain embodiments, $R^9$ is halogen, $-NR^{y3}R^{y4}$, $-N(R^{y3})C(O)R^{y2}$, $-N(R^{y3})S(O)_2R^{y2}$, or $-(C_1\text{-}C_6 \text{ alkylenyl})\text{-}S(O)_2R^{y1}$. In some such embodiments, $R^{y1}$ is $C_1\text{-}C_6$ alkyl. In some such embodiments, $R^{y3}$ is H. In certain embodiments wherein $R^9$ is $-NR^{y3}R^{y4}$ and $R^{y3}$ is H, an example of $R^{y4}$ is $-(C_1\text{-}C_6 \text{ alkylenyl})\text{-}G^3$. In certain embodiments wherein $R^9$ is $-N(R^{y3})C(O)R^{y2}$ and $R^{y3}$ is H, examples of $R^{y3}$ are $C_1\text{-}C_6$ alkyl and $-(C_1\text{-}C_6 \text{ alkylenyl})\text{-}G^3$. In certain embodiments wherein $R^9$ is $-N(R^{y3})S(O)_2R^{y2}$ and $R^{y3}$ is H, examples of $R^{y4}$ are $C_1\text{-}C_6$ alkyl and optionally substituted phenyl.

In certain embodiments, $R^{10}$ is H, $C_1\text{-}C_3$ alkyl, halogen, $C_1\text{-}C_3$ haloalkyl, or $-CN$.

In certain embodiments, $R^{10}$ is H, $C_1\text{-}C_3$ alkyl, or halogen.

In certain embodiments, $R^{10}$ is H.

Various embodiments of substituents $R^1$, $R^2$, $R^6$, $Y^1$, $Y^2$, $A^1$, $A^2$, $A^3$, and $A^4$ have been discussed above. These substituents embodiments can be combined to form various embodiments of compounds of formula (I). All embodiments of compounds of formula (I), formed by combining the substituent embodiments discussed above are within the scope of Applicant's invention, and some illustrative embodiments of the compounds of formula (I) are provided below.

In certain embodiments,
$Y^1$ is $CR^3$; and
$Y^2$ is $CR^4R^5$.

In some further embodiments, $A^1$ is $C(R^7)$, $A^2$ is $C(R^8)$, $A^3$ is $C(R^9)$, and $A^4$ is $C(R^{10})$; or $A^1$ is N, $A^2$ is $C(R^8)$, $A^3$ is $C(R^9)$, and $A^4$ is $C(R^{10})$; or $A^1$ is N, $A^2$ is $C(R^8)$, $A^3$ is N, and $A^4$ is $C(R^{10})$.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In certain embodiments,
$Y^1$ is $CR^3$;
$Y^2$ is $CR^4R^5$; and
$R^3$ is H, $-C(O)R^{3a}$, $-C(O)OR^{3a}$, $-C(O)NR^{3b}R^{3c}$, or $C_1\text{-}C_6$ alkyl, wherein the $C_1\text{-}C_6$ alkyl is optionally substituted with a substituent selected from the group consisting of $G^1$, $-NR^{3b}R^{3c}$, $N(R^{3b})C(O)R^{3d}$, $N(R^{3b})SO_2R^{3d}$, $N(R^{3b})C(O)OR^{3d}$, $N(R^{3b})C(O)NR^{3b}R^{3c}$, and $N(R^{3b})SO_2NR^{3b}R^{3c}$.

In some further embodiments, $A^1$ is $C(R^7)$, $A^2$ is $C(R^8)$, $A^3$ is $C(R^9)$, and $A^4$ is $C(R^{10})$; or $A^1$ is N, $A^2$ is $C(R^8)$, $A^3$ is $C(R^9)$, and $A^4$ is $C(R^{10})$; or $A^1$ is N, $A^2$ is $C(R^8)$, $A^3$ is N, and $A^4$ is $C(R^{10})$.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In certain embodiments,
$Y^1$ is $CR^3$;
$Y^2$ is $CR^4R^5$;
$R^4$ is H or deuterium; and
$R^5$ is H, deuterium, $C_1\text{-}C_6$ alkyl, $C_2\text{-}C_6$ alkenyl, $C_2\text{-}C_6$ alkynyl, $C_1\text{-}C_6$ haloalkyl, $-C(O)R^{5a}$, $-C(O)OR^{5a}$, or $G^1$; wherein the $C_1\text{-}C_6$ alkyl, $C_2\text{-}C_6$ alkenyl, and $C_2\text{-}C_6$ alkynyl are each independently unsubstituted or substituted with 1 or 2 substituents independently selected from the group consisting of $G^1$, $-C(O)R^{5a}$, $-C(O)OR^{5a}$, $-C(O)NR^{5b}R^{5c}$, $-C(O)N(R^{5b})NR^{5b}R^{5c}$, $-OR^{5a}$, $-OC(O)R^{5d}$, $-NR^{5b}R^{5c}$, $N(R^{5b})C(O)R^{5d}$, $N(R^{5b})SO_2R^{5d}$, $N(R^{5b})C(O)OR^{5d}$, $N(R^{5b})C(O)NR^{5b}R^{5c}$, and $N(R^{5b})SO_2NR^{5b}R^{5c}$.

In some further embodiments, $A^1$ is $C(R^7)$, $A^2$ is $C(R^8)$, $A^3$ is $C(R^9)$, and $A^4$ is $C(R^{10})$; or $A^1$ is N, $A^2$ is $C(R^8)$, $A^3$ is $C(R^9)$, and $A^4$ is $C(R^{10})$; or $A^1$ is N, $A^2$ is $C(R^8)$, $A^3$ is N, and $A^4$ is $C(R^{10})$.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In certain embodiments,
$Y^1$ is $CR^3$;
$Y^2$ is $CR^4R^5$; and
$R^6$ is H, $C_1\text{-}C_6$ alkyl, $C_2\text{-}C_6$ alkenyl, $-C(O)R^{6a}$, $-C(O)OR^{6a}$, $-C(O)NR^{6b}R^{6c}$, $-S(O)_2R^{6a}$, or $G^2$; wherein the $C_1\text{-}C_6$ alkyl and the $C_2\text{-}C_6$ alkenyl are each independently unsubstituted or substituted with 1 or 2 substituents independently selected from the group consisting of $G^2$, $-C(O)OR^{6a}$, $-NR^{6b}R^{6c}$, $N(R^{6b})C(O)R^{6d}$, $N(R^{6b})SO_2R^{6d}$, $N(R^{6b})C(O)OR^{6d}$, $N(R^{6b})C(O)NR^{6b}R^{6c}$, and $N(R^{6b})SO_2NR^{6b}R^{6c}$.

In some further embodiments, $A^1$ is $C(R^7)$, $A^2$ is $C(R^8)$, $A^3$ is $C(R^9)$, and $A^4$ is $C(R^{10})$; or $A^1$ is N, $A^2$ is $C(R^8)$, $A^3$ is $C(R^9)$, and $A^4$ is $C(R^{10})$; or $A^1$ is N, $A^2$ is $C(R^8)$, $A^3$ is N, and $A^4$ is $C(R^{10})$.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In certain embodiments,
$Y^1$ is $CR^3$;
$Y^2$ is $CR^4R^5$; and
$R^9$ is H, $C_1\text{-}C_6$ alkyl, halogen, $C_1\text{-}C_6$ haloalkyl, $-CN$, $-S(O)_2R^1$, $-S(O)_2NR^{y3}R^{y4}$, $-C(O)NR^{y3}R^{y4}$, $-NR^{y3}R^{y4}$, $-N(R^{y3})C(O)R^{y2}$, $-N(R^{y3})S(O)_2R^{y2}$, $-N(R^{y3})C(O)O(R^{y2})$, $-N(R^{y3})C(O)NR^{y3}R^{y4}$, $-N(R^{y3})S(O)_2NR^{y3}R^{y4}$, $-(C_1\text{-}C_6 \text{ alkylenyl})\text{-}S(O)_2R^{y1}$, $-(C_1\text{-}C_6 \text{ alkylenyl})\text{-}S(O)_2NR^{y3}R^{y4}$, $-(C_1\text{-}C_6 \text{ alkylenyl})\text{-}C(O)NR^{y3}R^{y4}$, $-(C_1\text{-}C_6 \text{ alkylenyl})\text{-}NR^{y3}R^{y4}$, $-(C_1\text{-}C_6 \text{ alkylenyl})\text{-}N(R^{y3})C(O)R^{y2}$, $-(C_1\text{-}C_6 \text{ alkylenyl})\text{-}N(R^{y3})S(O)_2R^{y2}$, $-(C_1\text{-}C_6 \text{ alkylenyl})\text{-}N(R^{y3})C(O)O(R^{y2})$, $-(C_1\text{-}C_6 \text{ alkylenyl})\text{-}N(R^{y3})C(O)NR^{y3}R^{y4}$, or $-(C_1\text{-}C_6 \text{ alkylenyl})\text{-}N(R^{y3})S(O)_2NR^{y3}R^{y4}$.

In some further embodiments, $A^1$ is $C(R^7)$, $A^2$ is $C(R^8)$, $A^3$ is $C(R^9)$, and $A^4$ is $C(R^{10})$; or $A^1$ is N, $A^2$ is $C(R^8)$, $A^3$ is $C(R^9)$, and $A^4$ is $C(R^{10})$; or $A^1$ is N, $A^2$ is $C(R^8)$, $A^3$ is N, and $A^4$ is $C(R^{10})$.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In certain embodiments,
$R^1$ is $C_1\text{-}C_3$ alkyl;
$R^2$ is H;
$Y^1$ is $CR^3$; and
$Y^2$ is $CR^4R^5$.

In some further embodiments, $R^1$ is methyl.
In certain embodiments,
$R^1$ is $C_1$-$C_3$ alkyl;
$R^2$ is H;
$Y^1$ is $CR^3$;
$Y^2$ is $CR^4R^5$;
$R^4$ is H; and
$R^5$ is H, —C(O)OR$^{5a}$, $G^1$, or $C_1$-$C_6$ alkyl which is unsubstituted or substituted with a substituent selected from the group consisting of $G^1$, —C(O)OR$^{5a}$, and —OR$^5$.

In some further embodiments, $R^1$ is methyl.
In some further embodiments, $A^1$ is $C(R^7)$, $A^2$ is $C(R^8)$, $A^3$ is $C(R^9)$, and $A^4$ is $C(R^{10})$; or $A^1$ is N, $A^2$ is $C(R^8)$, $A^3$ is $C(R^9)$, and $A^4$ is $C(R^{10})$; or $A^1$ is N, $A^2$ is $C(R^8)$, $A^3$ is N, and $A^4$ is $C(R^{10})$.
In some further embodiments, $A^1$ is $C(R^7)$, $A^2$ is $C(R^8)$, $A^3$ is $C(R^9)$, and $A^4$ is $C(R^{10})$.
In some further embodiments, $A^1$ is N, $A^2$ is $C(R^8)$, $A^3$ is $C(R^9)$, and $A^4$ is $C(R^{10})$.
In some further embodiments, $A^1$ is N, $A^2$ is $C(R^8)$, $A^3$ is N, and $A^4$ is $C(R^{10})$.
In certain embodiments,
$R^1$ is $C_1$-$C_3$ alkyl;
$R^2$ is H;
$Y^1$ is $CR^3$;
$Y^2$ is $CR^4R^5$; and
$R^3$ is H.

In some further embodiments, $A^1$ is $C(R^7)$, $A^2$ is $C(R^8)$, $A^3$ is $C(R^9)$, and $A^4$ is $C(R^{10})$; or $A^1$ is N, $A^2$ is $C(R^8)$, $A^3$ is $C(R^9)$, and $A^4$ is $C(R^{10})$; or $A^1$ is N, $A^2$ is $C(R^8)$, $A^3$ is N, and $A^4$ is $C(R^{10})$.
In some further embodiments, $A^1$ is $C(R^7)$, $A^2$ is $C(R^8)$, $A^3$ is $C(R^9)$, and $A^4$ is $C(R^{10})$.
In some further embodiments, $A^1$ is N, $A^2$ is $C(R^8)$, $A^3$ is $C(R^9)$, and $A^4$ is $C(R^{10})$.
In some further embodiments, $A^1$ is N, $A^2$ is $C(R^8)$, $A^3$ is N, and $A^4$ is $C(R^{10})$.
In some further embodiments, $R^1$ is methyl.
In certain embodiments,
$R^1$ is $C_1$-$C_3$ alkyl;
$R^2$ is H;
$Y^1$ is $CR^3$;
$Y^2$ is $CR^4R^5$; and
$R^{6}$ is H, $C_1$-$C_6$ alkyl, —C(O)R$^{6a}$, or $G^2$; wherein the $C_1$-$C_6$ alkyl is unsubstituted or substituted with a $G^2$ group.
In some further embodiments, $R^1$ is methyl.
In some further embodiments, $R^{6a}$ is $G^2$.
In some further embodiments, $R^{6a}$ is $G^2$ wherein $G^2$ is optionally substituted cycloalkyl.
In some further embodiments, $R^{6a}$ is $G^2$ wherein $G^2$ is optionally substituted cyclopropyl.
In some further embodiments, $A^1$ is $C(R^7)$, $A^2$ is $C(R^8)$, $A^3$ is $C(R^9)$, and $A^4$ is $C(R^{10})$; or $A^1$ is N, $A^2$ is $C(R^8)$, $A^3$ is $C(R^9)$, and $A^4$ is $C(R^{10})$; or $A^1$ is N, $A^2$ is $C(R^8)$, $A^3$ is N, and $A^4$ is $C(R^{10})$.
In some further embodiments, $A^1$ is $C(R^7)$, $A^2$ is $C(R^8)$, $A^3$ is $C(R^9)$, and $A^4$ is $C(R^{10})$.
In some further embodiments, $A^1$ is N, $A^2$ is $C(R^8)$, $A^3$ is $C(R^9)$, and $A^4$ is $C(R^{10})$.
In some further embodiments, $A^1$ is N, $A^2$ is $C(R^8)$, $A^3$ is N, and $A^4$ is $C(R^{10})$.
In certain embodiments,
$R^1$ is $C_1$-$C_3$ alkyl;
$R^2$ is H;
$Y^1$ is $CR^3$;
$Y^2$ is $CR^4R^5$; and $R^9$ is H, halogen, —S(O)$_2$R$^{y1}$, —C(O)NR$^{y3}$R$^{y4}$, —NR$^{y3}$R$^{y4}$, —N(R$^{y3}$)C(O)R$^{y2}$, —N(R$^{y3}$)S(O)$_2$R$^{y2}$, —N(R$^{y3}$)C(O)NR$^{y3}$R$^{y4}$, or —($C_1$-$C_6$ alkylenyl)-S(O)$_2$R$^{y1}$.
In some further embodiments, $A^1$ is $C(R^7)$, $A^2$ is $C(R^8)$, $A^3$ is $C(R^9)$, and $A^4$ is $C(R^{10})$; or $A^1$ is N, $A^2$ is $C(R^8)$, $A^3$ is $C(R^9)$, and $A^4$ is $C(R^{10})$; or $A^1$ is N, $A^2$ is $C(R^8)$, $A^3$ is N, and $A^4$ is $C(R^{10})$.
In some further embodiments, $A^1$ is $C(R^7)$, $A^2$ is $C(R^8)$, $A^3$ is $C(R^9)$, and $A^4$ is $C(R^{10})$.
In some further embodiments, $A^1$ is N, $A^2$ is $C(R^8)$, $A^3$ is $C(R^9)$, and $A^4$ is $C(R^{10})$.
In some further embodiments, $A^1$ is N, $A^2$ is $C(R^8)$, $A^3$ is N, and $A^4$ is $C(R^{10})$.
In some further embodiments, $R^1$ is methyl.
In certain embodiments,
$R^1$ is $C_1$-$C_3$ alkyl;
$R^2$ is H;
$Y^1$ is $CR^3$;
$Y^2$ is $CR^4R^5$; and
$A^1$ is $C(R^7)$, $A^2$ is $C(R^8)$, $A^3$ is $C(R^9)$, and $A^4$ is $C(R^{10})$; or
$A^1$ is N, $A^2$ is $C(R^8)$, $A^3$ is $C(R^9)$, and $A^4$ is $C(R^{10})$; or
$A^1$ is N, $A^2$ is $C(R^8)$, $A^3$ is N, and $A^4$ is $C(R^{10})$.
In some further embodiments, $A^1$ is $C(R^7)$, $A^2$ is $C(R^8)$, $A^3$ is $C(R^9)$, and $A^4$ is $C(R^{10})$.
In some further embodiments, $A^1$ is N, $A^2$ is $C(R^8)$, $A^3$ is $C(R^9)$, and $A^4$ is $C(R^{10})$.
In some further embodiments, $A^1$ is N, $A^2$ is $C(R^8)$, $A^3$ is N, and $A^4$ is $C(R^{10})$.
In yet some further embodiments, $R^1$ is methyl.
In certain embodiments,
$R^1$ is methyl;
$R^2$ is H;
$Y^1$ is $CR^3$;
$Y^2$ is $CR^4R^5$;
$A^1$ is $C(R^7)$, $A^2$ is $C(R^8)$, $A^3$ is $C(R^9)$, and $A^4$ is $C(R^{10})$; or
$A^1$ is N, $A^2$ is $C(R^8)$, $A^3$ is $C(R^9)$, and $A^4$ is $C(R^{10})$; or $A^1$ is N, $A^2$ is $C(R^8)$, $A^3$ is N, and $A^4$ is $C(R^{10})$;
$R^4$ is H or deuterium;
$R^7$ is H, halogen, $C_1$-$C_3$ alkyl, or optionally substituted cyclopropyl;
$R^8$ is H, $C_1$-$C_6$ alkyl, halogen, $C_1$-$C_6$ haloalkyl, —CN, optionally substituted heterocycle, —C(O)NR$^{y3}$R$^{y4}$, —($C_1$-$C_6$ alkylenyl)-NR$^{y3}$R$^{y4}$, —($C_1$-$C_6$ alkylenyl)-N(R$^{y3}$)C(O)R$^{y2}$, —($C_1$-$C_6$ alkylenyl)-N(R$^{y3}$)S(O)$_2$R$^{y2}$, —($C_1$-$C_6$ alkylenyl)-N(R$^{y3}$)C(O)O(R$^{y2}$), —($C_1$-$C_6$ alkylenyl)-N(R$^{y3}$)C(O)NR$^{y3}$R$^{y4}$, —($C_1$-$C_6$ alkylenyl)-N(R$^{y3}$)S(O)$_2$NR$^{y3}$R$^{y4}$, or —($C_1$-$C_6$ alkylenyl)-$G^3$ wherein $G^3$ is optionally substituted heterocycle; and
$R^{10}$ is H, $C_1$-$C_3$ alkyl, or halogen.
In some further embodiments, $A^1$ is $C(R^7)$, $A^2$ is $C(R^8)$, $A^3$ is $C(R^9)$, and $A^4$ is $C(R^{10})$.
In some further embodiments, $A^1$ is N, $A^2$ is $C(R^8)$, $A^3$ is $C(R^9)$, and $A^4$ is $C(R^{10})$.
In some further embodiments, $A^1$ is N, $A^2$ is $C(R^8)$, $A^3$ is N, and $A^4$ is $C(R^{10})$.
In certain embodiments,
$R^1$ is methyl;
$R^2$ is H;
$Y^1$ is $CR^3$;
$Y^2$ is $CR^4R^5$;
$A^1$ is $C(R^7)$, $A^2$ is $C(R^8)$, $A^3$ is $C(R^9)$, and $A^4$ is $C(R^{10})$; or
$A^1$ is N, $A^2$ is $C(R^8)$, $A^3$ is $C(R^9)$, and $A^4$ is $C(R^{10})$; or
$A^1$ is N, $A^2$ is $C(R^8)$, $A^3$ is N, and $A^4$ is $C(R^{10})$;
$R^4$ is H or deuterium;
$R^7$ is H, halogen, $C_1$-$C_3$ alkyl, or optionally substituted cyclopropyl;

$R^8$ is H, $C_1$-$C_6$ alkyl, halogen, $C_1$-$C_6$ haloalkyl, —CN, optionally substituted heterocycle, —C(O)NR$^{y3}$R$^{y4}$, —(C$_1$-C$_6$ alkylenyl)-NR$^{y3}$R$^{y4}$, —(C$_1$-C$_6$ alkylenyl)-N(R$^{y3}$)C(O)R$^{y2}$, —(C$_1$-C$_6$ alkylenyl)-N(R$^{y3}$)S(O)$_2$R$^{y2}$, —(C$_1$-C$_6$ alkylenyl)-N(R$^{y3}$)C(O)O(R$^{y2}$), —(C$_1$-C$_6$ alkylenyl)-N(R$^{y3}$)C(O)NR$^{y3}$R$^{y4}$, —(C$_1$-C$_6$ alkylenyl)-N(R$^{y3}$)S(O)$_2$NR$^{y3}$R$^{y4}$, or —(C$_1$-C$_6$ alkylenyl)-G$^3$ wherein G$^3$ is optionally substituted heterocycle;

$R^{10}$ is H, $C_1$-$C_3$ alkyl, or halogen; and $R^3$ is H or —C(O)NR$^{3b}$R$^{3c}$.

In some further embodiments, $R^{3b}$ and $R^{3c}$ are each independently H or $C_1$-$C_6$ alkyl.

In some further embodiments, $A^1$ is C(R$^7$), $A^2$ is C(R$^8$), $A^3$ is C(R$^9$), and $A^4$ is C(R$^{10}$).

In some further embodiments, $A^1$ is N, $A^2$ is C(R$^8$), $A^3$ is C(R$^9$), and $A^4$ is C(R$^{10}$).

In some further embodiments, $A^1$ is N, $A^2$ is C(R$^8$), $A^3$ is N, and $A^4$ is C(R$^{10}$).

In certain embodiments,
$R^1$ is methyl;
$R^2$ is H;
$Y^1$ is CR$^3$;
$Y^2$ is CR$^4$R$^5$;
$A^1$ is C(R$^7$), $A^2$ is C(R$^8$), $A^3$ is C(R$^9$), and $A^4$ is C(R$^{10}$); or
$A^1$ is N, $A^2$ is C(R$^8$), $A^3$ is C(R$^9$), and $A^4$ is C(R$^{10}$); or
$A^1$ is N, $A^2$ is C(R$^8$), $A^3$ is N, and $A^4$ is C(R$^{10}$);
$R^4$ is H or deuterium;
$R^7$ is H, halogen, $C_1$-$C_3$ alkyl, or optionally substituted cyclopropyl;
$R^8$ is H, $C_1$-$C_6$ alkyl, halogen, $C_1$-$C_6$ haloalkyl, —CN, optionally substituted heterocycle, —C(O)NR$^{y3}$R$^{y4}$, —(C$_1$-C$_6$ alkylenyl)-NR$^{y3}$R$^{y4}$, —(C$_1$-C$_6$ alkylenyl)-N(R$^{y3}$)C(O)R$^{y2}$, —(C$_1$-C$_6$ alkylenyl)-N(R$^{y3}$)S(O)$_2$R$^{y2}$, —(C$_1$-C$_6$ alkylenyl)-N(R$^{y3}$)C(O)O(R$^{y2}$), —(C$_1$-C$_6$ alkylenyl)-N(R$^{y3}$)C(O)NR$^{y3}$R$^{y4}$, —(C$_1$-C$_6$ alkylenyl)-N(R$^{y3}$)S(O)$_2$NR$^{y3}$R$^{y4}$, or —(C$_1$-C$_6$ alkylenyl)-G$^3$ wherein G$^3$ is optionally substituted heterocycle;
$R^{10}$ is H, $C_1$-$C_3$ alkyl, or halogen; and
$R^5$ is H, deuterium, or $C_1$-$C_6$ alkyl optionally substituted with a substituent selected from the group consisting of —C(O)OR$^{5a}$ and OR$^{5a}$.

In some further embodiments, $A^1$ is C(R$^7$), $A^2$ is C(R$^8$), $A^3$ is C(R$^9$), and $A^4$ is C(R$^{10}$).

In some further embodiments, $A^1$ is N, $A^2$ is C(R$^8$), $A^3$ is C(R$^9$), and $A^4$ is C(R$^{10}$).

In some further embodiments, $A^1$ is N, $A^2$ is C(R$^8$), $A^3$ is N, and $A^4$ is C(R$^{10}$).

In yet some further embodiments, $R^{y1}$ is $C_1$-$C_6$ alkyl.

In certain embodiments,
$R^1$ is methyl;
$R^2$ is H;
$Y^1$ is CR$^3$;
$Y^2$ is CR$^4$R$^5$;
$A^1$ is C(R$^7$), $A^2$ is C(R$^8$), $A^3$ is C(R$^9$), and $A^4$ is C(R$^{10}$); or
$A^1$ is N, $A^2$ is C(R$^8$), $A^3$ is C(R$^9$), and $A^4$ is C(R$^{10}$); or
$A^1$ is N, $A^2$ is C(R$^8$), $A^3$ is N, and $A^4$ is C(R$^{10}$);
$R^4$ is H or deuterium;
$R^7$ is H, halogen, $C_1$-$C_3$ alkyl, or optionally substituted cyclopropyl;
$R^8$ is H, $C_1$-$C_6$ alkyl, halogen, $C_1$-$C_6$ haloalkyl, —CN, optionally substituted heterocycle, —C(O)NR$^{y3}$R$^{y4}$, —(C$_1$-C$_6$ alkylenyl)-NR$^{y3}$R$^{y4}$, —(C$_1$-C$_6$ alkylenyl)-N(R$^{y3}$)C(O)R$^{y2}$, —(C$_1$-C$_6$ alkylenyl)-N(R$^{y3}$)S(O)$_2$R$^{y2}$, (C$_1$-C$_6$ alkylenyl)-N(R$^{y3}$)C(O)O(R$^{y2}$), (C$_1$-C$_6$ alkylenyl)-N(R$^{y3}$)C(O)NR$^{y3}$R$^{y4}$, —(C$_1$-C$_6$ alkylenyl)-N(R$^{y3}$)S(O)$_2$NR$^{y3}$R$^{y4}$, or —(C$_1$-C$_6$ alkylenyl)-G$^3$ wherein G$^3$ is optionally substituted heterocycle;

$R^{10}$ is H, $C_1$-$C_3$ alkyl, or halogen; and
$R^6$ is —C(O)R$^{6a}$, G$^2$, or $C_1$-$C_6$ alkyl which is unsubstituted or substituted with a G$^2$ group.

In some further embodiments, $A^1$ is C(R$^7$), $A^2$ is C(R$^8$), $A^3$ is C(R$^9$), and $A^4$ is C(R$^{10}$).

In some further embodiments, $A^1$ is N, $A^2$ is C(R$^8$), $A^3$ is C(R$^9$), and $A^4$ is C(R$^{10}$).

In some further embodiments, $A^1$ is N, $A^2$ is C(R$^8$), $A^3$ is N, and $A^4$ is C(R$^{10}$).

In some further embodiments, $R^{6a}$ is G$^2$.

In some further embodiments, $R^{6a}$ is G$^2$, and G$^2$ is optionally substituted cycloalkyl.

In some further embodiments, $R^{6a}$ is G$^2$, and G$^2$ is optionally substituted cyclopropyl.

In certain embodiments,
$R^1$ is methyl;
$R^2$ is H;
$Y^1$ is CR$^3$;
$Y^2$ is CR$^4$R$^5$;
$A^1$ is C(R$^7$), $A^2$ is C(R$^8$), $A^3$ is C(R$^9$), and $A^4$ is C(R$^{10}$); or
$A^1$ is N, $A^2$ is C(R$^8$), $A^3$ is C(R$^9$), and $A^4$ is C(R$^{10}$); or
$A^1$ is N, $A^2$ is C(R$^8$), $A^3$ is N, and $A^4$ is C(R$^{10}$);
$R^4$ is H or deuterium;
$R^7$ is H, halogen, $C_1$-$C_3$ alkyl, or optionally substituted cyclopropyl;
$R^8$ is H, $C_1$-$C_6$ alkyl, halogen, $C_1$-$C_6$ haloalkyl, —CN, optionally substituted heterocycle, —C(O)NR$^{y3}$R$^{y4}$, —(C$_1$-C$_6$ alkylenyl)-NR$^{y3}$R$^{y4}$, —(C$_1$-C$_6$ alkylenyl)-N(R$^{y3}$)C(O)R$^{y2}$, —(C$_1$-C$_6$ alkylenyl)-N(R$^{y3}$)S(O)$_2$R$^{y2}$, (C$_1$-C$_6$ alkylenyl)-N(R$^{y3}$)C(O)O(R$^{y2}$), (C$_1$-C$_6$ alkylenyl)-N(R$^{y3}$)C(O)NR$^{y3}$R$^{y4}$, —(C$_1$-C$_6$ alkylenyl)-N(R$^{y3}$)S(O)$_2$NR$^{y3}$R$^{y4}$, or —(C$_1$-C$_6$ alkylenyl)-G$^3$ wherein G$^3$ is optionally substituted heterocycle;

$R^{10}$ is H, $C_1$-$C_3$ alkyl, or halogen; and
$R^9$ is halogen, —NR$^{y3}$R$^{y4}$, —N(R$^{y3}$)C(O)R$^{y2}$, —N(R$^{y3}$)S(O)$_2$R$^{y2}$, or —(C$_1$-C$_6$ alkylenyl)-S(O)$_2$R$^{y1}$.

In some further embodiments, $A^1$ is C(R$^7$), $A^2$ is C(R$^8$), $A^3$ is C(R$^9$), and $A^4$ is C(R$^{10}$);

In some further embodiments, $A^1$ is N, $A^2$ is C(R$^8$), $A^3$ is C(R$^9$), and $A^4$ is C(R$^{10}$).

In some further embodiments, $A^1$ is N, $A^2$ is C(R$^8$), $A^3$ is N, and $A^4$ is C(R$^{10}$).

In some further embodiments, $R^{y3}$ is H.

In some further embodiments, $R^{y1}$ is $C_1$-$C_6$ alkyl.

In some further embodiments, $R^{y2}$ is $C_1$-$C_6$ alkyl.

In certain embodiments,
$R^1$ is methyl;
$R^2$ is H;
$Y^1$ is CR$^3$;
$Y^2$ is CR$^4$R$^5$;
$A^1$ is C(R$^7$), $A^2$ is C(R$^8$), $A^3$ is C(R$^9$), and $A^4$ is C(R$^{10}$); or
$A^1$ is N, $A^2$ is C(R$^8$), $A^3$ is C(R$^9$), and $A^4$ is C(R$^{10}$); or
$A^1$ is N, $A^2$ is C(R$^8$), $A^3$ is N, and $A^4$ is C(R$^{10}$);
$R^4$ is H;
$R^7$ is H or halogen;
$R^8$ is H; and
$R^{10}$ is H.

In some further embodiments, $A^1$ is C(R$^7$), $A^2$ is C(R$^8$), $A^3$ is C(R$^9$), and $A^4$ is C(R$^{10}$).

In some further embodiments, $A^1$ is N, $A^2$ is C(R$^8$), $A^3$ is C(R$^9$), and $A^4$ is C(R$^{10}$).

In some further embodiments, $A^1$ is N, $A^2$ is C(R$^8$), $A^3$ is N, and $A^4$ is C(R$^{10}$).

In certain embodiments,
$R^1$ is methyl;
$R^2$ is H;
$Y^1$ is CR$^3$;

$Y^2$ is $CR^4R^5$;
$A^1$ is $C(R^7)$, $A^2$ is $C(R^8)$, $A^3$ is $C(R^9)$, and $A^4$ is $C(R^{10})$; or
$A^1$ is N, $A^2$ is $C(R^8)$, $A^3$ is $C(R^9)$, and $A^4$ is $C(R^{10})$; or
$A^1$ is N, $A^2$ is $C(R^8)$, $A^3$ is N, and $A^4$ is $C(R^{10})$; and
$R^4$ is H;
$R^7$ is H or halogen;
$R^8$ is H;
$R^{10}$ is H; and
$R^9$ is halogen, $-NR^{y3}R^{y4}$, $-N(R^{y3})C(O)R^{y2}$, $-N(R^{y3})S(O)_2R^{y2}$, or $-(C_1-C_6$ alkylenyl$)-S(O)_2R^{y1}$.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In some further embodiments, $R^{y1}$ is $C_1-C_6$ alkyl and $R^{y3}$ is H.

In some further embodiments, $R^{y1}$ and $R^{y2}$ are $C_1-C_6$ alkyl, and $R^{y3}$ is H.

In certain embodiments,
$R^1$ is methyl;
$R^2$ is H;
$Y^1$ is $CR^3$;
$Y^2$ is $CR^4R^5$;
$A^1$ is $C(R^7)$, $A^2$ is $C(R^8)$, $A^3$ is $C(R^9)$, and $A^4$ is $C(R^{10})$; or
$A^1$ is N, $A^2$ is $C(R^8)$, $A^3$ is $C(R^9)$, and $A^4$ is $C(R^{10})$; or
$A^1$ is N, $A^2$ is $C(R^8)$, $A^3$ is N, and $A^4$ is $C(R^{10})$;
$R^4$ is H;
$R^7$ is H or halogen;
$R^8$ is H;
$R^{10}$ is H;
$R^9$ is halogen, $-NR^{y3}R^{y4}$, $-N(R^{y3})C(O)R^{y2}$, $-N(R^{y3})S(O)_2R^{y2}$, or $-(C_1-C_6$ alkylenyl$)-S(O)_2R^{y1}$; and
$R^6$ is $-C(O)R^{6a}$, $G^2$, or $C_1-C_6$ alkyl which is unsubstituted or substituted with a $G^2$ group.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In some further embodiments, $R^{y1}$ is $C_1-C_6$ alkyl, and $R^{y3}$ is H.

In some further embodiments, $R^{6a}$ is $G^2$.

In some further embodiments, $R^{6a}$ is $G^2$ wherein $G^2$ is optionally substituted cycloalkyl.

In some further embodiments, $R^{6a}$ is $G^2$ wherein $G^2$ is optionally substituted cyclopropyl.

In certain embodiments,
$R^1$ is methyl;
$R^2$ is H;
$Y^1$ is $CR^3$;
$Y^2$ is $CR^4R^5$;
$A^1$ is $C(R^7)$, $A^2$ is $C(R^8)$, $A^3$ is $C(R^9)$, and $A^4$ is $C(R^{10})$; or
$A^1$ is N, $A^2$ is $C(R^8)$, $A^3$ is $C(R^9)$, and $A^4$ is $C(R^{10})$; or
$A^1$ is N, $A^2$ is $C(R^8)$, $A^3$ is N, and $A^4$ is $C(R^{10})$;
$R^4$ is H;
$R^7$ is H or halogen;
$R^8$ is H;
$R^{10}$ is H;
$R^9$ is halogen, $-NR^{y3}R^{y4}$, $-N(R^{y3})C(O)R^{y2}$, $-N(R^{y3})S(O)_2R^{y2}$, or $-(C_1-C_6$ alkylenyl$)-S(O)_2R^{y1}$;
$R^6$ is $-C(O)R^{6a}$, $G^2$, or $C_1-C_6$ alkyl which is unsubstituted or substituted with a $G^2$ group;
$R^5$ is H or $C_1-C_6$ alkyl optionally substituted with a substituent selected from the group consisting of $-C(O)OR^{5a}$ and $OR^{5a}$.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In some further embodiments, $R^{y1}$ is $C_1-C_6$ alkyl, and $R^{y3}$ is H.

In some further embodiments, $R^{6a}$ is $G^2$.

In some further embodiments, $R^{6a}$ is $G^2$ wherein $G^2$ is optionally substituted cycloalkyl.

In some further embodiments, $R^{6a}$ is $G^2$ wherein $G^2$ is optionally substituted cyclopropyl.

In certain embodiments,
$R^1$ is methyl;
$R^2$ is H;
$Y^1$ is $CR^3$;
$Y^2$ is $CR^4R^5$;
$A^1$ is $C(R^7)$, $A^2$ is $C(R^8)$, $A^3$ is $C(R^9)$, and $A^4$ is $C(R^{10})$; or
$A^1$ is N, $A^2$ is $C(R^8)$, $A^3$ is $C(R^9)$, and $A^4$ is $C(R^{10})$; or
$A^1$ is N, $A^2$ is $C(R^8)$, $A^3$ is N, and $A^4$ is $C(R^{10})$;
$R^4$ is H;
$R^7$ is H or halogen;
$R^8$ is H;
$R^{10}$ is H;
$R^9$ is halogen, $-NR^{y3}R^{y4}$, $-N(R^{y3})C(O)R^{y2}$, $-N(R^{y3})S(O)_2R^{y2}$, or $-(C_1-C_6$ alkylenyl$)-S(O)_2R^{y1}$;
$R^6$ is $-C(O)R^{6a}$, $G^2$, or $C_1-C_6$ alkyl which is unsubstituted or substituted with a $G^2$ group;
$R^5$ is H or $C_1-C_6$ alkyl optionally substituted with a substituent selected from the group consisting of $-C(O)OR^{5a}$ and $OR^{5a}$; and
$R^3$ is H.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In some further embodiments, $R^{y1}$ is $C_1-C_6$ alkyl, and $R^{y3}$ is H.

In some further embodiments, $R^{6a}$ is $G^2$.

In some further embodiments, $R^{6a}$ is $G^2$ wherein $G^2$ is optionally substituted cyclopropyl.

In certain embodiments,
$R^1$ is methyl;
$R^2$ is H;
$Y^1$ is $CR^3$;
$Y^2$ is $CR^4R^5$;
$A^1$ is $C(R^2)$, $A^2$ is $C(R^8)$, $A^3$ is $C(R^9)$, and $A^4$ is $C(R^{10})$; or
$A^1$ is N, $A^2$ is $C(R^8)$, $A^3$ is $C(R^9)$, and $A^4$ is $C(R^{10})$; or
$A^1$ is N, $A^2$ is $C(R^8)$, $A^3$ is N, and $A^4$ is $C(R^{10})$;
$R^4$ is H;
$R^7$ is H;
$R^8$ is H;
$R^{10}$ is H;
$R^9$ is halogen, $-NR^{y3}R^{y4}$, $-N(R^{y3})C(O)R^{y2}$, $-N(R^{y3})S(O)_2R^{y2}$, or $-(C_1-C_6$ alkylenyl$)-S(O)_2R^{y1}$;
$R^6$ is $-C(O)R^{6a}$, $G^2$, or $C_1-C_6$ alkyl which is unsubstituted or substituted with a $G^2$ group;
$R^5$ is H or $C_1-C_6$ alkyl optionally substituted with a substituent selected from the group consisting of $-C(O)OR^{5a}$ and $OR^{5a}$;
$R^3$ is H;

$R^{5a}$ is $C_1$-$C_6$ alkyl;
$R^{y1}$ is $C_1$-$C_6$ alkyl; and
$R^{y3}$ is H.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In some further embodiments, $R^{6a}$ is $G^2$ wherein $G^2$ is optionally substituted cyclopropyl.

In some further embodiments, $R^{y2}$ is $C_1$-$C_6$ alkyl.

Compounds of formula (I) may contain one or more asymmetrically substituted atoms. Compounds of formula (I) may also exist as individual stereoisomers (including enantiomers and diastereomers) and mixtures thereof. Individual stereoisomers of compounds of formula (I) may be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

Compounds of formula (I) may also include the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen double bond are designated as being of Z or E configuration and substituents around a cycloalkyl or heterocycle are designated as being of cis or trans configuration.

Within the present invention it is to be understood that compounds disclosed herein may exhibit the phenomenon of tautomerism and all tautomeric isomers are included in the scope of the invention.

Thus, the formula drawings within this specification can represent only one of the possible tautomeric, geometric, or stereoisomeric forms. It is to be understood that the invention encompasses any tautomeric, geometric, or stereoisomeric form, and mixtures thereof, and is not to be limited merely to any one tautomeric, geometric, or stereoisomeric form utilized within the formula drawings.

Compounds of the invention are named using ChemDraw Ultra Version 12.

Exemplary compounds of formula (I) include, but are not limited to:

11-methyl-8-(methylsulfonyl)-2,4,5,11-tetrahydro-1H-2,5,11-triazadibenzo[cd,h]azulen-1-one;
5-(cyclopropylmethyl)-11-methyl-8-(methylsulfonyl)-2,4,5,11-tetrahydro-1H-2,5,11-triazadibenzo[cd,h]azulen-1-one;
5-(cyclopropylmethyl)-11-methyl-8-((methylsulfonyl)methyl)-2,4,5,11-tetrahydro-1H-2,5,11-triazadibenzo[cd,h]azulen-1-one;
5-(4-fluorophenyl)-11-methyl-8-((methylsulfonyl)methyl)-2,4,5,11-tetrahydro-1H-2,5,11-triazadibenzo[cd,h]azulen-1-one;
5-(2,4-difluorophenyl)-11-methyl-8-((methylsulfonyl)methyl)-2,4,5,11-tetrahydro-1H-2,5,11-triazadibenzo[cd,h]azulen-1-one;
5-(cyclopropanecarbonyl)-11-methyl-8-((methylsulfonyl)methyl)-2,4,5,11-tetrahydro-1H-2,5,11-triazadibenzo[cd,h]azulen-1-one;
5-benzoyl-11-methyl-8-((methylsulfonyl)methyl)-2,4,5,11-tetrahydro-1H-2,5,11-triazadibenzo[cd,h]azulen-1-one;
5-(4-fluorophenyl)-4-(2-methoxyethyl)-11-methyl-8-((methylsulfonyl)methyl)-2,4,5,11-tetrahydro-1H-2,5,11-triazadibenzo[cd,h]azulen-1-one;
methyl 3-(5-(4-fluorophenyl)-11-methyl-8-((methylsulfonyl)methyl)-1-oxo-2,4,5,11-tetrahydro-1H-2,5,11-triazadibenzo[cd,h]azulen-4-yl)propanoate;
5-(4-fluorophenyl)-11-methyl-8-((methylsulfonyl)methyl)-4-((tetrahydro-2H-pyran-4-yl)methyl)-2,4,5,11-tetrahydro-1H-2,5,11-triazadibenzo[cd,h]azulen-1-one;
5-(cyclopropylmethyl)-11-methyl-2,4,5,11-tetrahydro-1H-2,5,11-triazadibenzo[cd,h]azulen-1-one;
N-(5-(4-fluorophenyl)-11-methyl-1-oxo-2,4,5,11-tetrahydro-1H-2,5,11-triazadibenzo[cd,h]azulen-8-yl)ethanesulfonamide;
8-chloro-5-(4-fluorophenyl)-11-methyl-2,4,5,11-tetrahydro-1H-2,5,11-triazadibenzo[cd,h]azulen-1-one;
8-amino-5-(4-fluorophenyl)-11-methyl-2,4,5,11-tetrahydro-1H-2,5,6,11-tetraazadibenzo[cd,h]azulen-1-one;
ethyl 5-(4-fluorophenyl)-11-methyl-8-((methylsulfonyl)methyl)-1-oxo-2,4,5,11-tetrahydro-1H-2,5,11-triazadibenzo[cd,h]azulene-4-carboxylate;
8-fluoro-5-(4-fluorophenyl)-11-methyl-2,4,5,11-tetrahydro-1H-2,5,6,11-tetraazadibenzo[cd,h]azulen-1-one;
2-(2-chloro-5-fluorophenyl)-N-(5-(4-fluorophenyl)-11-methyl-1-oxo-2,4,5,11-tetrahydro-1H-2,5,6,11-tetraazadibenzo[cd,h]azulen-8-yl)acetamide;
2-(1,5-dimethyl-1H-pyrazol-3-yl)-N-(5-(4-fluorophenyl)-11-methyl-1-oxo-2,4,5,11-tetrahydro-1H-2,5,6,11-tetraazadibenzo[cd,h]azulen-8-yl)acetamide;
N-(5-(4-fluorophenyl)-11-methyl-1-oxo-2,4,5,11-tetrahydro-1H-2,5,6,11-tetraazadibenzo[cd,h]azulen-8-yl)-2-(3-(2-fluorophenyl)-1H-pyrazol-1-yl)acetamide;
2-(4-chloro-2-fluorophenyl)-N-(5-(4-fluorophenyl)-11-methyl-1-oxo-2,4,5,11-tetrahydro-1H-2,5,6,11-tetraazadibenzo[cd,h]azulen-8-yl)acetamide;
2-(chroman-6-yl)-N-(5-(4-fluorophenyl)-11-methyl-1-oxo-2,4,5,11-tetrahydro-1H-2,5,6,11-tetraazadibenzo[cd,h]azulen-8-yl)acetamide;
N-(5-(4-fluorophenyl)-11-methyl-1-oxo-2,4,5,11-tetrahydro-1H-2,5,6,11-tetraazadibenzo[cd,h]azulen-8-yl)-2-(1-methyl-1H-pyrazol-4-yl)acetamide;
8-amino-5-(4-fluorophenyl)-11-methyl-2,4,5,11-tetrahydro-1H-2,5,11-triazadibenzo[cd,h]azulen-1-one;
8-chloro-5-(4-fluorophenyl)-11-methyl-4-phenyl-2,4,5,11-tetrahydro-1H-2,5,11-triazadibenzo[cd,h]azulen-1-one;
11-methyl-8-((methylsulfonyl)methyl)-4-phenyl-2,4,5,11-tetrahydro-1H-2,5,11-triazadibenzo[cd,h]azulen-1-one;
N-(5-(4-fluorophenyl)-11-methyl-1-oxo-2,4,5,11-tetrahydro-1H-2,5,11-triazadibenzo[cd,h]azulen-8-yl)benzenesulfonamide;
N-(4-(N-(5-(4-fluorophenyl)-11-methyl-1-oxo-2,4,5,11-tetrahydro-1H-2,5,11-triazadibenzo[cd,h]azulen-8-yl)sulfamoyl)phenyl)acetamide;
N-(5-(4-fluorophenyl)-11-methyl-1-oxo-2,4,5,11-tetrahydro-1H-2,5,11-triazadibenzo[cd,h]azulen-8-yl)-2-(1-methyl-1H-pyrazol-4-yl)acetamide;
2-(4-chloro-2-fluorophenyl)-N-(5-(4-fluorophenyl)-11-methyl-1-oxo-2,4,5,11-tetrahydro-1H-2,5,11-triazadibenzo[cd,h]azulen-8-yl)acetamide;
2-(2-chloro-5-fluorophenyl)-N-(5-(4-fluorophenyl)-11-methyl-1-oxo-2,4,5,11-tetrahydro-1H-2,5,11-triazadibenzo[cd,h]azulen-8-yl)acetamide;

N-(5-(4-fluorophenyl)-11-methyl-1-oxo-2,4,5,11-tetrahydro-1H-2,5,11-triazadibenzo[cd,h]azulen-8-yl)-2-(3-(2-fluorophenyl)-1H-pyrazol-1-yl)acetamide;
N-(5-(4-fluorophenyl)-11-methyl-1-oxo-2,4,5,11-tetrahydro-1H-2,5,11-triazadibenzo[cd,h]azulen-8-yl)-2-(2-methylthiazol-5-yl)acetamide;
2-(1,5-dimethyl-1H-pyrazol-3-yl)-N-(5-(4-fluorophenyl)-11-methyl-1-oxo-2,4,5,11-tetrahydro-1H-2,5,11-triazadibenzo[cd,h]azulen-8-yl)acetamide;
$N^1$-(5-(4-fluorophenyl)-11-methyl-1-oxo-2,4,5,11-tetrahydro-1H-2,5,11-triazadibenzo[cd,h]azulen-8-yl)-$N^5$-phenylglutaramide;
N-(5-(4-fluorophenyl)-11-methyl-1-oxo-2,4,5,11-tetrahydro-1H-2,5,11-triazadibenzo[cd,h]azulen-8-yl)-5-methylpyrazine-2-carboxamide;
N-(5-(4-fluorophenyl)-11-methyl-1-oxo-2,4,5,11-tetrahydro-1H-2,5,11-triazadibenzo[cd,h]azulen-8-yl)-2-(4-methylpiperazin-1-yl)acetamide;
8-(((1-ethyl-1H-pyrazol-3-yl)methyl)amino)-5-(4-fluorophenyl)-11-methyl-2,4,5,11-tetrahydro-1H-2,5,11-triazadibenzo[cd,h]azulen-1-one;
5-(4-fluorophenyl)-11-methyl-8-(((1-methyl-1H-pyrazol-5-yl)methyl)amino)-2,4,5,11-tetrahydro-1H-2,5,11-triazadibenzo[cd,h]azulen-1-one;
8-((3-(1H-pyrazol-1-yl)propyl)amino)-5-(4-fluorophenyl)-11-methyl-2,4,5,11-tetrahydro-1H-2,5,11-triazadibenzo[cd,h]azulen-1-one;
5-(4-fluorophenyl)-11-methyl-8-(((6-methylpyridin-2-yl)methyl)amino)-2,4,5,11-tetrahydro-1H-2,5,11-triazadibenzo[cd,h]azulen-1-one;
methyl 4-((5-(4-fluorophenyl)-11-methyl-1-oxo-2,4,5,11-tetrahydro-1H-2,5,11-triazadibenzo[cd,h]azulen-8-yl)amino)butanoate;
5-(4-fluorophenyl)-11-methyl-8-(((1-methyl-1H-imidazol-5-yl)methyl)amino)-2,4,5,11-tetrahydro-1H-2,5,11-triazadibenzo[cd,h]azulen-1-one;
5-(4-fluorophenyl)-11-methyl-8-(((3-methylpyridin-2-yl)methyl)amino)-2,4,5,11-tetrahydro-1H-2,5,11-triazadibenzo[cd,h]azulen-1-one;
1-(5-(4-fluorophenyl)-11-methyl-1-oxo-2,4,5,11-tetrahydro-1H-2,5,11-triazadibenzo[cd,h]azulen-8-yl)-3-(3-phenoxyphenyl)urea;
1-(5-(4-fluorophenyl)-11-methyl-1-oxo-2,4,5,11-tetrahydro-1H-2,5,11-triazadibenzo[cd,h]azulen-8-yl)-3-(3-methoxyphenyl)urea;
2-(chroman-6-yl)-N-(5-(4-fluorophenyl)-11-methyl-1-oxo-2,4,5,11-tetrahydro-1H-2,5,11-triazadibenzo[cd,h]azulen-8-yl)acetamide;
N-(5-(4-fluorophenyl)-11-methyl-1-oxo-2,4,5,11-tetrahydro-1H-2,5,11-triazadibenzo[cd,h]azulen-8-yl)-3-(4-methylpiperazin-1-yl)propanamide;
N-(5-(4-fluorophenyl)-11-methyl-1-oxo-2,4,5,11-tetrahydro-1H-2,5,11-triazadibenzo[cd,h]azulen-8-yl)-3-(piperidin-1-yl)propanamide;
2-(2-bromo-5-fluorophenyl)-N-(5-(4-fluorophenyl)-11-methyl-1-oxo-2,4,5,11-tetrahydro-1H-2,5,11-triazadibenzo[cd,h]azulen-8-yl)acetamide;
2-(2,5-dichlorophenyl)-N-(5-(4-fluorophenyl)-11-methyl-1-oxo-2,4,5,11-tetrahydro-1H-2,5,11-triazadibenzo[cd,h]azulen-8-yl)acetamide;
2-(5-fluoro-2-(trifluoromethyl)phenyl)-N-(5-(4-fluorophenyl)-11-methyl-1-oxo-2,4,5,11-tetrahydro-1H-2,5,11-triazadibenzo[cd,h]azulen-8-yl)acetamide;
2-(2,5-difluorophenyl)-N-(5-(4-fluorophenyl)-11-methyl-1-oxo-2,4,5,11-tetrahydro-1H-2,5,11-triazadibenzo[cd,h]azulen-8-yl)acetamide;
2-(2,5-dimethylphenyl)-N-(5-(4-fluorophenyl)-11-methyl-1-oxo-2,4,5,11-tetrahydro-1H-2,5,11-triazadibenzo[cd,h]azulen-8-yl)acetamide;
N-(5-(4-fluorophenyl)-11-methyl-1-oxo-2,4,5,11-tetrahydro-1H-2,5,11-triazadibenzo[cd,h]azulen-8-yl)-2-phenylacetamide;
2-(5-chloro-2-phenoxyphenyl)-N-(5-(4-fluorophenyl)-11-methyl-1-oxo-2,4,5,11-tetrahydro-1H-2,5,11-triazadibenzo[cd,h]azulen-8-yl)acetamide;
N-(5-fluoro-2-methoxybenzyl)-5-(4-fluorophenyl)-11-methyl-1-oxo-2,4,5,11-tetrahydro-1H-2,5,11-triazadibenzo[cd,h]azulene-8-carboxamide;
N-(5-fluoro-2-methylbenzyl)-5-(4-fluorophenyl)-11-methyl-1-oxo-2,4,5,11-tetrahydro-1H-2,5,11-triazadibenzo[cd,h]azulene-8-carboxamide;
N-(2-bromo-5-fluorobenzyl)-5-(4-fluorophenyl)-11-methyl-1-oxo-2,4,5,11-tetrahydro-1H-2,5,11-triazadibenzo[cd,h]azulene-8-carboxamide;
5-(4-fluorophenyl)-N-(1-(4-fluorophenyl)ethyl)-11-methyl-1-oxo-2,4,5,11-tetrahydro-1H-2,5,11-triazadibenzo[cd,h]azulene-8-carboxamide;
N-(2-chloro-5-fluorobenzyl)-5-(4-fluorophenyl)-11-methyl-1-oxo-2,4,5,11-tetrahydro-1H-2,5,11-triazadibenzo[cd,h]azulene-8-carboxamide;
N-(1-(2,4-dichlorophenyl)ethyl)-5-(4-fluorophenyl)-11-methyl-1-oxo-2,4,5,11-tetrahydro-1H-2,5,11-triazadibenzo[cd,h]azulene-8-carboxamide;
N-((1-benzyl-1H-pyrazol-4-yl)methyl)-5-(4-fluorophenyl)-11-methyl-1-oxo-2,4,5,11-tetrahydro-1H-2,5,11-triazadibenzo[cd,h]azulene-8-carboxamide;
N-benzyl-5-(4-fluorophenyl)-11-methyl-1-oxo-2,4,5,11-tetrahydro-1H-2,5,11-triazadibenzo[cd,h]azulene-8-carboxamide;
N-(2,5-difluorobenzyl)-5-(4-fluorophenyl)-11-methyl-1-oxo-2,4,5,11-tetrahydro-1H-2,5,11-triazadibenzo[cd,h]azulene-8-carboxamide;
2-(5-fluoro-2-methoxyphenyl)-N-(5-(4-fluorophenyl)-11-methyl-1-oxo-2,4,5,11-tetrahydro-1H-2,5,11-triazadibenzo[cd,h]azulen-8-yl)acetamide;
2-(5-fluoro-2-nitrophenyl)-N-(5-(4-fluorophenyl)-11-methyl-1-oxo-2,4,5,11-tetrahydro-1H-2,5,11-triazadibenzo[cd,h]azulen-8-yl)acetamide;
8-amino-5-(2,4-difluorophenyl)-11-methyl-2,4,5,11-tetrahydro-1H-2,5,6,11-tetraazadibenzo[cd,h]azulen-1-one;
N-(5-(2,4-difluorophenyl)-11-methyl-1-oxo-2,4,5,11-tetrahydro-1H-2,5,6,11-tetraazadibenzo[cd,h]azulen-8-yl)ethanesulfonamide;
8-amino-5-(4-chlorophenyl)-11-methyl-2,4,5,11-tetrahydro-1H-2,5,6,11-tetraazadibenzo[cd,h]azulen-1-one;
N-(5-(4-chlorophenyl)-11-methyl-1-oxo-2,4,5,11-tetrahydro-1H-2,5,6,11-tetraazadibenzo[cd,h]azulen-8-yl)ethanesulfonamide;
N-(5-(4-chlorophenyl)-11-methyl-1-oxo-2,4,5,11-tetrahydro-1H-2,5,6,11-tetraazadibenzo[cd,h]azulen-8-yl)methanesulfonamide; and
N-(5-(4-chlorophenyl)-11-methyl-1-oxo-2,4,5,11-tetrahydro-1H-2,5,6,11-tetraazadibenzo[cd,h]azulen-8-yl)acetamide.

In certain embodiments, a compound of formula (I) is selected from the group consisting of:
5-(cyclopropylmethyl)-11-methyl-8-((methylsulfonyl)methyl)-2,4,5,11-tetrahydro-1H-2,5,11-triazadibenzo[cd,h]azulen-1-one;
5-(4-fluorophenyl)-11-methyl-8-((methylsulfonyl)methyl)-2,4,5,11-tetrahydro-1H-2,5,11-triazadibenzo[cd,h]azulen-1-one;

5-(2,4-difluorophenyl)-11-methyl-8-((methylsulfonyl)methyl)-2,4,5,11-tetrahydro-1H-2,5,11-triazadibenzo[cd,h]azulen-1-one;

5-(cyclopropanecarbonyl)-11-methyl-8-((methylsulfonyl)methyl)-2,4,5,11-tetrahydro-1H-2,5,11-triazadibenzo[cd,h]azulen-1-one;

5-(4-fluorophenyl)-4-(2-methoxyethyl)-11-methyl-8-((methylsulfonyl)methyl)-2,4,5,11-tetrahydro-1H-2,5,11-triazadibenzo[cd,h]azulen-1-one;

methyl 3-(5-(4-fluorophenyl)-11-methyl-8-((methylsulfonyl)methyl)-1-oxo-2,4,5,11-tetrahydro-1H-2,5,11-triazadibenzo[cd,h]azulen-4-yl)propanoate;

N-(5-(4-fluorophenyl)-11-methyl-1-oxo-2,4,5,11-tetrahydro-1H-2,5,11-triazadibenzo[cd,h]azulen-8-yl)ethanesulfonamide;

8-fluoro-5-(4-fluorophenyl)-11-methyl-2,4,5,11-tetrahydro-1H-2,5,6,11-tetraazadibenzo[cd,h]azulen-1-one;

2-(2-chloro-5-fluorophenyl)-N-(5-(4-fluorophenyl)-11-methyl-1-oxo-2,4,5,11-tetrahydro-1H-2,5,6,11-tetraazadibenzo[cd,h]azulen-8-yl)acetamide;

N-(5-(4-fluorophenyl)-11-methyl-1-oxo-2,4,5,11-tetrahydro-1H-2,5,6,11-tetraazadibenzo[cd,h]azulen-8-yl)-2-(1-methyl-1H-pyrazol-4-yl)acetamide;

8-amino-5-(4-fluorophenyl)-11-methyl-2,4,5,11-tetrahydro-1H-2,5,11-triazadibenzo[cd,h]azulen-1-one;

N-(5-(4-fluorophenyl)-11-methyl-1-oxo-2,4,5,11-tetrahydro-1H-2,5,11-triazadibenzo[cd,h]azulen-8-yl)benzenesulfonamide;

N-(4-(N-(5-(4-fluorophenyl)-11-methyl-1-oxo-2,4,5,11-tetrahydro-1H-2,5,11-triazadibenzo[cd,h]azulen-8-yl)sulfamoyl)phenyl)acetamide;

5-(4-fluorophenyl)-11-methyl-8-(((6-methylpyridin-2-yl)methyl)amino)-2,4,5,11-tetrahydro-1H-2,5,11-triazadibenzo[cd,h]azulen-1-one;

N-(5-(4-fluorophenyl)-11-methyl-1-oxo-2,4,5,11-tetrahydro-1H-2,5,11-triazadibenzo[cd,h]azulen-8-yl)-3-(piperidin-1-yl)propanamide;

N-(5-(2,4-difluorophenyl)-11-methyl-1-oxo-2,4,5,11-tetrahydro-1H-2,5,6,11-tetraazadibenzo[cd,h]azulen-8-yl)ethanesulfonamide;

N-(5-(4-chlorophenyl)-11-methyl-1-oxo-2,4,5,11-tetrahydro-1H-2,5,6,11-tetraazadibenzo[cd,h]azulen-8-yl)ethanesulfonamide;

N-(5-(4-chlorophenyl)-11-methyl-1-oxo-2,4,5,11-tetrahydro-1H-2,5,6,11-tetraazadibenzo[cd,h]azulen-8-yl)acetamide;

5-(1-acetylpiperidin-4-yl)-8-amino-11-methyl-2,4,5,11-tetrahydro-1H-2,5,11-triazadibenzo[cd,h]azulen-1-one;

N-(5-(1-acetylpiperidin-4-yl)-11-methyl-1-oxo-2,4,5,11-tetrahydro-1H-2,5,11-triazadibenzo[cd,h]azulen-8-yl)ethanesulfonamide;

N-(5-(1-acetylpiperidin-4-yl)-11-methyl-1-oxo-2,4,5,11-tetrahydro-1H-2,5,11-triazadibenzo[cd,h]azulen-8-yl)-2-(2-methylthiazol-5-yl)acetamide;

N-(5-(1-acetylpiperidin-4-yl)-11-methyl-1-oxo-2,4,5,11-tetrahydro-1H-2,5,11-triazadibenzo[cd,h]azulen-8-yl)-2-(2-chloro-5-fluorophenyl)acetamide;

N-(5-(1-acetylpiperidin-4-yl)-11-methyl-1-oxo-2,4,5,11-tetrahydro-1H-2,5,11-triazadibenzo[cd,h]azulen-8-yl)acetamide;

6-cyclopropyl-5-(2,4-difluorophenyl)-11-methyl-8-((methylsulfonyl)methyl)-2,4,5,11-tetrahydro-1H-2,5,11-triazadibenzo[cd,h]azulen-1-one;

11-methyl-8-((methylsulfonyl)methyl)-5-(pyridin-2-yl)-2,4,5,11-tetrahydro-1H-2,5,11-triazadibenzo[cd,h]azulen-1-one;

tert-butyl 4-(11-methyl-8-((methylsulfonyl)methyl)-1-oxo-1H-2,5,11-triazadibenzo[cd,h]azulen-5(2H,4H,11H)-yl)piperidine-1-carboxylate;

methyl 11-methyl-8-((methylsulfonyl)methyl)-1-oxo-4,11-dihydro-1H-2,5,11-triazadibenzo[cd,h]azulene-5(2H)-carboxylate; and N-(11-methyl-1-oxo-5-(pyridin-2-yl)-2,4,5,11-tetrahydro-1H-2,5,11-triazadibenzo[cd,h]azulen-8-yl)ethanesulfonamide.

Compounds of formula I can be used in the form of pharmaceutically acceptable salts. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts have been described in S. M. Berge et al. J. Pharmaceutical Sciences, 1977, 66: 1-19.

Compounds of formula (I) may contain either a basic or an acidic functionality, or both, and can be converted to a pharmaceutically acceptable salt, when desired, by using a suitable acid or base. The salts may be prepared in situ during the final isolation and purification of the compounds of the invention.

Examples of acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts may be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other examples of organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use.

The present invention contemplates compounds of formula (I) formed by synthetic means or formed by in vivo biotransformation of a prodrug.

Compounds described herein can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

General Synthesis

The compounds described herein, including compounds of general formula (I) and specific examples, may be prepared, for example, through the reaction routes depicted in schemes 1-5. The variables $A^1$, $A^2$, $A^3$, $A^4$, $Y^1$, $Y^2$, $R^1$, $R^2$, $R^3$, $R^4$, $R^5$, $R^6$, $R^{3b}$, $R^{3c}$, $R^{6a}$, $R^{6b}$, and $R^{6c}$ used in the following schemes have the meanings as set forth in the summary and detailed description sections unless otherwise noted.

Abbreviations used in the descriptions of the schemes and the specific examples have the following meanings: DMF for dimethylformamide, DMSO for dimethyl sulfoxide, TFA for trifluoroacetic acid, and HPLC for high performance liquid chromatography.

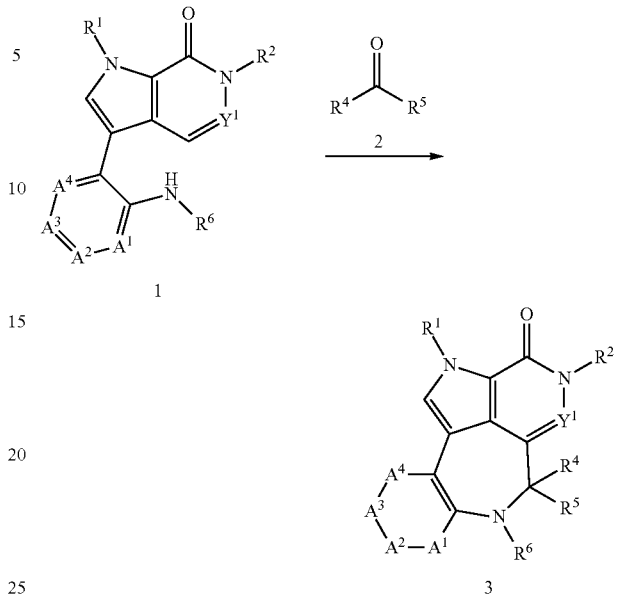

Scheme 1

Compounds of general formula (I) wherein $Y^2$ is $CR^4R^5$ may be prepared by treating compounds of the general formula (1) with an aldehyde or ketone (2) under acidic conditions, as illustrated in Scheme 1. Generally, this cyclization reaction may be effected in the presence of an acid, such as acetic acid or hydrochloric acid, in the absence or presence of a solvent such as, but not limited to, methanol or ethanol, at a temperature ranging from about 50° C. to about 150° C. Alternatively, this cyclization reaction may be effected in the presence of a reagent such as titanium tetrachloride in a solvent such as, but not limited to, tetrahydrofuran or dichloromethane, at a temperature ranging from about 0° C. to about 50° C.

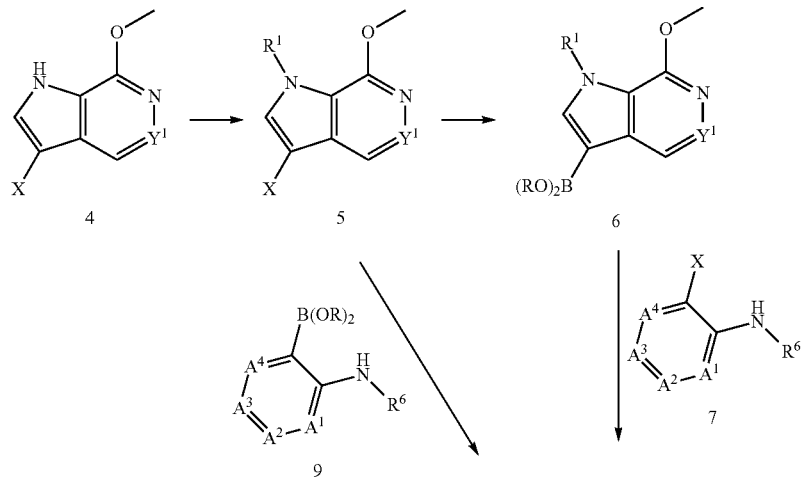

Scheme 2

-continued

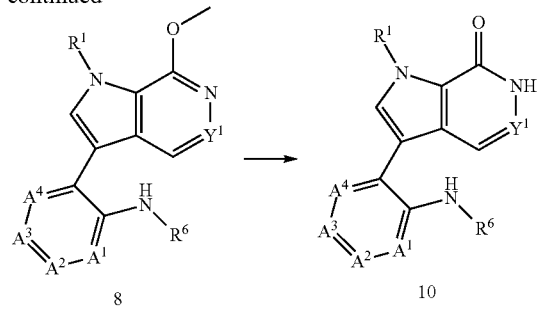

Compounds of formula (1) wherein $R^2$ is H may be prepared by general synthetic methods as shown in Scheme 2. Reaction of compounds of formula (4) wherein X is Br, Cl, I, or triflate with a $C_1$-$C_3$ alkyl halide, in the presence of a base such as, for example, carbonate of cesium, sodium, or potassium and in a solvent such as, for example, dimethylformamide, tetrahydrofuran, or dimethylsulfoxide, provides intermediates of formula (5) wherein $R^1$ is $C_1$-$C_3$ alkyl. The reaction may be conducted at temperature such as, for example, about 25° C. to about 60° C.

Pinacol esters of formula (6), may be synthesized, for example, by treatment of compounds of formula (5), wherein X is Br, Cl, I, or triflate, with a reagent such as, but not limited to, butyllithium followed by 2-isopropoxy-4,4,5,5-tetramethyl-1,3,2-dioxaborolane, in a solvent such as, for example, tetrahydrofuran, at a temperature such as, for example, about −78° C. (6) may be prepared by reaction of compounds of general formula (5), wherein X is Br, Cl, I, or triflate, with a reagent such as, but not limited to, bis(pinacolato)diboron or 4,4,5,5-tetramethyl-1,3,2-dioxaborolane in the presence of a palladium catalyst and a base, and optionally in the presence of a ligand, and in a suitable solvent at elevated temperature (about 80° C. to about 150° C.). The reaction may be facilitated by microwave irradiation. Examples of the palladium catalyst include, but are not limited to, tetrakis(triphenylphosphine)palladium(0), tris(dibenzylideneacetone)dipalladium(0), bis(triphenylphosphine)palladium(II) dichloride, and palladium(II) acetate. Examples of suitable bases that may be employed include, but not limited to, carbonates or phosphates of sodium, potassium, and cesium, and cesium fluoride. Examples of suitable ligands include, but are not limited to, 1,3,5,7-tetramethyl-6-phenyl-2,4,8-trioxa-6-phosphaadamantane, 2-dicyclohexylphosphino-2',4',6'-triisopropylbiphenyl (X-phos), and 1,1'-bis(diphenylphosphanyl) ferrocene. Non-limiting examples of suitable solvent include methanol, ethanol, dimethoxyethane, N,N-dimethylformamide, dimethylsulfoxide, dioxane, tetrahydrofuran, and water, or a mixture thereof. Preparation of compounds of formula (8) may be achieved by reaction of boronic acids or a derivative thereof (e.g., a pinacol ester) of formula (6) with compounds of formula (7), wherein X is Cl, Br, I, or triflate, under Suzuki coupling conditions (N. Miyama and A. Suzuki, Chem. Rev. 1995, 95:2457-2483, J. Organomet. Chem. 1999, 576:147-148). For example, the coupling reaction may be conducted in the presence of a palladium catalyst and a base, and optionally in the presence of a ligand, and in a suitable solvent at elevated temperature (about 80° C. to about 150° C.). The reaction may be facilitated by microwave irradiation. Examples of the palladium catalyst include, but are not limited to, tetrakis(triphenylphosphine)palladium(0), tris(dibenzylideneacetone)dipalladium(0), bis(triphenylphosphine)palladium(II) dichloride, and palladium(II) acetate. Examples of suitable bases that may be employed include, but not limited to, carbonates or phosphates of sodium, potassium, and cesium, and cesium fluoride. Examples of suitable ligands include, but are not limited to, 1,3,5,7-tetramethyl-6-phenyl-2,4,8-trioxa-6-phosphaadamantane, 2-dicyclohexylphosphino-2',4',6'-triisopropylbiphenyl (X-phos), and 1,1'-bis(diphenylphosphanyl) ferrocene. Non-limiting examples of suitable solvent include methanol, ethanol, dimethoxyethane, N,N-dimethylformamide, dimethylsulfoxide, dioxane, tetrahydrofuran, toluene, and water, or a mixture thereof. Compounds of general formula (8) may also be prepared from the reaction of boronic acids or a derivative thereof (e.g., a pinacol ester) (9) with halides (5) wherein X is Cl, Br, or I under Suzuki coupling conditions as described above. Compounds of general formula (10) may be synthesized by the treatment of compounds (8) with an acid such as, for example, hydrochloric acid, acetic acid, or p-toluene sulfonic acid in a solvent such as, for example, water, dioxane, or dimethylformamide, at a temperature such as, for example, about 25° C. to about 120° C. Alternatively, compounds of general formula (10) may be obtained from the reaction of compounds (8) with trimethylsilyl iodide in a solvent such as, for example, dichloromethane or chloroform, and at a temperature such as, for example, about 25° C. to about 75° C.

Scheme 3

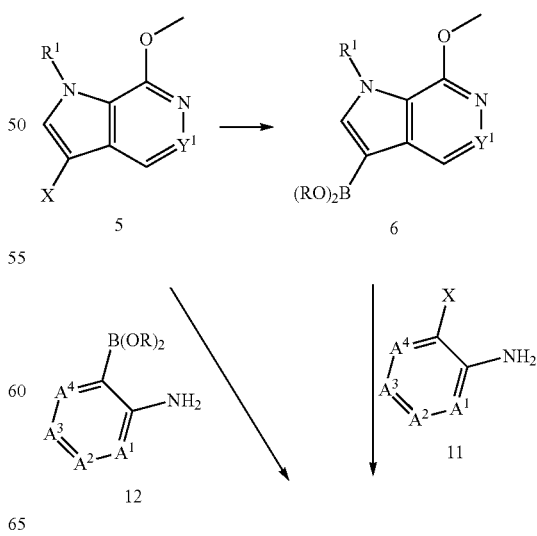

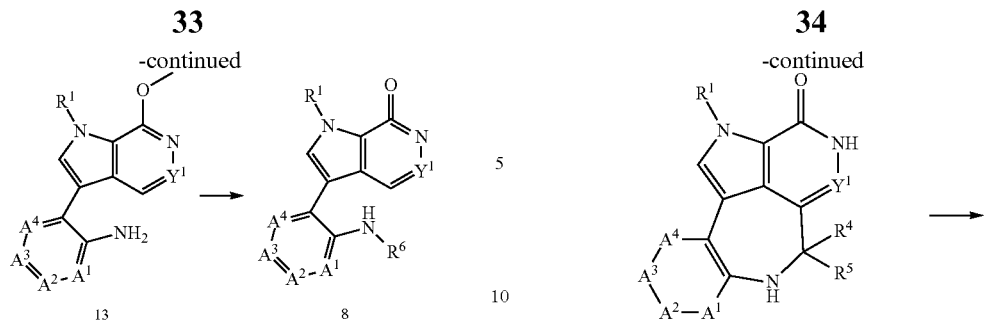

Compound of formula (8) may be prepared according to Scheme 3. Amines of formula (13) may be prepared from halides of formula (5) or boronic acid or derivatives thereof (e.g. pinacol ester) (6) using reaction conditions as described in Scheme 2. Reductive amination of amines of formula (13) with a suitable aldehyde or ketone in the presence of a reducing agent and an acid (e.g. acetic acid) provides compounds of formula (8) wherein $R^6$ is $C_1$-$C_6$ alkyl, $C_2$-$C_6$ alkenyl, or $C_2$-$C_6$ alkynyl, each of which is optionally substituted, or $R^6$ is $C_1$-$C_6$ haloalkyl. Examples of reducing agents that may be employed include, but are not limited to, sodium triacetoxyhydroborate, sodium borohydride, and sodium cyanoborohydride. The reaction is generally conducted in a solvent such as, for example, dichloromethane, methanol, or ethanol, at a temperature of about 0° C. to about 100° C.

Scheme 4

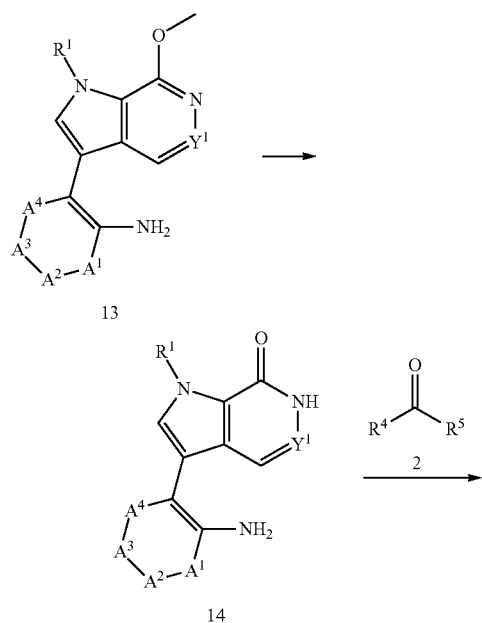

Compounds of formula (14) may be prepared by acid hydrolysis of compounds of formula (13), as described above in Scheme 2. Compounds of formula (15) may be prepared by treating compounds of formula (14) with an aldehyde or ketone (2) using conditions described in Scheme 1. Compounds of formula (16) wherein $R^6$ is optionally substituted $C_1$-$C_6$ alkyl, $C_2$-$C_6$ alkenyl, or $C_2$-$C_6$ alkynyl, or $R^6$ is $C_1$-$C_6$ haloalkyl may be prepared by the reductive amination reaction of compounds of formula (15) with a suitable aldehyde or ketone using reaction conditions as described in Scheme 3. Compounds of formula (16) wherein $R^6$ is $C(O)OR^{6a}$, $C(O)R^{6a}$, $S(O)_2R^{6a}$, and $C(O)NR^{6b}R^{6c}$ may be prepared by the reaction of compounds of formula (15) with chloroformates, acid chlorides, sulfonyl chlorides or isocyanates in the presence of a base such as, but not limited to, diisopropylethylamine, triethylamine, or cesium carbonate, in a solvent such as dimethylformamide, dimethylacetamide, 1,2-dichloroethane, or dichloromethane, at temperatures ranging from ambient temperature to about 100° C. for about 2 to about 72 hours.

Scheme 5

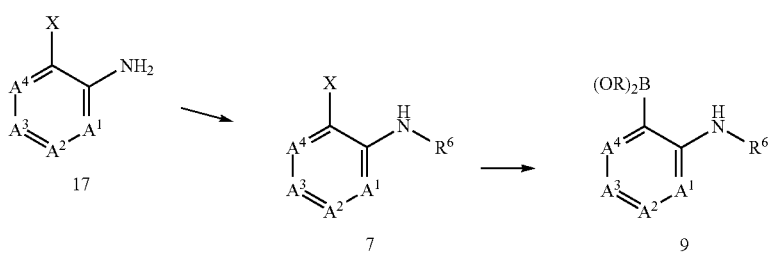

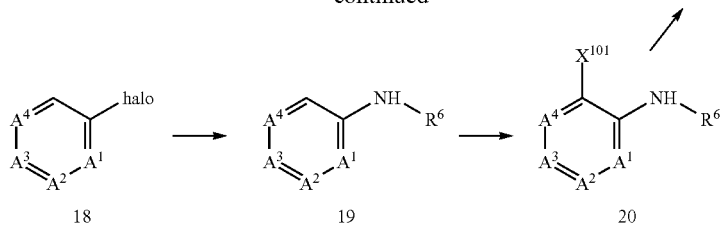

Compounds of formula (7) and formula (9) may be prepared according to the synthesis outlined in Scheme 5. Reductive amination of amines (17) wherein X is I, Br, or Cl with a suitable aldehyde or ketone provides compounds (7) wherein $R^6$ is $C_1$-$C_6$ alkyl, $C_2$-$C_6$ alkenyl, $C_2$-$C_6$ alkynyl, or $C_1$-$C_6$ haloalkyl. Compounds of formula (9) may be prepared from compounds of formula (7) under Suzuki coupling conditions as described in Scheme 2. Similarly, compound (20) wherein $X^{101}$ is I, Cl, or Br may be converted to (9).

Compound (19) may be prepared using Buchwald reaction conditions. For example, halides (18) may be treated with a suitable amine in the presence of a catalyst, a ligand, a base, and in a solvent to provide compounds (19). Examples of catalysts that may be employed include, but are not limited to, tetrakis(triphenylphosphine)palladium(0), tris(dibenzylideneacetone)dipalladium(0), bis(triphenylphosphine)palladium(II) dichloride, and palladium(II)acetate. Examples of suitable bases that may be employed include, but not limited to, carbonates or phosphates of sodium, potassium, and cesium, and cesium fluoride. Examples of suitable ligands include, but are not limited to, 1,3,5,7-tetramethyl-6-phenyl-2,4,8-trioxa-6-phosphaadamantane, 2-dicyclohexylphosphino-2',4',6'-triisopropylbiphenyl (X-phos), and 1,1'-bis(diphenylphosphanyl) ferrocene. Non-limiting examples of suitable solvent include toluene, tert-butanol, methanol, ethanol, dimethoxyethane, N,N-dimethylformamide, dimethylsulfoxide, dioxane, tetrahydrofuran, and water, or a mixture thereof. Halogenation of compounds of formula (19) by reaction with a reagent such as, but not limited to, N-bromosuccinimide, N-chlorosuccinimide, or N-iodosuccinimide, in a solvent such as, but not limited to, acetic acid, at temperatures from about 0° C. to about 50° C., provides compounds of formula (20).

It can be appreciated that the synthetic schemes and specific examples as illustrated in the synthetic examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step can vary depending on the particular reactants employed and substituents present in the reactants used. Unless otherwise specified, solvents, temperatures and other reaction conditions can be readily selected by one of ordinary skill in the art. Specific procedures are provided in the Synthetic Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Routine experimentations, including appropriate manipulation of the reaction conditions, reagents and sequence of the synthetic route, protection of any chemical functionality that can not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in T. Greene and P. Wuts, Protecting Groups in Organic Synthesis ($3^{rd}$ ed.), John Wiley & Sons, NY (1999), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be prepared by carrying out one of the above procedures using a pure geometric isomer as a starting material, or by resolution of a mixture of the geometric isomers of the compound or intermediates using a standard procedure such as chromatographic separation.

Pharmaceutical Compositions

This invention also provides for pharmaceutical compositions comprising a therapeutically effective amount of a compound of Formula I, or a pharmaceutically acceptable salt thereof together with a pharmaceutically acceptable carrier, diluent, or excipient therefor. The phrase "pharmaceutical composition" refers to a composition suitable for administration in medical or veterinary use.

The pharmaceutical compositions that comprise a compound of formula (I), alone or or in combination with a second active pharmaceutical agent, may be administered to the subjects orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents, which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally-administered drug form may be accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In certain embodiments, solid dosage forms may contain from 1% to 95% (w/w) of a compound of formula I. In certain embodiments, the compound of formula I may be present in the solid dosage form in a range of from 5% to 70% (w/w). In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

The pharmaceutical composition may be a unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form can be a capsule, tablet, cachet, or lozenge itself, or it can be the appropriate number of any of these in packaged form. The quantity of active component in a unit dose preparation may be varied or adjusted from 0.1 mg to 1000 mg, from 1 mg to 100 mg, or from 1% to 95% (w/w) of a unit dose, according to the particular application and the potency of the active component. The composition can, if desired, also contain other compatible therapeutic agents.

The dose to be administered to a subject may be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician can evaluate factors such as the circulating plasma levels of the compound, compound toxicities, and/or the progression of the disease, etc. In general, the dose equivalent of a compound is from about 1 µg/kg to 100 mg/kg for a typical subject.

For administration, compounds of the formula I can be administered at a rate determined by factors that can include, but are not limited to, the $LD_{50}$ of the compound, the pharmacokinetic profile of the compound, contraindicated drugs, and the side-effects of the compound at various concentrations, as applied to the mass and overall health of the subject. Administration can be accomplished via single or divided doses.

The compounds utilized in the pharmaceutical method of the invention can be administered at the initial dosage of about 0.001 mg/kg to about 100 mg/kg daily. In certain embodiments, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Treatment may be initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of formula I may also be administered in the form of liposomes. Liposomes generally may be derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form may contain, in addition to a compound of formula (I), stabilizers, preservatives, excipients and the like. Examples of lipids include, but are not limited to, natural and synthetic phospholipids and phosphatidyl cholines (lecithins), used separately or together.

Methods to form liposomes have been described, see example, Prescott, Ed., Methods in Cell Biology, Volume XIV, Academic Press, New York, N.Y. (1976), p. 33 et seq.

Dosage forms for topical administration of a compound described herein include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

Methods of Use

The compounds of formula I, or pharmaceutically acceptable salts thereof, and pharmaceutical compositions comprising a compound of formula I, or a pharmaceutically acceptable salt thereof, can be administered to a subject suffering from a bromodomain-mediated disorder or condition. The term "administering" refers to the method of contacting a compound with a subject. Thus, the compounds of formula I can be administered by injection, that is, intravenously, intramuscularly, intracutaneously, subcutaneously, intraduodenally, parentally, or intraperitoneally. Also, the compounds described herein can be administered by inhalation, for example, intranasally. Additionally, the compounds of formula I can be administered transdermally, topically, via implantation, transdermally, topically, and via implantation. In certain embodiments, the compounds of the formula I may be delivered orally. The compounds can also be delivered rectally, bucally, intravaginally, ocularly, andially, or by insufflation. Bromodomain-mediated disorders and conditions can be treated prophylactically, acutely, and chronically using compounds of formula I, depending on the nature of the disorder or condition. Typically, the host or subject in each of these methods is human, although other mammals can also benefit from the administration of a compound of formula I.

A "bromodomain-mediated disorder or condition" is characterized by the participation of one or more bromodomains (e.g., BRD4) in the inception, manifestation of one or more symptoms or disease markers, severity, or progression of a disorder or condition. Accordingly, compounds of formula I may be used to treat cancer, including, but not limited to acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor.

Further, compounds of formula I may be used to treat inflammatory diseases, inflammatory conditions, and autoimmune diseases, including, but not limited to: Addison's disease, acute gout, ankylosing spondylitis, asthma, atherosclerosis, Behcet's disease, bullous skin diseases, chronic obstructive pulmonary disease (COPD), Crohn's disease, dermatitis, eczema, giant cell arteritis, glomerulonephritis, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis.

Compounds of formula I, or pharmaceutically acceptable salts thereof, may be used to treat AIDS.

The compounds of formula I can be co-administered to a subject. The term "co-administered" means the administration of two or more different pharmaceutical agents or treatments (e.g., radiation treatment) that are administered to a subject by combination in the same pharmaceutical composition or separate pharmaceutical compositions. Thus co-administration involves administration at the same time of a single pharmaceutical composition comprising two or more pharmaceutical agents or administration of two or more different compositions to the same subject at the same or different times.

The compounds of the invention can be co-administered with a therapeutically effective amount of one or more agents to treat a cancer, where examples of the agents include, such as radiation, alkylating agents, angiogenesis inhibitors, antibodies, antimetabolites, antimitotics, antiproliferatives, antivirals, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs (dual variable domain antibodies), leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (bromodomain) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, *J. of Immunology* 1997, 158 (12), 5783).

SiRNAs are molecules having endogenous RNA bases and chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-((1R)-3-(dimethylamino)-1-((phenylsulfanyl)methyl) propyl)amino)-3-nitrobenzenesulfonamide) (ABT-737), N-(4-(4((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax), ABT-199, and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include EGFR antibodies, ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FCl, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-veMMAE, PSMA-ADC, MEDI-547, SGN-19Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806 (mAb-806), ErbB3 specific antibodies, BSG2 specific antibodies, DLL4 specific antibodies and C-met specific antibodies, and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirubicin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofuran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine)(ONCOVIN®; P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTATAAE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces staurospores*), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zoledronic acid), zorubicin and the like.

The compounds of the invention can also be co-administered with a therapeutically effective amount of one or more agents to treat an inflammatory disease or condition, or autoimmune disease, where examples of the agents include, such as methotrexate, 6-mercaptopurine, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g., NIK, IKK, p38 or MAP kinase inhibitors), IL-1β converting enzyme inhibitors, T-cell signalling inhibitors such as kinase inhibitors, metalloproteinase inhibitors, sulfasalazine, 6-mercaptopurines, angiotensin converting enzyme inhibitors, soluble cytokine receptors and derivatives thereof (e.g. soluble p55 or p75 TNF receptors and the derivatives p75TNFRIgG (etanercept) and p55TNFRIgG (Lenercept), sIL-1RI, sIL-1RII, sIL-6R), anti-inflammatory cytokines (e.g. IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL15, BIRB-796, SCIO-469, VX-702, AMG-548, VX-740, Roflumilast, IC-485, CDC-801, S1P1 agonists (such as FTY720), PKC family inhibitors (such as Ruboxistaurin or AEB-071) and Mesopram. In certain embodiments, combinations include methotrexate or leflunomide and in moderate or severe rheumatoid arthritis cases, cyclosporine and anti-TNF antibodies as noted above.

Non-limiting examples of therapeutic agents for inflammatory bowel disease with which a compound of Formula (I) of the invention may be co-administered include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-12, IL-15, IL-16, IL-23, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signalling by proinflammatory cytokines such as TNFα or IL-1 (e.g. NIK, IKK, or MAP kinase inhibitors); IL-1β converting enzyme inhibitors; TNFα converting enzyme inhibitors; T-cell signalling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-11, IL-13 and TGFβ). Preferred examples of therapeutic agents for Crohn's disease with which a compound of Formula (I) can be combined include the following: TNF antagonists, for example, anti-TNF antibodies, D2E7 (adalimumab), CA2 (infliximab), CDP 571, TNFR-Ig constructs, (p75TNFRIgG (etanercept) and p55TNFRIgG (LENERCEPT™) inhibitors and PDE4 inhibitors. A compound of Formula (I) can be combined with corticosteroids, for example, budenoside and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors; 6-mercaptopurine; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrosewater; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis with which a compound of Formula (I) may be co-administered include the following: corticosteroids; prednisolone; methylprednisolone; azathioprine; cyclophosphamide; cyclosporine; methotrexate; 4-aminopyridine; tizanidine; interferon-β1a (AVONEX®; Biogen); interferon-β1b (BETASERON®; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE®; Teva Pharmaceutical Industries, Inc.); hyperbaric oxygen; intravenous immunoglobulin; cladribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of Formula (I) can be combined with antibodies to cell surface molecules such as CD2, CD3, CD4, CD8, CD19, CD20, CD25, CD28, CD30, CD40, CD45, CD69, CD80, CD86, CD90 or their ligands. A compound of Formula (I) may also be combined with agents such as methotrexate, cyclosporine, FK506, rapamycin, mycophenolate mofetil, leflunomide, an S1P1 agonist, NSAIDs, for example, ibuprofen, corticosteroids such as prednisolone, phosphodiesterase inhibitors, adenosine agonists, antithrombotic agents, complement inhibitors, adrenergic agents, agents which interfere with signalling by proinflammatory cytokines such as TNFα or IL-1 (e.g., NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-13 and TGFβ).

A compound of Formula (I) may also be co-administered with agents, such as alemtuzumab, dronabinol, daclizumab, mitoxantrone, xaliproden hydrochloride, fampridine, glatiramer acetate, natalizumab, sinnabidol, α-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for ankylosing spondylitis with which a compound of Formula (I) can be co-administered include the following: ibuprofen, diclofenac, misoprostol, naproxen, meloxicam, indomethacin, diclofenac, celecoxib, rofecoxib, sulfasalazine, methotrexate, azathioprine, minocyclin, prednisone, and anti-TNF antibodies, D2E7 (HUMIRA®), CA2 (infliximab), CDP 571, TNFR-Ig constructs, (p75TNFRIgG (ENBREL®) and p55TNFRIgG (LENERCEPT®).

Non-limiting examples of therapeutic agents for asthma with which a compound of Formula (I) may be co-administered include the following: albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin HCl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, anti-IL-13 antibody, and metaproterenol sulfate.

Non-limiting examples of therapeutic agents for COPD with which a compound of Formula (I) may be co-administered include the following: albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, cilomilast and roflumilast.

Non-limiting examples of therapeutic agents for psoriasis with which a compound of Formula (I) may be co-administered include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874 and ustekinamab.

Non-limiting examples of therapeutic agents for psoriatic arthritis with which a compound of Formula (I) may be co-administered include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, D2E7 (adalimumab), and efalizumab.

Preferred examples of therapeutic agents for SLE (Lupus) with which a compound of Formula (I) may be co-administered include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept®. A compound of Formula (I) may also be combined with agents such as sulfasalazine, 5-aminosalicylic acid, olsalazine, Imuran® and agents which interfere with synthesis, production or action of proinflammatory cytokines such as IL-1, for example, caspase inhibitors like IL-1β converting enzyme inhibitors and IL-1ra. A compound of Formula (I) may also be used with T cell signaling inhibitors, for example, tyrosine kinase inhibitors; or molecules that target T cell activation molecules, for example, CTLA-4-IgG or anti-B7 family antibodies, anti-PD-1 family antibodies. A compound of Formula (I) can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. A compound of Formula (I) may also be used with UP 394 (abetimus), agents that deplete or inactivate B-cells, for example, Rituximab (anti-CD20 antibody), lymphostat-B (anti-BlyS antibody), TNF antagonists, for example, anti-TNF antibodies, D2E7 (adalimumab), CA2 (infliximab), CDP 571, TNFR-Ig constructs, (p75TNFRIgG (etanercept) and p55TNFRIgG (LENERCEPT™).

The compounds of the invention can also be co-administered with a therapeutically effective amount of one or more agents used in the prevention or treatment of AIDS, where examples of the agents include, HIV reverse transcriptase inhibitors, HIV protease inhibitors, immunomodulators, and other retroviral drugs. Examples of reverse transcriptase inhibitors include, but are not limited to, abacavir, adefovir, didanosine, dipivoxil delavirdine, efavirenz, lamivudine, nevirapine, stavudine zalcitabine, and zidovudine. Examples of protease inhibitors include, but are not limited to, amprenavir, indinavir, lopinavir, nelfinavir, ritonavir, and saquinavir.

A compound of Formula (I) may also be co-administered with insulin for the treatment of type I diabetes.

The compounds of the invention can also be co-administered with a therapeutically effective amount of one or more agents used in the prevention or treatment of AIDS, where examples of the agents include, HIV reverse transcriptase inhibitors, HIV protease inhibitors, immunomodulators, and other retroviral drugs. Examples of reverse transcriptase inhibitors include, but are not limited to, abacavir, adefovir, didanosine, dipivoxil delavirdine, efavirenz, emtricitabine, lamivudine, nevirapine, rilpivirine, stavudine, tenofovir, zalcitabine, and zidovudine. Examples of protease inhibitors include, but are not limited to, amprenavir, atazanavir, darunavir, indinavir, fosamprenavir, lopinavir, nelfinavir, ritonavir, saquinavir, and tipranavir. Examples of other retroviral drugs include, but are not limited to, elvitegravir, enfuvirtide, maraviroc and raltegravir.

The compounds of the invention can also be co-administered with a therapeutically effective amount of one or more agents used in the treatment of obesity, where examples of the agents include orlistat.

The compounds of the invention can also be co-administered with a therapeutically effective amount of one or more agents used in the treatment of type II diabetes, where examples of the agents include, alpha glucosidase inhibitors, insulin, metformin, sulfonylureas (e.g., carbutamide, acetohexamide, chlorpropamide, glibenclamide, glibornuride, gliclazide, glimepiride, glipizide, gliquidone, glisoxepide, glyclopyramide, tolbutamide, and tolazamide), nonsulfonylureas (e.g., nateglinide, and repaglinide), and thiazolidinediones (e.g., pioglitazone).

The compounds of the invention can be co-administered with a therapeutically effective amount of one or more agents to prevent or treat type II diabetes, hepatic steatosis, insulin resistance, metabolic syndrome and related disorders, where examples of the agents include, but are not limited to, insulin and insulins that have been modified to improve the duration of action in the body; agents that stimulate insulin secretion such as acetohexamide, chlorpropamide, glyburide, glimepiride, glipizide, glicazide, glycopyramide, gliquidone, rapaglinide, nataglinide, tolazamide and tolbutamide; agents that are glucagon-like peptide agonists such as exanatide, liraglutide and taspoglutide; agents that inhibit dipeptidyl-peptidase IV such as vildagliptin, sitagliptin, saxagliptin, linagliptin, allogliptin and septagliptin; agents that bind to the peroxisome proliferator-activated receptor gamma such as rosiglitazone and pioglitazone; agents that decrease insulin resistance such as metformin; agents that reduce glucose absorbance in the small intestine such as acarbose, miglitol and voglibose.

The compounds of the invention can be co-administered with a therapeutically effective amount of one or more agents to prevent or treat acute kidney disorders and chronic kidney diseases, where examples of the agents include, but are not limited to, dopamine, diuretics such as furosemide, bumetanide, thiazide and the like, mannitol, calcium gluconate, sodium bicarbonate, albuterol, paricalcitol, doxercalciferol, and cinacalcet.

The following Examples may be used for illustrative purposes and should not be deemed to narrow the scope of the invention.

EXAMPLES

Example 1

11-methyl-8-(methylsulfonyl)-2,4,5,11-tetrahydro-1H-2,5,11-triazadibenzo[cd,h]azulen-1-one Example 1a 3-iodo-7-methoxy-1-methyl-1H-pyrrolo[2,3-c]pyridine 3-Iodo-7-methoxy-1H-pyrrolo[2,3-c]pyridine (0.75 g, 2.74 mmol) in dimethylformamide (10 mL) was treated with 60% sodium hydride in mineral oil (0.219 g, 5.47 mmol) at ambient temperature for 20 minutes. To this solution was added methyl iodide (0.505 g, 3.56 mmol). The reaction mixture was stirred for 3 hours at ambient temperature. The reaction mixture was partitioned between water and ethyl acetate. The aqueous layer was extracted three times with ethyl acetate. The combined organic layers were washed with saturated aqueous sodium chloride, dried over anhydrous magnesium sulfate, filtered, and concentrated. The residue was purified by flash chromatography (silica gel, 10% ethyl acetate in hexanes) to afford the title compound (0.75 g, 95%).

Example 1b 7-methoxy-1-methyl-3-(4,4,5,5-tetramethyl-1,3,2-dioxaborolan-2-yl)-1H-pyrrolo[2,3-c]pyridine Example 1a (3.89 g, 13.5 mmol) was flow purged with nitrogen for 30 minutes, then treated with tetrahydrofuran (135 mL). The reaction mixture was cooled to −78° C. Butyllithium (5.40 mL, 13.5 mmol, 2.5 M butyllithium in hexanes) was added dropwise. The reaction mixture was stirred at −78° C. for 30 minutes. 2-Isopropoxy-4,4,5,5-tetramethyl-1,3,2-dioxaborolane (2.75 mL, 13.50 mmol) was added dropwise. The reaction mixture was stirred at −78° C. for 2.5 hours. The reaction mixture was poured onto water and extracted twice with ethyl acetate. The organic layer was washed with saturated aqueous sodium chloride, dried over anhydrous magnesium sulfate, filtered, and concentrated. The residue was purified by flash chromatography (silica gel, 0-30% ethyl acetate in heptanes) to afford the title compound (2.75 g, 70%).

Example 1c 2-(7-methoxy-1-methyl-1H-pyrrolo[2,3-c]pyridin-3-yl)-4-(methylsulfonyl)aniline Example 1b (1.00 g, 3.47 mmol), 2-bromo-4-methanesulfonylaniline (0.868 g, 3.47 mmol), tris(dibenzylideneacetone)dipalladium(0) (0.0950 g, 0.104 mmol), 1,3,5,7-tetramethyl-6-phenyl-2,4,8-trioxa-6-phosphaadamante (0.101 g, 0.347 mmol) and sodium carbonate (1.287 g, 12.15 mmol) were combined and sparged with argon for 15 minutes. Meanwhile a solution of 4:1 dioxane/water (35 mL) was sparged with nitrogen for 15 minutes and transferred by syringe into the reaction vessel under argon. The mixture was stirred at 60° C. for 4 hours, diluted with water and filtered to collect a solid. The solid was dissolved in 100 mL of hot 1:1 ethyl acetate/methanol, filtered to remove the solid palladium, and the filtrate was concentrated to afford the title compound (0.98 g, 85%).

Example 1d 11-methyl-8-(methylsulfonyl)-2,4,5,11-tetrahydro-1H-2,5,11-triazadibenzo[cd,h]azulen-1-one A 5 mL vial was charged with Example 1c (40 mg, 0.12 mmol), paraformaldehyde (18 mg, 0.60 mmol) and methanol (1 mL). To this suspension was added 4M HCl in dioxane (0.60 mL, 2.4 mmol). The vial was closed and stirred at 90° C. for 1 hour. The reaction mixture was cooled to ambient temperature and concentrated. The residue was purified by flash chromatography (silica gel, 2-8% methanol in dichloromethane) to afford the title compound (12 mg, 30%). $^1$H NMR (300 MHz, DMSO-$d_6$) δ 10.74 (d, J=5.09 Hz, 1H) 8.10 (d, J=2.37 Hz, 1H) 7.93 (s, 1H) 7.46 (dd, J=8.48, 2.03 Hz, 1H) 7.07 (d, J=8.48 Hz, 1H) 6.78 (d, J=5.43 Hz, 1H) 6.66 (s, 1H) 4.12 (s, 3H) 4.03 (s, 2H) 3.17 (s, 3H). MS (ESI+) m/z 330 (M+H)$^+$.

Example 2

5-(cyclopropylmethyl)-11-methyl-8-(methylsulfonyl)-2,4,5,11-tetrahydro-1H-2,5,11-triazadibenzo[cd,h]azulen-1-one

Example 2a

N-(cyclopropylmethyl)-2-(7-methoxy-1-methyl-1H-pyrrolo[2,3-c]pyridin-3-yl)-4-(methylsulfonyl)aniline Example 1c (0.100 g, 0.302 mmol), cyclopropanecarboxaldehyde (0.063 g, 0.91 mmol) and sodium triacetoxyhydroborate (0.192 g, 0.905 mmol) were combined in dichloromethane (1.0 mL) and acetic acid (1.0 mL) under nitrogen, stirred for 6 hours and partitioned in water/ethyl acetate. The organic layer was washed with 5% aqueous sodium bicarbonate, saturated aqueous sodium chloride, dried with anhydrous sodium sulfate, filtered, and concentrated to afford the title compound (0.116 g, 100%).

Example 2b

3-{2-[(cyclopropylmethyl)amino]-5-(methylsulfonyl)phenyl}-1-methyl-1,6-dihydro-7H-pyrrolo[2,3-c]pyridin-7-one Example 2a (0.035 g, 0.091 mmol) and 4M HCl in dioxane (5 mL, 20 mmol) were combined and heated at 70° C. for 24 hours, cooled and concentrated. Purification by reverse phase chromatography (C18, CH$_3$CN/water (0.1% TFA), 10-100%) afforded the title compound (0.024 g, 53%) as the TFA salt.

Example 2c 5-(cyclopropylmethyl)-11-methyl-8-(methylsulfonyl)-2,4,5,11-tetrahydro-1H-2,5,11-triazadibenzo[cd,h]azulen-1-one A 5 mL vial was charged with Example 2b (17 mg, 0.035 mmol), paraformaldehyde (5.3 mg, 0.18 mmol) and methanol (1 mL). To this suspension was added 4M HCl in dioxane (0.175 mL, 0.700 mmol). The vial was closed and stirred at 90° C. for 2 hours. The reaction mixture was cooled to ambient temperature and concentrated. The residue was purified by flash chromatography (silica gel, 2-8% methanol in dichloromethane) to afford the title compound (9.0 mg, 67%). $^1$H NMR (300 MHz, DMSO-$d_6$) δ 10.74 (d, J=4.7 Hz, 1H), 8.14 (d, J=2.2 Hz, 1H), 7.91 (s, 1H), 7.59 (dd, J=8.6, 2.2 Hz, 1H), 7.29 (d, J=8.6 Hz, 1H), 6.79 (d, J=5.4 Hz, 1H), 4.06-4.15 (m, 5H), 3.09-3.27 (m, 5H), 0.90-1.06 (m, 1H), 0.39-0.48 (m, 2H), 0.14-0.23 (m, 2H). MS (ESI+) m/z 384 (M+H)$^+$.

Example 3

5-(cyclopropylmethyl)-11-methyl-8-((methylsulfonyl)methyl)-2,4,5,11-tetrahydro-1H-2,5,11-triazadibenzo[cd,h]azulen-1-one

Example 3a 1-((methylsulfonyl)methyl)-4-nitrobenzene

To a solution of 4-nitrobenzyl bromide (10.0 g, 46.4 mmol) in dimethylformamide (25 mL) was added sodium methanesulfinate (7.10 g, 69.6 mmol). The reaction mixture was stirred at 65° C. for 1 hour. The reaction mixture was cooled to ambient temperature, diluted with water, stirred for 10 minutes and filtered to give the title compound (9.27 g, 93%).

Example 3b 4-((methylsulfonyl)methyl)aniline

Example 3a (8.2 g, 38 mmol) and tetrahydrofuran (200 mL) were added to wet 5% Pd/C (1.6 g, 0.376 mmol) in a pressure bottle. The reaction mixture was stirred at 50° C. for 2 hours under 30 psi of hydrogen. The reaction mixture was filtered through a nylon membrane, washed with a mixture of tetrahydrofuran and methanol, and concentrated to give the title compound (6.21 g, 88%).

Example 3C 2-iodo-4-((methylsulfonyl)methyl)aniline

To a solution of Example 3b (1.12 g, 6.03 mmol) in dimethylformamide (60.3 mL) was added N-iodosuccinimide (1.49 g, 6.63 mmol). The reaction mixture was stirred at ambient temperature for 90 minutes. The reaction mixture was quenched with 10% sodium thiosulfate and saturated aqueous sodium bicarbonate, and extracted with ethyl acetate three times. The combined organic layers were washed with saturated aqueous sodium chloride, dried with anhydrous magnesium sulfate, filtered, and concentrated. Water was added to the residue, and the mixture was stirred at ambient temperature for 10 minutes and filtered to give the title compound (1.55 g, 83%).

Example 3d

N-(cyclopropylmethyl)-2-iodo-4-((methylsulfonyl)methyl)aniline

Example 3c (311 mg, 1.00 mmol), cyclopropanecarbaldehyde (0.187 mL, 2.50 mmol) and acetic acid (0.572 mL, 10.0 mmol) were combined in a mixture of dichloromethane (5 mL) and methanol (5 mL). The reaction mixture was heated at 50° C. for 30 minutes, and then cooled to ambient temperature. MP-cyanoborohydride (1.27 g, 2.36 mmol/g, 3.00 mmol) was added and the reaction mixture was stirred at ambient temperature for 3 hours. The reaction mixture was filtered, washed with dichloromethane and concentrated. The residue was purified by flash chromatography (silica gel, 20-60% ethyl acetate in heptanes) to afford the title compound (296 mg, 81%).

Example 3e

N-(cyclopropylmethyl)-2-(7-methoxy-1-methyl-1H-pyrrolo[2,3-c]pyridin-3-yl)-4-((methylsulfonyl)methyl)aniline Example 3d (183 mg, 0.500 mmol), Example 1b (173 mg, 0.600 mmol), sodium carbonate (185 mg, 1.75 mmol), tris(dibenzylideneacetone)dipalladium (13.7 mg, 0.0150 mmol) and 1,3,5,7-tetramethyl-6-phenyl-2,4,8-trioxa-6-phosphaadamantane (13.1 mg, 0.0450 mmol) were combined in a microwave tube and purged with nitrogen for 15 minutes. A mixture of dioxane (2 mL) and water (0.5 mL) was purged with nitrogen for 15 minutes and transferred to the microwave tube. The reaction mixture was heated at 60° C. for 4 hours. The reaction mixture was partitioned in ethyl acetate and water. The organic layer was washed with saturated aqueous sodium chloride, dried with anhydrous sodium sulfate, treated with 3-mercaptopropyl functionalized silica gel, filtered, and concentrated. The residue was purified by flash chromatography (silica gel, 20-50% ethyl acetate in heptanes) to afford the title compound (140 mg, 70%).

Example 3f

3-{2-[(cyclopropylmethyl)amino]-5-[(methylsulfonyl)methyl]phenyl}-1-methyl-1,6-dihydro-7H-pyrrolo[2,3-c]pyridin-7-one Example 3e (136 mg, 0.340 mmol) in a solution of 4M HCl in dioxane (5 mL, 20.0 mmol) was heated at 70° C. for 2 hours. The reaction mixture was cooled and concentrated. The residue was purified by flash chromatography (silica gel, 2-6% methanol in dichloromethane) to afford the title compound (130 mg, 91%) as the HCl salt.

Example 3g 5-(cyclopropylmethyl)-11-methyl-8-((methylsulfonyl)methyl)-2,4,5,11-tetrahydro-1H-2,5,11-triazadibenzo[cd,h]azulen-1-one A 5 mL vial was charged with Example 3f (104 mg, 0.246 mmol), paraformaldehyde (37.0 mg, 1.23 mmol) and methanol (1 mL). To this suspension was added 4M HCl in dioxane (1.23 mL, 4.92 mmol). The vial was closed and stirred at 90° C. for 2 hours. The reaction mixture was cooled to ambient temperature and concentrated. The residue was purified by flash chromatography (silica gel, 2-8% methanol in dichloromethane) to give a solid. The solid was partitioned in saturated sodium bicarbonate and ethyl acetate. The organic layer was dried with anhydrous sodium sulfate, filtered, and concentrated to afford the title compound (41 mg, 42%). $^1$H NMR (300 MHz, DMSO-$d_6$) δ 10.68 (d, J=5.43 Hz, 1H) 7.68 (s, 1H) 7.63 (s, 1H) 7.09-7.17 (m, 2H) 6.72 (d, J=5.43 Hz, 1H) 4.39 (s, 2H) 4.11 (s, 3H) 4.03 (s, 2H) 2.96 (d, J=6.44 Hz, 2H) 2.91 (s, 3H) 0.82-0.99 (m, 1H) 0.35-0.46 (m, 2H) 0.05-0.12 (m, 2H). MS (ESI+) m/z 398 (M+H)$^+$.

Example 4

5-(4-fluorophenyl)-11-methyl-8-((methylsulfonyl)methyl)-2,4,5,11-tetrahydro-1H-2,5,11-triazadibenzo[cd,h]azulen-1-one Example 4a 2-(7-methoxy-1-methyl-1H-pyrrolo[2,3-c]pyridin-3-yl)-4-((methylsulfonyl)methyl)aniline Example 3c (1.25 g, 4.00 mmol), Example 1b (1.15 g, 4.00 mmol), potassium phosphate (2.97 g, 14.0 mmol), tris(dibenzylideneacetone)dipalladium (0.110 g, 0.120 mmol) and 1,3,5,7-tetramethyl-6-phenyl-2,4,8-trioxa-6-phosphaadamantane (0.105 g, 0.360 mmol) were combined in a microwave tube and purged with nitrogen for 15 minutes. A mixture of dioxane (12 mL) and water (3 mL) was purged with nitrogen for 15 minutes and transferred via cannula to the microwave tube. The reaction mixture was heated at 60° C. for 4 hours. The reaction mixture was partitioned in ethyl acetate and water. The organic layer was washed with saturated aqueous sodium chloride, dried with anhydrous sodium sulfate, treated with 3-mercaptopropyl functionalized silica gel, filtered, and concentrated. The residue was purified by flash chromatography (silica gel, 20-80% ethyl acetate in heptanes) to afford the title compound (0.985 g, 71%).

Example 4b

N-(4-fluorophenyl)-2-(7-methoxy-1-methyl-1H-pyrrolo[2,3-c]pyridin-3-yl)-4-((methylsulfonyl)methyl)aniline Example 4a (104 mg, 0.300 mmol), 1-bromo-4-fluorobenzene (105 mg, 0.600 mmol), diacetoxypalladium (2.7 mg, 0.012 mmol), dicyclohexyl(2',4',6'-triisopropyl-[1,1'-biphenyl]-2-yl)phosphine (11.4 mg, 0.0239 mmol) and cesium carbonate (195 mg, 0.600 mmol) were combined in a mixture of toluene (2.4 mL) and tert-butanol (0.6 mL). The reaction mixture was heated in a microwave reactor at 150° C. for 30 minutes. The reaction mixture was partitioned in ethyl acetate and water. The organic layer was washed with saturated aqueous sodium chloride, dried with anhydrous sodium sulfate, treated with 3-mercaptopropyl functionalized silica gel, filtered, and concentrated. The residue was purified by flash chromatography (silica gel, 2-4% methanol in dichloromethane) to afford the title compound (112 mg, 85%).

Example 4c

3-{2-[4-fluorophenyl)amino]-5-[(methylsulfonyl)methyl]phenyl}-1-methyl-1,6-dihydro-7H-pyrrolo[2,3-c]pyridin-7-one Example 4b (110 mg, 0.250 mmol) in a solution of 4M HCl in dioxane (5.0 mL, 20 mmol) was heated at 70° C. for 2 hours. The reaction mixture was cooled to ambient temperature and concentrated. The residue was partitioned in ethyl acetate and saturated aqueous sodium bicarbonate. The organic layer was washed with saturated aqueous sodium chloride, dried with anhydrous sodium sulfate, filtered, and concentrated. The residue was purified by flash chromatography (silica gel, 2-4% methanol in dichloromethane) to afford the title compound (86 mg, 81%).

Example 4d 5-(4-fluorophenyl)-11-methyl-8-((methylsulfonyl)methyl)-2,4,5,11-tetrahydro-1H-2,5,11-triazadibenzo[cd,h]azulen-1-one A 5 mL vial was charged with Example 4c (73 mg, 0.17 mmol), paraformaldehyde (52 mg, 1.7 mmol) and methanol (1 mL). To this suspension was added 4M HCl in dioxane (0.858 mL, 3.43 mmol). The vial was closed and stirred at 90° C. for 4 hours. The reaction mixture was cooled to ambient temperature and concentrated. To the residue was added water, and the pH was adjusted to about 7 by the addition of saturated aqueous sodium bicarbonate. The mixture was sonicated for 5 minutes and filtered to give a solid. The solid was purified by flash chromatography (silica gel, 2-4% methanol in dichloromethane) to afford the title compound (44 mg, 59%). $^1$H NMR (300 MHz, DMSO-$d_6$) δ 10.84 (d, J=5.43 Hz, 1H) 7.88 (s, 1H) 7.73 (s, 1H) 7.25-7.33 (m, 2H) 7.05 (d, J=5.76 Hz, 1H) 6.77-6.90 (m, 2H) 6.40-6.59 (m, 2H) 5.04 (s, 1H) 4.54 (s, 2H) 4.18 (s, 1H) 4.05 (s, 3H) 2.99 (s, 3H). MS (ESI+) m/z 438 (M+H)$^+$.

Example 5

5-(2,4-difluorophenyl)-11-methyl-8-((methylsulfonyl)methyl)-2,4,5,11-tetrahydro-1H-2,5,11-triazadibenzo[cd,h]azulen-1-one

Example 5a

N-(2,4-difluorophenyl)-2-(7-methoxy-1-methyl-1H-pyrrolo[2,3-c]pyridin-3-yl)-4-((methylsulfonyl)methyl)aniline Example 4a (104 mg, 0.300 mmol), 1-bromo-2,4-difluorobenzene (116 mg, 0.600 mmol), diacetoxypalladium (2.7 mg, 0.012 mmol), dicyclohexyl(2',4',6'-triisopropyl-[1,1'-biphenyl]-2-yl)phosphine (11.4 mg, 0.0239 mmol) and cesium carbonate (195 mg, 0.600 mmol) were combined in a mixture of toluene (2.4 mL) and tert-butanol (0.6 mL). The reaction mixture was heated in a microwave reactor at 150° C. for 1 hour. The reaction mixture was partitioned in ethyl acetate and water. The organic layer was washed with saturated aqueous sodium chloride, dried with anhydrous sodium sulfate, treated with 3-mercaptopropyl functionalized silica gel, filtered, and concentrated. The residue was purified by flash chromatography (silica gel, 1-2% methanol in dichloromethane) to afford the title compound (62 mg, 45%).

Example 5b

3-{2-[(2,4-difluorophenyl)amino]-5-[(methylsulfonyl)methyl]phenyl}-1-methyl-1,6-dihydro-7H-pyrrolo[2,3-c]pyridin-7-one Example 5a (60.0 mg, 0.131 mmol) in a solution of 4M HCl in dioxane (5.0 mL, 20 mmol) was heated at 70° C. for 2 hours. The reaction mixture was cooled to ambient temperature and concentrated. The residue was partitioned in ethyl acetate and saturated aqueous sodium bicarbonate. The organic layer was washed with saturated aqueous sodium chloride, dried with anhydrous sodium sulfate, filtered, and concentrated. The residue was purified by flash chromatography (silica gel, 2-4% methanol in dichloromethane) to afford the title compound (46 mg, 79%).

Example 5c 5-(2,4-difluorophenyl)-11-methyl-8-((methylsulfonyl)methyl)-2,4,5,11-tetrahydro-1H-2,5,11-triazadibenzo[cd,h]azulen-1-one A 5 mL vial was charged with Example 5b (37 mg, 0.083 mmol), paraformaldehyde (25 mg, 0.83 mmol) and methanol (1 mL). To this suspension was added 4M HCl in dioxane (0.417 mL, 1.67 mmol). The vial was closed and stirred at 90° C. for 4 hours. The reaction mixture was cooled to ambient temperature and concentrated. To the residue was added water, and the pH was adjusted to about 7 by the addition of saturated aqueous sodium bicarbonate. The mixture was sonicated for 5 minutes and filtered to give a solid. The solid was purified by flash chromatography (silica gel, 2-4% methanol in dichloromethane) to afford the title compound (16 mg, 42%). $^1$H NMR (300 MHz, DMSO-$d_6$) δ 10.75 (d, J=5.43 Hz, 1H) 7.69-7.93 (m, 2H) 7.05-7.22 (m, 2H) 6.80-6.98 (m, 2H) 6.66-6.76 (m, 2H) 4.57 (s, 2H) 4.46 (s, 2H) 4.11 (s, 3H) 2.95 (s, 3H). MS (ESI+) m/z 456 (M+H)$^+$.

Example 6

5-(cyclopropanecarbonyl)-11-methyl-8-((methylsulfonyl)methyl)-2,4,5,11-tetrahydro-1H-2,5,11-triazadibenzo[cd,h]azulen-1-one

Example 6a 11-methyl-8-((methylsulfonyl)methyl)-2,4,5,11-tetrahydro-1H-2,5,11-triazadibenzo[cd,h]azulen-1-one A 20 mL vial was charged with Example 4a (380 mg, 1.10 mmol), paraformaldehyde (330 mg, 11.0 mmol) and methanol (5 mL). To this suspension was added 4M HCl in dioxane (5.5 mL, 22 mmol). The vial was closed and stirred at 90° C. for 6 hours. The reaction mixture was cooled to ambient temperature and concentrated. Water was added to the residue, and the pH was adjusted to about 7 by the addition of saturated aqueous sodium bicarbonate. The mixture was sonicated for 5 minutes and filtered to give a solid. The solid was triturated with methanol/dichloromethane (1%) to afford the title compound (295 mg, 78%).

Example 6b 5-(cyclopropanecarbonyl)-11-methyl-8-((methylsulfonyl)methyl)-2,4,5,11-tetrahydro-1H-2,5,11-triazadibenzo[cd,h]azulen-1-one Example 6a (24 mg, 0.070 mmol), cyclopropanecarbonyl chloride (7.0 µL, 0.077 mmol) and triethylamine (0.029 mL, 0.210 mmol) were combined in dimethylformamide (2 mL). The reaction mixture was stirred at ambient temperature for 3 hours. Then another batch of cyclopropanecarbonyl chloride (3.2 µL, 0.035 mmol) was added. The reaction mixture was stirred at ambient temperature for another 3 hours. The reaction mixture was partitioned in ethyl acetate and 1M HCl. The organic layer was washed twice with saturated aqueous sodium chloride, dried with anhydrous sodium sulfate, filtered, and concentrated. The residue was purified by reverse phase HPLC(C8, $CH_3CN$/water (0.1% TFA), 20-55%) to afford the title compound (12 mg, 42%). $^1$H NMR (300 MHz, DMSO-$d_6$) δ 10.83 (d, J=5.76 Hz, 1H) 7.86 (d, J=2.03 Hz, 1H) 7.83 (s, 1H) 7.44 (d, J=8.16, 1 H) 7.31 (dd, J=8.14, 1.70 Hz, 1H) 6.82 (d, J=5.09 Hz, 1H) 5.34 (d, J=14.92 Hz, 1H) 4.42-4.63 (m, 2H) 4.13 (s, 3H) 3.81 (dd, J=14.92, 1.36 Hz, 1H) 2.98 (s, 3H) 1.13-1.34 (m, 1H) 0.55-0.85 (m, 3H) 0.37-0.49 (m, 1H). MS (ESI+) m/z 412 (M+H)$^+$.

Example 7

5-benzoyl-11-methyl-8-((methylsulfonyl)methyl)-2,4,5,11-tetrahydro-1H-2,5,11-triazadibenzo[cd,h]azulen-1-one Example 7 was prepared according to the procedure used for the preparation of Example 6b, substituting benzoyl chloride for cyclopropanecarbonyl chloride, to provide the title compound (10 mg, 32%). $^1$H NMR (400 MHz, DMSO-$d_6$) δ 10.91 (d, J=5.49 Hz, 1H) 7.94 (s, 1H) 7.83 (d, J=1.83 Hz, 1H) 7.18-7.26 (m, 1H) 7.08-7.15 (m, 2H) 6.79-7.00 (m, 5H) 5.65 (d, J=14.65 Hz, 1H) 4.30-4.53 (m, 2H) 4.18 (s, 3H) 3.96 (d, J=14.65 Hz, 1H) 2.82 (s, 3H). MS (ESI+) m/z 448 (M+H)$^+$.

Example 8

5-(4-fluorophenyl)-4-(2-methoxyethyl)-11-methyl-8-((methylsulfonyl)methyl)-2,4,5,11-tetrahydro-1H-2,5,11-triazadibenzo[cd,h]azulen-1-one A 5 mL vial was charged with Example 4b (22 mg, 0.050 mmol), 3-methoxypropanal (44 mg, 0.50 mmol) and methanol (1 mL). To this suspension was added 4M HCl in dioxane (0.25 mL, 1.0 mmol). The vial was closed and stirred at 90° C. for 2 hours. The reaction mixture was cooled to ambient temperature and concentrated. The residue was partitioned in ethyl acetate and saturated aqueous sodium bicarbonate. The organic layer was washed with saturated aqueous sodium chloride, dried with anhydrous sodium sulfate, filtered, and concentrated. The residue was purified by flash chromatography (silica gel, 2-4% methanol in dichloromethane) to afford the title compound (3 mg, 12%). $^1$H NMR (400 MHz, DMSO-$d_6$) δ 10.84 (d, J=5.49 Hz, 1H) 7.88 (d, J=1.83 Hz, 1H) 7.76 (s, 1H) 7.23-7.38 (m, 2H) 6.97 (d, J=5.80 Hz, 1H) 6.79-6.88 (m, 2H) 6.40-6.56 (m, 2H) 5.18 (t, J=7.48 Hz, 1H) 4.46-4.61 (m, 2H) 4.06 (s, 3H) 3.20-3.30 (m, 2H) 3.18 (s, 3H) 2.98 (s, 3H) 1.57-1.74 (m, 1H) 1.31-1.45 (m, 1H). MS (ESI+) m/z 496 (M+H)$^+$.

Example 9 methyl 3-(5-(4-fluorophenyl)-11-methyl-8-((methylsulfonyl)methyl)-1-oxo-2,4,5,11-tetrahydro-1H-2,5,11-triazadibenzo[cd,h]azulen-4-yl)propanoate A 5 mL vial was charged with Example 4b (22 mg, 0.050 mmol), methyl 4-oxobutanoate (58 mg, 0.50 mmol) and methanol (1 mL). To this suspension was added 4M HCl in dioxane (0.25 mL, 1.0 mmol). The vial was closed and stirred at 90° C. for 2 hours. The reaction mixture was cooled to ambient temperature and concentrated. The residue was partitioned in ethyl acetate and saturated aqueous sodium bicarbonate. The organic layer was washed with saturated aqueous sodium chloride, dried with anhydrous sodium sulfate, filtered, and concentrated. The residue was purified by flash chromatography (silica gel, 2-4% methanol in dichloromethane) to afford the title compound (7 mg, 27%). $^1$H NMR (400 MHz, DMSO-$d_6$) δ 10.86 (d, J=5.49 Hz, 1H) 7.89 (d, J=1.83 Hz, 1H) 7.76 (s, 1H) 7.26-7.36 (m, 2H) 7.00 (d, J=5.80 Hz, 1H) 6.79-6.91 (m, 2H) 6.43-6.54 (m, 2H) 5.09 (t, J=7.48 Hz, 1H) 4.46-4.61 (m, 2H) 4.06 (s, 3H) 3.49 (s, 3H) 2.97 (s, 3H) 2.24-2.45 (m, 2H) 1.61-1.74 (m, 1H) 1.36-1.54 (m, 1H). MS (ESI+) m/z 524 (M+H)$^+$.

Example 10

5-(4-fluorophenyl)-11-methyl-8-((methylsulfonyl)methyl)-4-((tetrahydro-2H-pyran-4-yl)methyl)-2,4,5,11-tetrahydro-1H-2,5,11-triazadibenzo[cd,h]azulen-1-one A 5 mL vial was charged with Example 4b (22 mg, 0.050 mmol), 2-(tetrahydro-2H-pyran-4-yl)acetaldehyde (64 mg, 0.50 mmol) and methanol (1 mL). To this suspension was added 4M HCl in dioxane (0.25 mL, 1.0 mmol). The vial was closed and was heated in a microwave reactor at 120° C. for 4 hours. The reaction mixture was cooled to ambient temperature and concentrated. The residue was partitioned in ethyl acetate and saturated aqueous sodium bicarbonate. The organic layer was washed with saturated aqueous sodium chloride, dried with anhydrous sodium sulfate, filtered, and concentrated. The residue was purified by flash chromatography (silica gel, 2-4% methanol in dichloromethane) to afford the title compound (9 mg, 34%). $^1$H NMR (300 MHz, DMSO-d$_6$) δ 10.84 (d, J=5.43 Hz, 1H) 7.87 (d, J=1.70 Hz, 1H) 7.74 (s, 1H) 7.25-7.37 (m, 2H) 7.08 (d, J=5.76 Hz, 1H) 6.74-6.89 (m, 2H) 6.47-6.59 (m, 2H) 5.18 (t, J=7.46 Hz, 1H) 4.45-4.65 (m, 2H) 4.06 (s, 3H) 3.69-3.81 (m, 2H) 3.14-3.27 (m, 2H) 2.96 (s, 3H) 0.95-1.61 (m, 7H). MS (ESI+) m/z 536 (M+H)$^+$.

Example 11

5-(cyclopropylmethyl)-11-methyl-2,4,5,11-tetrahydro-1H-2,5,11-triazadibenzo[cd,h]azulen-1-one Example 11a 2-bromo-N-(cyclopropylmethyl)aniline A 100 mL flask was charged with 2-bromoaniline (1.720 g, 10.00 mmol), cyclopropanecarbaldehyde (0.374 mL, 5.00 mmol), acetic acid (2.86 mL, 50.0 mmol) and dichloromethane (50 mL). The mixture was heated at 50° C. for 1 hour. The mixture was then cooled in an ice bath and the sodium triacetoxyborohydride (2.119 g, 10.00 mmol) was added in portionwise over a few minutes. After 15 minutes, the ice bath was removed and the mixture was stirred for 2 hours at ambient temperature. The reaction mixture was quenched with 2.5 M sodium hydroxide (16 mL) and then partitioned between saturated sodium bicarbonate solution (100 mL) and ethyl acetate (100 mL). The layers were separated and the organic layer was dried over anhydrous sodium sulfate, filtered, and concentrated.

The residue was purified by flash chromatography (silica gel, 0-10% ethyl acetate in heptanes) to provide the title compound (1.05 g, 93%).

Example 11b

N-(cyclopropylmethyl)-2-(7-methoxy-1-methyl-1H-pyrrolo[2,3-c]pyridin-3-yl)aniline A 25 mL vial was charged with Example 1b (160 mg, 0.556 mmol), Example 11a (128.8 mg, 0.570 mmol), tris(dibenzylideneacetone)dipalladium (0) (15.27 mg, 0.017 mmol), (1S,3R,5R,7S)-1,3,5,7-tetramethyl-8-phenyl-2,4,6-trioxa-8-phosphaadamantane (17.87 mg, 0.061 mmol) and potassium phosphate (354 mg, 1.667 mmol). This mixture was stirred under a stream of argon for 30 minutes. To this mixture was added a mixture of dioxane (4 mL) and water (1 mL) which had been degassed with argon for 30 minutes. The mixture was heated at 75° C. for 18 hours. Upon cooling to ambient temperature, the reaction mixture was partitioned between ethyl acetate (75 mL) and 50% saturated aqueous sodium chloride (100 mL). The organic layer was treated with 3-mercaptopropyl functionalized silica gel, dried over anhydrous sodium sulfate, filtered, and concentrated. This residue was purified by flash chromatography (silica gel, 0-5% methanol in dichloromethane) to provide the title compound (154 mg, 90%).

Example 11c 3-(2-((cyclopropylmethyl)amino)phenyl)-1-methyl-1H-pyrrolo[2,3-c]pyridin-7(6H)-one A 25 mL flask was charged with Example 11b (150 mg, 0.488 mmol), dioxane (4 mL) and hydrogen chloride (4M in dioxane, 4.88 mL, 19.52 mmol). The reaction mixture was heated at 70° C. overnight. Upon cooling, the reaction mixture was concentrated. The residue was purified by flash chromatography (silica gel, 0-7.5% methanol in dichloromethane) to provide the title compound (141 mg, 98%).

Example 11d 5-(cyclopropylmethyl)-11-methyl-2,4,5,11-tetrahydro-1H-2,5,11-triazadibenzo[cd,h]azulen-1-one A 5 mL vial was charged Example 11c (60 mg, 0.205 mmol), paraformaldehyde (92 mg, 1.023 mmol), methanol (2 mL) and hydrogen chloride, 4M in dioxane (1.023 mL, 4.09 mmol). The reaction mixture was heated at 90° C. for 2 hours. Upon cooling, the reaction mixture was partitioned between 50% saturated sodium bicarbonate solution (100 mL) and ethyl acetate (75 mL). The layers were separated and the aqueous layer was extracted with ethyl acetate (2×50 mL). The combined organic layers were dried over anhydrous sodium sulfate, filtered, and concentrated. The residue was purified by flash chromatography (silica gel, Gold Rf cartridge (12 g) eluting with a 0-5% methanol in dichloromethane) to provide the title compound (20.3 mg, 32%). $^1$H NMR (400 MHz, DMSO-d$_6$) δ 10.67 (d, J=4.88 Hz, 1H) 7.71 (s, 1H) 7.64 (dd, J=7.78, 1.37 Hz, 1H) 7.06-7.15 (m, 2H) 7.00-7.06 (m, 1H) 6.70 (d, J=5.19 Hz, 1H) 4.10 (s, 3H) 4.02 (s, 2H) 2.88 (d, J=6.41 Hz, 2H) 0.84-0.97 (m, 1H) 0.35-0.42 (m, 2H) 0.02-0.08 (m, 2H). MS (ESI+) m/z 306.1 (M+H)$^+$.

Example 12

N-(5-(4-fluorophenyl)-11-methyl-1-oxo-2,4,5,11-tetrahydro-1H-2,5,11-triazadibenzo[cd,h]azulen-8-yl)ethanesulfonamide Example 23e (0.0395 g, 0.11 mmol) in 1,2-dichloroethane (3 mL) was treated with ethanesulfonyl chloride (0.03 mL, 0.33 mmol) and triethylamine (0.06 mL, 0.44 mmol) and stirred at ambient temperature for 1 hour. Additional ethanesulfonyl chloride (0.03 mL, 0.33 mmol) and triethylamine (0.06 mL, 0.44 mmol) were added and stirring was continued overnight. The reaction mixture was concentrated. The residue was then treated with ethanesulfonyl chloride (0.3 mL, 3.3 mmol) and triethylamine (0.6 mL, 4.4 mmol), stirred for 7 hours and concentrated to dryness. The residue was taken up in tetrahydrofuran (3 mL), treated with sodium hydroxide (4 M aqueous solution, 0.14 mL, 0.55 mmol) and heated at 50° C. for 1.5 hours. The reaction mixture was then cooled to ambient temperature and neutralized with 2 N hydrochloric acid (aqueous). The reaction mixture was partitioned between ethyl acetate and water, washed with saturated aqueous sodium chloride, dried over anhydrous magnesium sulfate, filtered, and concentrated. The residue was purified by flash chromatography (silica gel, 0-17% methanol in dichloromethane) to provide 0.0069 g (14%) of the title compound. $^1$H NMR (400 MHz, DMSO-d$_6$) δ 10.80 (d, J=5.49 Hz, 1H), 9.87 (m, 1H), 7.63 (s, 1H), 7.60 (d, J=2.44 Hz, 1H), 7.21 (d, J=8.24 Hz, 1H), 7.09 (dd, J=8.54, 2.44 Hz, 1H), 7.03 (d, J=5.80 Hz, 1H), 6.82 (m, 2H), 6.49 (m, 2H), 5.01 (d, J=15.56 Hz, 1H), 4.16 (d, J=13.12 Hz, 1H), 4.05 (s, 3H), 3.18 (q, J=7.32 Hz, 2H), 1.27 (t, J=7.32 Hz, 3H). MS (ESI+) m/z 453.1 (M+H)$^+$.

Example 13

8-chloro-5-(4-fluorophenyl)-11-methyl-2,4,5,11-tetrahydro-1H-2,5,11-triazadibenzo[cd,h]azulen-1-one

Example 13a 4-chloro-2-(7-methoxy-1-methyl-1H-pyrrolo[2,3-c]pyridin-3-yl)aniline 2-Amino-5-chlorophenylboronic acid, pinacol ester (1.0 g, 3.94 mmol), Example 1a (1.136 g, 3.94 mmol), tris(dibenzylideneacetone)dipalladium (0) (0.108 g, 0.118 mmol), 1,3,5,7-tetramethyl-6-phenyl-2,4,8-trioxa-6-phosphaadamantane (0.115 g, 0.394 mmol) and sodium carbonate (1.463 g, 13.80 mmol) were combined and sparged with argon for 15 minutes. Meanwhile a solution of 4:1 dioxane/water (12 mL) was sparged with nitrogen for 15 minutes and transferred by syringe into the reaction vessel under argon. The mixture was stirred for 18 hours at 25° C., cooled to ambient temperature, and partitioned in 100 mL of water and 120 mL of ethyl acetate. The organic layer was washed with water, saturated aqueous sodium chloride, dried ($Na_2SO_4$), treated with 3-mercaptopropyl functionalized silica, filtered, and concentrated. Purification by chromatography (silica gel, 0-50% ethyl acetate in heptanes) afforded the title compound (0.8 g, 70%).

Example 13b 4-chloro-N-(4-fluorophenyl)-2-(7-methoxy-1-methyl-1H-pyrrolo[2,3-c]pyridin-3-yl)aniline Example 13b was prepared according to the procedure used for the preparation of Example 4b, substituting Example 13a for Example 4a. Purification by chromatography (silica gel, 0-40% ethyl acetate in heptanes) afforded the title compound (0.153 g, 77%).

Example 13c 8-chloro-5-(4-fluorophenyl)-11-methyl-2,4,5,11-tetrahydro-1H-2,5,11-triazadibenzo[cd,h]azulen-1-one A mixture of Example 13b (0.075 g, 0.196 mmol) and paraformaldehyde (0.059 g, 1.964 mmol) in methanol (1.964 mL) was treated with 4M hydrogen chloride in dioxane (1.47 mL, 5.89 mmol), heated to 95° C. for 3 hours in a sealed tube, cooled and concentrated. The residue was diluted with methanol (2 mL) and 5% aqueous sodium bicarbonate (10 mL), sonicated and the solid was collected by filtration to afford the title compound (0.072 g, 97%). $^1$H NMR (300 MHz, DMSO-$d_6$) δ 10.82 (d, J=5.43 Hz, 1H), 7.75-8.06 (m, 2H), 7.19-7.37 (m, 2H), 7.04 (d, J=5.76 Hz, 1H), 6.77-6.94 (m, 2H), 6.36-6.58 (m, 2H), 5.02 (s, 1H), 4.19-4.32 (m, 1H), 4.03 (s, 3H). MS (ESI+) m/z 379 (M+H)$^+$.

Example 14

8-amino-5-(4-fluorophenyl)-11-methyl-2,4,5,11-tetrahydro-1H-2,5,6,11-tetraazadibenzo[cd,h]azulen-1-one

Example 14a 3-bromo-N-(4-fluorophenyl)-5-nitropyridin-2-amine

3-Bromo-2-chloro-5-nitropyridine (3.936 g, 16.58 mmol), 4-fluoroaniline (5.53 g, 49.7 mmol) and dimethylsulfoxide (33.2 mL) were combined and stirred at 120° C. for 1 hour. The reaction mixture was cooled to ambient temperature producing a solid. Precipitation was induced further by the addition of 150 mL of water. The solid was collected by filtration and rinsed with 600 mL of water. The solid was purified by flash chromatography (silica gel, 0 to 20% ethyl acetate in heptanes) and then triturated in 15% ethyl acetate in heptanes to give 4.2 g (81%) of the title compound.

Example 14b

N-(4-fluorophenyl)-3-(7-methoxy-1-methyl-1H-pyrrolo[2,3-c]pyridin-3-yl)-5-nitropyridin-2-amine Example 14b was prepared according to the procedure used for the preparation of Example 23a, substituting Example 1b for Example 1a and Example 14a for (2-fluoro-5-nitrophenyl)boronic acid. Purification by flash chromatography (silica gel, 0 to 15% ethyl acetate in dichloromethane) gave 0.5 g (38%) of the title compound.

Example 14c 3-(2-((4-fluorophenyl)amino)-5-nitropyridin-3-yl)-1-methyl-1H-pyrrolo[2,3-c]pyridin-7(6H)-one A solution of Example 14b (0.5 g, 1.27 mmol) in 1,4-dioxane (7 mL) was treated with hydrogen chloride solution (4 M in 1,4-dioxane, 3.2 mL, 12.7 mmol) and stirred at 90° C. for 2 hours. The reaction mixture was concentrated and then treated again with hydrogen chloride solution (4 M in 1,4-dioxane, 3.2 mL, 12.7 mmol). The mixture was heated for 2 hours at 90° C. and then concentrated to dryness to give 0.482 g (100%) of the title compound.

Example 14d 5-(4-fluorophenyl)-11-methyl-8-nitro-2,4,5,11-tetrahydro-1H-2,5,6,11-tetraazadibenzo[cd,h]azulen-1-one To Example 14c (0.48 g, 1.27 mmol) in acetic acid (12.7 mL) was added paraformaldehyde (0.191 g, 6.36 mmol). The reaction mixture was heated at 90° C. for 15 minutes, partially concentrated and then slowly neutralized with saturated sodium carbonate solution. The resulting mixture was partitioned between ethyl acetate and water and washed with saturated aqueous sodium chloride. The combined aqueous layers were exhaustively extracted with ethyl acetate. The combined organic layers were dried over anhydrous magnesium sulfate, filtered, and concentrated. The residue was purified by flash chromatography (silica gel, 0 to 60% ethyl acetate in dichloromethane, then 10% ethyl acetate in dichloromethane with 3-15% methanol) to give the title compound as an impure mixture. The impure mixture was slurried in methanol (5 mL), treated with excess sodium hydroxide solution (4 M, aqueous) and heated at 70° C. for 1 hour. The reaction mixture was then cooled to ambient temperature, neutralized with hydrochloric acid solution (2 M, aqueous), and concentrated. The resulting solid was slurried in water, collected by filtration and dried under vacuum to give 0.187 g (38%) of the title compound.

Example 14e 8-amino-5-(4-fluorophenyl)-11-methyl-2,4,5,11-tetrahydro-1H-2,5,6,11-tetraazadibenzo[cd,h]azulen-1-one Example 14d (0.17 g, 0.43 mmol) in a mixture of ethanol (4 mL), tetrahydrofuran (4 mL) and water (1 mL) was treated with ammonium chloride (0.23 g, 4.3 mmol) and zinc dust (0.43 g, 6.5 mmol) and stirred at ambient temperature for 23 minutes and then filtered. The filtrate was evaporated and then slurried in ethyl acetate and water. The solid was collected by filtration. The filtrate was poured into a separatory funnel and the layers were separated. The organic layer was washed with saturated aqueous sodium chloride, dried over anhydrous magnesium sulfate, filtered, and concentrated. The two solids were combined and dried under vacuum to give 0.126 g (80%) of the title compound. $^1$H NMR (300 MHz, DMSO-$d_6$) δ 10.78 (d, J=5.43 Hz, 1H), 7.73 (d, J=2.71 Hz, 1H), 7.65 (s, 1H), 7.32 (d, J=3.05 Hz, 1H), 7.03 (d, J=5.76 Hz, 1H), 6.80 (m, 2H), 6.45 (m, 2H), 5.36 (s, 2H), 4.91 (m, 1H), 4.28 (m, 1H), 4.04 (s, 3H). MS (ESI+) m/z 362.2 (M+H)$^+$.

Example 15 ethyl 5-(4-fluorophenyl)-11-methyl-8-((methylsulfonyl)methyl)-1-oxo-2,4,5,11-tetrahydro-1H-2,5,11-triazadibenzo[cd,h]azulene-4-carboxylate A 5 mL vial was charged with Example 4c (85 mg, 0.20 mmol), 50% ethyl 2-oxoacetate in toluene (0.396 mL, 2.00 mmol) and ethanol (2 mL). To this suspension was added 4M HCl in dioxane (1.0 mL, 4.0 mmol). The vial was closed and stirred at 90° C. for 4 hours. The reaction mixture was cooled to ambient temperature and concentrated. The residue was partitioned in ethyl acetate and saturated aqueous sodium bicarbonate. The organic layer was washed with saturated aqueous sodium chloride, dried with anhydrous sodium sulfate, filtered, and concentrated. The residue was purified by flash chromatography (silica gel, 2-4% methanol in dichloromethane) to afford the title compound (21 mg, 21%). $^1$H NMR (300 MHz, DMSO-$d_6$) δ 10.90 (d, J=5.76 Hz, 1H) 7.79 (d, J=2.03 Hz, 1H) 7.71 (s, 1H) 7.16-7.30 (m, 2H) 7.10 (d, J=5.76 Hz, 1H) 6.85-6.96 (m, 2H) 6.59-6.68 (m, 2H) 6.18 (s, 1H) 4.39-4.58 (m, 2H) 4.07 (s, 3H) 3.72-3.90 (m, 2H) 2.91 (s, 3H) 0.86 (t, J=7.12 Hz, 3H). MS (ESI+) m/z 510 (M+H)$^+$.

Example 16

8-fluoro-5-(4-fluorophenyl)-11-methyl-2,4,5,11-tetrahydro-1H-2,5,6,11-tetraazadibenzo[cd,h]azulen-1-one

Example 16a 5-fluoro-3-(7-methoxy-1-methyl-1H-pyrrolo[2,3-c]pyridin-3-yl)pyridin-2-amine 3-Bromo-5-fluoropyridin-2-amine (0.25 g, 1.309 mmol), Example 1b (0.377 g, 1.309 mmol), tris(dibenzylideneacetone)dipalladium(0) (0.036 g, 0.039 mmol), 1,3,5,7-tetramethyl-6-phenyl-2,4,8-trioxa-6-phosphaadamantane (0.038 g, 0.131 mmol) and sodium carbonate (0.486 g, 4.58 mmol) were combined and sparged with argon for 15 minutes. Meanwhile a solution of 4:1 dioxane/water (9 mL) was sparged with nitrogen for 15 minutes and transferred by syringe into the reaction vessel under argon. The mixture was stirred for 4 hours at 60° C., cooled to ambient temperature, and partitioned in water and ethyl acetate. The organic layer was washed with water, saturated aqueous sodium chloride, dried (anhydrous Na$_2$SO$_4$), treated with 3-mercaptopropyl functionalized silica gel, filtered, and concentrated. Purification by chromatography (silica gel, 0-3% methanol in dichloromethane) afforded the title compound (0.23 g, 64%).

Example 16b 5-fluoro-N-(4-fluorophenyl)-3-(7-methoxy-1-methyl-1H-pyrrolo[2,3-c]pyridin-3-yl)pyridin-2-amine 1-Bromo-4-fluorobenzene (0.129 g, 0.735 mmol), Example 16a (0.1 g, 0.367 mmol), diacetoxypalladium (3.30 mg, 0.015 mmol), dicyclohexyl(2',4',6'-triisopropyl-[1,1'-biphenyl]-2-yl)phosphine (0.014 g, 0.029 mmol) and cesium carbonate (0.239 g, 0.735 mmol) were combined in t-butanol (0.360 mL)/toluene (1.80 mL) and heated by microwave at 150° C. for 40 minutes. The reaction mixture was cooled to ambient temperature and partitioned between ethyl acetate and water. The organic layer was washed with saturated aqueous sodium chloride, dried (anhydrous Na$_2$SO$_4$), treated with 3-mercaptopropyl functionalized silica gel, filtered, and concentrated. Purification by chromatography (silica gel, 0-40% ethyl acetate in heptanes) afforded the title compound (0.097 g, 72%).

Example 16c 3-(5-fluoro-2-((4-fluorophenyl)amino)pyridin-3-yl)-1-methyl-1H-pyrrolo[2,3-c]pyridin-7(6)-H-one Example 16b (0.097 g, 0.265 mmol) and 4M hydrogen chloride in dioxane (5 mL, 20.00 mmol) were heated at 90° C. for 4 hours, cooled and concentrated. Purification by trituration in diethyl ether afforded the title compound (0.11 g, 100%).

Example 16d 8-fluoro-5-(4-fluorophenyl)-11-methyl-2,4,5,11-tetrahydro-1H-2,5,6,11-tetraazadibenzo[cd,h]azulen-1-one Example 16c (0.04 g, 0.114 mmol), paraformaldehyde (0.068 g, 2.271 mmol) and 4M hydrogen chloride in dioxane (1.135 mL, 4.54 mmol) were heated in a sealed tube by microwave at 125° C. for 3 hours, cooled and concentrated. Purification by reverse phase HPLC(C18, CH$_3$CN/water (0.1% TFA), 0-100% gradient) afforded the title compound as a TFA salt (0.01 g, 18%). $^1$H NMR (400 MHz, DMSO-$d_6$) δ 10.54 (s, 1H), 8.21 (d, J=3.05 Hz, 1H), 8.10 (dd, J=9.61, 2.90 Hz, 1H), 7.87 (s, 1H), 6.99 (d, J=2.44 Hz, 1H), 6.81-6.87 (m, 2H), 6.62-6.67 (m, 2H), 4.60 (s, 2H), 4.07 (s, 3H). MS (ESI+) m/z 365 (M+H)$^+$.

Example 17

2-(2-chloro-5-fluorophenyl)-N-(5-(4-fluorophenyl)-11-methyl-1-oxo-2,4,5,11-tetrahydro-1H-2,5,6,11-tetraazadibenzo[cd,h]azulen-8-yl)acetamide A stock solution of Example 14e and N,N-diisopropylethylamine (0.11 M and 0.33 M in N,N-dimethylacetamide, respectively, 350 µL, 0.038 mmol Example 14e and 0.11 mmol N,N-diisopropylethylamine), 2-(3H-[1,2,3]triazolo[4,5-b]pyridin-3-yl)-1,1,3,3-tetramethylisouronium hexafluorophosphate(V) (0.13 M in N,N-dimethylacetamide, 350 µL, 0.046 mmol), and 2-(2-chloro-5-fluorophenyl)acetic acid (0.40 M in N,N-dimethylacetamide, 113 µL, 0.050 mmol) were aspirated from their respective source vials, mixed through a perfluoroalkoxy mixing tube (0.2 mm inner diameter), and loaded into an injection loop. The reaction segment was injected into the flow reactor (Hastelloy coil, 0.75 mm inner diameter, 1.8 mL internal volume) set at 100° C., and passed through the reactor at 180 μL per minute (10 minute residence time). Upon exiting the reactor, the reaction mixture was loaded directly into an injection loop and purified by reverse phase HPLC(C8, acetonitrile/water (0.1% ammonium acetate), 5-100%) to give 0.0062 g (30%) of the title compound. $^1$H NMR (400 MHz, DMSO-d$_6$/D$_2$O) δ 8.54 (d, J=2.75 Hz, 1H), 8.44 (d, J=2.75 Hz, 1H), 7.76 (s, 1H), 7.53 (dd, J=8.85, 5.19 Hz, 1H), 7.37 (dd, J=9.46, 3.05 Hz, 1H), 7.21 (m, 1H), 7.07 (s, 1H), 6.87 (m, 2H), 6.58 (m, 2H), 4.62 (m, 2H), 4.05 (s, 3H), 3.94 (s, 2H). MS (APCI+) m/z 532.0 (M+H)$^+$.

Example 18

2-(1,5-dimethyl-1H-pyrazol-3-yl)-N-(5-(4-fluorophenyl)-11-methyl-1-oxo-2,4,5,11-tetrahydro-1H-2,5,6,11-tetraazadibenzo[cd,h]azulen-8-yl)acetamide Example 18 was prepared according to the procedure used for the preparation of Example 17, substituting 2-(1,5-dimethyl-1H-pyrazol-3-yl)acetic acid for 2-(2-chloro-5-fluorophenyl)acetic acid, to give 0.0053 g (28%) of the title compound. $^1$H NMR (400 MHz, DMSO-d$_6$/D$_2$O) δ 8.50 (d, J=2.75 Hz, 1H), 8.45 (d, J=2.44 Hz, 1H), 7.77 (s, 1H), 7.07 (s, 1H), 6.86 (m, 2H), 6.57 (m, 2H), 6.02 (s, 1H), 4.61 (m, 2H), 4.06 (s, 3H), 3.67 (s, 3H), 3.59 (s, 2H), 2.23 (s, 3H). MS (APCI+) m/z 498.1 (M+H)$^+$.

Example 19

N-(5-(4-fluorophenyl)-11-methyl-1-oxo-2,4,5,11-tetrahydro-1H-2,5,6,11-tetraazadibenzo[cd,h]azulen-8-yl)-2-(3-(2-fluorophenyl)-1H-pyrazol-1-yl)acetamide Example 19 was prepared according to the procedure used for the preparation of Example 17, substituting 2-(3-(2-fluorophenyl)-1H-pyrazol-1-yl)acetic acid for 2-(2-chloro-5-fluorophenyl)acetic acid, to give 0.0108 g (50%) of the title compound. $^1$H NMR (400 MHz, DMSO-d$_6$/D$_2$O) δ 8.55 (d, J=2.44 Hz, 1H), 8.44 (d, J=2.75 Hz, 1H), 7.92 (m, 2H), 7.77 (s, 1H), 7.39 (m, 1H), 7.28 (m, 2H), 7.07 (s, 1H), 6.88 (m, 2H), 6.72 (dd, J=3.66, 2.44 Hz, 1H), 6.59 (m, 2H), 5.20 (s, 2H), 4.62 (s, 2H), 4.05 (s, 3H). MS (APCI+) m/z 564.0 (M+H)$^+$.

Example 20

2-(4-chloro-2-fluorophenyl)-N-(5-(4-fluorophenyl)-11-methyl-1-oxo-2,4,5,11-tetrahydro-1H-2,5,6,11-tetraazadibenzo[cd,h]azulen-8-yl)acetamide A stock solution of Example 14e and N,N-diisopropylethylamine (0.11 M and 0.33 M in N,N-dimethylacetamide, respectively, 350 μL, 0.038 mmol Example 14e and 0.11 mmol N,N-diisopropylethylamine), 2-(3H-[1,2,3]triazolo[4,5-b]pyridin-3-yl)-1,1,3,3-tetramethylisouronium hexafluorophosphate(V) (0.13 M in N,N-dimethylacetamide, 350 μL, 0.046 mmol), and 2-(4-chloro-2-fluorophenyl)acetic acid (0.40 M in N,N-dimethylacetamide, 113 μL, 0.050 mmol) were aspirated from their respective source vials, mixed through a perfluoroalkoxy mixing tube (0.2 mm inner diameter), and loaded into an injection loop. The reaction segment was injected into the flow reactor (Hastelloy coil, 0.75 mm inner diameter, 1.8 mL internal volume) set at 100° C., and passed through the reactor at 180 μL per minute (10 minute residence time). Upon exiting the reactor, the reaction mixture was loaded directly into an injection loop and purified by reverse phase HPLC(C8, acetonitrile/water (0.1% ammonium acetate), 5-100%) to yield the title compound as an impure mixture. The material was dissolved in methanol (1 mL) and manually injected into the HPLC(C8, acetonitrile/water (0.1% ammonium acetate), 5-100%) to give 0.0036 g (19%) of the title compound. $^1$H NMR (400 MHz, DMSO-d$_6$/D$_2$O) δ 8.52 (d, J=2.75 Hz, 1H), 8.43 (d, J=2.75 Hz, 1H), 7.76 (s, 1H), 7.47 (t, J=8.24 Hz, 1H), 7.42 (dd, J=9.77, 1.83 Hz, 1H), 7.30 (dd, J=8.09, 1.68 Hz, 1H), 7.07 (s, 1H), 6.87 (m, 2H), 6.58 (m, 2H), 4.61 (s, 2H), 4.05 (s, 3H), 3.82 (s, 2H). MS (APCI+) m/z 532.0 (M+H)$^+$.

Example 21

2-(chroman-6-yl)-N-(5-(4-fluorophenyl)-11-methyl-1-oxo-2,4,5,11-tetrahydro-1H-2,5,6,11-tetraazadibenzo[cd,h]azulen-8-yl)acetamide Example 21 was prepared according to the procedure used for the preparation of Example 20, substituting 2-(chroman-6-yl)acetic acid for 2-(4-chloro-2-fluorophenyl)acetic acid, to give 0.0066 g (34%) of the title compound. $^1$H NMR (400 MHz, DMSO-d$_6$/D$_2$O) δ 8.51 (d, J=2.44 Hz, 1H), 8.45 (d, J=2.44 Hz, 1H), 7.76 (s, 1H), 7.06 (d, J=6.71 Hz, 3H), 6.86 (m, 2H), 6.70 (m, 1H), 6.56 (m, 2H), 4.61 (m, 2H), 4.11 (m, 2H), 4.06 (s, 3H), 3.58 (s, 2H), 2.74 (t, J=6.41 Hz, 2H), 1.91 (m, 2H). MS (APCI+) m/z 535.7 (M+H)$^+$.

Example 22

N-(5-(4-fluorophenyl)-11-methyl-1-oxo-2,4,5,11-tetrahydro-1H-2,5,6,11-tetraazadibenzo[cd,h]azulen-8-yl)-2-(1-methyl-1H-pyrazol-4-yl)acetamide A stock solution of Example 14e and N,N-diisopropylethylamine (0.11 M and 0.33 M in N,N-dimethylacetamide, respectively, 350 μL, 0.038 mmol Example 14e and 0.11 mmol N,N-diisopropylethylamine), 2-(3H-[1,2,3]triazolo[4,5-b]pyridin-3-yl)-1,1,3,3-tetramethylisouronium hexafluorophosphate(V) (0.13 M in N,N-dimethylacetamide, 350 μL, 0.046 mmol), and 2-(1-methyl-1H-pyrazol-4-yl)acetic acid (0.40 M in N,N-dimethylacetamide, 113 μL, 0.050 mmol) were aspirated from their respective source vials, mixed through a perfluoroalkoxy mixing tube (0.2 mm inner diameter), and loaded into an injection loop. The reaction segment was injected into the flow reactor (Hastelloy coil, 0.75 mm inner diameter, 1.8 mL internal volume) set at 100° C., and passed through the reactor at 180 μL per minute (10 minute residence time). Upon exiting the reactor, the reaction mixture was loaded directly into an injection loop and purified by reverse phase HPLC(C8, acetonitrile/water (0.1% ammonium acetate), 5-100%) to yield the title compound as an impure mixture. The material was dissolved in methanol (1 mL) and manually injected into the HPLC(C8, acetonitrile/water (0.1% ammonium acetate), 5-100%) give 0.0067 g (38%) of the title compound. $^1$H NMR (400 MHz, DMSO-d$_6$/D$_2$O) δ 8.49 (d, J=2.44 Hz, 1H), 8.45 (d, J=2.75 Hz, 1H), 7.77 (s, 1H), 7.63 (s, 1H), 7.40 (s, 1H), 7.07 (s, 1H), 6.87 (m, 2H), 6.57 (m, 2H), 4.60 (m, 2H), 4.07 (s, 3H), 3.81 (s, 3H), 3.55 (s, 2H). MS (APCI+) m/z 484.1 (M+H)$^+$.

Example 23

8-amino-5-(4-fluorophenyl)-11-methyl-2,4,5,11-tetrahydro-1H-2,5,11-triazadibenzo[cd,h]azulen-1-one

Example 23a 3-(2-fluoro-5-nitrophenyl)-7-methoxy-1-methyl-1H-pyrrolo[2,3-c]pyridine Example 1a (2 g, 6.94 mmol), (2-fluoro-5-nitrophenyl) boronic acid (1.412 g, 7.64 mmol), tris(dibenzylideneacetone)dipalladium(0) (0.191 g, 0.208 mmol), (1S,3R,5R,7S)-1,3,5,7-tetramethyl-8-phenyl-2,4,6-trioxa-8-phosphaadamantane (0.203 g, 0.694 mmol) and potassium phosphate (5.16 g, 24.3 mmol) were combined and sparged with nitrogen for 30 minutes. To this mixture were added nitrogen-sparged dioxane (32 mL) and water (8 mL). The reaction mixture was stirred at 60° C. for 4 hours, partitioned between ethyl acetate and water and washed with saturated aqueous sodium chloride. The combined aqueous layers were exhaustively extracted with ethyl acetate. The combined organic layers were treated with 3-mercaptopropyl-functionalized silica gel for 20 minutes, dried over anhydrous magnesium sulfate, filtered through a plug of Celite and concentrated. The residue was purified by flash chromatography (silica gel, 0-3% ethyl acetate in dichloromethane) to give 1.9 g (91%) of the title compound.

Example 23b

N-(4-fluorophenyl)-2-(7-methoxy-1-methyl-1H-pyrrolo[2,3-c]pyridin-3-yl)-4-nitro aniline Example 23a (1.07 g, 3.55 mmol) and 4-fluoroaniline (0.434 g, 3.91 mmol) were dissolved in dimethyl sulfoxide (35.5 mL), treated with potassium 2-methylpropan-2-olate (0.8 g, 7.1 mmol) and stirred overnight at ambient temperature. The reaction mixture was partitioned between ethyl acetate and water and washed with saturated aqueous sodium chloride. The combined aqueous layers were extracted with ethyl acetate (2×150 mL). The combined organic layers were dried over anhydrous magnesium sulfate, filtered, and concentrated. The residue was purified by flash chromatography (silica gel, 0-2% ethyl acetate in dichloromethane) to provide 1.13 g (81%) of the title compound.

Example 23c 3-(2-((4-fluorophenyl)amino)-5-nitrophenyl)-1-methyl-1H-pyrrolo[2,3-c]pyridin-7(6H)-one Example 23b (1.126 g, 2.87 mmol) was treated with hydrogen chloride solution (4 M in 1,4-dioxane, 10.8 mL, 43 mmol) and heated at 90° C. for 1 hour. The reaction mixture was concentrated to dryness to give 1.09 g (100%) of the title compound.

Example 23d 5-(4-fluorophenyl)-11-methyl-8-nitro-2,4,5,11-tetrahydro-1H-2,5,11-triazadibenzo[cd,h]azulen-1-one To Example 23c (1.09 g, 2.87 mmol) in acetic acid (16 mL) was added paraformaldehyde (0.215 g, 7.18 mmol). The reaction mixture was heated at 90° C. for 13 minutes, cooled to ambient temperature, and diluted with water. The resulting solid was collected by filtration and dried under vacuum. The solid was then slurried in methanol (8 mL), treated with sodium hydroxide (4 M aqueous solution, 3 mL, 12 mmol) and heated at 70° C. for 2 hours. Methanol was removed under vacuum. Water was added to further induce precipitation and the solid was collected by filtration. The solid was then triturated with acetonitrile, collected by filtration and dried under high vacuum to give 0.93 g (83%) of the title compound.

Example 23e 8-amino-5-(4-fluorophenyl)-11-methyl-2,4,5,11-tetrahydro-1H-2,5,11-triazadibenzo[cd,h]azulen-1-one Example 23d (0.93 g, 2.38 mmol) was slurried in a mixture of tetrahydrofuran (8 mL), ethanol (4 mL) and water (2 mL), treated with ammonium chloride (1.274 g, 23.82 mmol) and zinc dust (2.336 g, 35.7 mmol), and stirred at ambient temperature for 30 minutes. The solids were removed by filtration. The filtrate was concentrated and the resulting solid was purified by sequential triturations with water, acetonitrile and diethyl ether to give 0.76 g (89%) of the title compound. $^1$H NMR (400 MHz, DMSO-$d_6$) δ 10.73 (d, J=5.49 Hz, 1H), 7.54 (s, 1H), 6.98 (d, J=5.49 Hz, 1H), 6.95 (d, J=2.44 Hz, 1H), 6.90 (d, J=8.24 Hz, 1H), 6.78 (m, J=8.85, 8.85 Hz, 2H), 6.49 (dd, J=8.39, 2.59 Hz, 1H), 6.45 (m, 2H), 5.11 (s, 2H), 4.95 (d, J=16.17 Hz, 1H), 4.14 (d, J=15.87 Hz, 1H), 4.03 (s, 3H). MS (ESI+) m/z 361.2 (M+H)$^+$.

Example 24

8-chloro-5-(4-fluorophenyl)-11-methyl-4-phenyl-2,4,5,11-tetrahydro-1H-2,5,11-triazadibenzo[cd,h]azulen-1-one

Example 24a 3-(5-chloro-2-((4-fluorophenyl)amino)phenyl)-1-methyl-1H-pyrrolo[2,3-c]pyridin-7(6H)-one Example 13b (0.76 g, 1.990 mmol) and 4M hydrogen chloride in dioxane (20 mL, 80 mmol) were heated at 70° C. for 18 hours, cooled, concentrated and azeotroped two times with toluene to afford the title compound (0.73 g, 100%).

Example 24b 8-chloro-5-(4-fluorophenyl)-11-methyl-4-phenyl-2,4,5,11-tetrahydro-1H-2,5,11-triazadibenzo[cd,h]azulen-1-one Example 24a (0.05 g, 0.136 mmol) and benzaldehyde (0.041 mL, 0.408 mmol) in acetic acid (1 mL) were heated in a sealed tube at 100° C. for 2 hours, cooled and concentrated. Purification by reverse phase HPLC(C18, CH$_3$CN/water (0.1% TFA), 0-100% gradient) afforded the title compound (0.002 g, 3%). $^1$H NMR (400 MHz, DMSO-$d_6$) δ 10.66 (s, 1H), 7.82 (s, 1H), 7.64 (d, J=2.44 Hz, 1H), 6.91-7.10 (m, 8H), 6.80-6.86 (m, 2H), 6.66-6.70 (m, 2H), 6.50 (s, 1H), 4.09 (s, 3H). MS (ESI+) m/z 456 (M+H)$^+$.

Example 25

11-methyl-8-((methylsulfonyl)methyl)-4-phenyl-2,4,5,11-tetrahydro-1H-2,5,11-triazadibenzo[cd,h]azulen-1-one A 5 mL vial was charged with Example 4a (104 mg, 0.300 mmol), benzaldehyde (159 mg, 1.50 mmol) and acetic acid (2 mL). The vial was closed and stirred at 80° C. for 6 hours. The reaction mixture was cooled to ambient temperature and concentrated. The residue was partitioned in ethyl acetate and saturated aqueous sodium bicarbonate. The organic layer was washed with saturated aqueous sodium chloride, dried with anhydrous sodium sulfate, filtered, and concentrated. The residue was purified by reverse phase HPLC(C18, $CH_3CN$/water (10 mM ammonium carbonate), 20-100%) to afford the title compound (19 mg, 15%). $^1$H NMR (300 MHz, DMSO-$d_6$) δ 10.72 (d, J=5.76 Hz, 1H) 7.68 (s, 1H) 7.57 (s, 1H) 7.03-7.29 (m, 5H) 6.90 (s, 2H) 6.41 (d, J=5.76 Hz, 1H) 6.28 (d, J=4.41 Hz, 1H) 5.30 (d, J=4.41 Hz, 1H) 4.26 (s, 2H) 4.16 (s, 3H) 2.80 (s, 3H). MS (ESI+) m/z 420 (M+H)$^+$.

Example 26

N-(5-(4-fluorophenyl)-11-methyl-1-oxo-2,4,5,11-tetrahydro-1H-2,5,11-triazadibenzo[cd,h]azulen-8-yl)benzenesulfonamide A stock solution of Example 23e and N,N-diisopropylethylamine (0.08 M and 0.16 M in dichloromethane, respectively, 500 µL, 0.042 mmol Example 23e and 0.083 mmol N,N-diisopropylethylamine), and benzenesulfonyl chloride (0.40 M in dichloromethane, 239 µL, 0.096 mmol) were mixed and stirred at ambient temperature overnight. The reaction mixture was concentrated, dissolved in methanol (1 mL) and injected on the reverse phase HPLC(C8, acetonitrile/water (0.1% TFA), 5-100%) to yield the title compound as an impure mixture.

The material was dissolved in methanol (1 mL) and manually injected into the HPLC(C8, acetonitrile/water (0.1% TFA), 5-100%) to give 0.0031 g (17%) of the title compound as the TFA salt. $^1$H NMR (400 MHz, DMSO-$d_6$/$D_2O$) δ 8.03 (m, 1H), 7.85 (m, 2H), 7.63 (m, 3H), 7.50 (d, J=2.44 Hz, 1H), 7.11 (d, J=8.54 Hz, 1H), 7.02 (s, 1H), 6.96 (dd, J=8.54, 2.44 Hz, 1H), 6.81 (m, 2H), 6.38 (m, 2H), 4.96 (s, 1H), 4.11 (s, 1H), 4.04 (s, 3H). MS (APCI+) m/z 501.0 (M+H)$^+$.

Example 27

N-(4-(N-(5-(4-fluorophenyl)-11-methyl-1-oxo-2,4,5,11-tetrahydro-1H-2,5,11-triazadibenzo[cd,h]azulen-8-yl)sulfamoyl)phenyl)acetamide A stock solution of Example 14e and N,N-diisopropylethylamine (0.08 M and 0.16 M in dichloromethane, respectively, 500 µL, 0.042 mmol Example 14e and 0.083 mmol N,N-diisopropylethylamine), and 4-acetamidobenzene-1-sulfonyl chloride (0.40 M in dichloromethane, 239 µL, 0.096 mmol) were mixed and stirred at ambient temperature overnight. The reaction mixture was concentrated, dissolved in methanol (1 mL) and injected on the reverse phase HPLC(C8, acetonitrile/water (0.1% TFA), 5-100%) to yield the title compound as an impure mixture. The material was dissolved in methanol (1 mL) and manually injected into the HPLC(C8, acetonitrile/water (0.1% TFA), 5-100%) to give 0.0071 g (32%) of the title compound as the TFA salt. $^1$H NMR (400 MHz, DMSO-$d_6$/$D_2O$) δ 7.75 (q, J=9.16 Hz, 4H), 7.57 (s, 1H), 7.48 (d, J=2.44 Hz, 1H), 7.11 (d, J=8.54 Hz, 1H), 7.02 (s, 1H), 6.95 (dd, J=8.54, 2.44 Hz, 1H), 6.80 (m, J=8.85, 8.85 Hz, 2H), 6.37 (m, 2H), 4.97 (s, 1H), 4.12 (m, 1H), 4.04 (s, 3H), 2.06 (s, 3H). MS (APCI+) m/z 558.0 (M+H)$^+$.

Example 28

N-(5-(4-fluorophenyl)-11-methyl-1-oxo-2,4,5,11-tetrahydro-1H-2,5,11-triazadibenzo[cd,h]azulen-8-yl)-2-(1-methyl-1H-pyrazol-4-yl)acetamide A stock solution of Example 23e and N,N-diisopropylethylamine (0.165 M and 0.47 M in N,N-dimethylacetamide, respectively, 275 µL, 0.042 mmol Example 23e and 0.13 mmol N,N-diisopropylethylamine), 2-(3H-[1,2,3]triazolo[4,5-b]pyridin-3-yl)-1,1,3,3-tetramethylisouronium hexafluorophosphate(V) (0.25 M in N,N-dimethylacetamide, 253 µL, 0.063 mmol), and 2-(1-methyl-1H-pyrazol-4-yl)acetic acid (0.40 M in N,N-dimethylacetamide, 125 µL, 0.05 mmol) were aspirated from their respective source vials, mixed through a perfluoroalkoxy mixing tube (0.2 mm inner diameter), and loaded into an injection loop. The reaction segment was injected into the flow reactor (Hastelloy coil, 0.75 mm inner diameter, 1.8 mL internal volume) set at 100° C., and passed through the reactor at 180 µL per minute (10 minute residence time). Upon exiting the reactor, the reaction mixture was loaded directly into an injection loop and purified using reverse phase HPLC(C8, acetonitrile/water (0.1% TFA), 5-100%) to give 0.0168 g (68%) of the title compound as the TFA salt. $^1$H NMR (400 MHz, DMSO-$d_6$/$D_2O$) δ 8.03 (d, J=2.14 Hz, 1H), 7.57 (s, 2H), 7.42 (dd, J=8.54, 2.44 Hz, 1H), 7.38 (s, 1H), 7.16 (d, J=8.54 Hz, 1H), 6.97 (s, 1H), 6.78 (m, 2H), 6.50 (m, 2H), 4.59 (m, 2H), 4.06 (s, 3H), 3.81 (s, 3H), 3.52 (s, 2H). MS (APCI+) m/z 483.1 (M+H)$^+$.

Example 29

2-(4-chloro-2-fluorophenyl)-N-(5-(4-fluorophenyl)-11-methyl-1-oxo-2,4,5,11-tetrahydro-1H-2,5,11-triazadibenzo[cd,h]azulen-8-yl)acetamide A stock solution of Example 23e and N,N-diisopropylethylamine (0.165 M and 0.47 M in N,N-dimethylacetamide, respectively, 275 µL, 0.042 mmol Example 23e and 0.13 mmol N,N-diisopropylethylamine), 2-(3H-[1,2,3]triazolo[4,5-b]pyridin-3-yl)-1,1,3,3-tetramethylisouronium hexafluorophosphate(V) (0.25 M in N,N-dimethylacetamide, 253 µL, 0.063 mmol), and 2-(4-chloro-2-fluorophenyl)acetic acid (0.40 M in N,N-dimethylacetamide, 125 µL, 0.05 mmol) were aspirated from their respective source vials, mixed through a perfluoroalkoxy mixing tube (0.2 mm inner diameter), and loaded into an injection loop. The reaction segment was injected into the flow reactor (Hastelloy coil, 0.75 mm inner diameter, 1.8 mL internal volume) set at 100° C., and passed through the reactor at 180 µL per minute (10 minute residence time). Upon exiting the reactor, the reaction mixture was loaded directly into an injection loop and purified using reverse phase HPLC(C8, acetonitrile/water (0.1% ammonium acetate), 5-100%) to give 0.0126 g (57%) of the title compound. $^1$H NMR (400 MHz, DMSO-$d_6$/$D_2O$) δ 8.06 (d, J=2.44 Hz, 1H), 7.56 (s, 1H), 7.45 (t, J=8.24 Hz, 1H), 7.40 (dd, J=8.54, 2.44 Hz, 1H), 7.31 (dd, J=9.77, 2.14 Hz, 1H), 7.25 (dd, J=8.24, 2.14 Hz, 1H), 7.17 (d, J=8.54 Hz, 1H), 6.97 (s, 1H), 6.78 (m, 2H), 6.50 (m, 2H), 4.58 (m, 2H), 4.05 (s, 3H), 3.77 (s, 2H). MS (APCI+) m/z 531.1 (M+H)$^+$.

Example 30

2-(2-chloro-5-fluorophenyl)-N-(5-(4-fluorophenyl)-11-methyl-1-oxo-2,4,5,11-tetrahydro-1H-2,5,11-triazadibenzo[cd,h]azulen-8-yl)acetamide Example 30 was prepared according to the procedure used for the preparation of Example 29, substituting 2-(2-chloro-5-fluorophenyl)acetic acid for 2-(4-chloro-2-fluorophenyl) acetic acid, to give 0.0108 g (49%) of the title compound. $^1$H NMR (400 MHz, DMSO-$d_6$/$D_2O$) δ 8.07 (d, J=2.44 Hz, 1H), 7.57 (s, 1H), 7.48 (dd, J=8.85, 5.19 Hz, 1H), 7.41 (dd, J=8.54, 2.44 Hz, 1H), 7.31 (dd, J=9.61, 3.20 Hz, 1H), 7.15 (m, 2H), 6.97 (s, 1H), 6.78 (m, 2H), 6.51 (m, 2H), 4.59 (m, 2H), 4.05 (s, 3H), 3.88 (m, 2H). MS (APCI+) m/z 531.0 (M+H)$^+$.

Example 31

N-(5-(4-fluorophenyl)-11-methyl-1-oxo-2,4,5,11-tetrahydro-1H-2,5,11-triazadibenzo[cd,h]azulen-8-yl)-2-(3-(2-fluorophenyl)-1H-pyrazol-1-yl)acetamide Example 31 was prepared according to the procedure used for the preparation of Example 29, substituting 2-(3-(2-fluorophenyl)-1H-pyrazol-1-yl)acetic acid for 2-(4-chloro-2-fluorophenyl)acetic acid, to give 0.0169 g (72%) of the title compound. $^1$H NMR (400 MHz, DMSO-$d_6$/$D_2O$) δ 8.09 (d, J=2.44 Hz, 1H), 7.91 (td, J=7.86, 1.98 Hz, 1H), 7.86 (d, J=2.14 Hz, 1H), 7.57 (s, 1H), 7.41 (dd, J=8.54, 2.44 Hz, 1H), 7.35 (m, 1H), 7.23 (m, 3H), 6.97 (s, 1H), 6.78 (m, 2H), 6.69 (dd, J=3.66, 2.44 Hz, 1H), 6.51 (m, 2H), 5.12 (s, 2H), 4.59 (m, 2H), 4.05 (s, 3H). MS (APCI+) m/z 563.0 (M+H)$^+$.

Example 32

N-(5-(4-fluorophenyl)-11-methyl-1-oxo-2,4,5,11-tetrahydro-1H-2,5,11-triazadibenzo[cd,h]azulen-8-yl)-2-(2-methylthiazol-5-yl)acetamide Example 32 was prepared according to the procedure used for the preparation of Example 29, substituting 2-(2-methylthiazol-5-yl)acetic acid for 2-(4-chloro-2-fluorophenyl) acetic acid, to give 0.0173 g (83%) of the title compound. $^1$H NMR (400 MHz, DMSO-$d_6$/$D_2O$) δ 8.03 (d, J=2.44 Hz, 1H), 7.58 (s, 1H), 7.48 (s, 1H), 7.41 (dd, J=8.54, 2.44 Hz, 1H), 7.18 (d, J=8.54 Hz, 1H), 6.97 (s, 1H), 6.78 (m, 2H), 6.50 (m, 2H), 4.58 (m, 2H), 4.06 (s, 3H), 3.90 (m, 2H), 2.61 (s, 3H). MS (APCI+) m/z 500.1 (M+H)$^+$.

Example 33

2-(1,5-dimethyl-1H-pyrazol-3-yl)-N-(5-(4-fluorophenyl)-11-methyl-1-oxo-2,4,5,11-tetrahydro-1H-2,5,11-triazadibenzo[cd,h]azulen-8-yl)acetamide Example 33 was prepared according to the procedure used for the preparation of Example 29, substituting 2-(1,5-dimethyl-1H-pyrazol-3-yl)acetic acid for 2-(4-chloro-2-fluorophenyl)acetic acid, to give 0.0165 g (80%) of the title compound. $^1$H NMR (400 MHz, DMSO-$d_6$/$D_2O$) δ 8.04 (d, J=2.44 Hz, 1H), 7.57 (s, 1H), 7.42 (dd, J=8.54, 2.44 Hz, 1H), 7.16 (d, J=8.54 Hz, 1H), 6.97 (s, 1H), 6.78 (m, 2H), 6.50 (m, 2H), 6.00 (s, 1H), 4.58 (m, 2H), 4.06 (s, 3H), 3.68 (s, 3H), 3.57 (s, 2H), 2.22 (s, 3H). MS (APCI+) m/z 497.1 (M+H)$^+$.

Example 34

$N^1$-(5-(4-fluorophenyl)-11-methyl-1-oxo-2,4,5,11-tetrahydro-1H-2,5,11-triazadibenzo[cd,h]azulen-8-yl)-$N^5$-phenylglutaramide Example 34 was prepared according to the procedure used for the preparation of Example 29, substituting 5-oxo-5-(phenylamino)pentanoic acid for 2-(4-chloro-2-fluorophenyl) acetic acid, to give 0.0158 g (69%) of the title compound. $^1$H NMR (400 MHz, DMSO-$d_6$/$D_2O$) δ 8.05 (d, J=2.44 Hz, 1H), 7.56 (m, 3H), 7.43 (dd, J=8.54, 2.44 Hz, 1H), 7.28 (m, 2H), 7.15 (d, J=8.54 Hz, 1H), 7.04 (m, 1H), 6.97 (s, 1H), 6.78 (m, 2H), 6.50 (m, 2H), 4.59 (m, 2H), 4.06 (s, 3H), 2.44 (q, J=7.02 Hz, 4H), 1.99 (m, 2H). MS (APCI+) m/z 550.1 (M+H)$^+$.

Example 35

N-(5-(4-fluorophenyl)-11-methyl-1-oxo-2,4,5,11-tetrahydro-1H-2,5,11-triazadibenzo[cd,h]azulen-8-yl)-5-methylpyrazine-2-carboxamide Example 35 was prepared according to the procedure used for the preparation of Example 29, substituting 5-methylpyrazine-2-carboxylic acid for 2-(4-chloro-2-fluorophenyl)acetic acid, to give 0.0066 g (33%) of the title compound. $^1$H NMR (400 MHz, DMSO-$d_6$/$D_2O$) δ 9.18 (d, J=1.22 Hz, 1H), 8.67 (d, J=0.92 Hz, 1H), 8.28 (d, J=2.44 Hz, 1H), 7.74 (dd, J=8.54, 2.44 Hz, 1H), 7.67 (s, 1H), 7.25 (d, J=8.54 Hz, 1H), 6.99 (s, 1H), 6.80 (m, 2H), 6.55 (m, 2H), 4.62 (m, 2H), 4.08 (s, 3H), 2.65 (s, 3H). MS (APCI+) m/z 481.1 (M+H)$^+$.

Example 36

N-(5-(4-fluorophenyl)-11-methyl-1-oxo-2,4,5,11-tetrahydro-1H-2,5,11-triazadibenzo[cd,h]azulen-8-yl)-2-(4-methylpiperazin-1-yl)acetamide Example 36 was prepared according to the procedure used for the preparation of Example 29, substituting 2-(4-methylpiperazin-1-yl)acetic acid for 2-(4-chloro-2-fluorophenyl) acetic acid, to give 0.0111 g (53%) of the title compound. $^1$H NMR (400 MHz, DMSO-$d_6$/$D_2O$) δ 8.03 (d, J=2.44 Hz, 1H), 7.62 (s, 1H), 7.48 (dd, J=8.54, 2.44 Hz, 1H), 7.18 (d, J=8.54 Hz, 1H), 6.97 (s, 1H), 6.78 (m, 2H), 6.51 (m, 2H), 4.59 (m, 2H), 4.06 (s, 3H), 3.16 (s, 2H), 2.60 (m, 4H), 2.45 (m, 4H), 2.21 (s, 3H). MS (APCI+) m/z 501.1 (M+H)$^+$.

Example 37

8-(((1-ethyl-1H-pyrazol-3-yl)methyl)amino)-5-(4-fluorophenyl)-11-methyl-2,4,5,11-tetrahydro-1H-2,5,11-triazadibenzo[cd,h]azulen-1-one A stock solution of Example 23e (0.164 M in N,N-dimethylacetamide, 255 mL, 0.042 mmol), acetic acid (4 M in methanol, 200 mL, 0.84 mmol), sodium cyanoborohydride (0.31 M in methanol, 200 mL, 0.063 mmol) and 1-ethyl-1H-pyrazole-3-carbaldehyde (0.40 M in N,N-dimethylacetamide, 156 mL, 0.063 mmol) were aspirated from their respective source vials, mixed through a perfluoroalkoxy mixing tube (0.2 mm inner diameter), and loaded into an injection loop. The reaction segment was injected into the flow reactor (Hastelloy coil, 0.75 mm inner diameter, 1.8 mL internal volume) set at 50° C., and passed through the reactor at 180 μL, min⁻¹ (10 minute residence time). Upon exiting the reactor, the reaction mixture was loaded directly into an injection loop and purified by reverse phase HPLC(C8, acetonitrile/water (0.1% ammonium acetate), 5-100%) to give 0.0081 g (41%) of the title compound. ¹H NMR (400 MHz, DMSO-$d_6$/$D_2O$) δ 7.57 (m, 2H), 7.07 (d, J=2.75 Hz, 1H), 6.95 (m, 2H), 6.74 (m, 2H), 6.60 (dd, J=8.54, 2.75 Hz, 1H), 6.46 (m, 2H), 6.22 (d, J=2.14 Hz, 1H), 4.28 (s, 2H), 4.10 (q, J=7.12 Hz, 2H), 4.04 (s, 3H), 2.88 (d, J=53.41 Hz, 2H), 1.38 (m, 3H). MS (APCI+) m/z 469.1 (M+H)⁺.

Example 38

5-(4-fluorophenyl)-11-methyl-8-(((1-methyl-1H-pyrazol-5-yl)methyl)amino)-2,4,5,11-tetrahydro-1H-2,5,11-triazadibenzo[cd,h]azulen-1-one Example 38 was prepared according to the procedure used for the preparation of Example 37, substituting 1-methyl-1H-pyrazole-5-carbaldehyde for 1-ethyl-1H-pyrazole-3-carbaldehyde, to give 0.0057 g (30%) of the title compound. ¹H NMR (400 MHz, DMSO-$d_6$/$D_2O$) δ 7.58 (s, 1H), 7.31 (d, J=1.83 Hz, 1H), 7.07 (d, J=2.75 Hz, 1H), 6.97 (d, J=8.54 Hz, 1H), 6.94 (s, 1H), 6.74 (m, 2H), 6.62 (dd, J=8.54, 2.75 Hz, 1H), 6.47 (m, 2H), 6.27 (d, J=1.83 Hz, 1H), 4.59 (m, 2H), 4.39 (s, 2H), 4.05 (s, 3H), 3.85 (s, 3H). MS (APCI+) m/z 455.1 (M+H)⁺.

Example 39

8-((3-(1H-pyrazol-1-yl)propyl)amino)-5-(4-fluorophenyl)-11-methyl-2,4,5,11-tetrahydro-1H-2,5,11-triazadibenzo[cd,h]azulen-1-one Example 39 was prepared according to the procedure used for the preparation of Example 37, substituting 3-(1H-pyrazol-1-yl)propanal for 1-ethyl-1H-pyrazole-3-carbaldehyde, to give 0.0072 g (37%) of the title compound. ¹H NMR (400 MHz, DMSO-$d_6$/$D_2O$) δ 7.68 (d, J=2.44 Hz, 1H), 7.57 (s, 1H), 7.46 (d, J=1.83 Hz, 1H), 6.94 (m, 3H), 6.74 (m, 2H), 6.50 (dd, J=8.39, 2.59 Hz, 1H), 6.46 (m, 2H), 6.26 (t, J=2.14 Hz, 1H), 4.64 (m, 2H), 4.26 (t, J=6.87 Hz, 2H), 4.05 (s, 3H), 3.13 (t, J=6.87 Hz, 2H), 2.12 (m, 2H). MS (APCI+) m/z 469.1 (M+H)⁺.

Example 40

5-(4-fluorophenyl)-11-methyl-8-(((6-methylpyridin-2-yl)methyl)amino)-2,4,5,11-tetrahydro-1H-2,5,11-triazadibenzo[cd,h]azulen-1-one A stock solution of Example 23e (0.164 M in N,N-dimethylacetamide, 255 mL, 0.042 mmol), acetic acid (4 M in methanol, 200 mL, 0.84 mmol), sodium cyanoborohydride (0.31 M in methanol, 200 mL, 0.063 mmol) and 6-methylpicolinaldehyde (0.40 M in N,N-dimethylacetamide, 156 mL, 0.063 mmol) were aspirated from their respective source vials, mixed through a perfluoroalkoxy mixing tube (0.2 mm inner diameter), and loaded into an injection loop. The reaction segment was injected into the flow reactor (Hastelloy coil, 0.75 mm inner diameter, 1.8 mL internal volume) set at 50° C., and passed through the reactor at 180 μL per minute (10 minute residence time). Upon exiting the reactor, the reaction mixture was loaded directly into an injection loop and purified by reverse phase HPLC(C8, acetonitrile/water (0.1% ammonium acetate), 5-100%) to give 0.0085 g (44%) of the title compound. ¹H NMR (400 MHz, DMSO-$d_6$/$D_2O$) δ 10.85 (s, 1H), 8.41 (d, J=1.83 Hz, 1H), 7.96 (s, 1H), 7.81 (dd, J=8.24, 1.83 Hz, 1H), 7.38 (m, 2H), 7.04 (s, 1H), 6.87 (m, J=9.00, 9.00 Hz, 3H), 6.58 (m, 3H), 4.58 (m, 2H), 4.06 (s, 3H), 3.90 (s, 3H), 3.17 (s, 2H). MS (APCI+) m/z 466.1 (M+H)⁺.

Example 41 methyl 4-((5-(4-fluorophenyl)-11-methyl-1-oxo-2,4,5,11-tetrahydro-1H-2,5,11-triazadibenzo[cd,h]azulen-8-yl)amino)butanoate Example 41 was prepared according to the procedure used for the preparation of Example 37, substituting methyl 4-oxobutanoate for 1-ethyl-1H-pyrazole-3-carbaldehyde, to give 0.0049 g (26%) of the title compound. ¹H NMR (400 MHz, DMSO-$d_6$/$D_2O$) δ 7.60 (s, 1H), 6.95 (m, 3H), 6.74 (m, 2H), 6.53 (dd, J=8.54, 2.75 Hz, 1H), 6.47 (m, 2H), 4.62 (m, 2H), 4.04 (s, 3H), 3.63 (s, 3H), 3.15 (t, J=6.87 Hz, 2H), 2.45 (t, J=7.17 Hz, 2H), 1.88 (m, 2H). MS (APCI+) m/z 461.1 (M+H)⁺.

Example 42

5-(4-fluorophenyl)-11-methyl-8-(((1-methyl-1H-imidazol-5-yl)methyl)amino)-2,4,5,11-tetrahydro-1H-2,5,11-triazadibenzo[cd,h]azulen-1-one Example 42 was prepared according to the procedure used for the preparation of Example 37, substituting 1-methyl-1H-imidazole-5-carbaldehyde for 1-ethyl-1H-pyrazole-3-carbaldehyde, to give 0.0056 g (30%) of the title compound. ¹H NMR (400 MHz, DMSO-$d_6$/$D_2O$) δ 7.59 (s, 1H), 7.52 (s, 1H), 7.08 (d, J=2.75 Hz, 1H), 6.97 (d, J=8.54 Hz, 1H), 6.93 (d, J=7.93 Hz, 2H), 6.75 (m, 2H), 6.63 (dd, J=8.54, 2.75 Hz, 1H), 6.47 (m, 2H), 4.45 (m, 2H), 4.33 (s, 2H), 4.05 (s, 3H), 3.67 (s, 3H). MS (APCI+) m/z 455.1 (M+H)⁺.

Example 43

5-(4-fluorophenyl)-11-methyl-8-(((3-methylpyridin-2-yl)methyl)amino)-2,4,5,11-tetrahydro-1H-2,5,11-triazadibenzo[cd,h]azulen-1-one Example 43 was prepared according to the procedure used for the preparation of Example 37, substituting 3-methylpicolinaldehyde for 1-ethyl-1H-pyrazole-3-carbaldehyde, to give 0.0086 g (45%) of the title compound. ¹H NMR (400 MHz, DMSO-$d_6$/$D_2O$) δ 8.40 (dd, J=4.73, 1.07 Hz, 1H), 7.63 (s, 1H), 7.60 (dd, J=7.48, 0.76 Hz, 1H), 7.23 (dd, J=7.48, 4.73 Hz, 1H), 7.16 (d, J=2.75 Hz, 1H), 6.98 (d, J=8.54 Hz, 1H), 6.94 (s, 1H), 6.74 (m, 2H), 6.68 (dd, J=8.39, 2.59 Hz, 1H), 6.47 (m, 2H), 4.43 (s, 2H), 4.06 (s, 3H), 4.25 (m, 2H), 2.41 (s, 3H). MS (APCI+) m/z 466.1 (M+H)⁺.

Example 44

1-(5-(4-fluorophenyl)-11-methyl-1-oxo-2,4,5,11-tetrahydro-1H-2,5,11-triazadibenzo[cd,h]azulen-8-yl)-3-(3-phenoxyphenyl)urea A stock solution of Example 23e and N,N-diisopropylethylamine (0.0875 M and 0.042 in N,N-dimethylacetamide, respectively, 497 μL, 0.042 mmol Example 23e and 0.126 mmol N,N-diisopropylethylamine) and 1-isocyanato-3-phenoxybenzene (0.40 M in N,N-dimethylacetamide, 208 μL, 0.084 mmol) were aspirated from their respective source vials, mixed through a perfluoroalkoxy mixing tube (0.2 mm inner diameter), and loaded into an injection loop. The reaction segment was injected into the flow reactor (Hastelloy coil, 0.75 mm inner diameter, 1.8 mL internal volume) set at 150° C., and passed through the reactor at 180 μL per minute (10 minute residence time). Upon exiting the reactor, the reaction mixture was loaded directly into an injection loop and purified by reverse phase HPLC(C8, acetonitrile/water (0.1% ammonium acetate), 5-100%) to give 0.0067 g (28%) of the title compound. $^1$H NMR (400 MHz, DMSO-$d_6$/$D_2$O) δ 7.90 (d, J=2.44 Hz, 1H), 7.60 (s, 1H), 7.40 (m, 2H), 7.27 (m, 3H), 7.16 (m, 3H), 7.03 (m, 2H), 6.97 (s, 1H), 6.78 (m, 2H), 6.64 (m, 1H), 6.51 (m, 2H), 4.60 (m, 2H), 4.06 (s, 3H). MS (APCI+) m/z 572.1 (M+H)$^+$.

Example 45

1-(5-(4-fluorophenyl)-11-methyl-1-oxo-2,4,5,11-tetrahydro-1H-2,5,11-triazadibenzo[cd,h]azulen-8-yl)-3-(3-methoxyphenyl)urea Example 45 was prepared according to the procedure used for the preparation of Example 44, substituting 1-isocyanato-3-methoxybenzene for 1-isocyanato-3-phenoxybenzene, to give 0.0013 g (6%) of the title compound. $^1$H NMR (400 MHz, DMSO-$d_6$/$D_2$O) δ 7.92 (d, J=2.75 Hz, 1H), 7.62 (s, 1H), 7.29 (m, 1H), 7.18 (m, 3H), 6.99 (m, 2H), 6.78 (m, 2H), 6.59 (m, 1H), 6.52 (m, 2H), 4.60 (s, 2H), 4.07 (s, 3H), 3.77 (s, 3H). MS (APCI+) m/z 510.1 (M+H)$^+$.

Example 46

2-(chroman-6-yl)-N-(5-(4-fluorophenyl)-11-methyl-1-oxo-2,4,5,11-tetrahydro-1H-2,5,11-triazadibenzo[cd,h]azulen-8-yl)acetamide Example 46 was prepared according to the procedure used for the preparation of Example 29, substituting 2-(chroman-6-yl)acetic acid for 2-(4-chloro-2-fluorophenyl)acetic acid, to give 0.0081 g (37%) of the title compound. $^1$H NMR (400 MHz, DMSO-$d_6$/$D_2$O) δ 8.05 (d, J=2.44 Hz, 1H), 7.56 (s, 1H), 7.42 (dd, J=8.54, 2.44 Hz, 1H), 7.15 (d, J=8.54 Hz, 1H), 7.05 (m, 2H), 6.97 (s, 1H), 6.77 (m, 2H), 6.68 (m, 1H), 6.50 (m, 2H), 4.58 (m, 2H), 4.11 (m, 2H), 4.05 (s, 3H), 3.55 (s, 2H), 2.74 (t, J=6.41 Hz, 2H), 1.93 (m, 2H). MS (APCI+) m/z 535.1 (M+H)$^+$.

Example 47

N-(5-(4-fluorophenyl)-11-methyl-1-oxo-2,4,5,11-tetrahydro-1H-2,5,11-triazadibenzo[cd,h]azulen-8-yl)-3-(4-methylpiperazin-1-yl)propanamide Example 47 was prepared according to the procedure used for the preparation of Example 29, substituting 3-(4-methylpiperazin-1-yl)propanoic acid for 2-(4-chloro-2-fluorophenyl)acetic acid, to give 0.0054 g (25%) of the title compound. $^1$H NMR (400 MHz, DMSO-$d_6$/$D_2$O) δ 8.03 (d, J=2.75 Hz, 1H), 7.56 (s, 1H), 7.39 (dd, J=8.54, 2.44 Hz, 1H), 7.16 (d, J=8.54 Hz, 1H), 6.97 (s, 1H), 6.77 (m, 2H), 6.50 (m, 2H), 4.59 (m, 2H), 4.06 (s, 3H), 4.04 (m, 2H), 2.70 (t, J=6.87 Hz, 2H), 2.49 (m, 5H), 2.37 (m, 4H), 2.18 (s, 3H). MS (APCI+) m/z 515.2 (M+H)$^+$.

Example 48

N-(5-(4-fluorophenyl)-11-methyl-1-oxo-2,4,5,11-tetrahydro-1H-2,5,11-triazadibenzo[cd,h]azulen-8-yl)-3-(piperidin-1-yl)propanamide A stock solution of Example 23e and N,N-diisopropylethylamine (0.165 M and 0.47 M in N,N-dimethylacetamide, respectively, 275 μL, 0.042 mmol Example 23e and 0.13 mmol N,N-diisopropylethylamine), 2-(3H-[1,2,3]triazolo[4,5-b]pyridin-3-yl)-1,1,3,3-tetramethylisouronium hexafluorophosphate(V) (0.25 M in N,N-dimethylacetamide, 253 μL, 0.063 mmol), and 3-(piperidin-1-yl)propanoic acid (0.40 M in N,N-dimethylacetamide, 125 μL, 0.05 mmol) were aspirated from their respective source vials, mixed through a perfluoroalkoxy mixing tube (0.2 mm inner diameter), and loaded into an injection loop. The reaction segment was injected into the flow reactor (Hastelloy coil, 0.75 mm inner diameter, 1.8 mL internal volume) set at 100° C., and passed through the reactor at 180 μL min$^{-1}$ (10 minute residence time). Upon exiting the reactor, the reaction mixture was loaded directly into an injection loop and purified using reverse phase HPLC(C8, acetonitrile/water (0.1% ammonium acetate), 5-100%) to give 0.0009 g (4%) of the title compound. $^1$H NMR (400 MHz, DMSO-$d_6$/$D_2$O) δ 8.03 (d, J=2.44 Hz, 1H), 7.56 (s, 1H), 7.38 (dd, J=8.54, 2.44 Hz, 1H), 7.16 (d, J=8.54 Hz, 1H), 6.97 (s, 1H), 6.78 (m, J=8.85, 8.85 Hz, 2H), 6.51 (m, J=9.31, 4.43 Hz, 2H), 4.59 (m, 2H), 4.06 (s, 3H), 2.71 (s, 1H), 2.67 (m, 3H), 2.44 (m, 4H), 1.54 (m, 4H), 1.43 (m, 2H). MS (APCI+) m/z 500.2 (M+H)$^+$.

Example 49

2-(2-bromo-5-fluorophenyl)-N-(5-(4-fluorophenyl)-11-methyl-1-oxo-2,4,5,11-tetrahydro-1H-2,5,11-triazadibenzo[cd,h]azulen-8-yl)acetamide A stock solution of Example 23e and N,N-diisopropylethylamine (0.14 M and 0.40 M in N,N-dimethylacetamide, respectively, 287 μL) and 2-(2-bromo-5-fluorophenyl)acetic acid (0.4 M in N,N-dimethylacetamide, 124 μL), and 2-(3H-[1,2,3]triazolo[4,5-b]pyridin-3-yl)-1,1,3,3-tetramethylisouronium hexafluorophosphate(V) (0.21 M in N,N-dimethylacetamide, 287 μL) were aspirated from their respective source vials, mixed through a perfluoroalkoxy mixing tube (0.2 mm inner diameter), and loaded into an injection loop. The reaction segment was injected into the flow reactor (Hastelloy coil, 0.75 mm inner diameter, 1.8 mL internal volume) set at 100° C. and passed through the reactor at 180 μL per minute (10 minute residence time). Upon exiting the reactor, the reaction mixture was loaded directly into an injection loop and purified by reverse phase HPLC(C8, acetonitrile/water (0.1% ammonium acetate), 5-100%) to give 0.0058 g (24%) of the title compound. $^1$H NMR (400 MHz, DMSO-$d_6$/$D_2$O) δ 8.14 (d, J=2.44 Hz, 1H), 7.68 (dd, J=8.85, 5.49 Hz, 1H), 7.65 (s, 1H), 7.42 (dd, J=8.54, 2.44 Hz, 1H), 7.36 (dd, J=9.61, 3.20 Hz, 1H), 7.21 (d, J=8.54 Hz, 1H), 7.14 (td, J=8.54, 3.36 Hz, 1H), 7.04 (s, 1H), 6.82 (m, 2H), 6.49 (m, 2H), 5.02 (d, J=15.87 Hz, 1H), 4.18 (d, J=16.78 Hz, 1H), 4.03 (s, 3H), 3.92 (s, 2H). MS (APCI+) m/z 575.1 (M+H)$^+$.

Example 50

2-(2,5-dichlorophenyl)-N-(5-(4-fluorophenyl)-11-methyl-1-oxo-2,4,5,11-tetrahydro-1H-2,5,11-triazadibenzo[cd,h]azulen-8-yl)acetamide Example 50 was prepared according to the procedure used for the preparation of Example 49, substituting 2-(2,5-dichlorophenyl)acetic acid for 2-(2-bromo-5-fluorophenyl)acetic acid, to give 0.0041 g (18%) of the title compound. $^1$H NMR (400 MHz, DMSO-$d_6$/$D_2$O) δ 8.13 (d, J=2.44 Hz, 1H), 7.65 (s, 1H), 7.57 (d, J=2.44 Hz, 1H), 7.52 (m, 1H), 7.41 (m, 2H), 7.21 (d, J=8.54 Hz, 1H), 7.04 (s, 1H), 6.82 (m, 2H), 6.48 (m, 2H), 5.02 (d, J=16.17 Hz, 1H), 4.18 (d, J=17.09 Hz, 1H), 4.03 (s, 3H), 3.91 (s, 2H). MS (APCI+) m/z 547.1 (M+H)$^+$.

Example 51

2-(5-fluoro-2-(trifluoromethyl)phenyl)-N-(5-(4-fluorophenyl)-11-methyl-1-oxo-2,4,5,11-tetrahydro-1H-2,5,11-triazadibenzo[cd,h]azulen-8-yl)acetamide Example 51 was prepared according to the procedure used for the preparation of Example 49, substituting 2-(5-fluoro-2-(trifluoromethyl)phenyl)acetic acid for 2-(2-bromo-5-fluorophenyl)acetic acid, to give 0.0111 g (47%) of the title compound. $^1$H NMR (400 MHz, DMSO-$d_6$/$D_2$O) δ 8.13 (d, J=2.44 Hz, 1H), 7.83 (dd, J=8.85, 5.49 Hz, 1H), 7.64 (s, 1H), 7.45 (dd, J=9.77, 2.44 Hz, 1H), 7.37 (m, 2H), 7.21 (d, J=8.54 Hz, 1H), 7.04 (s, 1H), 6.83 (m, 2H), 6.48 (m, 2H), 5.02 (d, J=16.78 Hz, 1H), 4.18 (d, J=16.48 Hz, 1H), 4.03 (s, 3H), 4.01 (s, 2H). MS (APCI+) m/z 565.2 (M+H)$^+$.

Example 52

2-(2,5-difluorophenyl)-N-(5-(4-fluorophenyl)-11-methyl-1-oxo-2,4,5,11-tetrahydro-1H-2,5,11-triazadibenzo[cd,h]azulen-8-yl)acetamide Example 52 was prepared according to the procedure used for the preparation of Example 49, substituting 2-(2,5-difluorophenyl)acetic acid for 2-(2-bromo-5-fluorophenyl)acetic acid, to give 0.0061 g (29%) of the title compound. $^1$H NMR (400 MHz, DMSO-$d_6$/$D_2$O) δ 8.12 (d, J=2.44 Hz, 1H), 7.65 (s, 1H), 7.42 (dd, J=8.54, 2.44 Hz, 1H), 7.25 (m, 4H), 7.04 (s, 1H), 6.83 (m, 2H), 6.48 (m, 2H), 5.02 (d, J=15.56 Hz, 1H), 4.18 (d, J=16.48 Hz, 1H), 4.04 (s, 3H), 3.80 (s, 2H). MS (APCI+) m/z 515.2 (M+H)$^+$.

Example 53

2-(2,5-dimethylphenyl)-N-(5-(4-fluorophenyl)-11-methyl-1-oxo-2,4,5,11-tetrahydro-1H-2,5,11-triazadibenzo[cd,h]azulen-8-yl)acetamide Example 53 was prepared according to the procedure used for the preparation of Example 49, substituting 2-(2,5-dimethylphenyl)acetic acid for 2-(2-bromo-5-fluorophenyl)acetic acid, to give 0.0086 g (41%) of the title compound. $^1$H NMR (400 MHz, DMSO-$d_6$/$D_2$O) δ 8.12 (d, J=2.14 Hz, 1H), 7.65 (s, 1H), 7.44 (dd, J=8.54, 2.44 Hz, 1H), 7.20 (d, J=8.54 Hz, 1H), 7.08 (m, 2H), 7.04 (s, 1H), 6.99 (dd, J=7.48, 1.37 Hz, 1H), 6.82 (m, 2H), 6.48 (m, 2H), 5.02 (d, J=17.09 Hz, 1H), 4.18 (d, J=16.17 Hz, 1H), 4.03 (s, 3H), 3.69 (s, 2H), 2.28 (s, 3H), 2.27 (s, 3H). MS (APCI+) m/z 507.3 (M+H)$^+$.

Example 54

N-(5-(4-fluorophenyl)-11-methyl-1-oxo-2,4,5,11-tetrahydro-1H-2,5,11-triazadibenzo[cd,h]azulen-8-yl)-2-phenylacetamide Example 54 was prepared according to the procedure used for the preparation of Example 49, substituting 2-phenylacetic acid for 2-(2-bromo-5-fluorophenyl)acetic acid, to give 0.0089 g, (44%) of the title compound. $^1$H NMR (400 MHz, DMSO-$d_6$/$D_2$O) δ 8.09 (d, J=2.44 Hz, 1H), 7.65 (s, 1H), 7.45 (dd, J=8.54, 2.44 Hz, 1H), 7.38 (m, 4H), 7.28 (m, 1H), 7.20 (d, J=8.54 Hz, 1H), 7.04 (s, 1H), 6.82 (m, 2H), 6.47 (m, 2H), 5.01 (d, J=16.17 Hz, 1H), 4.17 (d, J=16.17 Hz, 1H), 4.04 (s, 3H), 3.69 (s, 2H). MS (APCI+) m/z 479.2 (M+H)$^+$.

Example 55

2-(5-chloro-2-phenoxyphenyl)-N-(5-(4-fluorophenyl)-11-methyl-1-oxo-2,4,5,11-tetrahydro-1H-2,5,11-triazadibenzo[cd,h]azulen-8-yl)acetamide Example 55 was prepared according to the procedure used for the preparation of Example 49, substituting 2-(5-chloro-2-phenoxyphenyl)acetic acid for 2-(2-bromo-5-fluorophenyl)acetic acid, to give 0.0027 g (11%) of the title compound. $^1$H NMR (400 MHz, DMSO-$d_6$/$D_2$O) δ 8.03 (d, J=2.44 Hz, 1H), 7.59 (s, 1H), 7.52 (d, J=2.44 Hz, 1H), 7.36 (m, 4H), 7.16 (d, J=8.54 Hz, 1H), 7.12 (m, 1H), 7.04 (s, 1H), 6.99 (m, 2H), 6.88 (d, J=8.55 Hz, 1H), 6.81 (m, 2H), 6.46 (m, 2H), 5.01 (d, J=18.62 Hz, 1H), 4.17 (d, J=15.56 Hz, 1H), 4.04 (s, 3H), 3.79 (s, 2H). MS (APCI+) m/z 605.1 (M+H)$^+$.

Example 56

N-(5-fluoro-2-methoxybenzyl)-5-(4-fluorophenyl)-11-methyl-1-oxo-2,4,5,11-tetrahydro-1H-2,5,11-triazadibenzo[cd,h]azulene-8-carboxamide Example 56a methyl 4-amino-3-(7-methoxy-1-methyl-1H-pyrrolo[2,3-c]pyridin-3-yl)benzoate Example 56a was prepared according to the procedure used for the preparation of Example 23a, substituting Example 1b for Example 1a and methyl 4-amino-3-bromobenzoate for (2-fluoro-5-nitrophenyl)boronic acid. Purification by flash chromatography (silica gel, 0 to 45% ethyl acetate in dichloromethane) gave 0.44 g (81%) of the title compound.

Example 56b methyl 4-((4-fluorophenyl)amino)-3-(7-methoxy-1-methyl-1H-pyrrolo[2,3-c]pyridin-3-yl)benzoate Example 56a (0.44 g, 1.413 mmol), 1-bromo-4-fluorobenzene (0.495 g, 2.83 mmol), diacetoxypalladium (0.016 g, 0.071 mmol), dicyclohexyl(2',4',6'-triisopropyl-[1,1'-biphenyl]-2-yl)phosphine (X-PHOS) (0.067 g, 0.14 mmol) and cesium carbonate (0.921 g, 2.83 mmol) were combined. Toluene (6.5 mL) and tert-butanol (1.3 mL) were added. The mixture was reacted at 150° C. in a Biotage microwave reactor for 45 minutes. The mixture was cooled to ambient temperature, treated with 3-mercaptopropyl-functionalized silica gel for 10 minutes, filtered through a pad of Celite and concentrated. The residue was purified by flash chromatography (silica gel, 0 to 15% ethyl acetate in dichloromethane) to provide 0.55 g (96%) of the title compound.

Example 56c methyl 4-((4-fluorophenyl)amino)-3-(1-methyl-7-oxo-6,7-dihydro-1H-pyrrolo[2,3-c]pyridin-3-yl)benzoate Example 56b (0.546 g, 1.347 mmol) in methanol (4 mL) was treated with hydrogen chloride solution (4 M in 1,4- dioxane, 10 mL, 40 mmol) and heated at 60° C. for 1.5 hours. Additional hydrogen chloride solution (4 M in 1,4-dioxane, 6 mL, 24 mmol) was added and heating was continued at 65-70° C. The reaction mixture was concentrated, treated with hydrogen chloride solution (4 M in 1,4-dioxane, 6 mL, 24 mmol) and stirred at 80° C. for 2 hours and then at ambient temperature for 4 hours. The reaction mixture was concentrated, neutralized with saturated sodium bicarbonate solution, and partitioned between ethyl acetate and water. The organic layer was washed with saturated aqueous sodium chloride, dried over anhydrous magnesium sulfate, filtered, and concentrated. The concentrate was triturated with dichloromethane and dried under vacuum to give 0.47 g (88%) of the title compound.

Example 56d 5-(4-fluorophenyl)-11-methyl-1-oxo-2,4,5,11-tetrahydro-1H-2,5,11-triazadibenzo[cd,h]azulene-8-carboxylic acid Example 56c (0.504 g, 1.25 mmol) in a mixture of methanol (8 mL), dioxane (4 mL) and water (1 mL) was treated with lithium hydroxide monohydrate (0.524 g, 12.5 mmol) and heated at 80° C. for 1 hour. The reaction mixture was cooled to ambient temperature and neutralized with 2 N aqueous hydrochloric acid solution. A solid precipitated out of solution upon partitioning between ethyl acetate and water, and was isolated by filtration. The organic layer was concentrated to dryness. This residue was combined with the solid precipitate and the mixture was sequentially triturated with water, acetonitrile and methanol and then dried under high vacuum to give 0.25 g (52%) of the title compound.

Example 56e

N-(5-fluoro-2-methoxybenzyl)-5-(4-fluorophenyl)-11-methyl-1-oxo-2,4,5,11-tetrahydro-1H-2,5,11-triazadibenzo[cd,h]azulene-8-carboxamide A stock solution of Example 56d and N,N-diisopropylethylamine (0.15 M and 0.42 M in N,N-dimethylacetamide, respectively, 254 µL) and (5-fluoro-2-methoxyphenyl)-methanamine (0.4 M in N,N-dimethylacetamide, 115 µL), and 2-(3H-[1,2,3]triazolo[4,5-b]pyridin-3-yl)-1,1,3,3-tetramethylisouronium hexafluorophosphate(V) (0.22 M in N,N-dimethylacetamide, 254 µL) were aspirated from their respective source vials, mixed through a perfluoroalkoxy mixing tube (0.2 mm inner diameter), and loaded into an injection loop. The reaction segment was injected into the flow reactor (Hastelloy coil, 0.75 mm inner diameter, 1.8 mL internal volume) set at 100° C., and passed through the reactor at 180 µL min$^{-1}$ (10 minute residence time). Upon exiting the reactor, the reaction mixture was loaded directly into an injection loop and purified by reverse phase HPLC(C8, acetonitrile/water (0.1% ammonium acetate), 5-100%) to give 0.0016 g (8%) of the title compound. $^1$H NMR (400 MHz, DMSO-d$_6$/D$_2$O) δ 8.39 (d, J=2.14 Hz, 1H), 7.88 (s, 1H), 7.79 (dd, J=8.24, 2.14 Hz, 1H), 7.37 (d, J=8.24 Hz, 1H), 7.05 (m, 4H), 6.87 (m, 2H), 6.56 (m, 2H), 4.49 (s, 2H), 4.07 (s, 3H), 4.61 (m, 2H), 3.85 (s, 3H). MS (APCI+) m/z 527.2 (M+H)$^+$.

Example 57

N-(5-fluoro-2-methylbenzyl)-5-(4-fluorophenyl)-11-methyl-1-oxo-2,4,5,11-tetrahydro-1H-2,5,11-triazadibenzo[cd,h]azulene-8-carboxamide Example 57 was prepared according to the procedure used for the preparation of Example 56e, substituting (5-fluoro-2-methylphenyl)methanamine for (5-fluoro-2-methoxyphenyl)-methanamine, to give 0.0032 g (16%) of the title compound. $^1$H NMR (400 MHz, DMSO-d$_6$/D$_2$O) δ 8.39 (d, J=2.14 Hz, 1H), 7.87 (s, 1H), 7.79 (dd, J=8.24, 2.14 Hz, 1H), 7.37 (d, J=8.24 Hz, 1H), 7.24 (dd, J=8.24, 6.10 Hz, 1H), 7.06 (s, 1H), 7.01 (m, 2H), 6.87 (m, 2H), 6.56 (m, 2H), 4.50 (s, 2H), 4.64 (m, 2H), 4.07 (s, 3H), 2.33 (s, 3H). MS (APCI+) m/z 511.2 (M+H)$^+$.

Example 58

N-(2-bromo-5-fluorobenzyl)-5-(4-fluorophenyl)-11-methyl-1-oxo-2,4,5,11-tetrahydro-1H-2,5,11-triazadibenzo[cd,h]azulene-8-carboxamide Example 58 was prepared according to the procedure used for the preparation of Example 56e, substituting (2-bromo-5-fluorophenyl)methanamine for (5-fluoro-2-methoxyphenyl)-methanamine, to give 0.0037 g (17%) of the title compound. $^1$H NMR (400 MHz, DMSO-d$_6$/D$_2$O) δ 8.41 (d, J=2.14 Hz, 1H), 7.87 (s, 1H), 7.80 (dd, J=8.24, 2.14 Hz, 1H), 7.71 (dd, J=8.70, 5.34 Hz, 1H), 7.38 (d, J=8.24 Hz, 1H), 7.16 (m, 2H), 7.06 (s, 1H), 6.87 (m, 2H), 6.57 (m, 2H), 4.55 (s, 2H), 4.07 (s, 3H), 4.56 (m, 2H). MS (APCI+) m/z 575.1 (M+H)$^+$.

Example 59

5-(4-fluorophenyl)-N-(1-(4-fluorophenyl)ethyl)-11-methyl-1-oxo-2,4,5,11-tetrahydro-1H-2,5,11-triazadibenzo[cd,h]azulene-8-carboxamide Example 59 was prepared according to the procedure used for the preparation of Example 56e, substituting 1-(4-fluorophenyl)ethanamine for (5-fluoro-2-methoxyphenyl)-methanamine, to give 0.0085 g (43%) of the title compound. $^1$H NMR (400 MHz, DMSO-d$_6$/D$_2$O) δ 8.33 (d, J=2.14 Hz, 1H), 7.88 (s, 1H), 7.75 (dd, J=8.09, 1.98 Hz, 1H), 7.47 (m, 2H), 7.34 (d, J=8.24 Hz, 1H), 7.18 (m, 2H), 7.06 (s, 1H), 6.86 (m, 2H), 6.54 (m, 2H), 5.21 (q, J=7.02 Hz, 1H), 4.56 (m, 2H), 4.07 (s, 3H), 1.53 (d, J=7.02 Hz, 3H). MS (APCI+) m/z 511.1 (M+H)$^+$.

Example 60

N-(2-chloro-5-fluorobenzyl)-5-(4-fluorophenyl)-11-methyl-1-oxo-2,4,5,11-tetrahydro-1H-2,5,11-triazadibenzo[cd,h]azulene-8-carboxamide Example 60 was prepared according to the procedure used for the preparation of Example 56e, substituting (2-chloro-5-fluorophenyl)methanamine for (5-fluoro-2-methoxyphenyl)-methanamine, to give 0.0044 g (22%) of the title compound. $^1$H NMR (400 MHz, DMSO-d$_6$/D$_2$O) δ 8.40 (d, J=2.14 Hz, 1H), 7.87 (s, 1H), 7.79 (dd, J=8.09, 2.29 Hz, 1H), 7.54 (m, 1H), 7.38 (d, J=8.24 Hz, 1H), 7.21 (d, J=8.85 Hz, 2H), 7.06 (s, 1H), 6.87 (m, 2H), 6.57 (m, 2H), 4.59 (s, 2H), 4.07 (s, 3H), 4.66 (m, 2H). MS (APCI+) m/z 531.1 (M+H)$^+$.

Example 61

N-(1-(2,4-dichlorophenyl)ethyl)-5-(4-fluorophenyl)-11-methyl-1-oxo-2,4,5,11-tetrahydro-1H-2,5,11-triazadibenzo[cd,h]azulene-8-carboxamide Example 61 was prepared according to the procedure used for the preparation of Example 56e, substituting 1-(2,4-dichlorophenyl)ethanamine for (5-fluoro-2-methoxyphenyl)-methanamine, to give 0.0082 g (38%) of the title compound. $^1$H NMR (400 MHz, DMSO-$d_6$/D$_2$O) δ 8.34 (d, J=2.14 Hz, 1H), 7.88 (s, 1H), 7.75 (dd, J=8.24, 2.14 Hz, 1H), 7.59 (m, 2H), 7.45 (dd, J=8.54, 2.14 Hz, 1H), 7.35 (d, J=8.24 Hz, 1H), 7.06 (s, 1H), 6.87 (m, 2H), 6.55 (m, 2H), 5.43 (m, 1H), 4.08 (s, 3H), 4.40 (m, 2H), 1.50 (d, J=7.02 Hz, 3H). MS (APCI+) m/z 561.1 (M+H)$^+$.

Example 62

N-((1-benzyl-1H-pyrazol-4-yl)methyl)-5-(4-fluorophenyl)-11-methyl-1-oxo-2,4,5,11-tetrahydro-1H-2,5,11-triazadibenzo[cd,h]azulene-8-carboxamide Example 62 was prepared according to the procedure used for the preparation of Example 56e, substituting (1-benzyl-1H-pyrazol-4-yl)methanamine for (5-fluoro-2-methoxyphenyl)-methanamine, to give 0.0089 g (42%) of the title compound. $^1$H NMR (400 MHz, DMSO-$d_6$/D$_2$O) δ 8.32 (d, J=2.14 Hz, 1H), 7.85 (s, 1H), 7.77 (s, 1H), 7.72 (dd, J=8.24, 2.14 Hz, 1H), 7.47 (s, 1H), 7.32 (m, 6H), 7.05 (s, 1H), 6.86 (m, 2H), 6.54 (m, 2H), 5.28 (s, 2H), 4.37 (s, 2H), 4.06 (s, 3H), 4.44 (m, 2H). MS (APCI+) m/z 559.2 (M+H)$^+$.

Example 63

N-benzyl-5-(4-fluorophenyl)-11-methyl-1-oxo-2,4,5,11-tetrahydro-1H-2,5,11-triazadibenzo[cd,h]azulene-8-carboxamide Example 63 was prepared according to the procedure used for the preparation of Example 56e, substituting phenylmethanamine for (5-fluoro-2-methoxyphenyl)-methanamine, to give 0.0034 g (18%) of the title compound. $^1$H NMR (400 MHz, DMSO-$d_6$/D$_2$O) δ 8.37 (d, J=2.14 Hz, 1H), 7.86 (s, 1H), 7.77 (dd, J=8.24, 2.14 Hz, 1H), 7.37 (m, J=4.27 Hz, 5H), 7.28 (m, 1H), 7.06 (s, 1H), 6.86 (m, 2H), 6.55 (m, 2H), 4.55 (s, 2H), 4.06 (s, 3H), 4.58 (m, 2H). MS (APCI+) m/z 479.3 (M+H)$^+$.

Example 64

N-(2,5-difluorobenzyl)-5-(4-fluorophenyl)-11-methyl-1-oxo-2,4,5,11-tetrahydro-1H-2,5,11-triazadibenzo[cd,h]azulene-8-carboxamide Example 64 was prepared according to the procedure used for the preparation of Example 56e, substituting (2,5-difluorophenyl)methanamine for (5-fluoro-2-methoxyphenyl)-methanamine, to give 0.0043 g (22%) of the title compound. $^1$H NMR (400 MHz, DMSO-$d_6$/D$_2$O) δ 8.37 (d, J=2.14 Hz, 1H), 7.87 (s, 1H), 7.77 (dd, J=8.24, 2.14 Hz, 1H), 7.36 (m, 1H), 7.22 (m, 3H), 7.06 (s, 1H), 6.87 (m, 2H), 6.56 (m, 2H), 4.56 (s, 2H), 4.07 (s, 3H), 4.48 (m, 2H). MS (APCI+) m/z 515.2 (M+H)$^+$.

Example 65

2-(5-fluoro-2-methoxyphenyl)-N-(5-(4-fluorophenyl)-11-methyl-1-oxo-2,4,5,11-tetrahydro-1H-2,5,11-triazadibenzo[cd,h]azulen-8-yl)acetamide A stock solution of Example 23e and N,N-diisopropylethylamine (0.09 M and 0.25 M in N,N-dimethylacetamide, respectively, 450 µL, 0.2 mmol Example 23e and 0.6 mmol N,N-diisopropylethylamine), 2-(3H-[1,2,3]triazolo[4,5-b]pyridin-3-yl)-1,1,3,3-tetramethylisouronium hexafluorophosphate(V) (0.14 M in N,N-dimethylacetamide, 450 µL, 0.3 mmol), and 2-(5-fluoro-2-methoxyphenyl)acetic acid (0.40 M in N,N-dimethylacetamide, 125 µL, 0.24 mmol) were aspirated from their respective source vials, mixed through a perfluoroalkoxy mixing tube (0.2 mm inner diameter), and loaded into an injection loop. The reaction segment was injected into the flow reactor (Hastelloy coil, 0.75 mm inner diameter, 1.8 mL internal volume) set at 100° C., and passed through the reactor at 180 µL min$^{-1}$ (10 minute residence time). Upon exiting the reactor, the reaction mixture was loaded directly into an injection loop and purified using reverse phase HPLC(C8, acetonitrile/water (0.1% TFA), 5-100%) to give 0.0243 g (91%) of the title compound as the TFA salt. $^1$H NMR (400 MHz, DMSO-$d_6$/D$_2$O) δ 10.28 (s, 1H), 8.12 (d, J=2.44 Hz, 1H), 7.65 (s, 1H), 7.42 (dd, J=8.54, 2.44 Hz, 1H), 7.20 (d, J=8.54 Hz, 1H), 7.11 (m, 2H), 7.04 (s, 1H), 7.01 (m, 1H), 6.83 (m, 2H), 6.48 (m, 2H), 5.02 (d, J=15.56 Hz, 1H), 4.18 (d, J=15.87 Hz, 1H), 4.04 (s, 3H), 3.79 (s, 3H), 3.70 (s, 2H). MS (APCI+) m/z 527.1 (M+H)$^+$.

Example 66

2-(5-fluoro-2-nitrophenyl)-N-(5-(4-fluorophenyl)-11-methyl-1-oxo-2,4,5,11-tetrahydro-1H-2,5,11-triazadibenzo[cd,h]azulen-8-yl)acetamide Example 66 was prepared according to the procedure used for the preparation of Example 65, substituting 2-(5-fluoro-2-nitrophenyl)acetic acid for 2-(5-fluoro-2-methoxyphenyl) acetic acid, to give 0.0171 g (63%) of the title compound as the TFA salt. $^1$H NMR (400 MHz, DMSO-$d_6$/D$_2$O) δ 10.47 (s, 1H), 8.23 (dd, J=9.00, 5.34 Hz, 1H), 8.08 (d, J=2.44 Hz, 1H), 7.63 (s, 1H), 7.52 (dd, J=9.46, 2.75 Hz, 1H), 7.44 (m, 1H), 7.39 (dd, J=8.54, 2.44 Hz, 1H), 7.21 (d, J=8.54 Hz, 1H), 7.04 (s, 1H), 6.83 (m, 2H), 6.49 (m, 2H), 5.02 (d, J=15.87 Hz, 1H), 4.18 (m, 3H), 4.03 (s, 3H). MS (APCI+) m/z 542.0 (M+H)$^+$.

Example 67

8-amino-5-(2,4-difluorophenyl)-11-methyl-2,4,5,11-tetrahydro-1H-2,5,6,11-tetraazadibenzo[cd,h]azulen-1-one

Example 67a 3-bromo-N-(2,4-difluorophenyl)-5-nitropyridin-2-amine

A mixture of 3-bromo-2-chloro-5-nitropyridine (2.374 g, 10 mmol) and 2,4-difluoroaniline (2.58 g, 20 mmol) in dimethylsulfoxide (20 mL) was heated at 100° C. for 2 hours. After cooling, the reaction mixture was partitioned between water and ethyl acetate. The organic layer was separated, and the aqueous layer was extracted with additional ethyl acetate twice. The combined organic layers were washed with saturated aqueous sodium chloride, dried over anhydrous magnesium sulfate filtered, and concentrated. The residue was purified on silica gel eluting with 1:20 ethyl acetate/heptanes to give the title compound (1.75 g, 5.30 mmol, 53.0% yield) as yellow crystals.

Example 67b

N-(2,4-difluorophenyl)-3-(7-methoxy-1-methyl-1H-pyrrolo[2,3-c]pyridin-3-yl)-5-nitropyridin-2-amine A mixture of Example 1b (0.1 g, 0.347 mmol), Example 67a (0.137 g, 0.416 mmol), 1,3,5,7-tetramethyl-6-phenyl-2, 4,8-trioxa-6-phosphaadamantane (0.012 g, 0.041 mmol), tris(dibenzylideneacetone)dipalladium(0) (9.53 mg, 10.41 μmol), and potassium phosphate (0.184 g, 0.868 mmol) in dioxane (2 mL) and water (0.5 mL) was degassed and back-filled with nitrogen several times. The reaction was heated at 60° C. for 4 hours, during which time a solid formed. The reaction mixture was partitioned between water and ethyl acetate. Enough ethyl acetate was used to dissolve the solid completely. The aqueous layer was extracted with additional ethyl acetate twice. The combined organic layers were washed with saturated aqueous sodium chloride, dried over anhydrous magnesium sulfate, filtered, and concentrated. The residue triturated with 1:1 ethyl acetate/hexanes to give the title compound (0.095 g, 0.231 mmol, 66.5% yield).

Example 67c

A mixture of Example 67b (0.09 g, 0.219 mmol) and hydrogen chloride (5.47 mL, 21.88 mmol, 4 M) in dioxane (10 mL) was heated at 90° C. overnight. The solvent was evaporated to give the title compound, which was used directly for the next reaction.

Example 67d 5-(2,4-difluorophenyl)-11-methyl-8-nitro-2,4,5,11-tetrahydro-1H-2,5,6,11-tetraazadibenzo[cd,h]azulen-1-one A mixture of Example 67c (0.09 g, 0.227 mmol) and formaldehyde (0.034 g, 1.133 mmol) in acetic acid (5 mL) was heated at 100° C. for three days. The solvent was removed under reduced pressure to give the crude product, which was used for the next reaction directly.

Example 67e 8-amino-5-(2,4-difluorophenyl)-11-methyl-2,4,5,11-tetrahydro-1H-2,5,6,11-tetraazadibenzo[cd,h]azulen-1-one A mixture of Example 67d, iron powder (0.061 g, 1.099 mmol), and ammonia hydrochloride (0.024 g, 0.440 mmol) in tetrahydrofuran (2 mL), water (0.2 mL) and ethanol (2 mL) was heated at 90° C. for 2 hours. The solid was filtered off, and washed with ethyl acetate several times. The eluant was then poured into water. The organic layer was separated, and the aqueous layer was extracted with ethyl acetate several times. The combined organic layers were washed with saturated aqueous sodium chloride, dried over anhydrous magnesium sulfate, filtered, and concentrated. The residue was purified by reverse phase HPLC(C18, $CH_3CN$/water (0.1% TFA), 0-100%) to give the title compound as a bis TFA salt (0.045 g, 0.074 mmol, 33.7% yield). $^1$H NMR (500 MHz, DMSO-$d_6$) δ 10.83 (d, J=5.8 Hz, 1H), 7.83 (s, 1H), 7.68 (m, 1H), 7.59 (d, J=2.75 Hz, 1H), 7.10-7.16 (m, 1H), 6.90-7.02 (m, 2H), 6.82 (d, J=5.8 Hz, 1H), 4.62 9S, 2h), 4.12 (s, 3H). MS (DCI+) m/z 380.1 (M+H)$^+$.

Example 68

N-(5-(2,4-difluorophenyl)-11-methyl-1-oxo-2,4,5,11-tetrahydro-1H-2,5,6,11-tetraazadibenzo[cd,h]azulen-8-yl)ethanesulfonamide A mixture of Example 67e (0.045 g, 0.074 mmol), ethanesulfonyl chloride (0.038 g, 0.296 mmol), and triethylamine (0.060 g, 0.593 mmol) in dichloromethane (3 mL) was stirred at ambient temperature for 3 hours. The solvent was evaporated, and the residue was taken up in dioxane (4 mL) and 2.0 N NaOH (2 mL). The reaction mixture was heated at 90° C. for 1 hour. The solvents were partially removed, and the residue was partitioned between water and ethyl acetate. The aqueous layer was neutralized with 10% HCl and extracted with additional ethyl acetate twice. The combined organic layers were washed with saturated aqueous sodium chloride, dried over anhydrous magnesium sulfate, filtered, and concentrated under reduced pressure. The residue was purified by reverse phase HPLC(C18, $CH_3CN$/water (0.1% TFA), 0-100%) to afford 0.029 g (67%) of the title compound as a mono TFA salt. $^1$H NMR (500 MHz, DMSO-$d_6$) δ 10.78 (d, J=5.49, 1H), 9.75 (s, 1H), 7.91 (d, J=2.44 Hz, 1H), 7.83 (s, 1H), 7.80 (d, J=2.44 Hz, 1H), 7.23-7.33 (m, 1H), 7.11-7.16 (m, 1H), 7.01-7.05 (m, 1H), 6.81 (d, J=5.49 Hz, 1H), 4.61 (s, 2H), 4.14 (s, 3H), 3.12 (q, J=7.43 Hz, 2H), 1.25 (t, J=7.32 Hz, 3H). MS (DCI+) m/z 472.1 (M+H)$^+$.

Example 69

8-amino-5-(4-chlorophenyl)-11-methyl-2,4,5,11-tetrahydro-1H-2,5,6,11-tetraazadibenzo[cd,h]azulen-1-one Example 69a 3-bromo-N-(4-chlorophenyl)-5-nitropyridin-2-amine A mixture of 3-bromo-2-chloro-5-nitropyridine (2.374 g, 10 mmol) and 4-chloroaniline (2.55 g, 20.00 mmol) in dimethylsulfoxide (20 mL) was heated at 90° C. for 2 hours. After cooling to ambient temperature, the reaction mixture was partitioned between water and ethyl acetate. The organic layer was separated, and the aqueous layer was extracted with additional ethyl acetate twice. The combined organic layers were washed with saturated aqueous sodium chloride, dried over anhydrous magnesium sulfate, filtered, and concentrated. The residue was purified on silica gel eluting with 1:20 ethyl acetate/heptanes to give the crude product. This material was then triturated with 10% ethyl acetate in heptanes to give title compound (2.25 g, 6.85 mmol, 68.5% yield).

Example 69b

N-(4-chlorophenyl)-3-(7-methoxy-1-methyl-1H-pyrrolo[2,3-c]pyridin-3-yl)-5-nitropyridin-2-amine A mixture of Example 1b (0.2 g, 0.694 mmol), Example 69a (0.274 g, 0.833 mmol), 1,3,5,7-tetramethyl-6-phenyl-2,4,8-trioxa-6-phosphaadamantane (0.024 g, 0.081 mmol), tris(dibenzylideneacetone)dipalladium(0) (0.019 g, 0.021 mmol), and potassium phosphate (0.368 g, 1.735 mmol) in dioxane (4 mL) and water (1 mL) was degassed and back-filled with nitrogen several times. The reaction mixture was heated at 60° C. for 4 hours. The reaction mixture was partitioned between water and ethyl acetate. The aqueous layer was extracted with additional ethyl acetate three times. The combined organic layers were washed with saturated aqueous sodium chloride, dried over anhydrous magnesium sulfate, filtered, and concentrated. The residue was purified by flash column chromatography on silica gel eluting with 60% ethyl acetate in hexanes to give the title product (0.25 g, 0.610 mmol, 88% yield).

Example 69c 3-(2-((4-chlorophenyl)amino)-5-nitropyridin-3-yl)-1-methyl-1H-pyrrolo[2,3-c]pyridin-7(6H)-one A mixture of Example 69b (0.25 g, 0.610 mmol) and hydrogen chloride (12.20 mL, 48.8 mmol, 4 M in dioxane) was heated at 90° C. overnight. The reaction mixture was cooled to ambient temperature, and the solvent was removed under reduced pressure to give the crude product, which was used directly for the next reaction.

Example 69d

A mixture of Example 69c (0.250 g, 0.632 mmol) and formaldehyde (0.095 g, 3.16 mmol) in acetic acid (15 mL) was heated at 90° C. for 2 hours. The reaction mixture was cooled to ambient temperature. The solvent was removed under reduced pressure to give the crude product, which was used directly for the next reaction.

Example 69e 8-amino-5-(4-chlorophenyl)-11-methyl-2,4,5,11-tetrahydro-1H-2,5,6,11-tetraazadibenzo[cd,h]azulen-1-one A mixture of Example 69d (0.25 g, 0.613 mmol), iron (0.171 g, 3.07 mmol), and ammonia hydrochloride (0.066 g, 1.226 mmol) in tetrahydrofuran (5 mL), water (1 mL) and ethanol (5 mL) was heated at 90° C. for 2 hours. The solid was filtered off, and washed with ethyl acetate several times. The eluant was then poured into water. The organic layer was separated, and the aqueous layer was extracted with ethyl acetate several times. The combined organic layers were washed with saturated aqueous sodium chloride, dried over anhydrous magnesium sulfate, filtered, and concentrated. The residue was purified by flash chromatography on silica gel eluting with 20% methanol in ethyl acetate to give the title product. $^1$H NMR (500 MHz, DMSO-$d_6$) δ 10.90 (d, J=5.49, 1H), 7.76-7.77 (m, 2H), 7.61 (d, J=1.83 Hz, 1H), 7.05-7.09 (m, 1H), 6.55 (d, J=9.16 Hz, 2H), 4.88 (s, 2H), 4.06 (s, 3H). MS (DCI+) m/z 378.2 (M+H)$^+$.

Example 70

N-(5-(4-chlorophenyl)-11-methyl-1-oxo-2,4,5,11-tetrahydro-1H-2,5,6,11-tetraazadibenzo[cd,h]azulen-8-yl)ethanesulfonamide A mixture of Example 69e (0.04 g, 0.106 mmol), ethanesulfonyl chloride (0.054 g, 0.2423 mmol), and triethylamine (0.064 g, 0.635 mmol) in dichloromethane (3 mL) was stirred at ambient temperature for 2 hours. The solvent was removed, and the residue was treated with dioxane (3 mL) and 2.0 N NaOH (2 mL). The reaction mixture was heated at 90° C. for 2 hours. The solvents were partially removed, and the residue was partitioned between water and ethyl acetate. The aqueous layer was neutralized with 10% HCl and extracted with additional ethyl acetate twice. The combined organic layers were washed with saturated aqueous sodium chloride, dried over anhydrous magnesium sulfate, filtered, and concentrated under reduced pressure. The residue was purified by reverse phase HPLC(C18, CH$_3$CN/water (0.1% TFA), 0-100%) to afford 0.035 g (56.6%) of the title compound as the TFA salt. $^1$H NMR (500 MHz, DMSO-$d_6$) δ 10.87 (d, J=5.8, 1H), 10.15 (s, 1H), 8.17 (d, J=2.75 Hz, 1H), 8.00 (d, J=2.75 Hz, 1H), 7.82 (s, 1H), 7.09 (d, J=5.8 Hz, 1H), 7.03-7.07 (m, 2H), 6.58-6.62 (m, 2H), 4.62 (s, 2H), 4.07 (s, 3H), 3.26 (q, J=7.32 Hz, 2H), 1.29 (t, J=7.32 Hz, 3H). MS (DCI+) m/z 470.1 (M+H)$^+$.

Example 71

N-(5-(4-chlorophenyl)-11-methyl-1-oxo-2,4,5,11-tetrahydro-1H-2,5,6,11-tetraazadibenzo[cd,h]azulen-8-yl)methanesulfonamide Example 71 was prepared according to the procedure used for the preparation of Example 68, substituting Example 69e for Example 67e, and methanesulfonyl chloride for ethanesulfonyl chloride, respectively, to provide the mono TFA salt of the title compound. $^1$H NMR (500 MHz, DMSO-$d_6$) δ 10.88 (d, J=5.49, 1H), 10.11 (s, 1H), 8.17 (d, J=2.44 Hz, 1H), 8.01 (d, J=2.44 Hz, 1H), 7.83 (s, 1H), 7.09 (d, J=5.49 Hz, 1H), 7.03-7.07 (m, 2H), 6.59-6.63 (m, 2H), 4.63 (s, 2H), 4.07 (s, 3H), 3.17 (s, 3H). MS (DCI+) m/z 456.1 (M+H)$^+$.

Example 72

N-(5-(4-chlorophenyl)-11-methyl-1-oxo-2,4,5,11-tetrahydro-1H-2,5,6,11-tetraazadibenzo[cd,h]azulen-8-yl)acetamide A mixture of Example 69e (0.02 g, 0.053 mmol), triethylamine (53.6 mg, 0.53 mmol), and acetyl chloride (0.019 mL, 0.265 mmol) in dichloromethane (2 mL) was stirred at ambient temperature for 2 hours. Additional acetyl chloride (0.057 mL, 0.795 mmol) and triethylamine (161 mg, 1.59 mmol) were added, and the reaction mixture was stirred for additional 3 hours. The solvent was evaporated, and the residue was treated with dioxane (3 mL) and 2.0 NaOH (1 mL). The reaction mixture was heated at 80° C. for three hours. The solvents were partially removed, and the residue was partitioned between water and ethyl acetate. The aqueous layer was neutralized with 10% HCl and extracted with additional ethyl acetate twice. The combined organic layers were washed with saturated aqueous sodium chloride, dried over anhydrous magnesium sulfate, filtered, and concentrated under reduced pressure. The residue was purified by reverse phase HPLC(C18, CH$_3$CN/water (0.1% TFA), 0-100%) to afford 0.018 g (67.3%) of the title compound as the TFA salt. $^1$H NMR (500 MHz, DMSO-$d_6$) δ 10.87 (d, J=5.8, 1H), 10.31 (s, 1H), 8.53 (d, J=2.75 Hz, 1H), 8.42 (d, J=2.44 Hz, 1H), 7.74 (s, 1H), 7.09 (d, J=5.49 Hz, 1H), 7.03-7.07 (m, 2H), 6.57-6.60 (m, 2H), 4.65 (br s, 2H), 4.07 (s, 3H), 2.13 (s, 3H). MS (DCI+) m/z 420.2 (M+H)$^+$.

Example 73

5-(1-acetylpiperidin-4-yl)-8-amino-11-methyl-2,4,5,11-tetrahydro-1H-2,5,11-triazadibenzo[cd,h]azulen-1-one

Example 73a 1-(4-((2-(7-methoxy-1-methyl-1H-pyrrolo[2,3-c]pyridin-3-yl)-4-nitrophenyl)amino)piperidin-1-yl)ethanone Example 23a (0.1 g, 0.332 mmol) and 1-(4-aminopiperidin-1-yl)ethanone (0.052 g, 0.365 mmol) were dissolved in dimethyl sulfoxide (0.6 mL), treated with N-ethyl-N-isopropylpropan-2-amine (0.29 mL, 1.66 mmol) and stirred at 90° C. overnight. Additional 1-(4-aminopiperidin-1-yl)ethanone (0.052 g, 0.365 mmol) and N-ethyl-N-isopropylpropan-2-amine (0.29 mL, 1.66 mmol) were added and heating was continued at 90° C. for another 24 hours. The reaction mixture was partitioned between ethyl acetate and water. The organic layer was washed with saturated aqueous sodium chloride, treated with mercapto-functionalized silica gel for 20 minutes, dried over anhydrous magnesium sulfate, filtered through a plug of Celite and concentrated. The residue was purified by flash chromatography (silica gel, 0-7% methanol in dichloromethane) to provide 0.156 g (>100%) of the title compound with ethyl acetate as an excipient.

Example 73b 3-(2-((1-acetylpiperidin-4-yl)amino)-5-nitrophenyl)-1-methyl-1H-pyrrolo[2,3-c]pyridin-7(6H)-one Example 73a (0.99 g, 2.16 mmol) was dissolved in 1,4-dioxane (5 mL) and treated with hydrogen chloride solution (4 M in 1,4-dioxane) (10.8 mL, 43.2 mmol). The mixture was stirred for 10 minutes at 80° C. Methanol (1 mL) was added and heating was continued at 80° C. for two hours. The reaction mixture was concentrated to dryness. The residue was converted to the free base using a Varian ion exchange Bond Elut Plex column (1-7 N ammonia in methanol). The material from the ion exchange procedure was concentrated, slurried in methanol, and the solid collected by filtration to give 0.092 g (>100%) of the title compound as the ammonium salt.

Example 73c 5-(1-acetylpiperidin-4-yl)-11-methyl-8-nitro-2,4,5,11-tetrahydro-1H-2,5,11-triazadibenzo[cd,h]azulen-1-one To Example 73b (0.41 g, 1 mmol) and paraformaldehyde (0.06 g, 2 mmol) in a 20-mL microwave vial was added acetic acid (5 mL). The vial was capped and heated at 90° C. for 1 hour. The reaction mixture was concentrated and dried under high vacuum to give the title compound.

Example 73d 5-(1-acetylpiperidin-4-yl)-8-amino-11-methyl-2,4,5,11-tetrahydro-1H-2,5,11-triazadibenzo[cd,h]azulen-1-one To Example 73c (0.421 g, 1 mmol) in tetrahydrofuran (4 mL), ethanol (2 mL) and water (1 mL) was added zinc dust (0.981 g, 15 mmol) and ammonium chloride (0.535 g, 10 mmol). The mixture was stirred for 45 minutes at ambient temperature. The reaction mixture was filtered through Celite rinsing with tetrahydrofuran and methanol. The filtrate was concentrated and partitioned between ethyl acetate and water. The aqueous layer was exhaustively extracted with ethyl acetate and combinations of dichloromethane and isopropanol. The combined organic layers were washed with saturated aqueous sodium chloride, dried over anhydrous magnesium sulfate, filtered, and concentrated. The residue was purified by flash chromatography (silica gel, 0-20% methanol in dichloromethane) to give 0.1 g (24%) of the title compound. $^1$H NMR (400 MHz, DMSO-$d_6$) δ 10.71 (d, J=5.19 Hz, 1H), 7.52 (s, 1H), 6.80 (d, J=2.44 Hz, 1H), 6.77 (dd, J=8.39, 1.68 Hz, 1H), 6.72 (d, J=5.19 Hz, 1H), 6.31 (dd, J=8.24, 2.75 Hz, 1H), 4.84 (s, 2H), 4.15 (m, 2H), 4.10 (s, 3H), 3.82 (d, J=15.87 Hz, 1H), 3.64 (dd, J=27.77, 13.73 Hz, 1H), 2.77 (m, 2H), 2.38 (m, 1H), 1.88 (m, 4H), 1.17 (m, 3H). MS (ESI+) m/z 392.2 (M+H)$^+$.

Example 74

N-(5-(1-acetylpiperidin-4-yl)-11-methyl-1-oxo-2,4,5,11-tetrahydro-1H-2,5,11-triazadibenzo[cd,h]azulen-8-yl)ethanesulfonamide Example 73d (0.02 g, 0.051 mmol) in pyridine (0.5 mL) was treated sequentially with ethanesulfonyl chloride (0.015 ml, 0.153 mmol) and N,N-dimethylpyridin-4-amine (0.00156 g, 0.013 mmol). The mixture was stirred at ambient temperature for 2 hours and 20 minutes. Ethanol (0.5 mL) and potassium carbonate (0.071 g, 0.511 mmol) were added and the mixture was stirred at ambient temperature for 4.5 hours and then at 50° C. overnight. The reaction mixture was cooled to room temperature, partitioned between ethyl acetate and water, washed with saturated aqueous sodium chloride, dried over anhydrous magnesium sulfate, filtered, and concentrated. The residue was purified by flash chromatography (silica gel, 0-10% methanol in dichloromethane) to give 0.0094 g (38%) of the title compound. $^1$H NMR (400 MHz, DMSO-$d_6$) δ 10.73 (d, J=5.49 Hz, 1H), 9.59 (s, 1H), 7.56 (s, 1H), 7.44 (d, J=2.44 Hz, 1H), 7.06 (d, J=8.54 Hz, 1H), 6.92 (dd, J=8.39, 2.59 Hz, 1H), 6.77 (d, J=5.80 Hz, 1H), 4.25 (t, J=13.89 Hz, 2H), 4.11 (s, 3H), 3.72 (m, 2H), 3.07 (m, J=7.32, 7.32, 7.32 Hz, 3H), 2.87 (m, 1H), 2.42 (t, J=12.05 Hz, 1H), 1.93 (s, 3H), 1.75 (m, 1H), 1.30 (m, 3H), 1.23 (t, J=7.32 Hz, 3H). MS (ESI+) m/z 484.2 (M+H)$^+$.

Example 75

N-(5-(1-acetylpiperidin-4-yl)-11-methyl-1-oxo-2,4,5,11-tetrahydro-1H-2,5,11-triazadibenzo[cd,h]azulen-8-yl)-2-(2-methylthiazol-5-yl)acetamide A mixture of Example 73d (0.02 g, 0.051 mmol), 2-(2-methylthiazol-5-yl)acetic acid (0.012 g, 0.077 mmol), and 2-(3H-[1,2,3]triazolo[4,5-b]pyridin-3-yl)-1,1,3,3-tetramethylisouronium hexafluorophosphate(V) (0.029 g, 0.077 mmol) in N,N-dimethyl acetamide (0.5 mL) was treated with N-ethyl-N-isopropylpropan-2-amine (0.027 mL, 0.153 mmol) and stirred at ambient temperature for 22 hours. The reaction mixture was partitioned between ethyl acetate and water and washed with saturated aqueous sodium chloride. The aqueous layers were combined, saturated with solid sodium chloride and extracted with ethyl acetate (4×100 mL). The organic layers were combined, dried over anhydrous magnesium sulfate, filtered and concentrated. The residue was purified by flash chromatography (silica gel, 0-15% methanol in dichloromethane). The material was further purified by reverse phase HPLC(C18, acetonitrile/water (0.1% TFA), 10-100%) to provide 0.0258 g (78%) of the title compound as the TFA salt. $^1$H NMR (400 MHz, PYRIDINE-$d_5$) δ 11.24 (s, 1H), 10.34 (s, 1H), 8.34 (d, J=2.44 Hz, 1H), 7.62 (s, 1H), 7.54 (d, J=2.75 Hz, 1H), 7.35 (s, 1H), 7.21 (d, J=8.54 Hz, 1H), 6.89 (s, 1H), 4.20 (s, 2H), 4.13 (s, 3H), 4.07 (s, 2H), 3.64 (m, 1H), 3.25 (m, 1H), 2.63 (m, 2H), 2.55 (s, 3H), 2.59 (m, 1H), 1.93 (s, 3H), 1.69 (m, 2H), 1.50 (m, 2H). MS (ESI+) m/z 531.1 (M+H)$^+$.

Example 76

N-(5-(1-acetylpiperidin-4-yl)-11-methyl-1-oxo-2,4,5,11-tetrahydro-1H-2,5,11-triazadibenzo[cd,h]azulen-8-yl)-2-(2-chloro-5-fluorophenyl)acetamide Example 73d (0.02 g, 0.051 mmol) in dichloromethane (0.5 mL) was treated with a solution of 2-(2-chloro-5-fluorophenyl)acetyl chloride (0.022 g, 0.106 mmol) in dichloromethane (0.2 mL) and triethylamine (0.025 mL, 0.179 mmol) and stirred at ambient temperature for 22 hours. The reaction mixture was concentrated. The residue was purified by flash chromatography (silica gel, 0-10% methanol in dichloromethane). It was further purified by reverse phase HPLC(C18, acetonitrile/water (0.1% TFA), 0-90%) to provide 0.0228 g (66%) of the title compound as the TFA salt. $^1$H NMR (400 MHz, PYRIDINE-d$_5$) δ 11.20 (s, 1H), 10.31 (s, 1H), 8.38 (d, J=2.44 Hz, 1H), 7.55 (dd, J=8.54, 2.44 Hz, 1H), 7.42 (dd, J=9.46, 3.05 Hz, 1H), 7.32 (m, 2H), 7.21 (d, J=8.54 Hz, 1H), 6.93 (m, 1H), 6.89 (s, 1H), 4.50 (m, 1H), 4.20 (s, 2H), 4.13 (s, 3H), 4.04 (m, 2H), 3.65 (s, 1H), 3.25 (m, 1H), 2.62 (m, 2H), 1.93 (s, 3H), 1.69 (m, 2H), 1.49 (m, J=23.42, 11.83, 4.12 Hz, 2H). MS (ESI+) m/z 562.1 (M+H)$^+$.

Example 77

N-(5-(1-acetylpiperidin-4-yl)-11-methyl-1-oxo-2,4,5,11-tetrahydro-1H-2,5,11-triazadibenzo[cd,h]azulen-8-yl)acetamide Example 23d (0.0278 g, 0.071 mmol) was treated with a solution of acetyl chloride (0.0101 mL, 0.142 mmol) in dichloromethane (1.5 mL), followed by triethylamine (0.059 mL, 0.426 mmol). The resulting mixture was stirred at ambient temperature for 2.5 hours and then concentrated. The residue was purified by flash chromatography (silica gel, 0-17% methanol in dichloromethane). It was further purified by reverse phase HPLC(C18, acetonitrile/water (0.1% TFA), 0-100%) to provide 0.0296 g (78%) of the title compound as the TFA salt. $^1$H NMR (400 MHz, DMSO-d$_6$) δ 10.42 (s, 1H), 9.54 (s, 1H), 7.86 (d, J=2.44 Hz, 1H), 7.48 (s, 1H), 7.22 (dd, J=8.54, 2.44 Hz, 1H), 7.05 (d, J=8.54 Hz, 1H), 6.74 (s, 1H), 4.26 (m, 1H), 4.12 (s, 3H), 4.08 (m, 2H), 3.76 (m, 2H), 3.09 (m, 1H), 2.79 (m, 1H), 2.04 (s, 3H), 1.91 (s, 3H), 1.57 (m, 2H), 1.36 (m, J=1.22 Hz, 2H). MS (ESI+) m/z 434.1 (M+H)$^+$.

Example 78

6-cyclopropyl-5-(2,4-difluorophenyl)-11-methyl-8-((methylsulfonyl)methyl)-2,4,5,11-tetrahydro-1H-2,5,11-triazadibenzo[cd,h]azulen-1-one

Example 78a 1-bromo-4-((methylsulfonyl)methyl)benzene

A 250 mL round-bottomed flask was charged with 4-bromobenzyl bromide (5 g, 20 mmol) and N,N-dimethylformamide (10.81 mL). Sodium methanesulfinate (3.06 g, 30 mmol) was added. The reaction mixture was stirred at 65° C. for 1 hour. The reaction mixture was cooled to ambient temperature and diluted with water. The resulting suspension was stirred for 10 minutes and filtered. The solid was rinsed with water and dried under house vacuum over the weekend to provide 4.75 g (95%) of the title compound.

Example 78b 2,4-difluoro-N-(4-((methylsulfonyl)methyl)phenyl)aniline

A 100 mL microwave tube was charged with 2,4-difluoroaniline (1.235 mL, 12.26 mmol), Example 78a (3.05 g, 12.26 mmol), diacetoxypalladium (0.055 g, 0.245 mmol), dicyclohexyl(2',4',6'-triisopropyl-[1,1'-biphenyl]-2-yl)phosphine (0.234 g, 0.49 mmol), cesium carbonate (5.59 g, 17.16 mmol), toluene (40.9 mL) and t-butanol (8.17 mL). The tube was sealed, and the reaction mixture was heated in a Milestone Ethos microwave, 5 minute ramp to 150° C., then 10 minutes fixed hold time. The reaction mixture was filtered through a 10 g Celite SPE column and rinsed with ethyl acetate. The filtrate was concentrated. The residue was purified by flash chromatography (20-100% ethyl acetate in heptanes) to provide 3.44 g (94%) of the title compound.

Example 78c 2-bromo-N-(2,4-difluorophenyl)-4-((methylsulfonyl)methyl)aniline A 500 mL round-bottomed flask was charged with Example 78b (3.44 g, 11.57 mmol) and acetic acid (116 mL). The reaction mixture was placed into a water bath. N-bromosuccinimide (2.06 g, 11.57 mmol) was added in 2 portions 10 minutes apart. The reaction mixture was stirred at ambient temperature for 1.5 hours. The reaction mixture was quenched with 200 mL 10% aqueous sodium thiosulfate solution and diluted with water. The reaction mixture was extracted twice with ethyl acetate. The combined organic layers were washed twice with 2 N aqueous sodium hydroxide solution (until the pH of the aqueous was >7) and once with saturated aqueous sodium chloride solution, dried over anhydrous magnesium sulfate, filtered and concentrated. The residue was taken up into ethyl acetate, then treated with heptanes. The resulting slurry was stirred for 30 minutes and filtered to provide 3.82 g (88% yield) of the title compound.

Example 78d 2-cyclopropyl-N-(2,4-difluorophenyl)-4-((methylsulfonyl)methyl)aniline A 5 mL microwave vial was charged with Example 78c (0.2287 g, 0.608 mmol), cyclopropylboronic acid (0.209 g, 2.432 mmol), cesium carbonate (0.99 g, 3.04 mmol) and bis(triphenylphosphine)palladium(II) dichloride (0.021 g, 0.03 mmol). The tube was sealed and the mixture was sparged with nitrogen for 30 minutes. Degassed 1,4-dioxane (2.53 mL) and water (0.507 mL) were added. The reaction mixture was heated at 100° C. overnight. The reaction mixture was partitioned between ethyl acetate and water. The organic layer was washed with saturated aqueous sodium chloride solution, dried over anhydrous magnesium sulfate, filtered and concentrated. The residue was purified by flash chromatography (silica gel, 10-70% ethyl acetate in heptanes) to provide 0.143 g (70%) of the title compound.

Example 78e 2-bromo-6-cyclopropyl-N-(2,4-difluorophenyl)-4-((methylsulfonyl)methyl)aniline Example 78e was prepared according to the procedure used for the preparation of Example 78c, substituting Example 78d for Example 78b, to provide 0.111 g (63%) of the title compound.

Example 78f 2-cyclopropyl-N-(2,4-difluorophenyl)-6-(7-methoxy-1-methyl-1H-pyrrolo[2,3-c]pyridin-3-yl)-4-((methylsulfonyl)methyl)aniline Example 1b (0.066 g, 0.228 mmol), Example 78e (0.1 g, 0.24 mmol), tris(dibenzylideneacetone)dipalladium(0)

(0.00627 g, 0.00685 mmol), (1S,3R,5R,7S)-1,3,5,7-tetramethyl-8-phenyl-2,4,6-trioxa-8-phosphaadamantane (0.00667 g, 0.023 mmol) and sodium carbonate (0.104 g, 0.982 mmol) were combined and sparged with nitrogen for 30 minutes. To this were added nitrogen-sparged 1,4-dioxane (1.1 mL) and water (0.275 mL) via syringe. The reaction mixture was stirred at 60° C. for 5 hours. The reaction mixture was partitioned between ethyl acetate and water. The organic layer was washed with saturated aqueous sodium chloride, treated with 3-mercaptopropyl-functionalized silica gel for 20 minutes, dried over anhydrous magnesium sulfate, filtered through a plug of Celite and concentrated. The residue was purified by flash chromatography (silica gel, 0-10% ethyl acetate in dichloromethane) to give 0.0941 g (83%) of the title compound.

Example 78g 3-(3-cyclopropyl-2-((2,4-difluorophenyl)amino)-5-((methylsulfonyl)methyl)phenyl)-1-methyl-1H-pyrrolo[2,3-c]pyridin-7(6H)-one Example 78f (0.094 g, 0.189 mmol) in methanol (2 mL) was treated with hydrogen chloride solution (4 M in 1,4-dioxane) (0.945 mL, 3.78 mmol) and heated at 90° C. for 3.67 hours. The reaction mixture was cooled to ambient temperature and concentrated. The residue was purified by flash chromatography (silica gel, 0-6% methanol in dichloromethane) to give 0.1 g (>100%) of the title compound.

Example 78h 6-cyclopropyl-5-(2,4-difluorophenyl)-11-methyl-8-((methylsulfonyl)methyl)-2,4,5,11-tetrahydro-1H-2,5,11-triazadibenzo[cd,h]azulen-1-one To a 5-mL microwave vial equipped with a magnetic stirbar was added Example 78g (0.0541 g, 0.112 mmol), paraformaldehyde (0.02 g, 0.671 mmol), and acetic acid (5 mL). The vial was capped and heated at 70° C. for 45 minutes. The reaction mixture was concentrated. The residue was purified by reverse phase HPLC(C18, acetonitrile/water (0.1% TFA), 10-90%). The material was then taken up in tetrahydrofuran (1 mL) and methanol (0.1 mL), treated with sodium hydroxide solution (4 M aqueous) (0.048 mL, 0.191 mmol) and heated at 70° C. for 2 hours. The reaction mixture was cooled to ambient temperature and neutralized with hydrochloric acid solution (2 M aqueous). The resulting mixture was partitioned between ethyl acetate and water, washed with saturated aqueous sodium chloride, dried over anhydrous magnesium sulfate, filtered and concentrated to provide 0.019 g (33.9%) of the title compound. $^1$H NMR (400 MHz, DMSO-$d_6$) δ 10.73 (d, J=5.19 Hz, 1H), 7.76 (s, 1H), 7.67 (s, 1H), 7.06 (m, 1H), 6.83 (s, 1H), 6.75 (d, J=5.19 Hz, 1H), 6.65 (m, 1H), 6.20 (m, 1H), 5.03 (d, J=16.17 Hz, 1H), 4.44 (m, 2H), 4.21 (d, J=16.17 Hz, 1H), 4.09 (s, 3H), 2.94 (s, 3H), 2.01 (m, 1H), 0.83 (m, 1H), 0.67 (m, 1H), 0.58 (m, 1H), 0.23 (m, 1H). MS (ESI+) m/z 496.1 (M+H)$^+$.

Example 79

11-methyl-8-((methylsulfonyl)methyl)-5-(pyridin-2-yl)-2,4,5,11-tetrahydro-1H-2,5,11-triazadibenzo[cd,h]azulen-1-one Example 79a N-(2-(7-methoxy-1-methyl-1H-pyrrolo[2,3-c]pyridin-3-yl)-4-((methylsulfonyl)methyl)phenyl)pyridin-2-amine Example 4a (0.05 g, 0.145 mmol), 2-bromopyridine (0.028 mL, 0.29 mmol), diacetoxypalladium (0.0016 g, 0.00724 mmol), dicyclohexyl(2',4',6'-triisopropyl-[1,1'-biphenyl]-2-yl)phosphine (0.0069 g, 0.014 mmol), and cesium carbonate (0.094 g, 0.29 mmol) were combined in a 5-mL microwave vial. Toluene (1.2 mL) and t-butanol (0.3 mL) were added. The vial was capped and the mixture was reacted at 150° C. for 30 minutes in a Biotage microwave reactor. Additional 2-bromopyridine (0.028 mL, 0.29 mmol), diacetoxypalladium (0.0016 g, 0.00724 mmol) and dicyclohexyl(2',4',6'-triisopropyl-[1,1'-biphenyl]-2-yl)phosphine (0.0069 g, 0.014 mmol) were added and the mixture was reacted in a Biotage microwave reactor for another 40 minutes at 150° C. The reaction mixture was partitioned between ethyl acetate and water. The organic layer was washed with saturated aqueous sodium chloride, treated with 3-mercaptopropyl-functionalized silica gel for 20 minutes, dried over anhydrous magnesium sulfate, filtered through a plug of Celite and concentrated. The residue was purified by flash chromatography (silica gel, 0-90% ethyl acetate in dichloromethane) to give 0.04 g (65.4%) of the title compound.

Example 79b 1-methyl-3-(5-((methylsulfonyl)methyl)-2-(pyridin-2-ylamino)phenyl)-1H-pyrrolo[2,3-c]pyridin-7(6H)-one A mixture of Example 79a (0.062 g, 0.147 mmol) in methanol (1 mL) was treated with hydrogen chloride solution (4 M in 1,4-dioxane) (1 mL, 4 mmol) and heated at 75° C. for 2.5 hours. Additional hydrogen chloride solution (4 M in 1,4-dioxane) (1 mL, 4 mmol) was added and heating was continued for another 3.5 hours. The reaction mixture was concentrated to dryness to provide 0.06 g (92%) of the title compound as the HCl salt.

Example 79c 11-methyl-8-((methylsulfonyl)methyl)-5-(pyridin-2-yl)-2,4,5,11-tetrahydro-1H-2,5,11-triazadibenzo[cd,h]azulen-1-one A mixture of Example 79b (0.06 g, 0.135 mmol) and paraformaldehyde (0.066 g, 2.2 mmol) in acetic acid (1 mL) was heated at 85° C. for 1 hour. The reaction mixture was concentrated to ⅓ of the original volume, treated with sodium hydroxide solution (4 M aqueous) (0.169 mL, 0.674 mmol) until pH 10 was obtained and stirred overnight at ambient temperature. The mixture was heated at 50° C. for 1 hour, basified further to pH 12 and heated at 70° C. for 3 hours. The mixture was cooled to ambient temperature, neutralized with hydrochloric acid solution (2 M aqueous) and partitioned between ethyl acetate and water. The aqueous layer was extracted with ethyl acetate. The organic layers were combined and concentrated. The residue was purified by reverse phase HPLC(C18, acetonitrile/water (0.1% TFA), 0-45%) to provide 0.013 g (18%) of the title compound as the TFA salt. $^1$H NMR (400 MHz, DMSO-$d_6$) δ 10.86 (d, J=5.19 Hz, 1H), 8.00 (d, J=4.88 Hz, 1H), 7.91 (s, 1H), 7.79 (s, 1H), 7.54 (s, 1H), 7.41 (m, 1H), 7.35 (m, 1H), 7.00 (d, J=5.19 Hz, 1H), 6.70 (m, 1H), 6.54 (s, 1H), 5.52 (d, J=15.56 Hz, 1H), 4.56 (m, 2H), 4.19 (d, J=15.26 Hz, 1H), 4.08 (s, 3H), 3.00 (s, 3H). MS (ESI+) m/z 421.1 (M+H)$^+$.

Example 80 tert-butyl 4-(11-methyl-8-((methylsulfonyl)methyl)-1-oxo-1H-2,5,11-triazadibenzo[cd,h]azulen-5(2H, 4H,11H)-yl)piperidine-1-carboxylate To a mixture of Example 6a (0.015 g, 0.044 mmol) and tert-butyl 4-oxopiperidine-1-carboxylate (0.017 g, 0.087 mmol) was added dichloroethane (1 mL) and acetic acid (0.03 mL, 0.524 mmol). The reaction mixture was heated at 50° C. for 2 hours, treated with sodium triacetoxyhydroborate (0.028 g, 0.131 mmol) and heated overnight at 50° C. Additional tert-butyl 4-oxopiperidine-1-carboxylate (0.017 g, 0.087 mmol) was added and the mixture was heated for 1 hour. Additional sodium triacetoxyhydroborate (0.028 g, 0.131 mmol) was added and the mixture was heated over a second night at 50° C. The reaction mixture was cooled to ambient temperature, partitioned between ethyl acetate and water, washed with saturated aqueous sodium chloride, dried over anhydrous magnesium sulfate, filtered and concentrated. The residue was purified by flash chromatography (silica gel, 0-6% methanol in dichloromethane) to give 0.0194 g (84%) of the title compound. $^1$H NMR (500 MHz, DMSO-$d_6$) δ 10.71 (d, J=5.49 Hz, 1H), 7.69 (s, 1H), 7.64 (s, 1H), 7.13 (s, 1H), 6.79 (d, J=5.49 Hz, 1H), 4.40 (m, 2H), 4.11 (s, 3H), 3.87 (m, 2H), 3.73 (m, 1H), 3.63 (m, 1H), 3.19 (m, 1H), 2.91 (s, 3H), 2.66 (m, 2H), 1.67 (m, 1H), 1.58 (m, 1H), 1.45 (m, 2H), 1.38 (s, 9H), 1.23 (m, 1H). MS (ESI+) m/z 526.8 (M+H)$^+$.

Example 81 methyl 11-methyl-8-((methylsulfonyl)methyl)-1-oxo-4,11-dihydro-1H-2,5,11-triazadibenzo[cd,h]azulene-5(2H)-carboxylate A mixture of Example 6a (0.0145 g, 0.042 mmol) in N,N-dimethylacetamide (0.5 mL) was treated sequentially with methyl carbonochloridate (0.016 mL, 0.211 mmol) and N-ethyl-N-isopropylpropan-2-amine (0.074 mL, 0.422 mmol) and stirred overnight at ambient temperature. The reaction mixture was then diluted with methanol (1.2 mL), treated with sodium carbonate (0.011 g, 0.105 mmol) and stirred at ambient temperature for 4 hours. The reaction mixture was partitioned between ethyl acetate and water and washed with saturated aqueous sodium chloride. The aqueous layers were combined and exhaustedly extracted with ethyl acetate. The combined organic layers were dried over anhydrous magnesium sulfate, filtered and concentrated. The residue was purified by reverse phase HPLC(C18, acetonitrile/water (0.1% TFA), 0-50%) to provide 0.0069 g (40.7%) of the title compound. $^1$H NMR (400 MHz, DMSO-$d_6$) δ 10.51 (s, 1H), 7.76 (d, J=1.53 Hz, 1H), 7.69 (s, 1H), 7.29 (m, 1H), 7.23 (m, 1H), 6.79 (s, 1H), 5.00 (d, J=15.56 Hz, 1H), 4.44 (m, 2H), 4.12 (s, 3H), 3.94 (d, J=15.26 Hz, 1H), 3.50 (s, 3H), 2.93 (s, 3H). MS (ESI+) m/z 402.1 (M+H)$^+$.

Example 82

N-(11-methyl-1-oxo-5-(pyridin-2-yl)-2,4,5,11-tetrahydro-1H-2,5,11-triazadibenzo[cd,h]azulen-8-yl)ethanesulfonamide

Example 82a

N-(2-(7-methoxy-1-methyl-1H-pyrrolo[2,3-c]pyridin-3-yl)-4-nitrophenyl)pyridin-2-amine A mixture of Example 23a (0.122 g, 0.405 mmol) and 2-aminopyridine (0.042 g, 0.445 mmol) in dimethyl sulfoxide (6 mL) was treated with potassium 2-methylpropan-2-olate (0.091 g, 0.81 mmol) and stirred at ambient temperature for 23.5 hours. The reaction mixture was partitioned between ethyl acetate and water, washed with saturated aqueous sodium chloride, dried over anhydrous magnesium sulfate, filtered and concentrated. The residue was purified by flash chromatography (silica gel, 0-15% ethyl acetate in dichloromethane) to give 0.117 g (77%) of the title compound.

Example 82b 1-methyl-3-(5-nitro-2-(pyridin-2-ylamino)phenyl)-1H-pyrrolo[2,3-c]pyridin-7(6H)-one A mixture of Example 82a (0.1163 g, 0.31 mmol) in methanol (3.1 mL) was treated with hydrogen chloride solution (4 M in 1,4-dioxane) (1.55 mL, 6.2 mmol) and heated at 75° C. overnight and then for another 10 hours at 67° C. The reaction mixture was concentrated to give 0.151 g (>100%) of the title compound as the HCl salt

Example 82c 11-methyl-8-nitro-5-(pyridin-2-yl)-2,4,5,11-tetrahydro-1H-2,5,11-triazadibenzo[cd,h]azulen-1-one To a 20-mL microwave vial equipped with a magnetic stirbar was added Example 82b (0.132 g, 0.365 mmol), paraformaldehyde (0.033 g, 1.1 mmol), and acetic acid (6 mL). The vial was capped and heated at 75° C. for 1 hour and 25 minutes. The reaction mixture was concentrated, diluted with 1,4-dioxane, treated with sodium hydroxide solution (4 N aqueous) (1.83 mL, 7.3 mmol) and heated at 75° C. for 1 hour. The reaction mixture was cooled to ambient temperature and neutralized with hydrochloric acid solution (2 N aqueous). The resulting mixture was partitioned between ethyl acetate and water, washed with saturated aqueous sodium chloride, dried over anhydrous magnesium sulfate, filtered and concentrated to give 0.104 g (76%) of the title compound as an impure mixture.

Example 82d 8-amino-11-methyl-5-(pyridin-2-yl)-2,4,5,11-tetrahydro-1H-2,5,11-triazadibenzo[cd,h]azulen-1-one A mixture of Example 82c (0.09 g, 0.241 mmol), zinc dust (0.236 g, 3.62 mmol) and ammonium chloride (0.129 g, 2.411 mmol) in tetrahydrofuran (2.6 mL), ethanol (1.3 mL), and water (0.65 mL) was stirred at ambient temperature for 1 hour and then filtered to remove the solid. The filtrate was concentrated and then slurried in water. The solid was collected by filtration and dried in a vacuum oven at 70° C. to give 0.0732 g (88%) of the title compound as an impure mixture.

Example 82e

N-(11-methyl-1-oxo-5-(pyridin-2-yl)-2,4,5,11-tetrahydro-1H-2,5,11-triazadibenzo[cd,h]azulen-8-yl)ethanesulfonamide A mixture of Example 82d (0.09 g, 0.262 mmol) in dichloroethane (2 mL) and 1,4-dioxane (4 mL) was treated with ethanesulfonyl chloride (0.075 mL, 0.786 mmol) and triethylamine (0.183 mL, 1.31 mmol). The mixture was stirred at ambient temperature overnight and then concentrated. The mixture was redissolved in 1,4-dioxane (4 mL), treated with sodium hydroxide solution (4 M aqueous) (0.655 ml, 2.62 mmol) and heated at 50° C. for 1.75 hours. The mixture was then cooled to ambient temperature and neutralized with hydrochloric acid solution (2 M aqueous). The mixture was partitioned between ethyl acetate and water. The aqueous layer was extracted with ethyl acetate (2×60 mL). The organic layers were combined, dried over anhydrous magnesium sulfate, filtered and concentrated. The residue was purified by reverse phase HPLC(C18, acetonitrile/water (0.1% TFA), 10-60%) to provide 0.0477 g (33%) of the title compound as the TFA salt. $^1$H NMR (400 MHz, DMSO-d$_6$) δ 10.48 (s, 1H), 9.56 (s, 1H), 7.98 (dd, J=5.19, 1.22 Hz, 1H), 7.64 (d, J=2.44 Hz, 1H), 7.58 (s, 1H), 7.41 (m, 1H), 7.27 (d, J=8.54 Hz, 1H), 7.13 (dd, J=8.54, 2.44 Hz, 1H), 6.90 (s, 1H), 6.60 (dd, J=6.56, 5.65 Hz, 1H), 6.42 (d, J=8.85 Hz, 1H), 5.53 (s, 1H), 4.08 (s, 3H), 3.97 (s, 1H), 3.19 (q, J=7.32 Hz, 2H), 1.29 (t, J=7.32 Hz, 3H). MS (ESI+) m/z 436.2 (M+H)$^+$.

Biological Examples

Bromodomain Domain Binding Assay

A time-resolved fluorescence resonance energy transfer (TR-FRET) assay was used to determine the affinities of compounds of the Examples listed in Table 1 for each bromodomain of BRD4. His-tagged first (BD1: amino acids K57-E168) and second (BD2: amino acids E352-E168) bromodomains of BRD4 were expressed and purified. An Alexa647-labeled BET-inhibitor was used as the fluorescent probe in the assay.

Synthesis of Alexa647-labeled bromodomain inhibitor compound 2-((6S,Z)-4-(4-chlorophenyl)-2,3,9-trimethyl-6H-thieno[3,2f][1,2,4]triazolo[4,3-a][1,4]diazepin-6-yl)acetic acid Methyl 2-((6S,Z)-4-(4-chlorophenyl)-2,3,9-trimethyl-6H-thieno[3,2-f][1,2,4]triazolo[4,3-a][1,4]diazepin-6-yl)acetate (see e.g., WO 2006129623)(100.95 mg, 0.243 mmol was suspended in 1 mL methanol to which was added a freshly prepared solution of lithium hydroxide monohydrate (0.973 mL, 0.5 M, 0.487 mmol) and shaken at ambient temperature for 3 hours. The methanol was evaporated and the pH adjusted with aqueous hydrochloric acid (1 M, 0.5 mL, 0.5 mmol) and extracted four times with ethyl acetate. The combined ethyl acetate layers were dried over magnesium sulfate and evaporated to afford 2-((6S,Z)-4-(4-chlorophenyl)-2,3,9-trimethyl-6H-thieno[3,2-f][1,2,4]triazolo[4,3-a][1,4]diazepin-6-yl)acetic acid (85.3 mg, 87.0%); ESI-MS m/z=401.1 [(M+H)$^+$] which was used directly in the next reaction.

N-(2-(2-(2-aminoethoxy)ethoxy)ethyl)-2-065,Z)-4-(4-chlorophenyl)-2,3,9-trimethyl-6H-thieno[3,2-f][1,2,4]triazolo[4,3-a][1,4]diazepin-6-yl)acetamide bis(2,2,2-trifluoroacetate)

2-((6S,Z)-4-(4-chlorophenyl)-2,3,9-trimethyl-6H-thieno[3,2f][1,2,4]triazolo[4,3-a][1,4]diazepin-6-yl)acetic acid) (85.3 mg, 0.213 mmol) was combined with 2,2'-(ethane-1,2-diylbis(oxy))diethanamine (Sigma-Aldrich, 0.315 mg, 2.13 mmol) were combined in 5 mL anhydrous dimethylformamide. (1H-benzo[d][1,2,3]triazol-1-yloxy)tripyrrolidin-1-ylphosphonium hexafluorophosphate(V) (PyBOB, CSBio, Menlo Park Calif.; 332 mg, 0.638 mmol) was added and the reaction shaken at ambient temperature for 16 hours. The reaction was diluted to 6 mL with dimethylsulfoxide:water (9:1, v:v) and purified in two injections with time collection Waters Deltapak C18 200×25 mm column eluted with a gradient of 0.1% trifluoroacetic acid (v/v) in water and acetonitrile. The fractions containing the two purified products were lyophilized to afford N-(2-(2-(2-aminoethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide bis(2,2,2-trifluoroacetate) (134.4 mg, 82.3%); ESI-MS m/z=531.1 [(M+H)$^+$]; 529.1 [(M−H)$^−$] and (S,Z)—N,N'-(2,2'-(ethane-1,2-diylbis(oxy))bis(ethane-2,1-diyl))bis(2-((6S,Z)-4-(4-chlorophenyl)-2,3,9-trimethyl-6H-thieno[3,2-f][1,2,4]triazolo[4,3-a][1,4]diazepin-6-yl)acetamide)bis(2,2,2-trifluoroacetate) (3.0 mg, 1.5%); ESI-MS m/z=913.2 [(M+H)$^+$]; 911.0 [(M−H)$^−$].

N-(2-(2-(2-amido-(Alexa647)-ethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide(2,2,2-trifluoroacetate).

N-(2-(2-(2-aminoethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide bis(2,2,2-trifluoroacetate) (5.4 mg, 0.0071 mmol) was combined with Alexa Fluor® 647 carboxylic Acid, succinimidyl ester (Life Technologies, Grand Island, N.Y.; 3 mg, 0.0024 mmol) were combined in 1 mL anhydrous dimethylsulfoxide containing diisopropylethylamine (1% v/v) and shaken at ambient temperature for 16 hours. The reaction was diluted to 3 mL with dimethylsulfoxide:water (9:1, v:v) and purified in one injection with time collection Waters Deltapak C18 200×25 mm column eluted with a gradient of 0.1% trifluoroacetic acid (v/v) in water and acetonitrile. The fractions containing the purified product were lyophilized to afford N-(2-(2-(2-amido-(Alexa647)-ethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide(2,2,2-trifluoroacetate) (1.8 mg); MALDI-MS m/z=1371.1, 1373.1 [(M+H)$^+$] as a dark blue powder.

Assay

Compound dilution series were prepared in DMSO via an approximately 3-fold serial dilution from one of the following:
Assay method C: 1250 µM-21 nM
Assay method D: 500 µM-8.5 nM
Assay method E: 0.47 mM to 7.8 nM
Assay method F: 250 µM-4.2 nM
Assay method G: 0.047 mM to 0.78 nM
or 5-fold serial dilution from one of the following:
Assay method A: 2.5 mM-800 nM
Assay method B: 2.5 mM-797 nM For Assay methods A, C, D, and F: Compounds were then diluted 6:100 in assay buffer (20 mM Sodium Phosphate, pH 6.0, 50 mM NaCl, 1 mM Ethylenediaminetetraacetic acid, 0.01% Triton X-100, 1 mM DL-Dithiothreitol) to yield 3× working solutions. Six microliters (µL) of the working solution was then transferred to white, low-volume assay plates (Costar #3673). A 1.5× assay mixture containing His-tagged bromodomain, Europium-conjugated anti-His antibody (Invitrogen PV5596) and the Alexa-647-conjugated probe molecule was also prepared. Twelve µL of this solution was added to the assay plate to reach a final volume of 18 µL.

For Assay methods B, E, and G: Compound dilutions were added directly into white, low-volume assay plates (Perkin Elmer Proxiplate 384 Plus#6008280) using a Labcyte Echo in conjunction with Labcyte Access and Thermo Multidrop CombinL robotics. Compounds were then suspended in eight microliters (μL) of assay buffer (20 mM Sodium Phosphate, pH 6.0, 50 mM NaCl, 1 mM Ethylenediaminetetraacetic acid disodium salt dihydrate, 0.01% Triton X-100, 1 mM DL-Dithiothreitol) containing His-tagged bromodomain, Europium-conjugated anti-His antibody (Invitrogen PV5596) and Alexa-647-conjugated probe.

The final concentration of 1× assay mixture for assay methods A, B, C, D, E, F, and G contains 2% DMSO, 8 nM His-tagged bromodomain, 1 nM Europium-conjugated anti-His-tag antibody and 100 nM or 30 nM probe (for BDI or BDII, respectively) and compound concentration in the range of: 50 μM-16 nM for method A, 49.02 μM-15.63 nM for method B, 25 μM-423 pM for method C, 10 μM-169 pM for method D, 9.19 μM 150 pM for method E, 5 μM-85 pM for method F, and 0.92 μM-15 pM for method G.

After a one-hour equilibration at room temperature, TR-FRET ratios were determined using an Envision multilabel plate reader (Ex 340, Em 495/520).

TR-FRET data were normalized to the means of 24 no-compound controls ("high") and 8 controls containing 1 μM un-labeled probe ("low"). Percent inhibition was plotted as a function of compound concentration and the data were fit with the 4 parameter logistic equation to obtain $IC_{50}$s Inhibition constants ($K_i$) were calculated from the $IC_{50}$s, probe $K_d$ and probe concentration. Typical Z' values were between 0.65 and 0.75. The minimum significant ratio was determined to evaluate assay reproducibility (Eastwood et al., (2006) J Biomol Screen, 11: 253-261). The MSR was determined to be 2.03 for BDI and 1.93 for BDII, and a moving MSR (last six run MSR overtime) for both BDI and BDII was typically <3. The $K_i$ values are reported in Table 1.

MX-1 Cell Line Proliferation Assay

The impact of compounds of the Examples on cancer cell proliferation was determined using the breast cancer cell line MX-1 (ATCC) in a 3-day proliferation assay and the data are reported in Table 1. MX-1 cells were maintained in RPMI 1640 medium (Sigma) supplemented with 10% FBS at 37 C.° and an atmosphere of 5% $CO_2$. For compound testing, MX-1 cells were plated in 96-well black bottom plates at a density of 5000 cells/well in 90 μL of culture media and incubated at 37° overnight to allow cell adhesion and spreading. Compound dilution series were prepared in DMSO via a 3-fold serial dilution from 3 mM to 0.1 μM. The DMSO dilution series were then diluted 1:100 in phosphate buffered saline, and 10 μL of the resulted solution were added to the appropriate wells of the MX-1 cell plate. The final compound concentrations in the wells were 3, 1, 0.3, 0.1, 0.03, 0.01, 0.003, 0.001, 0.0003 and 0.0001 μM. After the addition of compounds, the cells were incubated for 72 more hours and the amounts of viable cells were determined using the Cell Titer Glo assay kit (Promega) according to manufacturer suggested protocol.

Luminescence readings from the Cell Titer Glo assay were normalized to the DMSO treated cells and analyzed using the GraphPad Prism software with sigmoidal curve fitting to obtain $EC_{50}$s. The minimum significant ratio (MSR) was determined to evaluate assay reproducibility (Eastwood et al., (2006) J Biomol Screen, 11: 253-261). The overall MSR was determined to be 2.1 and a moving MSR (last six run MSR overtime) has been <2.

TABLE 1

| Compounds of Example # | TR-FRET assay protocol | TR-FRET Binding Ki: BRD4 (BDI_K57-E168) (μM) | TR-FRET Binding Ki: BRD4 (BDII_E352-M457) (μM) | Cellular proliferation: $EC_{50}$ (μM) |
|---|---|---|---|---|
| 1 | D | 1.35 | 2.82 | >3 |
| 2 | D | 0.021 | 0.43 | 0.144 |
| 3 | D | 0.00439 | 0.00755 | 0.0193 |
| 4 | F | 0.00061 | 0.00215 | 0.00139 |
| 5 | F | 0.00176 | 0.00195 | 0.00395 |
| 6 | F | 0.00353 | 0.00244 | 0.0164 |
| 7 | D | 0.0591 | 0.0975 | 0.273 |
| 8 | F | 0.00581 | 0.0252 | 0.0466 |
| 9 | F | 0.00629 | 0.0182 | 0.805 |
| 10 | F | 0.00823 | 0.0574 | 0.0816 |
| 11 | F | 0.00714 | 0.0189 | 0.0568 |
| 12 | F | 0.00218 | 0.0043 | 0.00563 |
| 13 | D | 0.00274 | 0.0341 | 0.072 |
| 14 | D | 0.003 | 0.00369 | 0.00278 |
| 15 | F | 0.00914 | 0.0269 | 0.0363 |
| 16 | D | 0.00079 | 0.00507 | 0.00555 |
| 17 | F | 0.00143 | 0.00248 | 0.0199 |
| 18 | D | 0.00182 | 0.00346 | 0.00702 |
| 19 | F | 0.00132 | 0.0116 | 0.0687 |
| 20 | D | 0.00176 | 0.00469 | 0.0365 |
| 21 | F | 0.00105 | 0.00269 | 0.0166 |
| 22 | D | 0.00129 | 0.00303 | 0.0165 |
| 23 | F | 0.00138 | 0.00754 | 0.00479 |
| 24 | F | 0.178 | >0.408 | ND |
| 25 | F | 0.192 | 0.124 | >1 |
| 26 | F | 0.00027 | 0.00312 | 0.00948 |
| 27 | F | 0.0002 | 0.00173 | 0.00856 |
| 28 | F | 0.00117 | 0.00821 | 0.0135 |
| 29 | F | 0.00303 | 0.0224 | ND |
| 30 | F | 0.00353 | 0.0218 | 0.0512 |
| 31 | F | 0.0115 | 0.0795 | ND |
| 32 | F | 0.00137 | 0.0116 | 0.0123 |
| 33 | F | 0.00149 | 0.00639 | 0.0174 |
| 34 | F | 0.0022 | 0.0249 | 0.0479 |
| 35 | F | 0.00201 | 0.0189 | 0.0264 |
| 36 | F | 0.00134 | 0.0232 | 0.0168 |
| 37 | F | 0.00107 | 0.00742 | 0.019 |
| 38 | F | 0.00152 | 0.0093 | 0.0090 |
| 39 | F | 0.00194 | 0.0123 | 0.0232 |
| 40 | F | 0.00086 | 0.00727 | 0.0255 |
| 41 | F | 0.00173 | 0.0125 | 0.0556 |
| 42 | F | 0.00207 | 0.0134 | 0.00983 |
| 43 | F | 0.00125 | 0.00649 | 0.0173 |
| 44 | F | 0.0533 | >0.408 | >1 |
| 45 | F | 0.00712 | 0.13 | ND |
| 46 | F | 0.00329 | 0.0197 | ND |
| 47 | F | 0.00114 | 0.0133 | 0.0143 |
| 48 | F | 0.00239 | 0.0195 | 0.0295 |
| 49 | F | 0.00274 | 0.0298 | 0.0651 |
| 50 | F | 0.00594 | 0.0331 | 0.0637 |
| 51 | F | 0.00512 | 0.0848 | ND |
| 52 | F | 0.00276 | 0.0559 | 0.0559 |
| 53 | F | 0.00261 | 0.0501 | ND |
| 54 | F | 0.00207 | 0.0179 | ND |
| 55 | F | 0.00931 | 0.24 | ND |
| 56 | F | 0.00174 | 0.0574 | ND |
| 57 | F | 0.00172 | 0.029 | 0.0549 |
| 58 | F | 0.00183 | 0.0127 | 0.0633 |
| 59 | F | 0.00289 | 0.0715 | ND |
| 60 | F | 0.0032 | 0.0461 | 0.0755 |
| 61 | F | 0.00517 | 0.147 | ND |
| 62 | F | 0.00162 | 0.0331 | 0.0656 |
| 63 | F | 0.00198 | 0.022 | 0.0499 |
| 64 | F | 0.00173 | 0.0469 | ND |
| 65 | F | 0.00392 | 0.0449 | 0.0555 |
| 66 | F | 0.00214 | 0.0301 | 0.0446 |
| 67 | F | 0.0212 | 0.007 | ND |
| 68 | F | 0.00126 | 0.00179 | 0.0175 |
| 69 | F | 0.00078 | 0.00189 | 0.0044 |
| 70 | F | 0.00079 | 0.000708 | 0.0244 |
| 71 | F | 0.00165 | 0.00221 | 0.0356 |
| 72 | F | 0.00256 | 0.00441 | 0.0101 |
| 73 | F | 0.00708 | 0.0418 | ND |
| 74 | F | 0.00361 | 0.017 | >1.0 |

TABLE 1-continued

| Compounds of Example # | TR-FRET assay protocol | TR-FRET Binding Ki: BRD4 (BDI_K57-E168) (µM) | TR-FRET Binding Ki: BRD4 (BDII_E352-M457) (µM) | Cellular proliferation: $EC_{50}$ (µM) |
|---|---|---|---|---|
| 75 | F | 0.00254 | 0.0546 | >1.0 |
| 76 | F | 0.00346 | 0.0175 | 0.332 |
| 77 | F | 0.0046 | 0.112 | >1.0 |
| 78 | F | 0.00129 | 0.00085 | 0.00628 |
| 79 | F | 0.00109 | 0.00208 | 0.00548 |
| 80 | F | 0.00304 | 0.0145 | 0.106 |
| 81 | F | 0.00497 | 0.0111 | 0.0779 |
| 82 | F | 0.00083 | 0.00147 | 0.00493 |

ND = Not Determined

LPS (Lipopolysaccharide) Induced IL-6 Production Mouse Assay

Compounds of the Examples listed in Table 2 were assayed for their ability to inhibit LPS (lipopolysaccharide) induced IL-6 (Interleukin-6) production in mice. Fox Chase SCID® female mice (Charles Rivers Labs, 5 per group) or CD1 female mice (5 mice per group) received an intraperitoneal challenge of lipopolysaccharide (2.5 mg/kg, L2630 E. coli 0111:B4) one hour after oral administration of compounds. Mice were euthanized 2 hours after lipopolysaccharide injection, blood was removed by cardiac puncture, and then the serum harvested from the blood samples was frozen at −80° C. On the day of the assay the serum samples were brought to room temperature and then diluted 1:20 in phosphate-buffered saline containing 2% bovine serum albumin. Interleukin-6 measurements were performed using a cytokine assay from Meso Scale Discovery (Gaithersburg, Md.) for mouse serum analysis according to the manufacturer's protocol and read on a SECTOR Imager 6000 (Meso Scale Discovery, Gaithersburg, Md.) instrument. Statistical analysis was performed using Prism software (version 5.0) incorporating Dunnett's one way ANOVA. The IL-6 mean and standard deviation of the group of vehicle treated animals were compared with the IL-6 mean and standard deviation of the group treated with drug. A p value <0.05 means that there is less than a 5% probability that the mean values in the two groups are equal. The % inhibition values in Table 2 all exhibited a p value less than 0.05.

TABLE 2

Inhibition of LPS induced IL-6 production

| Compound of Example # | % inhibition at 3 mg/kg | Mouse Strain |
|---|---|---|
| 4 | 70 | SCID |
| 5 | 71 | SCID |
| 36 | 68 | CD1 |
| 72 | 63 | CD1 |
| 79 | 61 | CD1 |

Xenograft Tumor Growth Inhibition Assay

The effect of compounds of the examples to inhibit the growth of OPM-2 xenograft tumors implanted in mice was evaluated. A suspension of cancer cells ($5 \times 10^6$ per 0.1 mL) prepared in RPMI culture medium (Invitrogen, Carlsbad, Calif.) was diluted 1:1 with a solution of Matrigel™ (BD Biosciences, Franklin Lakes, N.J.) and inoculated subcutaneously into the right hind flank of female SCID-beige (Charles River Labs) mice. Randomization into treatment and vehicle control groups (9 or 10/group) occurred when the mean tumor volume reached approximately 250 mm³ Compounds were formulated in 2.5% DMSO, 10% EtOH, 27.5% PEG 400, 60% Phosol 53 MCT. Administration of compound or vehicle was initiated on the day following randomization and continued for 21 days. Tumors were measured twice a week throughout the treatment period using a pair of calipers and tumor volumes were calculated according to the formula $V = L \times W^2 / 2$ (V: volume, $mm^3$; L: length, mm. W: width, m) Tumor growth inhibition was calculated based on the mean tumor volume measured on the first day that the mean volume of the vehicle group exceeded 2000 $mm^3$ according to the formula % TGI=100−mean tumor volume of treatment group/mean tumor volume of control group×100. Results are given in Table 3.

TABLE 3

OPM-2 human multiple myeloma cancer xenograft model

| Compound of example # | Dose mg/kg | route, regimen | % TGI[a] | % removed from study[b] |
|---|---|---|---|---|
| 4 | 3.75 | PO, QDx21 | 68*** | 11 |
| 4 | 7.5 | PO, QDx21 | 84*** | 44 |
| 5 | 2.5 | PO, QDx21 | 66*** | 0 |
| 5 | 5.0 | PO, QDx21 | 81*** | 44 |
| 79 | 1.25 | PO, QDx21 | 71*** | 11 |
| 79 | 2.5 | PO, QDx21 | 79*** | 0 |

[a]The p values (as indicated by asterisks) are derived from Student's T test comparison of treatment group vs. control group.
***p < 0.001.
[b]Percentage of treatment group that were removed from study due to morbidity or weight loss in excess of 20%.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof. All publications, patents, and patent applications cited herein are hereby incorporated by reference in their entirety for all purposes.

The invention claimed is:
1. A compound of formula (I) or a pharmaceutically acceptable salt thereof,

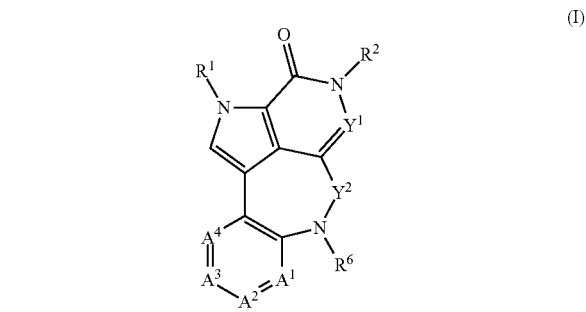

(I)

wherein
$R^1$ is $CD_3$, $C_1$-$C_3$ alkyl, or $C_1$-$C_3$ haloalkyl;
$R^2$ is H or $C_1$-$C_3$ alkyl;
$Y^1$ is N or $CR^3$;
$R^3$ is H, $C_1$-$C_6$ alkyl, $C_2$-$C_6$ alkenyl, $C_2$-$C_6$ alkynyl, halogen, $C_1$-$C_6$ haloalkyl, —C(O)$R^{3a}$, —C(O)O$R^{3a}$, —C(O)N$R^{3b}R^{3c}$, —C(O)N($R^{3b}$)N$R^{3b}R^{3c}$, —S(O)$R^{3d}$, —S(O)$_2$R$^{3a}$, —S(O)$_2$NR$^{3b}$R$^{3c}$ or G$^1$; wherein the C$_1$-C$_6$ alkyl, C$_2$-C$_6$ alkenyl, and C$_2$-C$_6$ alkynyl are each independently unsubstituted or substituted with 1 or 2 substituents independently selected from the group consisting of G$^1$, —C(O)R$^{3a}$, —C(O)OR$^{3a}$, —C(O)NR$^{3b}$R$^{3c}$, —S(O)R$^{3d}$, —S(O)$_2$R$^{3a}$, —S(O)$_2$NR$^{3b}$R$^{3c}$, —OR$^{3a}$, —OC(O)R$^{3d}$, —NR$^{3b}$R$^{3c}$, N(R$^{3b}$)C(O)R$^{3d}$, N(R$^{3b}$)SO$_2$R$^{3d}$, N(R$^{3b}$)C(O)OR$^{3d}$, N(R$^{3b}$)C(O)NR$^{3b}$R$^{3c}$, N(R$^{3b}$)SO$_2$NR$^{3b}$R$^{3c}$, and N(R$^{3b}$)C(NR$^{3b}$R$^{3c}$)=NR$^{3b}$R$^{3c}$;

Y$^2$ is C(O), S(O)$_2$, or CR$^4$R$^5$;

R$^4$ is H, deuterium, C$_1$-C$_6$ alkyl, halogen, or C$_1$-C$_6$ haloalkyl; and R$^5$ is H, deuterium, C$_1$-C$_6$ alkyl, C$_2$-C$_6$ alkenyl, C$_2$-C$_6$ alkynyl, halogen, C$_1$-C$_6$ haloalkyl, —C(O)R$^{5a}$, —C(O)OR$^{5a}$, —C(O)NR$^{5b}$R$^{5c}$, —S(O)R$^{5d}$, —S(O)$_2$R$^{5a}$, —S(O)$_2$NR$^{5b}$R$^{5c}$, or G$^1$; wherein the C$_1$-C$_6$ alkyl, C$_2$-C$_6$ alkenyl, and C$_2$-C$_6$ alkynyl are each independently unsubstituted or substituted with 1 or 2 substituents independently selected from the group consisting of G$^1$, —C(O)R$^{5a}$, —C(O)OR$^{5a}$, —C(O)NR$^{5b}$R$^{5c}$, —C(O)N(R$^{5b}$)NR$^{5b}$R$^{5c}$, —S(O)R$^{5d}$, —S(O)$_2$R$^{5a}$, —S(O)$_2$NR$^{5b}$R$^{5c}$, —OR$^{5a}$, —OC(O)R$^{5d}$—NR$^{5b}$R$^{5c}$, N(R$^{5b}$)C(O)R$^{5d}$, N(R$^{5b}$)SO$_2$R$^{5d}$, N(R$^{5b}$)C(O)OR$^{5d}$, N(R$^{5b}$)C(O)NR$^{5b}$R$^{5c}$, N(R$^{5b}$)SO$_2$NR$^{5b}$R$^{5c}$, and N(R$^{5b}$)C(NR$^{5b}$R$^{5c}$)=NR$^{5b}$R$^{5c}$;

R$^{3a}$, R$^{3b}$, R$^{3c}$, R$^{5a}$, R$^{5b}$, and R$^{5C}$, at each occurrence, are each independently H, C$_1$-C$_6$ alkyl, C$_2$-C$_6$ alkenyl, C$_2$-C$_6$ alkynyl, C$_1$-C$_6$ haloalkyl, G$^1$, or —(C$_1$-C$_6$ alkylenyl)-G$^1$;

R$^{3d}$ and R$^{5d}$, at each occurrence, are each independently C$_1$-C$_6$ alkyl, C$_2$-C$_6$ alkenyl, C$_2$-C$_6$ alkynyl, C$_1$-C$_6$ haloalkyl, G$^1$, or —(C$_1$-C$_6$ alkylenyl)-G$^1$;

G$^1$, at each occurrence, is independently aryl, heteroaryl, heterocycle, cycloalkyl, or cycloalkenyl; and each G$^1$ is optionally substituted with 1, 2, 3, 4, or 5 R$^{1g}$ groups;

R$^6$ is H, C$_1$-C$_6$ alkyl, C$_2$-C$_6$ alkenyl, C$_2$-C$_6$ alkynyl, halogen, C$_1$-C$_6$ haloalkyl, —C(O)R$^{6a}$, —C(O)OR$^{6a}$, —C(O)NR$^{6b}$R$^{6c}$, —S(O)$_2$R$^{6a}$, —S(O)$_2$NR$^{6b}$R$^{6c}$, or G$^2$; wherein the C$_1$-C$_6$ alkyl, C$_2$-C$_6$ alkenyl, and C$_2$-C$_6$ alkynyl are each independently unsubstituted or substituted with 1 or 2 substituents independently selected from the group consisting of G$^2$, —C(O)R$^{6a}$, —C(O)OR$^{6a}$, —C(O)NR$^{6b}$R$^{6c}$, —C(O)N(R$^{6b}$)NR$^{6b}$R$^{6c}$, —S(O)R$^{6d}$, —S(O)$_2$R$^{6a}$, —S(O)$_2$NR$^{6b}$R$^{6c}$, —OR$^{6a}$, —OC(O)R$^{6d}$, —NR$^{6b}$R$^{6c}$, N(R$^{6b}$)C(O)R$^{6d}$, N(R$^{6b}$)SO$_2$R$^{6d}$, N(R$^{6b}$)C(O)OR$^{6d}$, N(R$^{6b}$)C(O)NR$^{6b}$R$^{6c}$, N(R$^{6b}$)SO$_2$NR$^{6b}$R$^{6C}$, and N(R$^{6b}$)C(NR$^{6b}$R$^{6c}$)=NR$^{6b}$R$^{6c}$;

R$^{6a}$, R$^{6b}$, and R$^{6c}$, at each occurrence, are each independently H, alkyl, C$_2$-C$_6$ alkenyl, C$_2$-C$_6$ alkynyl, haloalkyl, G$^2$, —(C$_1$-C$_6$ alkylenyl)-G$^2$, —(C$_1$-C$_6$ alkylenyl)-OR$^a$, —(C$_1$-C$_6$ alkylenyl)-S(O)$_2$R$^a$, —(C$_1$-C$_6$ alkylenyl)-S(O)$_2$NR$^c$R$^d$, —(C$_1$-C$_6$ alkylenyl)-C(O)R$^a$, —(C$_1$-C$_6$ alkylenyl)-C(O)OR$^a$, —(C$_1$-C$_6$ alkylenyl)-C(O)NR$^c$R$^d$, —(C$_1$-C$_6$ alkylenyl)-NR$^c$R$^d$, —(C$_1$-C$_6$ alkylenyl)-N(R$^e$)C(O)R$^b$, —(C$_1$-C$_6$ alkylenyl)-N(R$^e$)S(O)$_2$R$^b$, —(C$_1$-C$_6$ alkylenyl)-N(R$^e$)C(O)O(R$^b$), —(C$_1$-C$_6$ alkylenyl)-N(R$^e$)C(O)NR$^c$R$^d$, or —(C$_1$-C$_6$ alkylenyl)-N(R$^e$)S(O)$_2$NR$^c$R$^d$;

R$^{6d}$, at each occurrence, is independently alkyl, C$_2$-C$_6$ alkenyl, C$_2$-C$_6$ alkynyl, haloalkyl, G$^2$, —(C$_1$-C$_6$ alkylenyl)-G$^2$, —(C$_1$-C$_6$ alkylenyl)-OR$^a$, —(C$_1$-C$_6$ alkylenyl)-S(O)$_2$R$^a$, —(C$_1$-C$_6$ alkylenyl)-S(O)$_2$NR$^c$R$^d$, —(C$_1$-C$_6$ alkylenyl)-C(O)R$^a$, —(C$_1$-C$_6$ alkylenyl)-C(O)OR$^a$, —(C$_1$-C$_6$ alkylenyl)-C(O)NR$^c$R$^d$, —(C$_1$-C$_6$ alkylenyl)-NR$^c$R$^d$, —(C$_1$-C$_6$ alkylenyl)-N(R$^e$)C(O)R$^b$, —(C$_1$-C$_6$ alkylenyl)-N(R$^e$)S(O)$_2$R$^b$, —(C$_1$-C$_6$ alkylenyl)-N(R$^e$)C(O)O(R$^b$), —(C$_1$-C$_6$ alkylenyl)-N(R$^e$)C(O)NR$^c$R$^d$, or —(C$_1$-C$_6$ alkylenyl)-N(R$^e$)S(O)$_2$NR$^c$R$^d$;

G$^2$, at each occurrence, is independently aryl, heteroaryl, heterocycle, cycloalkyl, or cycloalkenyl; and each G$^2$ is optionally substituted with 1, 2, 3, 4, or 5 R$^{2g}$ groups;

A$^1$ is C(R$^7$) or N; A$^2$ is C(R$^8$) or N; A$^3$ is C(R$^9$) or N; and A$^4$ is C(R$^{10}$) or N; wherein zero, one, or two of A$^1$, A$^2$, A$^3$, and A$^4$ are N;

R$^7$, R$^8$, and R$^9$, are each independently H, C$_1$-C$_6$ alkyl, C$_2$-C$_6$ alkenyl, C$_2$-C$_6$ alkynyl, halogen, C$_1$-C$_6$ haloalkyl, —CN, NO$_2$, —OR$^{y1}$, —OC(O)R$^{y2}$, —OC(O)NR$^{y3}$R$^{y4}$, —SR$^{y1}$, —S(O)$_2$R$^{y1}$, —S(O)$_2$NR$^{y3}$R$^{y4}$, —C(O)R$^{y1}$, —C(O)OR$^{y1}$, —C(O)NR$^{y3}$R$^{y4}$, —NR$^{y3}$R$^{y4}$, —N(R$^{y3}$)C(O)R$^{y2}$, —N(R$^{y3}$)S(O)$_2$R$^{y2}$, —N(R$^{y3}$)C(O)O(R$^{y2}$), —N(R$^{y3}$)C(O)NR$^{y3}$R$^{y4}$, —N(R$^{y3}$)S(O)$_2$NR$^{y3}$R$^{y4}$, G$^3$, —(C$_1$-C$_6$ alkylenyl)-CN, —(C$_1$-C$_6$ alkylenyl)-OR$^{y1}$, —(C$_1$-C$_6$ alkylenyl)-OC(O)R$^{y2}$, —(C$_1$-C$_6$ alkylenyl)-OC(O)NR$^{y3}$R$^{y4}$, —(C$_1$-C$_6$ alkylenyl)-S(O)$_2$R$^{y1}$, —(C$_1$-C$_6$ alkylenyl)-S(O)$_2$NR$^{y3}$R$^{y4}$, —(C$_1$-C$_6$ alkylenyl)-C(O)R$^{y1}$, —(C$_1$-C$_6$ alkylenyl)-C(O)OR$^{y1}$, —(C$_1$-C$_6$ alkylenyl)-C(O)NR$^{y3}$R$^{y4}$, —(C$_1$-C$_6$ alkylenyl)-NR$^{y3}$R$^{y4}$, —(C$_1$-C$_6$ alkylenyl)-N(R$^{y3}$)C(O)R$^{y2}$, —(C$_1$-C$_6$ alkylenyl)-N(R$^{y3}$)S(O)$_2$R$^{y2}$, —(C$_1$-C$_6$ alkylenyl)-N(R$^{y3}$)C(O)O(R$^{y2}$), —(C$_1$-C$_6$ alkylenyl)-N(R$^{y3}$)C(O)NR$^{y3}$R$^{y4}$, —(C$_1$-C$_6$ alkylenyl)-N(R$^{y3}$)S(O)$_2$NR$^{y3}$R$^{y4}$, —(C$_1$-C$_6$ alkylenyl)-CN, or —(C$_1$-C$_6$ alkylenyl)-G$^3$;

R$^{y1}$, R$^{y3}$, and R$^{y4}$, at each occurrence, are each independently H, C$_1$-C$_6$ alkyl, C$_2$-C$_6$ alkenyl, C$_2$-C$_6$ alkynyl, C$_1$-C$_6$ haloalkyl, G$^3$, —(C$_1$-C$_6$ alkylenyl)-G$^3$, —(C$_1$-C$_6$ alkylenyl)-OR$^a$, —(C$_1$-C$_6$ alkylenyl)-S(O)$_2$R$^a$, —(C$_1$-C$_6$ alkylenyl)-S(O)$_2$NR$^c$R$^d$, —(C$_1$-C$_6$ alkylenyl)-C(O)R$^a$, —(C$_1$-C$_6$ alkylenyl)-C(O)OR$^a$, —(C$_1$-C$_6$ alkylenyl)-C(O)NR$^c$R$^d$, —(C$_1$-C$_6$ alkylenyl)-NR$^c$R$^d$, —(C$_1$-C$_6$ alkylenyl)-N(R$^e$)C(O)R$^b$, —(C$_1$-C$_6$ alkylenyl)-N(R$^e$)S(O)$_2$R$^b$, —(C$_1$-C$_6$ alkylenyl)-N(R$^e$)C(O)O(R$^b$), —(C$_1$-C$_6$ alkylenyl)-N(R$^e$)C(O)NR$^c$R$^d$, or —(C$_1$-C$_6$ alkylenyl)-N(R$^e$)S(O)$_2$NR$^c$R$^d$;

R$^{y2}$, at each occurrence, is independently C$_1$-C$_6$ alkyl, C$_2$-C$_6$ alkenyl, C$_2$-C$_6$ alkynyl, C$_1$-C$_6$ haloalkyl, G$^3$, —(C$_1$-C$_6$ alkylenyl)-G$^3$, —(C$_1$-C$_6$ alkylenyl)-OR$^a$, —(C$_1$-C$_6$ alkylenyl)-S(O)$_2$R$^a$, —(C$_1$-C$_6$ alkylenyl)-S(O)$_2$NR$^c$R$^d$, —(C$_1$-C$_6$ alkylenyl)-C(O)R$^a$, —(C$_1$-C$_6$ alkylenyl)-C(O)OR$^a$, —(C$_1$-C$_6$ alkylenyl)-C(O)NR$^c$R$^d$, —(C$_1$-C$_6$ alkylenyl)-NR$^c$R$^d$, —(C$_1$-C$_6$ alkylenyl)-N(R$^e$)C(O)R$^b$, —(C$_1$-C$_6$ alkylenyl)-N(R$^e$)S(O)$_2$R$^b$, —(C$_1$-C$_6$ alkylenyl)-N(R$^e$)C(O)O(R$^b$), —(C$_1$-C$_6$ alkylenyl)-N(R$^e$)C(O)NR$^c$R$^d$, or —(C$_1$-C$_6$ alkylenyl)-N(R$^e$)S(O)$_2$NR$^c$R$^d$;

G$^3$, at each occurrence, is independently aryl, heteroaryl, cycloalkyl, cycloalkenyl, or heterocycle; and each G$^3$ group is optionally substituted with 1, 2, 3, 4, or 5 R$^{4g}$ groups;

R$^{10}$ is H, C$_1$-C$_3$ alkyl, halogen, C$_1$-C$_3$ haloalkyl, or —CN;

R$^{1g}$, R$^{2g}$, and R$^{4g}$, at each occurrence, is independently selected from the group consisting of oxo, C$_1$-C$_6$ alkyl, C$_2$-C$_6$ alkenyl, C$_2$-C$_6$ alkynyl, halogen, C$_1$-C$_6$ haloalkyl, —CN, NO$_2$, G$^{2a}$, —OR$^a$, —OC(O)R$^b$, —OC(O)NR$^c$R$^d$, —SR$^a$, —S(O)$_2$R$^a$, —S(O)$_2$NR$^c$R$^d$, —C(O)R$^a$, —C(O)OR$^a$, —C(O)NR$^c$R$^d$, —NR$^c$R$^d$, —N(R$^e$)C(O)R$^b$, —N(R$^e$)S(O)$_2$R$^b$, —N(R$^e$)C(O)O(R$^b$), —N(R$^e$)C(O)NR$^c$R$^d$, —N(R$^e$)S(O)$_2$NR$^c$R$^d$, —(C$_1$-C$_6$ alkylenyl)-CN, —(C$_1$-C$_6$ alkylenyl)-G$^{2a}$, —(C$_1$-C$_6$ alkylenyl)-OR$^a$, —(C$_1$-C$_6$ alkylenyl)-OC(O)R$^b$, —(C$_1$-C$_6$ alkylenyl)-OC(O)NR$^c$R$^d$, —(C$_1$-C$_6$ alkylenyl)-S(O)$_2$R$^a$, —(C$_1$-C$_6$ alkylenyl)-S(O)$_2$NR$^c$R$^d$, —(C$_1$-C$_6$ alkylenyl)-C(O)R$^a$, —(C$_1$-C$_6$ alkylenyl)-C(O)OR$^a$, —(C$_1$-C$_6$ alkylenyl)-C(O)NR$^c$R$^d$, —(C$_1$-C$_6$ alkylenyl)-

NR$^c$R$^d$, —(C$_1$-C$_6$ alkylenyl)-N(R$^e$)C(O)R$^b$, —(C$_1$-C$_6$ alkylenyl)-N(R$^e$)S(O)$_2$R$^b$, —(C$_1$-C$_6$ alkylenyl)-N(R$^e$)C(O)O(R$^b$), —(C$_1$-C$_6$ alkylenyl)-N(R$^e$)C(O)NR$^c$R$^d$, —(C$_1$-C$_6$ alkylenyl)-N(R$^e$)S(O)$_2$NR$^c$R$^d$, or —(C$_1$-C$_6$ alkylenyl)-CN;

R$^a$, R$^c$, R$^d$, and R$^e$, at each occurrence, are each independently H, C$_1$-C$_6$ alkyl, C$_2$-C$_6$ alkenyl, C$_2$-C$_6$ alkynyl, C$_1$-C$_6$ haloalkyl, G$^{2a}$, or —(C$_1$-C$_6$ alkylenyl)-G$^{2a}$;

R$^b$, at each occurrence, is independently C$_1$-C$_6$ alkyl, C$_2$-C$_6$ alkenyl, C$_2$-C$_6$ alkynyl, C$_1$-C$_6$ haloalkyl, G$^{2a}$, or —(C$_1$-C$_6$ alkylenyl)-G$^{2a}$;

G$^{2a}$, at each occurrence, are each independently aryl, heteroaryl, heterocycle, cycloalkyl, or cycloalkenyl; and each G$^{2a}$ group is optionally substituted with 1, 2, 3, 4, or 5 R$^{3g}$ groups;

R$^{3g}$, at each occurrence, is independently oxo, C$_1$-C$_6$ alkyl, C$_2$-C$_6$ alkenyl, C$_2$-C$_6$ alkynyl, halogen, C$_1$-C$_6$ haloalkyl, —CN, NO$_2$, —OR$^{z1}$, —OC(O)R$^{z2}$, —OC(O)NR$^{z3}$R$^{z4}$, —SR$^{z1}$, —S(O)$_2$R$^{z1}$, —S(O)$_2$NR$^{z3}$R$^{z4}$, —C(O)R$^{z1}$, —C(O)OR$^{z1}$, —C(O)NR$^{z3}$R$^{z4}$, —NR$^{z3}$R$^{z4}$, —N(R$^{z3}$)C(O)R$^{z2}$, —N(R$^{z3}$)S(O)$_2$R$^{z2}$, —N(R$^{z3}$)C(O)O(R$^{z2}$), —N(R$^{z3}$)C(O)NR$^{z3}$R$^{z4}$, —N(R$^{z3}$)S(O)$_2$NR$^{z3}$R$^{z4}$, —(C$_1$-C$_6$ alkylenyl)-OR$^{z1}$, —(C$_1$-C$_6$ alkylenyl)-OC(O)R$^{z2}$, —(C$_1$-C$_6$ alkylenyl)-OC(O)NR$^{z3}$R$^{z4}$, —(C$_1$-C$_6$ alkylenyl)-S(O)$_2$R$^{z1}$, —(C$_1$-C$_6$ alkylenyl)-S(O)$_2$NR$^{z3}$R$^{z4}$, —(C$_1$-C$_6$ alkylenyl)-C(O)R$^{z2}$, —(C$_1$-C$_6$ alkylenyl)-C(O)OR$^{z1}$, —(C$_1$-C$_6$ alkylenyl)-C(O)NR$^{z3}$R$^{z4}$, —(C$_1$-C$_6$ alkylenyl)-NR$^{z3}$R$^{z4}$, —(C$_1$-C$_6$ alkylenyl)-N(R$^{z3}$)C(O)R$^{z2}$, —(C$_1$-C$_6$ alkylenyl)-N(R$^{z3}$)S(O)$_2$R$^{z2}$, —(C$_1$-C$_6$ alkylenyl)-N(R$^{z3}$)C(O)O(R$^{z2}$), —(C$_1$-C$_6$ alkylenyl)-N(R$^{z3}$)C(O)NR$^{z3}$R$^{z4}$, —(C$_1$-C$_6$ alkylenyl)-N(R$^{z3}$)S(O)$_2$NR$^{z3}$R$^{z4}$, or —(C$_1$-C$_6$ alkylenyl)-CN;

R$^{z1}$, R$^{z3}$, and R$^{z4}$, at each occurrence, are each independently H, C$_1$-C$_6$ alkyl, C$_2$-C$_6$ alkenyl, C$_2$-C$_6$ alkynyl, or C$_1$-C$_6$ haloalkyl; and R$^{z2}$, at each occurrence, is independently C$_1$-C$_6$ alkyl, C$_2$-C$_6$ alkenyl, C$_2$-C$_6$ alkynyl, or C$_1$-C$_6$ haloalkyl.

2. The compound of claim 1, or a pharmaceutically acceptable salt thereof, wherein
R$^1$ is C$_1$-C$_3$ alkyl.

3. The compound of claim 1, or a pharmaceutically acceptable salt thereof, wherein
R$^2$ is H.

4. The compound of claim 1, or a pharmaceutically acceptable salt thereof, wherein
Y$^1$ is CR$^3$; and
Y$^2$ is CR$^4$R$^5$.

5. The compound of claim 4, or a pharmaceutically acceptable salt thereof, wherein
R$^3$ is H, —C(O)R$^{3a}$, —C(O)OR$^{3a}$, —C(O)NR$^{3b}$R$^{3c}$ or C$_1$-C$_6$ alkyl, wherein the C$_1$-C$_6$ alkyl is optionally substituted with a substituent selected from the group consisting of G$^1$, NR$^{3b}$R$^{3c}$, N(R$^{3b}$)C(O)R$^{3d}$, N(R$^{3b}$)SO$_2$R$^{3d}$, N(R$^{3b}$)C(O)OR$^{3d}$, N(R$^{3b}$)C(O)NR$^{3b}$R$^{3c}$, and N(R$^{3b}$)SO$_2$NR$^{3b}$R$^{3c}$.

6. The compound of claim 4, or a pharmaceutically acceptable salt thereof, wherein
R$^4$ is H or deuterium; and
R$^5$ is H, deuterium, C$_1$-C$_6$ alkyl, C$_2$-C$_6$ alkenyl, C$_2$-C$_6$ alkynyl, C$_1$-C$_6$ haloalkyl, —C(O)R$^{5a}$, —C(O)OR$^{5a}$, or G$^1$; wherein the C$_1$-C$_6$ alkyl, C$_2$-C$_6$ alkenyl, and C$_2$-C$_6$ alkynyl are each independently unsubstituted or substituted with 1 or 2 substituents independently selected from the group consisting of G$^1$, —C(O)R$^{5a}$, —C(O)OR$^{5c}$, —C(O)NR$^{5b}$R$^{5c}$, —C(O)N(R$^{5b}$)NR$^{5b}$R$^{5c}$, —OR$^{5a}$, —OC(O)R$^{5d}$, —NR$^{5b}$R$^{5c}$, N(R$^{5b}$)C(O)R$^{5d}$, N(R$^{5b}$)SO$_2$R$^{5d}$, N(R$^{5b}$)C(O)OR$^{5d}$, N(R$^{5b}$)C(O)NR$^{5b}$R$^{5c}$, and N(R$^{5b}$)SO$_2$NR$^{5b}$R$^{5c}$.

7. The compound of claim 4, or a pharmaceutically acceptable salt thereof, wherein
R$^6$ is H, C$_1$-C$_6$ alkyl, C$_2$-C$_6$ alkenyl, —C(O)R$^{6a}$, —C(O)OR$^{6a}$, —C(O)NR$^{6b}$R$^{6c}$, —S(O)$_2$R$^{6a}$, or G$^2$; wherein the C$_1$-C$_6$ alkyl and the C$_2$-C$_6$ alkenyl are each independently unsubstituted or substituted with 1 or 2 substituents independently selected from the group consisting of G$^2$, —C(O)OR$^{6a}$, —NR$^{6b}$R$^{6c}$, N(R$^{6b}$)C(O)R$^{6d}$, N(R$^{6b}$)SO$_2$R$^{6d}$, N(R$^{6b}$)C(O)OR$^{6d}$, N(R$^{6b}$)C(O)NR$^{6b}$R$^{6e}$, and N(R$^{6b}$)SO$_2$NR$^{6b}$R$^{6c}$.

8. The compound of claim 4, or a pharmaceutically acceptable salt thereof, wherein
A$^1$ is C(R$^7$), A$^2$ is C(R$^8$), A$^3$ is C(R$^9$), and A$^4$ is C(R$^{10}$); or
A$^1$ is N, A$^2$ is C(R$^8$), A$^3$ is C(R$^9$), and A$^4$ is C(R$^{10}$); or
A$^1$ is N, A$^2$ is C(R$^8$), A$^3$ is N, and A$^4$ is C(R$^{10}$).

9. The compound of claim 4, or a pharmaceutically acceptable salt thereof, wherein
R$^9$ is H, C$_1$-C$_6$ alkyl, halogen, C$_1$-C$_6$ haloalkyl, —CN, —S(O)$_2$R$^{y1}$, —S(O)$_2$NR$^{y3}$R$^{y4}$, —C(O)NR$^{y3}$R$^{y4}$, —NR$^{y3}$R$^{y4}$, —N(R$^{y3}$)C(O)R$^{y2}$, —N(R$^{y3}$)S(O)$_2$R$^{y2}$, —N(R$^{y3}$)C(O)O(R$^{y2}$), —N(R$^{y3}$)C(O)NR$^{y3}$R$^{y4}$, —N(R$^{y3}$)S(O)$_2$NR$^{y3}$R$^{y4}$, —(C$_1$-C$_6$ alkylenyl)-S(O)$_2$R$^{y1}$, —(C$_1$-C$_6$ alkylenyl)-S(O)$_2$NR$^{y3}$R$^{y4}$, —(C$_1$-C$_6$ alkylenyl)-C(O)NR$^{y3}$R$^{y4}$, —(C$_1$-C$_6$ alkylenyl)-NR$^{y3}$R$^{y4}$, —(C$_1$-C$_6$ alkylenyl)-N(R$^{y3}$)C(O)R$^{y2}$, —(C$_1$-C$_6$ alkylenyl)-N(R$^{y3}$)S(O)$_2$R$^{y2}$, —(C$_1$-C$_6$ alkylenyl)-N(R$^{y3}$)C(O)O(R$^{y2}$), —(C$_1$-C$_6$ alkylenyl)-N(R$^{y3}$)C(O)NR$^{y3}$R$^{y4}$, or —(C$_1$-C$_6$ alkylenyl)-N(R$^{y3}$)S(O)$_2$NR$^{y3}$R$^{y4}$.

10. The compound of claim 1, or a pharmaceutically acceptable salt thereof, wherein
R$^1$ is C$_1$-C$_3$ alkyl;
R$^2$ is H;
Y$^1$ is CR$^3$; and
Y$^2$ is CR$^4$R$^5$.

11. The compound of claim 10, or a pharmaceutically acceptable salt thereof, wherein
R$^4$ is H; and
R$^5$ is H, —C(O)OR$^{5a}$, G$^1$, or C$_1$-C$_6$ alkyl which is unsubstituted or substituted with a substituent selected from the group consisting of G$^1$, —C(O)OR$^{5a}$, and —OR$^{5a}$.

12. The compound of claim 10, or a pharmaceutically acceptable salt thereof, wherein
R$^3$ is H.

13. The compound of claim 10, or a pharmaceutically acceptable salt thereof, wherein
R$^6$ is H, C$_1$-C$_6$ alkyl, —C(O)R$^{6a}$, or G$^2$; wherein the C$_1$-C$_6$ alkyl is unsubstituted or substituted with a G$^2$ group.

14. The compound of claim 10, or a pharmaceutically acceptable salt thereof, wherein
R$^9$ is H, halogen, —S(O)$_2$R$^{y1}$, —C(O)NR$^{y3}$R$^{y4}$, —NR$^{y3}$R$^{y4}$, —N(R$^{y3}$)C(O)R$^{y2}$, —N(R$^{y3}$)S(O)$_2$R$^{y2}$, —N(R$^{y3}$)C(O)NR$^{y3}$R$^{y4}$, or —(C$_1$-C$_6$ alkylenyl)-S(O)$_2$R$^{y1}$.

15. The compound of claim 10, or a pharmaceutically acceptable salt thereof, wherein
A$^1$ is C(R$^7$), A$^2$ is C(R$^8$), A$^3$ is C(R$^9$), and A$^4$ is C(R$^{10}$); or
A$^1$ is N, A$^2$ is C(R$^8$), A$^3$ is C(R$^9$), and A$^4$ is C(R$^{10}$); or
A$^1$ is N, A$^2$ is C(R$^8$), A$^3$ is N, and A$^4$ is C(R$^{10}$).

16. The compound of claim 15, or a pharmaceutically acceptable salt thereof, wherein
R$^1$ is methyl;
R$^4$ is H or deuterium;
R$^7$ is H, halogen, C$_1$-C$_3$ alkyl, or optionally substituted cyclopropyl;

107

R⁸ is H, C₁-C₆ alkyl, halogen, C₁-C₆ haloalkyl, —CN, optionally substituted heterocycle, —C(O)NR^{y3}R^{y4}, —(C₁-C₆ alkylenyl)-NR^{y3}R^{y4}, —(C₁-C₆ alkylenyl)-N(R^{y3})C(O)R^{y2}, —(C₁-C₆ alkylenyl)-N(R^{y3})S(O)₂R^{y2}, (C₁-C₆ alkylenyl)-N(R^{y3})C(O)O(R^{y2}), (C₁-C₆ alkylenyl)-N(R^{y3})C(O)NR^{y3}R^{y4}, —(C₁-C₆ alkylenyl)-N(R^{y3})S(O)₂NR^{y3}R^{y4}, or —(C₁-C₆ alkylenyl)-G³ wherein G³ is optionally substituted heterocycle; and R¹⁰ is H, C₁-C₃ alkyl, or halogen.

17. The compound of claim 16, or a pharmaceutically acceptable salt thereof, wherein
R³ is H or —C(O)NR^{3b}R^{3c}.

18. The compound of claim 16, or a pharmaceutically acceptable salt thereof, wherein
R⁵ is H, deuterium, or C₁-C₆ alkyl optionally substituted with a substituent selected from the group consisting of —C(O)OR^{5a} and OR^{5a}.

19. The compound of claim 16, or a pharmaceutically acceptable salt thereof, wherein
R⁶ is —C(O)R^{6a}, G², or C₁-C₆ alkyl which is unsubstituted or substituted with a G² group.

20. The compound of claim 16, or a pharmaceutically acceptable salt thereof, wherein
R⁹ is halogen, —NR^{y3}R^{y4}, —N(R^{y3})C(O)R^{y2}, —N(R^{y3})S(O)₂R^{y2}, or —(C₁-C₆ alkylenyl)-S(O)₂R^{y1}.

21. The compound of claim 16, or a pharmaceutically acceptable salt thereof, wherein
R⁴ is H;
R⁷ is H or halogen;
R⁸ is H; and
R¹⁰ is H.

22. The compound of claim 21, or a pharmaceutically acceptable salt thereof, wherein
R⁹ is halogen, —NR^{y3}R^{y4}, —N(R^{y3})C(O)R^{y2}, —N(R^{y3})S(O)₂R^{y2}, or —(C₁-C₆ alkylenyl)-S(O)₂R^{y1}.

23. The compound of claim 22, or a pharmaceutically acceptable salt thereof, wherein
R⁶ is —C(O)R^{6a}, G², or C₁-C₆ alkyl which is unsubstituted or substituted with a G² group.

24. The compound of claim 23, or a pharmaceutically acceptable salt thereof, wherein
R⁵ is H or C₁-C₆ alkyl which is optionally substituted with a substituent selected from the group consisting of —C(O)OR^{5a} and OR^{5a}.

25. The compound of claim 24, or a pharmaceutically acceptable salt thereof, wherein
R³ is H.

26. The compound of claim 25, or a pharmaceutically acceptable salt thereof, wherein
R⁷ is hydrogen;
R^{5a} is C₁-C₆ alkyl;
R^{y1} is C₁-C₆ alkyl; and
R^{y3} is H.

27. The compound of claim 1, or a pharmaceutically acceptable salt thereof, wherein
A¹ is C(R⁷), A² is C(R⁸), A³ is C(R⁹), and A⁴ is C(R¹⁰).

28. The compound of claim 1, or a pharmaceutically acceptable salt thereof, wherein
A¹ is N, A² is C(R⁸), A³ is C(R⁹), and A⁴ is C(R¹⁰).

29. The compound of claim 1, or a pharmaceutically acceptable salt thereof, wherein
A¹ is N, A² is C(R⁸), A³ is N, and A⁴ is C(R¹⁰).

30. The compound of claim 1 or a pharmaceutically acceptable salt thereof, wherein the compound is selected from the group consisting of:
11-methyl-8-(methylsulfonyl)-2,4,5,11-tetrahydro-1H-2,5,11-triazadibenzo[cd,h]azulen-1-one;

108

5-(cyclopropylmethyl)-11-methyl-8-(methylsulfonyl)-2,4,5,11-tetrahydro-1H-2,5,11-triazadibenzo[cd,h]azulen-1-one;
5-(cyclopropylmethyl)-11-methyl-8-((methylsulfonyl)methyl)-2,4,5,11-tetrahydro-1H-2,5,11-triazadibenzo[cd,h]azulen-1-one;
5-(4-fluorophenyl)-11-methyl-8-((methylsulfonyl)methyl)-2,4,5,11-tetrahydro-1H-2,5,11-triazadibenzo[cd,h]azulen-1-one;
5-(2,4-difluorophenyl)-11-methyl-8-((methylsulfonyl)methyl)-2,4,5,11-tetrahydro-1H-2,5,11-triazadibenzo[cd,h]azulen-1-one;
5-(cyclopropanecarbonyl)-11-methyl-8-((methylsulfonyl)methyl)-2,4,5,11-tetrahydro-1H-2,5,11-triazadibenzo[cd,h]azulen-1-one;
5-benzoyl-11-methyl-8-((methylsulfonyl)methyl)-2,4,5,11-tetrahydro-1H-2,5,11-triazadibenzo[cd,h]azulen-1-one;
5-(4-fluorophenyl)-4-(2-methoxyethyl)-11-methyl-8-((methylsulfonyl)methyl)-2,4,5,11-tetrahydro-1H-2,5,11-triazadibenzo[cd,h]azulen-1-one;
methyl 3-(5-(4-fluorophenyl)-11-methyl-8-((methylsulfonyl)methyl)-1-oxo-2,4,5,11-tetrahydro-1H-2,5,11-triazadibenzo[cd,h]azulen-4-yl)propanoate;
5-(4-fluorophenyl)-11-methyl-8-((methylsulfonyl)methyl)-4-((tetrahydro-2H-pyran-4-yl)methyl)-2,4,5,11-tetrahydro-1H-2,5,11-triazadibenzo[cd,h]azulen-1-one;
5-(cyclopropylmethyl)-11-methyl-2,4,5,11-tetrahydro-1H-2,5,11-triazadibenzo[cd,h]azulen-1-one;
N-(5-(4-fluorophenyl)-11-methyl-1-oxo-2,4,5,11-tetrahydro-1H-2,5,11-triazadibenzo[cd,h]azulen-8-yl)ethanesulfonamide;
8-chloro-5-(4-fluorophenyl)-11-methyl-2,4,5,11-tetrahydro-1H-2,5,11-triazadibenzo[cd,h]azulen-1-one;
8-amino-5-(4-fluorophenyl)-11-methyl-2,4,5,11-tetrahydro-1H-2,5,6,11-tetraazadibenzo[cd,h]azulen-1-one;
ethyl 5-(4-fluorophenyl)-11-methyl-8-((methylsulfonyl)methyl)-1-oxo-2,4,5,11-tetrahydro-1H-2,5,11-triazadibenzo[cd,h]azulene-4-carboxylate;
8-fluoro-5-(4-fluorophenyl)-11-methyl-2,4,5,11-tetrahydro-1H-2,5,6,11-tetraazadibenzo[cd,h]azulen-1-one;
2-(2-chloro-5-fluorophenyl)-N-(5-(4-fluorophenyl)-11-methyl-1-oxo-2,4,5,11-tetrahydro-1H-2,5,6,11-tetraazadibenzo[cd,h]azulen-8-yl)acetamide;
2-(1,5-dimethyl-1H-pyrazol-3-yl)-N-(5-(4-fluorophenyl)-11-methyl-1-oxo-2,4,5,11-tetrahydro-1H-2,5,6,11-tetraazadibenzo[cd,h]azulen-8-yl)acetamide;
N-(5-(4-fluorophenyl)-11-methyl-1-oxo-2,4,5,11-tetrahydro-1H-2,5,6,11-tetraazadibenzo[cd,h]azulen-8-yl)-2-(3-(2-fluorophenyl)-1H-pyrazol-1-yl)acetamide;
2-(4-chloro-2-fluorophenyl)-N-(5-(4-fluorophenyl)-11-methyl-1-oxo-2,4,5,11-tetrahydro-1H-2,5,6,11-tetraazadibenzo[cd,h]azulen-8-yl)acetamide;
2-(chroman-6-yl)-N-(5-(4-fluorophenyl)-11-methyl-1-oxo-2,4,5,11-tetrahydro-1H-2,5,6,11-tetraazadibenzo[cd,h]azulen-8-yl)acetamide;
N-(5-(4-fluorophenyl)-11-methyl-1-oxo-2,4,5,11-tetrahydro-1H-2,5,6,11-tetraazadibenzo[cd,h]azulen-8-yl)-2-(1-methyl-1H-pyrazol-4-yl)acetamide;
8-amino-5-(4-fluorophenyl)-11-methyl-2,4,5,11-tetrahydro-1H-2,5,11-triazadibenzo[cd,h]azulen-1-one;
8-chloro-5-(4-fluorophenyl)-11-methyl-4-phenyl-2,4,5,11-tetrahydro-1H-2,5,11-triazadibenzo[cd,h]azulen-1-one;

11-methyl-8-((methylsulfonyl)methyl)-4-phenyl-2,4,5,11-tetrahydro-1H-2,5,11-triazadibenzo[cd,h]azulen-1-one;

N-(5-(4-fluorophenyl)-11-methyl-1-oxo-2,4,5,11-tetrahydro-1H-2,5,11-triazadibenzo[cd,h]azulen-8-yl)benzenesulfonamide;

N-(4-(N-(5-(4-fluorophenyl)-11-methyl-1-oxo-2,4,5,11-tetrahydro-1H-2,5,11-triazadibenzo[cd,h]azulen-8-yl)sulfamoyl)phenyl)acetamide;

N-(5-(4-fluorophenyl)-11-methyl-1-oxo-2,4,5,11-tetrahydro-1H-2,5,11-triazadibenzo[cd,h]azulen-8-yl)-2-(1-methyl-1H-pyrazol-4-yl)acetamide;

2-(4-chloro-2-fluorophenyl)-N-(5-(4-fluorophenyl)-11-methyl-1-oxo-2,4,5,11-tetrahydro-1H-2,5,11-triazadibenzo[cd,h]azulen-8-yl)acetamide;

2-(2-chloro-5-fluorophenyl)-N-(5-(4-fluorophenyl)-11-methyl-1-oxo-2,4,5,11-tetrahydro-1H-2,5,11-triazadibenzo[cd,h]azulen-8-yl)acetamide;

N-(5-(4-fluorophenyl)-11-methyl-1-oxo-2,4,5,11-tetrahydro-1H-2,5,11-triazadibenzo[cd,h]azulen-8-yl)-2-(3-(2-fluorophenyl)-1H-pyrazol-1-yl)acetamide;

N-(5-(4-fluorophenyl)-11-methyl-1-oxo-2,4,5,11-tetrahydro-1H-2,5,11-triazadibenzo[cd,h]azulen-8-yl)-2-(2-methylthiazol-5-yl)acetamide;

2-(1,5-dimethyl-1H-pyrazol-3-yl)-N-(5-(4-fluorophenyl)-11-methyl-1-oxo-2,4,5,11-tetrahydro-1H-2,5,11-triazadibenzo[cd,h]azulen-8-yl)acetamide;

$N^1$-(5-(4-fluorophenyl)-11-methyl-1-oxo-2,4,5,11-tetrahydro-1H-2,5,11-triazadibenzo[cd,h]azulen-8-yl)-$N^5$-phenylglutaramide;

N-(5-(4-fluorophenyl)-11-methyl-1-oxo-2,4,5,11-tetrahydro-1H-2,5,11-triazadibenzo[cd,h]azulen-8-yl)-5-methylpyrazine-2-carboxamide;

N-(5-(4-fluorophenyl)-11-methyl-1-oxo-2,4,5,11-tetrahydro-1H-2,5,11-triazadibenzo[cd,h]azulen-8-yl)-2-(4-methylpiperazin-1-yl)acetamide;

8-(((1-ethyl-1H-pyrazol-3-yl)methyl)amino)-5-(4-fluorophenyl)-11-methyl-2,4,5,11-tetrahydro-1H-2,5,11-triazadibenzo[cd,h]azulen-1-one;

5-(4-fluorophenyl)-11-methyl-8-(((1-methyl-1H-pyrazol-5-yl)methyl)amino)-2,4,5,11-tetrahydro-1H-2,5,11-triazadibenzo[cd,h]azulen-1-one;

8-((3-(1H-pyrazol-1-yl)propyl)amino)-5-(4-fluorophenyl)-11-methyl-2,4,5,11-tetrahydro-1H-2,5,11-triazadibenzo[cd,h]azulen-1-one;

5-(4-fluorophenyl)-11-methyl-8-(((6-methylpyridin-2-yl)methyl)amino)-2,4,5,11-tetrahydro-1H-2,5,11-triazadibenzo[cd,h]azulen-1-one;

methyl 445-(4-fluorophenyl)-11-methyl-1-oxo-2,4,5,11-tetrahydro-1H-2,5,11-triazadibenzo[cd,h]azulen-8-yl)amino)butanoate;

5-(4-fluorophenyl)-11-methyl-8-(((1-methyl-1H-imidazol-5-yl)methyl)amino)-2,4,5,11-tetrahydro-1H-2,5,11-triazadibenzo[cd,h]azulen-1-one;

5-(4-fluorophenyl)-11-methyl-8-(((3-methylpyridin-2-yl)methyl)amino)-2,4,5,11-tetrahydro-1H-2,5,11-triazadibenzo[cd,h]azulen-1-one;

1-(5-(4-fluorophenyl)-11-methyl-1-oxo-2,4,5,11-tetrahydro-1H-2,5,11-triazadibenzo[cd,h]azulen-8-yl)-3-(3-phenoxyphenyl)urea;

1-(5-(4-fluorophenyl)-11-methyl-1-oxo-2,4,5,11-tetrahydro-1H-2,5,11-triazadibenzo[cd,h]azulen-8-yl)-3-(3-methoxyphenyl)urea;

2-(chroman-6-yl)-N-(5-(4-fluorophenyl)-11-methyl-1-oxo-2,4,5,11-tetrahydro-1H-2,5,11-triazadibenzo[cd,h]azulen-8-yl)acetamide;

N-(5-(4-fluorophenyl)-11-methyl-1-oxo-2,4,5,11-tetrahydro-1H-2,5,11-triazadibenzo[cd,h]azulen-8-yl)-3-(4-methylpiperazin-1-yl)propanamide;

N-(5-(4-fluorophenyl)-11-methyl-1-oxo-2,4,5,11-tetrahydro-1H-2,5,11-triazadibenzo[cd,h]azulen-8-yl)-3-(piperidin-1-yl)propanamide;

2-(2-bromo-5-fluorophenyl)-N-(5-(4-fluorophenyl)-11-methyl-1-oxo-2,4,5,11-tetrahydro-1H-2,5,11-triazadibenzo[cd,h]azulen-8-yl)acetamide;

2-(2,5-dichlorophenyl)-N-(5-(4-fluorophenyl)-11-methyl-1-oxo-2,4,5,11-tetrahydro-1H-2,5,11-triazadibenzo[cd,h]azulen-8-yl)acetamide;

2-(5-fluoro-2-(trifluoromethyl)phenyl)-N-(5-(4-fluorophenyl)-11-methyl-1-oxo-2,4,5,11-tetrahydro-1H-2,5,11-triazadibenzo[cd,h]azulen-8-yl)acetamide;

2-(2,5-difluorophenyl)-N-(5-(4-fluorophenyl)-11-methyl-1-oxo-2,4,5,11-tetrahydro-1H-2,5,11-triazadibenzo[cd,h]azulen-8-yl)acetamide;

2-(2,5-dimethylphenyl)-N-(5-(4-fluorophenyl)-11-methyl-1-oxo-2,4,5,11-tetrahydro-1H-2,5,11-triazadibenzo[cd,h]azulen-8-yl)acetamide;

N-(5-(4-fluorophenyl)-11-methyl-1-oxo-2,4,5,11-tetrahydro-1H-2,5,11-triazadibenzo[cd,h]azulen-8-yl)-2-phenylacetamide;

2-(5-chloro-2-phenoxyphenyl)-N-(5-(4-fluorophenyl)-11-methyl-1-oxo-2,4,5,11-tetrahydro-1H-2,5,11-triazadibenzo[cd,h]azulen-8-yl)acetamide;

N-(5-fluoro-2-methoxybenzyl)-5-(4-fluorophenyl)-11-methyl-1-oxo-2,4,5,11-tetrahydro-1H-2,5,11-triazadibenzo[cd,h]azulene-8-carboxamide;

N-(5-fluoro-2-methylbenzyl)-5-(4-fluorophenyl)-11-methyl-1-oxo-2,4,5,11-tetrahydro-1H-2,5,11-triazadibenzo[cd,h]azulene-8-carboxamide;

N-(2-bromo-5-fluorobenzyl)-5-(4-fluorophenyl)-11-methyl-1-oxo-2,4,5,11-tetrahydro-1H-2,5,11-triazadibenzo[cd,h]azulene-8-carboxamide;

5-(4-fluorophenyl)-N-(1-(4-fluorophenyl)ethyl)-11-methyl-1-oxo-2,4,5,11-tetrahydro-1H-2,5,11-triazadibenzo[cd,h]azulene-8-carboxamide;

N-(2-chloro-5-fluorobenzyl)-5-(4-fluorophenyl)-11-methyl-1-oxo-2,4,5,11-tetrahydro-1H-2,5,11-triazadibenzo[cd,h]azulene-8-carboxamide;

N-(1-(2,4-dichlorophenyl)ethyl)-5-(4-fluorophenyl)-11-methyl-1-oxo-2,4,5,11-tetrahydro-1H-2,5,11-triazadibenzo[cd,h]azulene-8-carboxamide;

N-((1-benzyl-1H-pyrazol-4-yl)methyl)-5-(4-fluorophenyl)-11-methyl-1-oxo-2,4,5,11-tetrahydro-1H-2,5,11-triazadibenzo[cd,h]azulene-8-carboxamide;

N-benzyl-5-(4-fluorophenyl)-11-methyl-1-oxo-2,4,5,11-tetrahydro-1H-2,5,11-triazadibenzo[cd,h]azulene-8-carboxamide;

N-(2,5-difluorobenzyl)-5-(4-fluorophenyl)-11-methyl-1-oxo-2,4,5,11-tetrahydro-1H-2,5,11-triazadibenzo[cd,h]azulene-8-carboxamide;

2-(5-fluoro-2-methoxyphenyl)-N-(5-(4-fluorophenyl)-11-methyl-1-oxo-2,4,5,11-tetrahydro-1H-2,5,11-triazadibenzo[cd,h]azulen-8-yl)acetamide;

2-(5-fluoro-2-nitrophenyl)-N-(5-(4-fluorophenyl)-11-methyl-1-oxo-2,4,5,11-tetrahydro-1H-2,5,11-triazadibenzo[cd,h]azulen-8-yl)acetamide;

8-amino-5-(2,4-difluorophenyl)-11-methyl-2,4,5,11-tetrahydro-1H-2,5,6,11-tetraazadibenzo[cd,h]azulen-1-one;

N-(5-(2,4-difluorophenyl)-11-methyl-1-oxo-2,4,5,11-tetrahydro-1H-2,5,6,11-tetraazadibenzo[cd,h]azulen-8-yl)ethanesulfonamide;

8-amino-5-(4-chlorophenyl)-11-methyl-2,4,5,11-tetrahydro-1H-2,5,6,11-tetraazadibenzo[cd,h]azulen-1-one;
N-(5-(4-chlorophenyl)-11-methyl-1-oxo-2,4,5,11-tetrahydro-1H-2,5,6,11-tetraazadibenzo[cd,h]azulen-8-yl)ethanesulfonamide;
N-(5-(4-chlorophenyl)-11-methyl-1-oxo-2,4,5,11-tetrahydro-1H-2,5,6,11-tetraazadibenzo[cd,h]azulen-8-yl)methanesulfonamide;
N-(5-(4-chlorophenyl)-11-methyl-1-oxo-2,4,5,11-tetrahydro-1H-2,5,6,11-tetraazadibenzo[cd,h]azulen-8-yl)acetamide;
5-(1-acetylpiperidin-4-yl)-8-amino-11-methyl-2,4,5,11-tetrahydro-1H-2,5,11-triazadibenzo[cd,h]azulen-1-one;
N-(5-(1-acetylpiperidin-4-yl)-11-methyl-1-oxo-2,4,5,11-tetrahydro-1H-2,5,11-triazadibenzo[cd,h]azulen-8-yl)ethanesulfonamide;
N-(5-(1-acetylpiperidin-4-yl)-11-methyl-1-oxo-2,4,5,11-tetrahydro-1H-2,5,11-triazadibenzo[cd,h]azulen-8-yl)-2-(2-methylthiazol-5-yl)acetamide;
N-(5-(1-acetylpiperidin-4-yl)-11-methyl-1-oxo-2,4,5,11-tetrahydro-1H-2,5,11-triazadibenzo[cd,h]azulen-8-yl)-2-(2-chloro-5-fluorophenyl)acetamide;
N-(5-(1-acetylpiperidin-4-yl)-11-methyl-1-oxo-2,4,5,11-tetrahydro-1H-2,5,11-triazadibenzo[cd,h]azulen-8-yl)acetamide;
6-cyclopropyl-5-(2,4-difluorophenyl)-11-methyl-8-((methylsulfonyl)methyl)-2,4,5,11-tetrahydro-1H-2,5,11-triazadibenzo[cd,h]azulen-1-one;
11-methyl-8-((methylsulfonyl)methyl)-5-(pyridin-2-yl)-2,4,5,11-tetrahydro-1H-2,5,11-triazadibenzo[cd,h]azulen-1-one;
tert-butyl 4-(11-methyl-8-((methylsulfonyl)methyl)-1-oxo-1H-2,5,11-triazadibenzo[cd,h]azulen-5(2H,4H,11H)-yl)piperidine-1-carboxylate;
methyl 11-methyl-8-((methylsulfonyl)methyl)-1-oxo-4,11-dihydro-1H-2,5,11-triazadibenzo[cd,h]azulene-5(2H)-carboxylate; and
N-(11-methyl-1-oxo-5-(pyridin-2-yl)-2,4,5,11-tetrahydro-1H-2,5,11-triazadibenzo[cd,h]azulen-8-yl)ethanesulfonamide.

31. The compound of claim 1 or a pharmaceutically acceptable salt thereof, wherein the compound is selected from the group consisting of
5-(cyclopropylmethyl)-11-methyl-8-((methylsulfonyl)methyl)-2,4,5,11-tetrahydro-1H-2,5,11-triazadibenzo[cd,h]azulen-1-one;
5-(4-fluorophenyl)-11-methyl-8-((methylsulfonyl)methyl)-2,4,5,11-tetrahydro-1H-2,5,11-triazadibenzo[cd,h]azulen-1-one;
5-(2,4-difluorophenyl)-11-methyl-8-((methylsulfonyl)methyl)-2,4,5,11-tetrahydro-1H-2,5,11-triazadibenzo[cd,h]azulen-1-one;
5-(cyclopropanecarbonyl)-11-methyl-8-((methylsulfonyl)methyl)-2,4,5,11-tetrahydro-1H-2,5,11-triazadibenzo[cd,h]azulen-1-one;
5-(4-fluorophenyl)-4-(2-methoxyethyl)-11-methyl-8-((methylsulfonyl)methyl)-2,4,5,11-tetrahydro-1H-2,5,11-triazadibenzo[cd,h]azulen-1-one;
methyl 3-(5-(4-fluorophenyl)-11-methyl-8-((methylsulfonyl)methyl)-1-oxo-2,4,5,11-tetrahydro-1H-2,5,11-triazadibenzo[cd,h]azulen-4-yl)propanoate;
N-(5-(4-fluorophenyl)-11-methyl-1-oxo-2,4,5,11-tetrahydro-1H-2,5,11-triazadibenzo[cd,h]azulen-8-yl)ethanesulfonamide;
8-fluoro-5-(4-fluorophenyl)-11-methyl-2,4,5,11-tetrahydro-1H-2,5,6,11-tetraazadibenzo[cd,h]azulen-1-one;
2-(2-chloro-5-fluorophenyl)-N-(5-(4-fluorophenyl)-11-methyl-1-oxo-2,4,5,11-tetrahydro-1H-2,5,6,11-tetraazadibenzo[cd,h]azulen-8-yl)acetamide;
N-(5-(4-fluorophenyl)-11-methyl-1-oxo-2,4,5,11-tetrahydro-1H-2,5,6,11-tetraazadibenzo[cd,h]azulen-8-yl)-2-(1-methyl-1H-pyrazol-4-yl)acetamide;
8-amino-5-(4-fluorophenyl)-11-methyl-2,4,5,11-tetrahydro-1H-2,5,11-triazadibenzo[cd,h]azulen-1-one;
N-(5-(4-fluorophenyl)-11-methyl-1-oxo-2,4,5,11-tetrahydro-1H-2,5,6,11-tetraazadibenzo[cd,h]azulen-8-yl)benzenesulfonamide;
N-(4-(N-(5-(4-fluorophenyl)-11-methyl-1-oxo-2,4,5,11-tetrahydro-1H-2,5,11-triazadibenzo[cd,h]azulen-8-yl)sulfamoyl)phenyl)acetamide;
5-(4-fluorophenyl)-11-methyl-8-(((6-methylpyridin-2-yl)methyl)amino)-2,4,5,11-tetrahydro-1H-2,5,11-triazadibenzo[cd,h]azulen-1-one;
N-(5-(4-fluorophenyl)-11-methyl-1-oxo-2,4,5,11-tetrahydro-1H-2,5,11-triazadibenzo[cd,h]azulen-8-yl)-3-(piperidin-1-yl)propanamide;
N-(5-(2,4-difluorophenyl)-11-methyl-1-oxo-2,4,5,11-tetrahydro-1H-2,5,6,11-tetraazadibenzo[cd,h]azulen-8-yl)ethanesulfonamide;
N-(5-(4-chlorophenyl)-11-methyl-1-oxo-2,4,5,11-tetrahydro-1H-2,5,6,11-tetraazadibenzo[cd,h]azulen-8-yl)ethanesulfonamide;
N-(5-(4-chlorophenyl)-11-methyl-1-oxo-2,4,5,11-tetrahydro-1H-2,5,6,11-tetraazadibenzo[cd,h]azulen-8-yl)acetamide;
6-cyclopropyl-5-(2,4-difluorophenyl)-11-methyl-8-((methylsulfonyl)methyl)-2,4,5,11-tetrahydro-1H-2,5,11-triazadibenzo[cd,h]azulen-1-one;
11-methyl-8-((methylsulfonyl)methyl)-5-(pyridin-2-yl)-2,4,5,11-tetrahydro-1H-2,5,11-triazadibenzo[cd,h]azulen-1-one; and
N-(11-methyl-1-oxo-5-(pyridin-2-yl)-2,4,5,11-tetrahydro-1H-2,5,11-triazadibenzo[cd,h]azulen-8-yl)ethanesulfonamide.

32. A pharmaceutical composition comprising a therapeutically effective amount of a compound of formula (I) according to claim 1, or a pharmaceutically acceptable salt thereof, and a pharmaceutically acceptable carrier.

* * * * *